United States Patent
Banchereau et al.

(10) Patent No.: US 9,315,580 B2
(45) Date of Patent: Apr. 19, 2016

(54) VACCINES DIRECTED TO LANGERHANS CELLS

(71) Applicant: Baylor Research Institute, Dallas, TX (US)

(72) Inventors: Jacques F. Banchereau, Dallas, TX (US); Gerard Zurawski, Midlothian, TX (US); Sandra Zurawski, Midlothian, TX (US); Eynav Klechevsky, Haifa (IL); SangKon Oh, Baltimore, MD (US)

(73) Assignee: Baylor Research Institute, Dallas, TX (US)

( * ) Notice: Subject to any disclaimer, the term of this patent is extended or adjusted under 35 U.S.C. 154(b) by 185 days.

(21) Appl. No.: 13/863,131

(22) Filed: Apr. 15, 2013

(65) Prior Publication Data

US 2014/0030264 A1    Jan. 30, 2014

Related U.S. Application Data

(63) Continuation of application No. 12/882,052, filed on Sep. 14, 2010, now abandoned.

(60) Provisional application No. 61/242,283, filed on Sep. 14, 2009.

(51) Int. Cl.
| | | |
|---|---|---|
| *C07K 16/00* | (2006.01) | |
| *C12P 21/08* | (2006.01) | |
| *C07K 16/28* | (2006.01) | |
| *A61K 39/00* | (2006.01) | |
| *A61K 39/145* | (2006.01) | |
| *A61K 39/21* | (2006.01) | |
| *C07K 14/47* | (2006.01) | |
| *C12N 7/00* | (2006.01) | |
| *C07K 14/005* | (2006.01) | |
| *A61K 39/12* | (2006.01) | |

(52) U.S. Cl.
CPC ......... *C07K 16/2896* (2013.01); *A61K 39/0011* (2013.01); *A61K 39/12* (2013.01); *A61K 39/145* (2013.01); *A61K 39/21* (2013.01); *C07K 14/005* (2013.01); *C07K 14/4748* (2013.01); *C07K 16/2851* (2013.01); *C12N 7/00* (2013.01); *A61K 2039/505* (2013.01); *A61K 2039/5154* (2013.01); *A61K 2039/55561* (2013.01); *A61K 2039/6056* (2013.01); *C07K 2319/00* (2013.01); *C07K 2319/33* (2013.01); *C12N 2740/16034* (2013.01); *C12N 2760/16134* (2013.01)

(58) Field of Classification Search
None
See application file for complete search history.

(56) References Cited

U.S. PATENT DOCUMENTS

| | | | |
|---|---|---|---|
| 6,685,930 B1 | 2/2004 | Chang | 424/85.2 |
| 7,247,615 B2 | 7/2007 | Schlom et al. | 514/15 |
| 7,560,534 B2 | 7/2009 | Deo et al. | 530/388.73 |
| 2005/0214312 A1 | 9/2005 | Flechtner et al. | 424/185.1 |
| 2006/0257412 A1 | 11/2006 | Bowdish et al. | 424/178.1 |
| 2007/0014807 A1 | 1/2007 | Maida | 424/185.1 |
| 2008/0254044 A1 | 10/2008 | Zurawski et al. | 424/178.1 |
| 2008/0260735 A1 | 10/2008 | Ellis et al. | 424/133.1 |
| 2010/0322929 A1 | 12/2010 | Zurawski et al. | 424/134.1 |

FOREIGN PATENT DOCUMENTS

| | | |
|---|---|---|
| AU | 2010291939 | 3/2013 |
| CN | 1452636 A | 10/2003 |
| CN | 101155914 A | 4/2008 |
| WO | WO 9404679 A1 * | 3/1994 |
| WO | 01/85798 | 11/2001 |
| WO | 2006/127150 | 11/2006 |
| WO | 2008/097817 | 8/2008 |
| WO | 2009/061996 | 5/2009 |
| WO | 2010/009346 | 1/2010 |

OTHER PUBLICATIONS

Banchereau, Jacques, et al., "Dendritic Cells and the Control of Immunity", Nature, Mar. 19, 1998, vol. 392, pp. 245-252.

Caux, Christophe, et al., "CD34+ Hematopoietic Progenitors from Human Cord Blood Differentiate Along Two Independent Dendritic Cell Pathways in Response to GM-CSF+TNFalpha", J. Exp. Med., Aug. 1996, vol. 184, pp. 695-706.

Caux, Christophe, et al., "CD34+ Hematopoietic Progenitors from Human Cord Blood Differentiate Along Two Indepenent Dendritic Cell Pathways in Response to Granulocyte-Macrophage Colony-Stimulating Factor Plus Tumor Necrosis Pacter alpha:II. Functional Analysis", Blood, 1997, 90:1458-1470.

Chomarat, Pascale, et al., "TNF Skews Monocyte Differentiation Dendritic Cells", J. Immunol., (2003), 171:2262-2269.

Dudziak, Diana, et al., "Differential Antigen Processing by Dendritic Cell Subsets in Vivo", Science, Jan. 5, 2007, vol. 315, pp. 107-111.

Fonteneau, Jean-Francois, et al., "Activation of Influenza—Virus-Specific CD4+ and CD8+ T Cells: A New Role for Plasmacytoid Dendritic Cells in Adaptive Immunity", Blood, May 1, 2003, vol. 101, No. 9, pp. 3520-3526.

He, Bing, et al., "Intestinal Bacteria Trigger T Cell-Independent Immunoglobulin A2 class Switching by Inducing Epithelial-Cell Secretion of the Cytokine April", Immunity, Jun. 2007, 26, pp. 812-826, Kadowaki, Norimitsu, et al., "Natural Interferon alpha/Beta-Producing Cells Link Innate and Adaptive Immunity", J. Exp. Med., Jul. 17, 2000, vol. 192, No. 2, pp. 219-225.

(Continued)

*Primary Examiner* — Hong Sang
(74) *Attorney, Agent, or Firm* — Norton Rose Fulbright US LLP

(57) ABSTRACT

The present invention includes isolated anti-Langerin vaccines, methods for making and using an isolated anti-Langerin antibody or binding fragment thereof and one or more antigenic peptides at the carboxy-terminus of the isolated anti-Langerin antibody, wherein when two or more antigenic peptides are present, the peptides are separated by the one or more linker peptides that comprise at least one glycosylation site. The present invention also includes isolated vectors for the expression of the anti-Langerin antigen delivery vectors and their manufactures and use.

7 Claims, 17 Drawing Sheets

(56) References Cited

OTHER PUBLICATIONS

Luft, Thomas, et al., "Functionally Distinct Dendritic Cell (DS) Populations Induced by Physiologic Stimuli: Prostaglandin E2 Regulates the Migratory Subsets", Blood, (2002), 100:1362-1372.
Maldonado-Lopez, Roberto, et al., "CD8alpha+ and CD8alpha-subclasses of Dendritic Cells Direct the Development of Distinct T Helper Cells in Vivo", J. Exp. Med., Feb. 1, 1999, vol. 189, No. 3, pp. 587-592.
Mohamadzadeh, Mansour, et al., "Interleukin 15 Skews Monocyte Differentiation into Dendritic Cells with Features of Langerhans Cells", J. Exp. Med., Oct. 1, 2001, vol. 194, No. 7, pp. 1013-1019.
Paquette, Ronald L, et al., "Interferon-alpha and Granulocyte-Macrophage Colony-Stimulating Factor Differentiate Peripheral Blood Monocytes into Potent Antigen-Presenting Cells", J. Leukoc. Biol., ( Sep. 1998), 64:358-367.
Di Pucchio, Tiziana, et al., "Direct Proteasome-Independent Cross-Presentation of Viral Antigen by Plasmacytoid Dendritic Cells on Major Histocompatibility Complex Class 1", Nat. Immunol., May 2008, 9(5):551-557.
Pulendran, B., et al., "Distinct Dendritic Cell Subsets Differentially Regulate the Class of Immune Reponse in Vivo", Proc. Natl. Acad, Sci, Feb. 1999, vol. 96, pp. 1036-1041.
Pulendran, Bali, et al., "Lipopolysaccharides from Distinct Pathogens Induce Different Classes of Immune Responses in Vivo", J. Immunol., (2001), 167:5067-5076.
Rissoan, Marie-Ciotilde, et al., "Reciprocal Control of T Helper Cell and Dendritic Cell Differentiation", Science, Feb. 19, 1999, vol. 283, pp. 1183-1186.
Romani, Nikolaus, et al., "Proliferating Dendritic Cell Progenitors in Human Blood", J. Exp. Med., Jul. 1994, vol. 180, pp. 83-93.
Sallusto, Federica, et al., "Efficient Presentation of Soluble Antigen by Cultured Human Dendritic Cells is Maintained by Granulocyte/Macrophage Colony-Stimulating Factor Plus Interleukin 4 and Downregulated by Tumor Nectosis Factor alpha", J. Exp. Med., Apr. 1994, vol. 179, pp. 1109-1118.
Seifert, Ulrike, et al., "An Essential Role for Tripeptidyl Peptidase in the Generation of an MHC Class I Epitop", Nature Immunology, vol. 4, No. 4, (Apr. 2003), pp. 375-379.
Shortman, Ken, et al., "Mouse and Human Dendritic Cell Subtypes", Nature Reviews: Immunology, Mar. 2002, vol. 2, pp. 151-161.
Peters, J.H., et al., "Signals Required for Differentiating Dendritic Cells from Human Monocytes in Vitro", Adv. Exp. Med. Biol (1993), vol. 329:275-280 (Abstract Only).
Altin, J.G., et al., "Targeting dendritic cells with atigen-containing liposomes:antitumour immunity.", Expert Opin. Biol. Ther. 4(11):1735-1747 (Nov. 2004).
Idoyaga, J. et al. "Antibody to Langerin/CD207 localized large numbers of CD8alpha+ dendritic cells to the marginal zone of mouse spleen." Proc. Natl. Acad. Sci. U.S.A. 106(5): 1524-1529 (Feb. 3, 2009).
Koski, G.K. et al., "Reengineering dendritic cell-based anti-cancer vaccines." Immunol. Rev. 222:256-276 (Apr. 2008).
Ramakrishna, V., et al., "Toll-like receptor activation enhances cell-mediated immunity induced by an antibody vaccine targeting human dendritic cells." J. Transl. Med. 5:5 doi:10.1186/1479-5876-5-5 (Jan. 25, 2007).
Seo, N., et al., "Vaccine therapy for cutaneous T-cell lymphoma." Hematol. Oncol. Clin. North. Am. 17(6):1467-1474 (Dec. 2003).
Shortman, K., et al., "Improving vaccines by targeting antigens to dendritic cells." Exp. Mol. Med. 41(2): 61-66 (Feb. 28, 2009).

Stoitzner, P., et al., "Vizualization and characterization of migratory Langerhans cells in murine skin and lymph nodes by antibodies against Langerin/CD207." J. Invest. Dermatol. 120(2):266-274 (Feb. 2003).
International Search Report and Written Opinion for PCT/US2010/048800 dated May 30, 2011 (15 pages).
Komenaka, et al., "HM 1.24—Utilizing Cancer Vaccines," Clinics in Dermatology, 2004, 22:251-265.
Evans, et al., Q.J. Med 1999: 92:299-307.
Paul, "Fundamental Immunology," 3rd Edition, 1993, pp. 292-295.
Rudikoff, et al., "Single Amino Acid Substitution Altering Antigen-binding Specificity," Proc. Natl. Acad. Scie. USA. 79(6): 1979-1983, Mar. 1982.
Coleman, Research in Immunology, 145:33-36, 1994.
Bending, Methods: A Companion to Methods in Enzymology, 1995; 8:83-93.
Cheong, et al, "Production of Monoclonal Antibodies that Recognize the Extracellular Domain of Mouse Langerin/CD207," Journal of Immunological Methods, vol. 324, No. 1-2, Jul. 2, 2007, pp. 48-62.
Flacher, Vincent, et al., "Expression of Langerin/CD207 reveals dendritic cell heterogeneity between inbred mouse strains," Immunology, vol. 123, No. 3, pp. 339-347, Mar. 1, 2008.
Geijtenbeek, Teunis B.H., et al., "Rhesus macaque and Chimpanzee DC-Sign act as HIV/SIV gp120 trans-receptors, similar to human DC-SIGN," Immunology Letters, vol. 79, No. 1-2, pp. 101-107, Nov. 1, 2001.
Tacken, Paul J. et al., "Dendritic-cell Immunotherapy: from ex vivo loading in vivo targeting," The Journal of Immunology, Nature Pub. Group, vol. 7, No. 10, pp. 790-802; Oct. 1, 2007.
Pereira, Candida F. et al., "In vivo targeting of DC-SIGN-positive antigen-presenting cells in a nonhuman primate model," Journal of Immunotherapy, vol. 30, No. 7; Oct. 1, 2007.
Banchereau, J., et al., "Immune and Clinical Responses in Patients with Metastatic Melanoma to CD34+ Progenitor-derived Dendritic Cell Vaccine" *Canser Res.* 61:6451-6458 (2001).
Robertson, M., et al., "Efficient Antigen Presentation to Cytotozic T Lymphocytes by Cells Transduced with a Retroviral Vector Expressing the HIV-1 Nef Protein" *AIDS Search and Human Retroviruses* 9(12): 1217-1223 (1993).
Van Broekhoven, C., et al., "Targeting Dendritic Cells with Antigen-Containing Liposomes: A Highly Effecetive Procedure for Induction of Antitumor Immunity and for Tumor Immunotherapy" *Cancer Res.* 64:4357-4365 (2004).
Idoyaga, J., et al. "Cutting Edge: Langerin/CD207 Receptor on Dendritic Cells Mediates Efficient Antigen Presentation on MHC I and II Products in Vivo" *J of Immunology*, 180(6):2647-3650 (2008).
Hawiger, D., et al. "Dendritic Cells Induce Peripheral T Cell Unresponsiveness Under Stead State Conditions in Vivo" *JEM*, 194(6):769-779 (2001).
Dudziak, D., et al "Differential Antigen Processing by Dendritic Cell Subsets in Vivo" *Science*, 315(5808):107-111 (2007).
Bonifaz, Laura C. et al. "In Vivo Targeting of Antigens to Maturing Dendritic Cells via the DEC-205 Receptor Improves T Cell Vaccination" *JEM*, 199(6):815-824 (2004).
Trumpfheller, C., et al. "Intensified and protective CD4+ T cell immunity in mice with anti-dendritic cell HIV gag fusion antibody vaccine" *JEM*, 203(3):607-617 (2006).
Bozzacco, Leonla et al. "DEC-205 receptor on dendritic cells mediates presentation of HIV gag protein to CD8+ T cells in a spectrum of human MHC 1 haplotypes" *PNAS*, 104(4):1289-1294 (2007).

\* cited by examiner

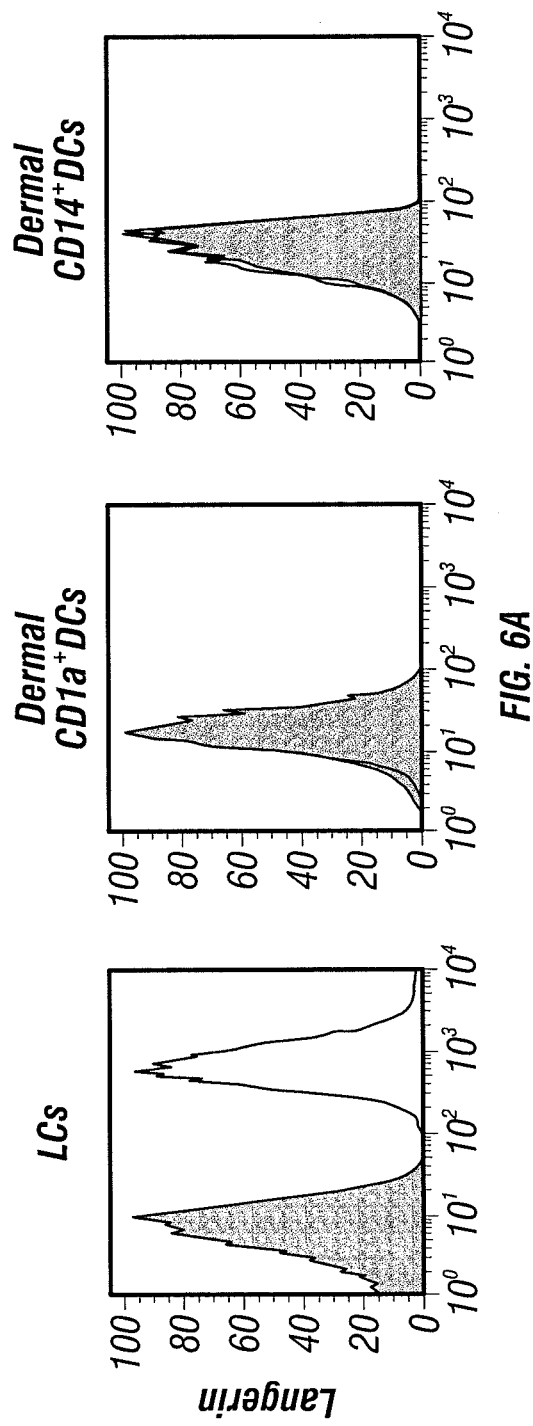
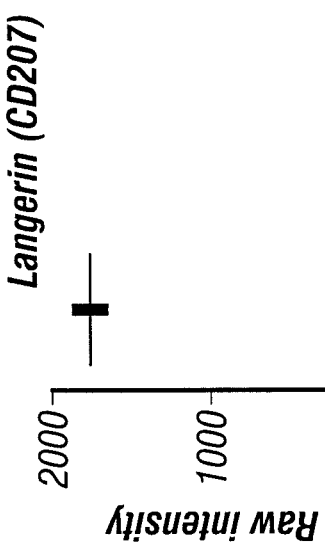
FIG. 6A
FIG. 6C
FIG. 6B

Human Epithelial Sheet

DR-FITC
Anti-Langerin 15b10-Alexa568

Confocal 63x objective

```
                         SEQUENCE LISTING

<160> NUMBER OF SEQ ID NOS: 82

<210> SEQ ID NO 1
<211> LENGTH: 717
<212> TYPE: DNA
<213> ORGANISM: Artificial Sequence
<220> FEATURE:
<223> OTHER INFORMATION: Synthetic oligonucleotide.

<400> SEQUENCE: 1
atgaagttgc ctgttaggct gttggtgctg atgttctgga ttcctgcttc cagcagtgat      60
gttgtgatga cccaaactcc actctccctg cctgtccgtc ttggagatca agcctccatc     120
tcttgcagat ctagtcagag ccttgtacac agtaatggaa acacctattt acattggtac     180
ctgcagaagc caggccagtc tccaaagctc ctgatctaca agtttccaa ccgatttct      240 ggggtcccag acaggttcag tggcagtgga tcagggacaa atttcacact caagatcagc     300
agagtggagg ctgaggatct gggactttat ttctgctctc aaagtacaca tgttccgtac     360
acgttcggag gggggaccaa gctggaaata aaacgggctg atgctgcacc aactgtatcc     420 atcttccac catccagtga gcagttaaca tctggaggtg cctcagtcgt gtgcttcttg      480
aacaacttct accccaaaga catcaatgtc aagtggaaga ttgatggcag tgaacgacaa     540
aatggcgtcc tgaacagttg gactgatcag gacagcaaag acagcaccta cagcatgaac     600
agcaccctca cgttgaccaa ggacgagtat gaacgacata cagctatac ctgtgaggcc      660 actcacaaga catcaacttc acccatcgtc aagagcttca caggaatga gtgttag        717

<210> SEQ ID NO 2
<211> LENGTH: 219
<212> TYPE: PRT
<213> ORGANISM: Artificial Sequence
<220> FEATURE:
<223> OTHER INFORMATION: Synthetic peptide.

<400> SEQUENCE: 2

Asp Val Val Met Thr Gln Thr Pro Leu Ser Leu Pro Val Arg Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45
```

```
Pro Lys Leu Leu Ile Tyr Lys Val Ser Asn Arg Phe Ser Gly Val Pro
     50                  55                  60

Asp Arg Phe Ser Gly Ser Gly Ser Gly Thr Asn Phe Thr Leu Lys Ile
 65                  70                  75                  80

Ser Arg Val Glu Ala Glu Asp Leu Gly Leu Tyr Phe Cys Ser Gln Ser
                 85                  90                  95

Thr His Val Pro Tyr Thr Phe Gly Gly Gly Thr Lys Leu Glu Ile Lys
                100                 105                 110

Arg Ala Asp Ala Ala Pro Thr Val Ser Ile Phe Pro Pro Ser Ser Glu
            115                 120                 125

Gln Leu Thr Ser Gly Gly Ala Ser Val Val Cys Phe Leu Asn Asn Phe
        130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Asn Ser Thr Leu Thr Leu Thr Lys Asp Glu Tyr Glu
                180                 185                 190

Arg His Asn Ser Tyr Thr Cys Glu Ala Thr His Lys Thr Ser Thr Ser
            195                 200                 205

Pro Ile Val Lys Ser Phe Asn Arg Asn Glu Cys
        210                 215

<210> SEQ ID NO 3
<211> LENGTH: 1395
<212> TYPE: DNA
<213> ORGANISM: Artificial Sequence
<220> FEATURE:
<223> OTHER INFORMATION: Syntehtic oligonucleotide.

<400> SEQUENCE: 3
atggaatgga ggatctttct cttcatcctg tcaggaactg caggtgtcca ctcccaggtt     60
cagctgcggc agtctggacc tgagctggtg aagcctgggg cttcagtgaa gatgtcctgc    120
aaggcttctg gatacacatt tactgactat gttataagtt gggtgaagca gagaactgga    180
cagggccttg agtggattgg agatatttat cctggaagtg gttattcttt ctacaatgag    240
aacttcaagg gcaaggccac actgactgca gacaaatcct ccaccacagc ctacatgcag    300
ctcagcagcc tgacatctga ggactctgcg gtctatttct gtgcaaccta ctataactac    360 cctttttgctt actggggcca agggactctg gtcactgtct ctgcagccaa acaacgggc    420 ccatccgtct tccccctggc gccctgctcc aggagcacct ccgagagcac agccgccctg    480
ggctgcctgg tcaaggacta cttccccgaa ccggtgacgg tgtcgtggaa ctcaggcgcc    540
ctgaccagcg gcgtgcacac cttcccggct gtcctacagt cctcaggact ctactccctc    600
agcagcgtgg tgaccgtgcc ctccagcagc ttgggcacga agacctacac ctgcaacgta    660
gatcacaagc ccagcaacac caaggtggac aagagagttg agtccaaata tggtccccca    720
tgcccaccct gcccagcacc tgagttcgaa ggggaccat cagtcttcct gttcccccca    780
aaacccaagg acactctcat gatctcccgg acccctgagg tcacgtgcgt ggtggtggac    840
gtgagccagg aagaccccga ggtccagttc aactggtacg tggatggcgt ggaggtgcat    900
aatgccaaga caaagccgcg ggaggagcag ttcaacagca cgtaccgtgt ggtcagcgtc    960
ctcaccgtcc tgcaccagga ctggctgaac ggcaaggagt acaagtgcaa ggtctccaac   1020
aaaggcctcc cgtcctccat cgagaaaacc atctccaaag ccaaagggca gccccgagag   1080
```

-continued

```
ccacaggtgt acaccctgcc cccatcccag gaggagatga ccaagaacca ggtcagcctg    1140
acctgcctgg tcaaaggctt ctaccccagc gacatcgccg tggagtggga gagcaatggg    1200
cagccggaga caactacaa gaccacgcct cccgtgctgg actccgacgg ctccttcttc     1260
ctctacagca ggctaaccgt ggacaagagc aggtggcagg aggggaatgt cttctcatgc    1320
tccgtgatgc atgaggctct gcacaaccac tacacacaga gagcctctc cctgtctctg    1380 ggtaaagcta gctga                                                     1395

<210> SEQ ID NO 4
<211> LENGTH: 446
<212> TYPE: PRT
<213> ORGANISM: Artificial Sequence
<220> FEATURE:
<223> OTHER INFORMATION: Synthetic peptide.

<400> SEQUENCE: 4

Gln Val Gln Leu Arg Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Val Ile Ser Trp Val Lys Gln Arg Thr Gly Gln Gly Leu Glu Trp Ile
        35                  40                  45

Gly Asp Ile Tyr Pro Gly Ser Gly Tyr Ser Phe Tyr Asn Glu Asn Phe
    50                  55                  60

Lys Gly Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Phe Cys
                85                  90                  95

Ala Thr Tyr Tyr Asn Tyr Pro Phe Ala Tyr Trp Gly Gln Gly Thr Leu
            100                 105                 110

Val Thr Val Ser Ala Ala Lys Thr Thr Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300
```

```
Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
            325                 330                 335

Lys Gly Gln Pro Arg Glu Pro Gln Val Tyr Thr Leu Pro Pro Ser Gln
        340                 345                 350

Glu Glu Met Thr Lys Asn Gln Val Ser Leu Thr Cys Leu Val Lys Gly
    355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys Ala Ser
        435                 440                 445
```

```
<210> SEQ ID NO 5
<211> LENGTH: 705
<212> TYPE: DNA
<213> ORGANISM: Artificial Sequence
<220> FEATURE:
<223> OTHER INFORMATION: Synthetic oligonucleotide.

<400> SEQUENCE: 5
atggcctgga tttcacttat actctctctc ctggctctca gctcaggggc catttcccag    60
gctgttgtga ctcaggaatc tgcactcacc acatcacctg gtgaaacagt cacactcact   120
tgtcgctcaa gtactgggac tgttacaact agtaactatg ccaactgggt ccaagaaaaa   180
ccagatcatt tattcactgg tctaataggt ggtaccaaca accgagtttc aggtgttcct   240
gccagattct caggctccct gattggagac aaggctgccc tcaccatcac aggggcacag   300
actgaggatg aggcaatata tttctgtgct ctatggtaca gcaaccattg ggtgttcggt   360
ggaggaacca aactgactgt cctaggccag cccaagtctt cgccatcagt caccctgttt   420
ccaccttcct ctgaagagct cgagactaac aaggccacac tggtgtgtac gatcactgat   480
ttctacccag gtgtggtgac agtggactgg aaggtagatg gtacccctgt cactcagggt   540
atggagacaa cccagccttc caaacagagc aacaacaagt acatggctag cagctacctg   600
accctgacag caagagcatg ggaaaggcat agcagttaca gctgccaggt cactcatgaa   660
ggtcacactg tggagaagag tttgtcccgt gctgactgtt cctag                   705
```

```
<210> SEQ ID NO 6
<211> LENGTH: 215
<212> TYPE: PRT
<213> ORGANISM: Artificial Sequence
<220> FEATURE:
<223> OTHER INFORMATION: Synthetic peptide.

<400> SEQUENCE: 6

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
```

```
                35                  40                  45
Leu Ile Gly Gly Thr Asn Asn Arg Val Ser Gly Val Pro Ala Arg Phe
 50                  55                  60

Ser Gly Ser Leu Ile Gly Asp Lys Ala Ala Leu Thr Ile Thr Gly Ala
 65                  70                  75                  80

Gln Thr Glu Asp Glu Ala Ile Tyr Phe Cys Ala Leu Trp Tyr Ser Asn
                 85                  90                  95

His Trp Val Phe Gly Gly Gly Thr Lys Leu Thr Val Leu Gly Gln Pro
                100                 105                 110

Lys Ser Ser Pro Ser Val Thr Leu Phe Pro Pro Ser Ser Glu Glu Leu
            115                 120                 125

Glu Thr Asn Lys Ala Thr Leu Val Cys Thr Ile Thr Asp Phe Tyr Pro
130                 135                 140

Gly Val Val Thr Val Asp Trp Lys Val Asp Gly Thr Pro Val Thr Gln
145                 150                 155                 160

Gly Met Glu Thr Thr Gln Pro Ser Lys Gln Ser Asn Asn Lys Tyr Met
                165                 170                 175

Ala Ser Ser Tyr Leu Thr Leu Thr Ala Arg Ala Trp Glu Arg His Ser
            180                 185                 190

Ser Tyr Ser Cys Gln Val Thr His Glu Gly His Thr Val Glu Lys Ser
        195                 200                 205

Leu Ser Arg Ala Asp Cys Ser
210                 215
```

<210> SEQ ID NO 7
<211> LENGTH: 1401
<212> TYPE: DNA
<213> ORGANISM: Artificial Sequence
<220> FEATURE:
<223> OTHER INFORMATION: Syntehtic oligonucleotide.

<400> SEQUENCE: 7

```
atgacattga acatgctgtt ggggctgaag tgggttttct tgttgttttt ttatcaaggt     60
gtgcattgtg aggtgcagct tgttgagtct ggtggaggat tggtgcagcc taaagggtca   120
ttgaaactct catgtgcagc ctctggatta accttcaata tctacgccat gaactgggtc   180
cgccaggctc caggaaaggg tttggaatgg gttgctcgca taagaaataa agtaataat   240 tatgcaacat attatgccga ttcagtgaaa gacaggttca ccatctccag agatgattca   300
caaagcttgc tctatctgca aatgaacaac ttgaaaactg aggacacagc catgtattac   360
tgtgtgggac gggactggtt tgattactgg ggccaaggga ctctggtcac tgtctctgca   420
gccaaaacga cacccccatc tgtctatcca ctggcccctg gatctgctgc ccaaactaac   480
tccatggtga ccctgggatg cctggtcaag ggctatttcc ctgagccagt gacagtgacc   540
tggaactctg gatccctgtc cagcggtgtg cacaccttcc cagctgtcct gcagtctgac   600
ctctacactc tgagcagctc agtgactgtc cctccagca cctggcccag cgagaccgtc   660
acctgcaacg ttgcccaccc ggccagcagc accaaggtgg acaagaaaat tgtgcccagg   720
gattgtggtt gtaagccttg catatgtaca gtcccagaag tatcatctgt cttcatcttc   780
cccccaaagc ccaaggatgt gctcaccatt actctgactc ctaaggtcac gtgtgttgtg   840
gtagacatca gcaaggatga tcccgaggtc cagttcagct ggtttgtaga tgatgtggag   900
gtgcacacag ctcagacgca accccgggag gagcagttca acagcacttt ccgctcagtc   960
agtgaacttc ccatcatgca ccaggactgg ctcaatggca aggagttcaa atgcagggtc  1020
```

```
aacagtgcag ctttccctgc ccccatcgag aaaaccatct ccaaaaccaa aggcagaccg    1080
aaggctccac aggtgtacac cattccacct cccaaggagc agatggccaa ggataaagtc    1140
agtctgacct gcatgataac agacttcttc cctgaagaca ttactgtgga gtggcagtgg    1200
aatgggcagc cagcggagaa ctacaagaac actcagccca tcatggacac agatggctct    1260
tacttcgtct acagcaagct caatgtgcag aagagcaact gggaggcagg aaatactttc    1320
acctgctctg tgttacatga gggcctgcac aaccaccata ctgagaagag cctctcccac    1380
tctcctggta aagctagctg a                                              1401
```

<210> SEQ ID NO 8
<211> LENGTH: 443
<212> TYPE: PRT
<213> ORGANISM: Artificial Sequence
<220> FEATURE:
<223> OTHER INFORMATION: Synthetic peptide.

<400> SEQUENCE: 8

```
Glu Val Gln Leu Val Glu Ser Gly Gly Gly Leu Val Gln Pro Lys Gly
1               5                   10                  15

Ser Leu Lys Leu Ser Cys Ala Ala Ser Gly Leu Thr Phe Asn Ile Tyr
            20                  25                  30

Ala Met Asn Trp Val Arg Gln Ala Pro Gly Lys Gly Leu Glu Trp Val
        35                  40                  45

Ala Arg Ile Arg Asn Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Leu
65                  70                  75                  80

Leu Tyr Leu Gln Met Asn Asn Leu Lys Thr Glu Asp Thr Ala Met Tyr
                85                  90                  95

Tyr Cys Val Gly Arg Asp Trp Phe Asp Tyr Trp Gly Gln Gly Thr Leu
            100                 105                 110

Val Thr Val Ser Ala Ala Lys Thr Thr Pro Pro Ser Val Tyr Pro Leu
        115                 120                 125

Ala Pro Gly Ser Ala Ala Gln Thr Asn Ser Met Val Thr Leu Gly Cys
    130                 135                 140

Leu Val Lys Gly Tyr Phe Pro Glu Pro Val Thr Val Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Pro Ser Ser Thr Trp
            180                 185                 190

Pro Ser Glu Thr Val Thr Cys Asn Val Ala His Pro Ala Ser Ser Thr
        195                 200                 205

Lys Val Asp Lys Lys Ile Val Pro Arg Asp Cys Gly Cys Lys Pro Cys
    210                 215                 220

Ile Cys Thr Val Pro Glu Val Ser Ser Val Phe Ile Phe Pro Pro Lys
225                 230                 235                 240

Pro Lys Asp Val Leu Thr Ile Thr Leu Thr Pro Lys Val Thr Cys Val
                245                 250                 255

Val Val Asp Ile Ser Lys Asp Asp Pro Glu Val Gln Phe Ser Trp Phe
            260                 265                 270

Val Asp Asp Val Glu Val His Thr Ala Gln Thr Gln Pro Arg Glu Glu
        275                 280                 285

Gln Phe Asn Ser Thr Phe Arg Ser Val Ser Glu Leu Pro Ile Met His
```

```
                            290                 295                 300
Gln Asp Trp Leu Asn Gly Lys Glu Phe Lys Cys Arg Val Asn Ser Ala
305                 310                 315                 320

Ala Phe Pro Ala Pro Ile Glu Lys Thr Ile Ser Lys Thr Lys Gly Arg
                325                 330                 335

Pro Lys Ala Pro Gln Val Tyr Thr Ile Pro Pro Lys Glu Gln Met
            340                 345                 350

Ala Lys Asp Lys Val Ser Leu Thr Cys Met Ile Thr Asp Phe Phe Pro
            355                 360                 365

Glu Asp Ile Thr Val Glu Trp Gln Trp Asn Gly Gln Pro Ala Glu Asn
            370                 375                 380

Tyr Lys Asn Thr Gln Pro Ile Met Asp Thr Asp Gly Ser Tyr Phe Val
385                 390                 395                 400

Tyr Ser Lys Leu Asn Val Gln Lys Ser Asn Trp Glu Ala Gly Asn Thr
                405                 410                 415

Phe Thr Cys Ser Val Leu His Glu Gly Leu His Asn His His Thr Glu
                420                 425                 430

Lys Ser Leu Ser His Ser Pro Gly Lys Ala Ser
            435                 440
```

<210> SEQ ID NO 9
<211> LENGTH: 60
<212> TYPE: PRT
<213> ORGANISM: Artificial Sequence
<220> FEATURE:
<223> OTHER INFORMATION: Synthetic peptide.

<400> SEQUENCE: 9

```
Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
                20                  25                  30

Lys His Ser Gln Pro Trp Gln Val Leu Val Ala Ser Arg Gly Arg Ala
            35                  40                  45

Val Cys Gly Gly Val Leu Val His Pro Gln Trp Val
        50                  55                  60
```

<210> SEQ ID NO 10
<211> LENGTH: 60
<212> TYPE: PRT
<213> ORGANISM: Artificial Sequence
<220> FEATURE:
<223> OTHER INFORMATION: Syhthetic peptide.

<400> SEQUENCE: 10

```
Leu Thr Ala Ala His Cys Ile Arg Asn Lys Ser Val Ile Leu Leu Gly
1               5                   10                  15

Arg His Ser Leu Phe His Pro Glu Asp Thr Gly Gln Val Phe Gln Val
                20                  25                  30

Ser His Ser Phe Pro His Pro Leu Tyr Asp Met Ser Leu Leu Lys Asn
            35                  40                  45

Arg Phe Leu Arg Pro Gly Asp Asp Ser Ser His Asp
        50                  55                  60
```

<210> SEQ ID NO 11
<211> LENGTH: 60
<212> TYPE: PRT
<213> ORGANISM: Artificial Sequence
<220> FEATURE:

<223> OTHER INFORMATION: Synthetic peptide.

<400> SEQUENCE: 11

Leu Met Leu Leu Arg Leu Ser Glu Pro Ala Glu Leu Thr Asp Ala Val
1               5                   10                  15

Lys Val Met Asp Leu Pro Thr Gln Glu Pro Ala Leu Gly Thr Thr Cys
            20                  25                  30

Tyr Ala Ser Gly Trp Gly Ser Ile Glu Pro Glu Glu Phe Leu Thr Pro
        35                  40                  45

Lys Lys Leu Gln Cys Val Asp Leu His Val Ile Ser
    50                  55                  60

<210> SEQ ID NO 12
<211> LENGTH: 60
<212> TYPE: PRT
<213> ORGANISM: Artificial Sequence
<220> FEATURE:
<223> OTHER INFORMATION: Synthetic peptide.

<400> SEQUENCE: 12

Asn Asp Val Cys Ala Gln Val His Pro Gln Lys Val Thr Lys Phe Met
1               5                   10                  15

Leu Cys Ala Gly Arg Trp Thr Gly Gly Lys Ser Thr Cys Ser Gly Asp
            20                  25                  30

Ser Gly Gly Pro Leu Val Cys Asn Gly Val Leu Gln Gly Ile Thr Ser
        35                  40                  45

Trp Gly Ser Glu Pro Cys Ala Leu Pro Glu Arg Pro
    50                  55                  60

<210> SEQ ID NO 13
<211> LENGTH: 21
<212> TYPE: PRT
<213> ORGANISM: Artificial Sequence
<220> FEATURE:
<223> OTHER INFORMATION: Synthetic peptide.

<400> SEQUENCE: 13

Ser Leu Tyr Thr Lys Val Val His Tyr Arg Lys Trp Ile Lys Asp Thr
1               5                   10                  15

Ile Val Ala Asn Pro
            20

<210> SEQ ID NO 14
<211> LENGTH: 9
<212> TYPE: PRT
<213> ORGANISM: Artificial Sequence
<220> FEATURE:
<223> OTHER INFORMATION: Synthetic peptide.

<400> SEQUENCE: 14

Ile Met Asp Gln Val Pro Phe Ser Val
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic peptide.

<400> SEQUENCE: 15

Ile Thr Asp Gln Val Pro Phe Ser Val
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic peptide.

<400> SEQUENCE: 16

```
Tyr Leu Glu Pro Gly Pro Val Thr Val
1               5
```

<210> SEQ ID NO 17
<211> LENGTH: 9
<212> TYPE: PRT
<213> ORGANISM: Artificial Sequence
<220> FEATURE:
<223> OTHER INFORMATION: Synthetic peptide.

<400> SEQUENCE: 17

```
Tyr Leu Glu Pro Gly Pro Val Thr Ala
1               5
```

<210> SEQ ID NO 18
<211> LENGTH: 9
<212> TYPE: PRT
<213> ORGANISM: Artificial Sequence
<220> FEATURE:
<223> OTHER INFORMATION: Syntehtic peptide.

<400> SEQUENCE: 18

```
Lys Thr Trp Gly Gln Tyr Trp Gln Val
1               5
```

<210> SEQ ID NO 19
<211> LENGTH: 244
<212> TYPE: PRT
<213> ORGANISM: Artificial Sequence
<220> FEATURE:
<223> OTHER INFORMATION: Synthetic peptide.

<400> SEQUENCE: 19

```
Ala Pro Leu Ile Leu Ser Arg Ile Val Gly Gly Trp Glu Cys Glu Lys
1               5                   10                  15

His Ser Gln Pro Trp Gln Val Leu Val Ala Ser Arg Gly Arg Ala Val
            20                  25                  30

Cys Gly Gly Val Leu Val His Pro Gln Trp Val Leu Thr Ala Ala His
        35                  40                  45

Cys Ile Arg Asn Lys Ser Val Ile Leu Leu Gly Arg His Ser Leu Phe
    50                  55                  60

His Pro Glu Asp Thr Gly Gln Val Phe Gln Val Ser His Ser Phe Pro
65                  70                  75                  80

His Pro Leu Tyr Asp Met Ser Leu Leu Lys Asn Arg Phe Leu Arg Pro
                85                  90                  95

Gly Asp Asp Ser Ser His Asp Leu Met Leu Leu Arg Leu Ser Glu Pro
            100                 105                 110

Ala Glu Leu Thr Asp Ala Val Lys Val Met Asp Leu Pro Thr Gln Glu
        115                 120                 125

Pro Ala Leu Gly Thr Thr Cys Tyr Ala Ser Gly Trp Gly Ser Ile Glu
    130                 135                 140

Pro Glu Glu Phe Leu Thr Pro Lys Lys Leu Gln Cys Val Asp Leu His
145                 150                 155                 160
```

```
Val Ile Ser Asn Asp Val Cys Ala Gln Val His Pro Gln Lys Val Thr
                165                 170                 175

Lys Phe Met Leu Cys Ala Gly Arg Trp Thr Gly Lys Ser Thr Cys
            180                 185                 190

Ser Gly Asp Ser Gly Gly Pro Leu Val Cys Asn Gly Val Leu Gln Gly
        195                 200                 205

Ile Thr Ser Trp Gly Ser Glu Pro Cys Ala Leu Pro Glu Arg Pro Ser
    210                 215                 220

Leu Tyr Thr Lys Val Val His Tyr Arg Lys Trp Ile Lys Asp Thr Ile
225                 230                 235                 240

Val Ala Asn Pro

<210> SEQ ID NO 20
<211> LENGTH: 230
<212> TYPE: PRT
<213> ORGANISM: Artificial Sequence
<220> FEATURE:
<223> OTHER INFORMATION: Synthetic peptide.

<400> SEQUENCE: 20

Asp Thr Thr Glu Pro Ala Thr Pro Thr Thr Pro Val Thr Thr Pro Thr
1               5                   10                  15

Thr Thr Lys Val Pro Arg Asn Gln Asp Trp Leu Gly Val Ser Arg Gln
            20                  25                  30

Leu Arg Thr Lys Ala Trp Asn Arg Gln Leu Tyr Pro Glu Trp Thr Glu
        35                  40                  45

Ala Gln Arg Leu Asp Cys Trp Arg Gly Gly Gln Val Ser Leu Lys Val
    50                  55                  60

Ser Asn Asp Gly Pro Thr Leu Ile Gly Ala Asn Ala Ser Phe Ser Ile
65                  70                  75                  80

Ala Leu Asn Phe Pro Gly Ser Gln Lys Val Leu Pro Asp Gly Gln Val
                85                  90                  95

Ile Trp Val Asn Asn Thr Ile Ile Asn Gly Ser Gln Val Trp Gly Gly
            100                 105                 110

Gln Pro Val Tyr Pro Gln Glu Thr Asp Asp Ala Cys Ile Phe Pro Asp
        115                 120                 125

Gly Gly Pro Cys Pro Ser Gly Ser Trp Ser Gln Lys Arg Ser Phe Val
    130                 135                 140

Tyr Val Trp Lys Thr Trp Gly Gln Tyr Trp Gln Val Leu Gly Gly Pro
145                 150                 155                 160

Val Ser Gly Leu Ser Ile Gly Thr Gly Arg Ala Met Leu Gly Thr His
                165                 170                 175

Thr Met Glu Val Thr Val Tyr His Arg Arg Gly Ser Gln Ser Tyr Val
            180                 185                 190

Pro Leu Ala His Ser Ser Ser Ala Phe Thr Ile Thr Asp Gln Val Pro
        195                 200                 205

Phe Ser Val Ser Val Ser Gln Leu Arg Ala Leu Asp Gly Gly Asn Lys
    210                 215                 220

His Phe Leu Arg Asn Gln
225                 230

<210> SEQ ID NO 21
<211> LENGTH: 73
<212> TYPE: PRT
<213> ORGANISM: Artificial Sequence
<220> FEATURE:
```

```
<223> OTHER INFORMATION: Synthetic peptide.
<220> FEATURE:
<221> NAME/KEY: misc_feature
<222> LOCATION: (38)..(38)
<223> OTHER INFORMATION: Xaa can be any naturally occurring amino acid

<400> SEQUENCE: 21

Pro Leu Thr Phe Ala Leu Gln Leu His Asp Pro Ser Gly Tyr Leu Ala
1               5                   10                  15

Glu Ala Asp Leu Ser Tyr Thr Trp Asp Phe Gly Asp Ser Ser Gly Thr
            20                  25                  30

Leu Ile Ser Arg Ala Xaa Val Val Thr His Thr Tyr Leu Glu Pro Gly
        35                  40                  45

Pro Val Thr Ala Gln Val Val Leu Gln Ala Ala Ile Pro Leu Thr Ser
    50                  55                  60

Cys Gly Ser Ser Pro Val Pro Ala Ser
65                  70

<210> SEQ ID NO 22
<211> LENGTH: 109
<212> TYPE: PRT
<213> ORGANISM: Artificial Sequence
<220> FEATURE:
<223> OTHER INFORMATION: Synthetic peptide.

<400> SEQUENCE: 22

Gly Thr Thr Asp Gly His Arg Pro Thr Ala Glu Ala Pro Asn Thr Thr
1               5                   10                  15

Ala Gly Gln Val Pro Thr Thr Glu Val Val Gly Thr Thr Pro Gly Gln
            20                  25                  30

Ala Pro Thr Ala Glu Pro Ser Gly Thr Thr Ser Val Gln Val Pro Thr
        35                  40                  45

Thr Glu Val Ile Ser Thr Ala Pro Val Gln Met Pro Thr Ala Glu Ser
    50                  55                  60

Thr Gly Met Thr Pro Glu Lys Val Pro Val Ser Glu Val Met Gly Thr
65                  70                  75                  80

Thr Leu Ala Glu Met Ser Thr Pro Glu Ala Thr Gly Met Thr Pro Ala
                85                  90                  95

Glu Val Ser Ile Val Val Leu Ser Gly Thr Thr Ala Ala
            100                 105

<210> SEQ ID NO 23
<211> LENGTH: 75
<212> TYPE: PRT
<213> ORGANISM: Artificial Sequence
<220> FEATURE:
<223> OTHER INFORMATION: Synthetic peptide.

<400> SEQUENCE: 23

Gln Val Thr Thr Thr Glu Trp Val Glu Thr Thr Ala Arg Glu Leu Pro
1               5                   10                  15

Ile Pro Glu Pro Glu Gly Pro Asp Ala Ser Ser Ile Met Ser Thr Glu
            20                  25                  30

Ser Ile Thr Gly Ser Leu Gly Pro Leu Leu Asp Gly Thr Ala Thr Leu
        35                  40                  45

Arg Leu Val Lys Arg Gln Val Pro Leu Asp Cys Val Leu Tyr Arg Tyr
    50                  55                  60

Gly Ser Phe Ser Val Thr Leu Asp Ile Val Gln
65                  70                  75
```

```
<210> SEQ ID NO 24
<211> LENGTH: 109
<212> TYPE: PRT
<213> ORGANISM: Artificial Sequence
<220> FEATURE:
<223> OTHER INFORMATION: Synthetic peptide.

<400> SEQUENCE: 24

Gly Ile Glu Ser Ala Glu Ile Leu Gln Ala Val Pro Ser Gly Glu Gly
1               5                   10                  15

Asp Ala Phe Glu Leu Thr Val Ser Cys Gln Gly Gly Leu Pro Lys Glu
            20                  25                  30

Ala Cys Met Glu Ile Ser Ser Pro Gly Cys Gln Pro Pro Ala Gln Arg
        35                  40                  45

Leu Cys Gln Pro Val Leu Pro Ser Pro Ala Cys Gln Leu Val Leu His
    50                  55                  60

Gln Ile Leu Lys Gly Gly Ser Gly Thr Tyr Cys Leu Asn Val Ser Leu
65                  70                  75                  80

Ala Asp Thr Asn Ser Leu Ala Val Val Ser Thr Gln Leu Ile Val Pro
                85                  90                  95

Gly Ile Leu Leu Thr Gly Gln Glu Ala Gly Leu Gly Gln
            100                 105

<210> SEQ ID NO 25
<211> LENGTH: 50
<212> TYPE: PRT
<213> ORGANISM: ARtificial Sequence
<220> FEATURE:
<223> OTHER INFORMATION: Synthetic peptide.

<400> SEQUENCE: 25

Met Glu Met Lys Ile Leu Arg Ala Leu Asn Phe Gly Leu Gly Arg Pro
1               5                   10                  15

Leu Pro Leu His Phe Leu Arg Arg Ala Ser Lys Ile Gly Glu Val Asp
            20                  25                  30

Val Glu Gln His Thr Leu Ala Lys Tyr Leu Met Glu Leu Thr Met Leu
        35                  40                  45

Asp Tyr
    50

<210> SEQ ID NO 26
<211> LENGTH: 36
<212> TYPE: PRT
<213> ORGANISM: Artificial Sequence
<220> FEATURE:
<223> OTHER INFORMATION: Synthetic peptide.

<400> SEQUENCE: 26

Asp Trp Leu Val Gln Val Gln Met Lys Phe Arg Leu Leu Gln Glu Thr
1               5                   10                  15

Met Tyr Met Thr Val Ser Ile Ile Asp Arg Phe Met Gln Asn Asn Cys
            20                  25                  30

Val Pro Lys Lys
        35

<210> SEQ ID NO 27
<211> LENGTH: 48
<212> TYPE: PRT
<213> ORGANISM: Artificial Sequence
<220> FEATURE:
<223> OTHER INFORMATION: Syntehtic peptide.
```

<400> SEQUENCE: 27

Met Glu His Gln Leu Leu Cys Cys Glu Val Glu Thr Ile Arg Arg Ala
1               5                   10                  15

Tyr Pro Asp Ala Asn Leu Leu Asn Asp Arg Val Leu Arg Ala Met Leu
                20                  25                  30

Lys Ala Glu Glu Thr Cys Ala Pro Ser Val Ser Tyr Phe Lys Cys Val
            35                  40                  45

<210> SEQ ID NO 28
<211> LENGTH: 95
<212> TYPE: PRT
<213> ORGANISM: Artificial Sequence
<220> FEATURE:
<223> OTHER INFORMATION: Synthetic peptide.

<400> SEQUENCE: 28

Gln Lys Glu Val Leu Pro Ser Met Arg Lys Ile Val Ala Thr Trp Met
1               5                   10                  15

Leu Glu Val Cys Glu Glu Gln Lys Cys Glu Glu Val Phe Pro Leu
                20                  25                  30

Ala Met Asn Tyr Leu Asp Arg Phe Leu Ser Leu Glu Pro Val Lys Lys
            35                  40                  45

Ser Arg Leu Gln Leu Leu Gly Ala Thr Cys Met Phe Val Ala Ser Lys
        50                  55                  60

Met Lys Glu Thr Ile Pro Leu Thr Ala Glu Lys Leu Cys Ile Tyr Thr
65                  70                  75                  80

Asp Asn Ser Ile Arg Pro Glu Glu Leu Leu Gln Met Glu Leu Leu
                85                  90                  95

<210> SEQ ID NO 29
<211> LENGTH: 60
<212> TYPE: PRT
<213> ORGANISM: Artificial Sequence
<220> FEATURE:
<223> OTHER INFORMATION: Synthetic peptide.

<400> SEQUENCE: 29

Leu Val Asn Lys Leu Lys Trp Asn Leu Ala Ala Met Thr Pro His Asp
1               5                   10                  15

Phe Ile Glu His Phe Leu Ser Lys Met Pro Glu Ala Glu Glu Asn Lys
                20                  25                  30

Gln Ile Ile Arg Lys His Ala Gln Thr Phe Val Ala Leu Cys Ala Thr
            35                  40                  45

Asp Val Lys Phe Ile Ser Asn Pro Pro Ser Met Val
        50                  55                  60

<210> SEQ ID NO 30
<211> LENGTH: 92
<212> TYPE: PRT
<213> ORGANISM: Artificial Sequence
<220> FEATURE:
<223> OTHER INFORMATION: Synthetic peptide.

<400> SEQUENCE: 30

Ala Ala Gly Ser Val Val Ala Ala Val Gln Gly Leu Asn Leu Arg Ser
1               5                   10                  15

Pro Asn Asn Phe Leu Ser Tyr Tyr Arg Leu Thr Arg Phe Leu Ser Arg
                20                  25                  30

Val Ile Lys Cys Asp Pro Asp Cys Leu Arg Ala Cys Gln Glu Gln Ile

```
            35                  40                  45
Glu Ala Leu Leu Glu Ser Ser Leu Arg Gln Ala Gln Gln Asn Met Asp
 50                  55                  60

Pro Lys Ala Ala Glu Glu Glu Glu Glu Glu Glu Glu Val Asp Leu
 65                  70                  75                  80

Ala Cys Thr Pro Thr Asp Val Arg Asp Val Asp Ile
                 85                  90

<210> SEQ ID NO 31
<211> LENGTH: 32
<212> TYPE: PRT
<213> ORGANISM: Artificial Sequence
<220> FEATURE:
<223> OTHER INFORMATION: Synthetic peptide.

<400> SEQUENCE: 31

Val Gly Phe Pro Val Thr Pro Gln Val Pro Leu Arg Pro Met Thr Tyr
 1               5                  10                  15

Lys Ala Ala Val Asp Leu Ser His Phe Leu Lys Glu Lys Gly Gly Leu
                 20                  25                  30

<210> SEQ ID NO 32
<211> LENGTH: 30
<212> TYPE: PRT
<213> ORGANISM: Artificial Sequence
<220> FEATURE:
<223> OTHER INFORMATION: Synthetic peptide.

<400> SEQUENCE: 32

His Thr Gln Gly Tyr Phe Pro Asp Trp Gln Asn Tyr Thr Pro Gly Pro
 1               5                  10                  15

Gly Val Arg Tyr Pro Leu Thr Phe Gly Trp Leu Tyr Lys Leu
                 20                  25                  30

<210> SEQ ID NO 33
<211> LENGTH: 19
<212> TYPE: PRT
<213> ORGANISM: Artificial Sequence
<220> FEATURE:
<223> OTHER INFORMATION: Synthetic peptide.

<400> SEQUENCE: 33

Glu Lys Ile Arg Leu Arg Pro Gly Gly Lys Lys Lys Tyr Lys Leu Lys
 1               5                  10                  15

His Ile Val

<210> SEQ ID NO 34
<211> LENGTH: 32
<212> TYPE: PRT
<213> ORGANISM: Artificial Sequence
<220> FEATURE:
<223> OTHER INFORMATION: Syntehtic peptide.

<400> SEQUENCE: 34

Asn Pro Pro Ile Pro Val Gly Glu Ile Tyr Lys Arg Trp Ile Ile Leu
 1               5                  10                  15

Gly Leu Asn Lys Ile Val Arg Met Tyr Ser Pro Thr Ser Ile Leu Asp
                 20                  25                  30

<210> SEQ ID NO 35
<211> LENGTH: 31
<212> TYPE: PRT
<213> ORGANISM: Artificial Sequence
```

```
<220> FEATURE:
<223> OTHER INFORMATION: Syntehtic peptide.

<400> SEQUENCE: 35

Ala Ile Phe Gln Ser Ser Met Thr Lys Ile Leu Glu Pro Phe Arg Lys
1               5                   10                  15

Gln Asn Pro Asp Ile Val Ile Tyr Gln Tyr Met Asp Asp Leu Tyr
            20                  25                  30

<210> SEQ ID NO 36
<211> LENGTH: 314
<212> TYPE: PRT
<213> ORGANISM: Artificial Sequence
<220> FEATURE:
<223> OTHER INFORMATION: Syntehtic peptide.

<400> SEQUENCE: 36

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Ser His Asn Gly Lys Leu Cys Arg Leu Lys Gly Ile Ala
        35                  40                  45

Pro Leu Gln Leu Gly Lys Cys Asn Ile Ala Gly Trp Leu Leu Gly Asn
    50                  55                  60

Pro Glu Cys Asp Pro Leu Leu Pro Val Arg Ser Trp Ser Tyr Ile Val
65                  70                  75                  80

Glu Thr Pro Asn Ser Glu Asn Gly Ile Cys Tyr Pro Gly Asp Phe Ile
                85                  90                  95

Asp Tyr Glu Glu Leu Arg Glu Gln Leu Ser Ser Val Ser Ser Phe Glu
            100                 105                 110

Arg Phe Glu Ile Phe Pro Lys Glu Ser Ser Trp Pro Asn His Asn Thr
        115                 120                 125

Asn Gly Val Thr Ala Ala Cys Ser His Glu Gly Lys Ser Ser Phe Tyr
    130                 135                 140

Arg Asn Leu Leu Trp Leu Thr Glu Lys Glu Gly Ser Tyr Pro Lys Leu
145                 150                 155                 160

Lys Asn Ser Tyr Val Asn Lys Gly Lys Glu Val Leu Val Leu Trp
                165                 170                 175

Gly Ile His His Pro Pro Asn Ser Lys Glu Gln Gln Asn Leu Tyr Gln
            180                 185                 190

Asn Glu Asn Ala Tyr Val Ser Val Val Thr Ser Asn Tyr Asn Arg Arg
        195                 200                 205

Phe Thr Pro Glu Ile Ala Glu Arg Pro Lys Val Arg Asp Gln Ala Gly
    210                 215                 220

Arg Met Asn Tyr Tyr Trp Thr Leu Leu Lys Pro Gly Asp Thr Ile Ile
225                 230                 235                 240

Phe Glu Ala Asn Gly Asn Leu Ile Ala Pro Met Tyr Ala Phe Ala Leu
                245                 250                 255

Ser Arg Gly Phe Gly Ser Gly Ile Ile Thr Ser Asn Ala Ser Met His
            260                 265                 270

Glu Cys Asn Thr Lys Cys Gln Thr Pro Leu Gly Ala Ile Asn Ser Ser
        275                 280                 285

Leu Pro Tyr Gln Asn Ile His Pro Val Thr Ile Gly Glu Cys Pro Lys
    290                 295                 300

Tyr Val Arg Ser Ala Lys Leu Arg Met Val
```

```
<210> SEQ ID NO 37
<211> LENGTH: 314
<212> TYPE: PRT
<213> ORGANISM: Artificial Sequence
<220> FEATURE:
<223> OTHER INFORMATION: Syntehtic peptide.

<400> SEQUENCE: 37

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Lys His Asn Gly Lys Leu Cys Asp Leu Asp Gly Val Lys
        35                  40                  45

Pro Leu Ile Leu Arg Asp Cys Ser Val Ala Gly Trp Leu Leu Gly Asn
50                  55                  60

Pro Met Cys Asp Glu Phe Ile Asn Val Pro Glu Trp Ser Tyr Ile Val
65                  70                  75                  80

Glu Lys Ala Asn Pro Val Asn Asp Leu Cys Tyr Pro Gly Asp Phe Asn
                85                  90                  95

Asp Tyr Glu Glu Leu Lys His Leu Leu Ser Arg Ile Asn His Phe Glu
            100                 105                 110

Lys Ile Gln Ile Ile Pro Lys Ser Ser Trp Ser Ser His Glu Ala Ser
        115                 120                 125

Leu Gly Val Ser Ser Ala Cys Pro Tyr Gln Gly Lys Ser Ser Phe Phe
130                 135                 140

Arg Asn Val Val Trp Leu Ile Lys Lys Asn Ser Thr Tyr Pro Thr Ile
145                 150                 155                 160

Lys Arg Ser Tyr Asn Asn Thr Asn Gln Glu Asp Leu Leu Val Leu Trp
                165                 170                 175

Gly Ile His His Pro Asn Asp Ala Ala Glu Gln Thr Lys Leu Tyr Gln
            180                 185                 190

Asn Pro Thr Thr Tyr Ile Ser Val Gly Thr Ser Thr Leu Asn Gln Arg
        195                 200                 205

Leu Val Pro Arg Ile Ala Thr Arg Ser Lys Val Asn Gly Gln Ser Gly
210                 215                 220

Arg Met Glu Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Thr Ile Met Lys Ser Glu Leu Glu Tyr Gly
            260                 265                 270

Asn Cys Asn Thr Lys Cys Gln Thr Pro Met Gly Ala Ile Asn Ser Ser
        275                 280                 285

Met Pro Phe His Asn Ile His Pro Leu Thr Ile Gly Glu Cys Pro Lys
290                 295                 300

Tyr Val Lys Ser Asn Arg Leu Val Leu Ala
305                 310

<210> SEQ ID NO 38
<211> LENGTH: 231
<212> TYPE: PRT
<213> ORGANISM: Artificial Sequence
<220> FEATURE:
<223> OTHER INFORMATION: Syntehtic peptide.
```

<400> SEQUENCE: 38

Pro Ile Val Gln Asn Ile Gln Gly Gln Met Val His Gln Ala Ile Ser
1               5                   10                  15

Pro Arg Thr Leu Asn Ala Trp Val Lys Val Val Glu Glu Lys Ala Phe
            20                  25                  30

Ser Pro Glu Val Ile Pro Met Phe Ser Ala Leu Ser Glu Gly Ala Thr
        35                  40                  45

Pro Gln Asp Leu Asn Thr Met Leu Asn Thr Val Gly Gly His Gln Ala
    50                  55                  60

Ala Met Gln Met Leu Lys Glu Thr Ile Asn Glu Glu Ala Ala Glu Trp
65                  70                  75                  80

Asp Arg Val His Pro Val His Ala Gly Pro Ile Ala Pro Gly Gln Met
                85                  90                  95

Arg Glu Pro Arg Gly Ser Asp Ile Ala Gly Thr Thr Ser Thr Leu Gln
            100                 105                 110

Glu Gln Ile Gly Trp Met Thr Asn Asn Pro Pro Ile Pro Val Gly Glu
        115                 120                 125

Ile Tyr Lys Arg Trp Ile Ile Leu Gly Leu Asn Lys Ile Val Arg Met
130                 135                 140

Tyr Ser Pro Thr Ser Ile Leu Asp Ile Arg Gln Gly Pro Lys Glu Pro
145                 150                 155                 160

Phe Arg Asp Tyr Val Asp Arg Phe Tyr Lys Thr Leu Arg Ala Glu Gln
                165                 170                 175

Ala Ser Gln Glu Val Lys Asn Trp Met Thr Glu Thr Leu Leu Val Gln
            180                 185                 190

Asn Ala Asn Pro Asp Cys Lys Thr Ile Leu Lys Ala Leu Gly Pro Ala
        195                 200                 205

Ala Thr Leu Glu Glu Met Met Thr Ala Cys Gln Gly Val Gly Gly Pro
    210                 215                 220

Gly His Lys Ala Arg Val Leu
225                 230

<210> SEQ ID NO 39
<211> LENGTH: 25
<212> TYPE: PRT
<213> ORGANISM: Artificial Sequence
<220> FEATURE:
<223> OTHER INFORMATION: Synthetic peptide.

<400> SEQUENCE: 39

Ser Ser Val Ser Pro Thr Thr Ser Val His Pro Thr Pro Thr Ser Val
1               5                   10                  15

Pro Pro Thr Pro Thr Lys Ser Ser Pro
            20                  25

<210> SEQ ID NO 40
<211> LENGTH: 25
<212> TYPE: PRT
<213> ORGANISM: Artificial Sequence
<220> FEATURE:
<223> OTHER INFORMATION: Synthetic peptide.

<400> SEQUENCE: 40

Pro Thr Ser Thr Pro Ala Asp Ser Ser Thr Ile Thr Pro Thr Ala Thr
1               5                   10                  15

Pro Thr Ala Thr Pro Thr Ile Lys Gly
            20                  25

<210> SEQ ID NO 41
<211> LENGTH: 25
<212> TYPE: PRT
<213> ORGANISM: Artificial Sequence
<220> FEATURE:
<223> OTHER INFORMATION: Synthetic peptide.

<400> SEQUENCE: 41

Thr Val Thr Pro Thr Ala Thr Ala Pro Ser Ala Ile Val Thr Thr
1               5                   10                  15

Ile Thr Pro Thr Ala Thr Thr Lys Pro
            20                  25

<210> SEQ ID NO 42
<211> LENGTH: 25
<212> TYPE: PRT
<213> ORGANISM: Artificial Sequence
<220> FEATURE:
<223> OTHER INFORMATION: Synthetic peptide.

<400> SEQUENCE: 42

Thr Asn Gly Ser Ile Thr Val Ala Ala Thr Ala Pro Thr Val Thr Pro
1               5                   10                  15

Thr Val Asn Ala Thr Pro Ser Ala Ala
            20                  25

<210> SEQ ID NO 43
<211> LENGTH: 9
<212> TYPE: PRT
<213> ORGANISM: Artificial Sequence
<220> FEATURE:
<223> OTHER INFORMATION: Synthetic peptide.

<400> SEQUENCE: 43

Gly Ile Leu Gly Phe Val Phe Thr Leu
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic peptide.

<400> SEQUENCE: 44

Lys Leu Gln Cys Val Asp Leu His Val
1               5

<210> SEQ ID NO 45
<211> LENGTH: 76
<212> TYPE: PRT
<213> ORGANISM: Artificial Sequence
<220> FEATURE:
<223> OTHER INFORMATION: Synthetic peptide.

<400> SEQUENCE: 45

Ala Ser Ile Ser Cys Arg Ser Ser Gln Ser Leu Val His Ser Asn Gly
1               5                   10                  15

Asn Thr Tyr Leu His Trp Tyr Leu Gln Lys Pro Gly Gln Ser Pro Lys
            20                  25                  30

Leu Leu Ile Tyr Lys Val Ser Asn Arg Phe Ser Gly Val Pro Asp Arg
        35                  40                  45

Phe Ser Gly Ser Gly Ser Gly Thr Asn Phe Thr Leu Lys Ile Ser Arg

```
                50                  55                  60
Val Glu Ala Glu Asp Leu Gly Leu Tyr Phe Cys Ser
 65                  70                  75
```

<210> SEQ ID NO 46
<211> LENGTH: 81
<212> TYPE: PRT
<213> ORGANISM: Artificial Sequence
<220> FEATURE:
<223> OTHER INFORMATION: Synthetic peptide.

<400> SEQUENCE: 46

```
Ser Val Lys Met Ser Cys Lys Ala Ser Gly Tyr Thr Phe Thr Asp Tyr
 1               5                  10                  15

Val Ile Ser Trp Val Lys Gln Arg Thr Gly Gln Gly Leu Glu Trp Ile
                20                  25                  30

Gly Asp Ile Tyr Pro Gly Ser Gly Tyr Ser Phe Tyr Asn Glu Asn Phe
            35                  40                  45

Lys Gly Lys Ala Thr Leu Thr Ala Asp Lys Ser Ser Thr Thr Ala Tyr
 50                  55                  60

Met Gln Leu Ser Ser Leu Thr Ser Glu Asp Ser Ala Val Tyr Phe Cys
 65                  70                  75                  80

Ala
```

<210> SEQ ID NO 47
<211> LENGTH: 74
<212> TYPE: PRT
<213> ORGANISM: Artificial Sequence
<220> FEATURE:
<223> OTHER INFORMATION: Synthetic peptide.

<400> SEQUENCE: 47

```
Val Thr Leu Thr Cys Arg Ser Ser Thr Gly Ala Val Thr Thr Ser Asn
 1               5                  10                  15

Tyr Ala Asn Trp Val Gln Glu Lys Pro Asp His Leu Phe Thr Gly Leu
                20                  25                  30

Ile Gly Gly Thr Asn Asn Arg Val Ser Gly Val Pro Ala Arg Phe Ser
            35                  40                  45

Gly Ser Leu Ile Gly Asp Lys Ala Ala Leu Thr Ile Thr Gly Ala Gln
 50                  55                  60

Thr Glu Asp Glu Ala Ile Tyr Phe Cys Ala
 65                  70
```

<210> SEQ ID NO 48
<211> LENGTH: 82
<212> TYPE: PRT
<213> ORGANISM: Artificial Sequence
<220> FEATURE:
<223> OTHER INFORMATION: Synthetic peptide.

<400> SEQUENCE: 48

```
Ser Leu Lys Leu Ser Cys Ala Ala Ser Gly Leu Thr Phe Asn Ile Tyr
 1               5                  10                  15

Ala Met Asn Trp Val Arg Gln Ala Pro Gly Lys Gly Leu Glu Trp Val
                20                  25                  30

Ala Arg Ile Arg Asn Lys Ser Asn Asn Tyr Ala Thr Tyr Tyr Ala Asp
            35                  40                  45

Ser Val Lys Asp Arg Phe Thr Ile Ser Arg Asp Asp Ser Gln Ser Leu
 50                  55                  60
```

Leu Tyr Leu Gln Met Asn Asn Leu Lys Thr Glu Asp Thr Ala Met Tyr
65                  70                  75                  80

Tyr Cys

<210> SEQ ID NO 49
<211> LENGTH: 717
<212> TYPE: DNA
<213> ORGANISM: Artificial Sequence
<220> FEATURE:
<223> OTHER INFORMATION: Syntehtic oligonucleotide.

<400> SEQUENCE: 49
atgaagttgc ctgttaggct gttggtgctg atgttctgga ttcctgcttc cagcagtgat      60
gttgtgatga cccaaactcc actctccctg cctgtccgtc ttggagatca agcctccatc     120
tcttgcagat ctagtcagag ccttgtacac agtaatggaa acacctattt acattggtac     180
ctgcagaagc caggccagtc tccaaagctc ctgatctaca agtttccaa ccgattttct      240 ggggtcccag acaggttcag tggcagtgga tcaggacaa atttcacact caagatcagc      300
agagtggagg ctgaggatct gggactttat ttctgctctc aaagtacaca tgttccgtac     360
acgttcggag gggggaccaa gctggaaata aaacgggctg atgctgcacc aactgtatcc     420
atcttcccac catccagtga gcagttaaca tctggaggtg cctcagtcgt gtgcttcttg     480
aacaacttct accccaaaga catcaatgtc aagtggaaga ttgatggcag tgaacgacaa     540
aatggcgtcc tgaacagttg gactgatcag gacagcaaag acagcaccta cagcatgaac     600 agcacccta cgttgaccaa ggacgagtat aacgacata acagctatac ctgtgaggcc      660
actcacaaga catcaacttc acccatcgtc aagagcttca caggaatga gtgttag        717

<210> SEQ ID NO 50
<211> LENGTH: 219
<212> TYPE: PRT
<213> ORGANISM: Artificial Sequence
<220> FEATURE:
<223> OTHER INFORMATION: Syntehtic peptide.

<400> SEQUENCE: 50

Asp Val Val Met Thr Gln Thr Pro Leu Ser Leu Pro Val Arg Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asn Phe Thr Leu Lys Ile
65                  70                  75                  80

Ser Arg Val Glu Ala Glu Asp Leu Gly Leu Tyr Phe Cys Ser Gln Ser
                85                  90                  95

Thr His Val Pro Tyr Thr Phe Gly Gly Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
            165                 170                 175

Thr Tyr Ser Met Asn Ser Thr Leu Thr Leu Lys Asp Glu Tyr Glu
        180                 185                 190

Arg His Asn Ser Tyr Thr Cys Glu Ala Thr His Lys Thr Ser Thr Ser
            195                 200                 205

Pro Ile Val Lys Ser Phe Asn Arg Asn Glu Cys
        210                 215

<210> SEQ ID NO 51
<211> LENGTH: 714
<212> TYPE: DNA
<213> ORGANISM: Artificial Sequence
<220> FEATURE:
<223> OTHER INFORMATION: Synthetic oligonucleotide.

<400> SEQUENCE: 51
atggattttc agatgcagat tatcagcttg ctgctaatca gtgtcacagt catagtgtct    60
aatggagaaa ttgtgctcac ccagtctcca accaccatgg ctgcatctcc cggggagaag   120
atcactatca cctgcagtgc cagctcaagt ataagttccc attacttaca ttggtatcag   180
cagaagccag gattctcccc taaactcttg atttatagga catccaatct ggcttctgga   240
gtcccagctc gcttcagtgg cagtgggtct gggacctctt actctctcac aattgacacc   300
atggaggctg aagatgttgc cacttactac tgccagcagg gtagtagtat accattcacg   360
ttcggctcgg ggacaaagtt ggaaataaaa cgggctgatg ctgcaccaac tgtatccatc   420
ttcccaccat ccagtgagca gttaacatct ggaggtgcct cagtcgtgtg cttcttgaac   480
aacttctacc ccaaagacat caatgtcaag tggaagattg atggcagtga acgacaaaat   540
ggcgtcctga acagttggac tgatcaggac agcaaagaca gcacctacag catgagcagc   600
accctcacgt tgaccaagga cgagtatgaa cgacataaca gctatacctg tgaggccact   660
cacaagacat caacttcacc catcgtcaag agcttcaaca ggaatgagtg ttag          714

<210> SEQ ID NO 52
<211> LENGTH: 215
<212> TYPE: PRT
<213> ORGANISM: Artificial Sequence
<220> FEATURE:
<223> OTHER INFORMATION: Synthetic peptide.

<400> SEQUENCE: 52

Glu Ile Val Leu Thr Gln Ser Pro Thr Thr Met Ala Ala Ser Pro Gly
1               5                   10                  15

Glu Lys Ile Thr Ile Thr Cys Ser Ala Ser Ser Ser Ile Ser Ser His
            20                  25                  30

Tyr Leu His Trp Tyr Gln Gln Lys Pro Gly Phe Ser Pro Lys Leu Leu
        35                  40                  45

Ile Tyr Arg Thr Ser Asn Leu Ala Ser Gly Val Pro Ala Arg Phe Ser
    50                  55                  60

Gly Ser Gly Ser Gly Thr Ser Tyr Ser Leu Thr Ile Asp Thr Met Glu
65                  70                  75                  80

Ala Glu Asp Val Ala Thr Tyr Tyr Cys Gln Gln Gly Ser Ser Ile Pro
                85                  90                  95

Phe Thr Phe Gly Ser Gly Thr Lys Leu Glu Ile Lys Arg Ala Asp Ala
            100                 105                 110

Ala Pro Thr Val Ser Ile Phe Pro Pro Ser Ser Glu Gln Leu Thr Ser
        115                 120                 125

Gly Gly Ala Ser Val Val Cys Phe Leu Asn Asn Phe Tyr Pro Lys Asp
            130                 135                 140

Ile Asn Val Lys Trp Lys Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
                165                 170                 175

Ser Ser Thr Leu Thr Leu Thr Lys Asp Glu Tyr Glu Arg His Asn Ser
            180                 185                 190

Tyr Thr Cys Glu Ala Thr His Lys Thr Ser Thr Ser Pro Ile Val Lys
            195                 200                 205

Ser Phe Asn Arg Asn Glu Cys
            210                 215

<210> SEQ ID NO 53
<211> LENGTH: 1479
<212> TYPE: DNA
<213> ORGANISM: Artificial Sequence
<220> FEATURE:
<223> OTHER INFORMATION: Synthetic oligonucleotide.

<400> SEQUENCE: 53

| | |
|---|---|
| atgagatcac tgttctcttt acagttactg agcacacagg acctcgccat gggatggagc | 60 |
| tgtatcatcc tcttcttggt agcaacagct acaggtgtcc actctcaggt ccaactgcag | 120 |
| cagcctgggg ctgaacttgt gaagcctggg gcttcagtga agctgtcctg caaggcttct | 180 |
| ggctacacct tcaccagtta ctggatgcag tgggtaaagc agaggcctgg acagggcctt | 240 |
| gagtggatcg gagagattga tccttctgat agctatacta actacaatca aaggttcaag | 300 |
| ggcaaggcca cattgactgt ggacacatcc tccagcacag cctacataca gctcagcagc | 360 |
| ctgacgtctg aggactctgc ggtctgtttc tgtgcaagac gctactatgg taactacgat | 420 |
| gggtttgctt actggggcca agggactctg gtcactgtct ctgcagccaa acaacagcc | 480 |
| ccatcggtct atccactggc ccctgtgtgt ggaggtacaa ctggctcctc ggtgactcta | 540 |
| ggatgcctgg tcaagggtta tttccctgag ccagtgacct tgacctggaa ctctggatcc | 600 |
| ctgtccagtg gtgtgcacac cttcccagct ctcctgcagt ctggcctcta cacctcagc | 660 |
| agctcagtga ctgtaacctc gaacaccctg cccagccaga ccatcacctg caatgtggcc | 720 |
| cacccggcaa gcagcaccaa agtggacaag aaaattgagc ccagagtgcc cataacacag | 780 |
| aaccctgtc ctccactcaa agagtgtccc catgcgcag ctccagacct cttgggtgga | 840 |
| ccatccgtct tcatcttccc tccaaagatc aaggatgtac tcatgatctc cccgagcccc | 900 |
| atggtcacat gtgtggtggt ggatgtgagc gaggatgacc cagacgtcca gatcagctgg | 960 |
| tttgtgaaca acgtggaagt acacacagct cagacacaaa cccatagaga ggattacaac | 1020 |
| agtactctcc gggtggtcag tgccctcccc atccagcacc aggactggat gagtggcaag | 1080 |
| gagttcaaat gcaaggtcaa caacagagcc ctcccatccc catcgagaa aaccatctca | 1140 |
| aaacccagag ggccagtaag agctccacag gtatatgtct tgcctccacc agcagaagag | 1200 |
| atgactaaga aagagttcag tctgacctgc atgatcacag gcttcttacc tgccgaaatt | 1260 |
| gctgtggact ggaccagcaa tgggcgtaca gagcaaaact acaagaacac cgcaacagtc | 1320 |
| ctggactctg atggttctta cttcatgtac agcaagctca gagtacaaaa gagcacttgg | 1380 |
| gaaagaggaa gtcttttcgc ctgctcagtg gtccacgagg gtctgcacaa tcaccttacg | 1440 |
| actaagacca tctcccggtc tctgggtaaa gctagctga | 1479 |

<210> SEQ ID NO 54
<211> LENGTH: 457
<212> TYPE: PRT
<213> ORGANISM: Artificial Sequence
<220> FEATURE:
<223> OTHER INFORMATION: Synthetic peptide.

<400> SEQUENCE: 54

```
Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Trp Ile
        35                  40                  45

Gly Glu Ile Asp Pro Ser Asp Ser Tyr Thr Asn Tyr Asn Gln Arg Phe
    50                  55                  60

Lys Gly Lys Ala Thr Leu Thr Val Asp Thr Ser Ser Ser Thr Ala Tyr
65                  70                  75                  80

Ile Gln Leu Ser Ser Leu Thr Ser Glu Asp Ser Ala Val Cys Phe Cys
                85                  90                  95

Ala Arg Arg Tyr Tyr Gly Asn Tyr Asp Gly Phe Ala Tyr Trp Gly Gln
            100                 105                 110

Gly Thr Leu Val Thr Val Ser Ala Ala Lys Thr Thr Ala Pro Ser Val
        115                 120                 125

Tyr Pro Leu Ala Pro Val Cys Gly Thr Thr Gly Ser Ser Val Thr
    130                 135                 140

Leu Gly Cys Leu Val Lys Gly Tyr Phe Pro Glu Pro Val Thr Leu Thr
145                 150                 155                 160

Trp Asn Ser Gly Ser Leu Ser Ser Gly Val His Thr Phe Pro Ala Leu
                165                 170                 175

Leu Gln Ser Gly Leu Tyr Thr Leu Ser Ser Ser Val Thr Val Thr Ser
            180                 185                 190

Asn Thr Trp Pro Ser Gln Thr Ile Thr Cys Asn Val Ala His Pro Ala
        195                 200                 205

Ser Ser Thr Lys Val Asp Lys Lys Ile Glu Pro Arg Val Pro Ile Thr
    210                 215                 220

Gln Asn Pro Cys Pro Pro Leu Lys Glu Cys Pro Pro Cys Ala Ala Pro
225                 230                 235                 240

Asp Leu Leu Gly Gly Pro Ser Val Phe Ile Phe Pro Pro Lys Ile Lys
                245                 250                 255

Asp Val Leu Met Ile Ser Pro Ser Pro Met Val Thr Cys Val Val Val
            260                 265                 270

Asp Val Ser Glu Asp Asp Pro Asp Val Gln Ile Ser Trp Phe Val Asn
        275                 280                 285

Asn Val Glu Val His Thr Ala Gln Thr Gln Thr His Arg Glu Asp Tyr
    290                 295                 300

Asn Ser Thr Leu Arg Val Val Ser Ala Leu Pro Ile Gln His Gln Asp
305                 310                 315                 320

Trp Met Ser Gly Lys Glu Phe Lys Cys Lys Val Asn Asn Arg Ala Leu
                325                 330                 335

Pro Ser Pro Ile Glu Lys Thr Ile Ser Lys Pro Arg Gly Pro Val Arg
            340                 345                 350

Ala Pro Gln Val Tyr Val Leu Pro Pro Ala Glu Glu Met Thr Lys
        355                 360                 365
```

```
Lys Glu Phe Ser Leu Thr Cys Met Ile Thr Gly Phe Leu Pro Ala Glu
    370                 375                 380

Ile Ala Val Asp Trp Thr Ser Asn Gly Arg Thr Glu Gln Asn Tyr Lys
385                 390                 395                 400

Asn Thr Ala Thr Val Leu Asp Ser Asp Gly Ser Tyr Phe Met Tyr Ser
                405                 410                 415

Lys Leu Arg Val Gln Lys Ser Thr Trp Glu Arg Gly Ser Leu Phe Ala
            420                 425                 430

Cys Ser Val Val His Glu Gly Leu His Asn His Leu Thr Thr Lys Thr
        435                 440                 445

Ile Ser Arg Ser Leu Gly Lys Ala Ser
    450                 455

<210> SEQ ID NO 55
<211> LENGTH: 705
<212> TYPE: DNA
<213> ORGANISM: Artificial Sequence
<220> FEATURE:
<223> OTHER INFORMATION: Synthetic oligonucleotide.

<400> SEQUENCE: 55
atgagggccc ctgctcagtt ttttgggatc ttgttgctct ggtttccagg tatcagatgt    60
gacatcaaga tgacccagtc tccatcctcc atgtatgcat cgctgggaga gagagtcact   120
attacttgca aggcgagtca ggacattaaa agctatttaa cttggtacca gcagaaacca   180
tggaaatctc ctaagaccct gatcaattat gcaacaagct ggcagatggg gtcccatca   240 agattcagtg gcagtggatc tggacaagat tattctctaa ccatcagcag cctggagtct   300
gacgatacag caacttatta ctgtctacag catggtcaga gtccgttcac gttcggaggg   360
gggaccaggc tggagataaa acgggctgat gctgcaccaa ctgtatccat cttcccacca   420
tccagtgagc agttaacatc tggaggtgcc tcggtcgtgt gcttcttgaa caacttctac   480
cccaaagaca tcaatgtcaa gtggaagatt gatggcagtg aacgacaaaa tggcgtcctg   540
aacagttgga ctgatcagga cagcaaagac agcacctaca gcatgagcag caccctcacg   600
ttgaccaagg acgagtatga acgacataac agctatacct gtgaggccac tcacaagaca   660
tcaacttcac ccatcgtcaa gagcttcaac aggaatgagt gttag              705

<210> SEQ ID NO 56
<211> LENGTH: 214
<212> TYPE: PRT
<213> ORGANISM: Artificial Sequence
<220> FEATURE:
<223> OTHER INFORMATION: Synthetic peptide.

<400> SEQUENCE: 56

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Lys Ser Tyr
            20                  25                  30

Leu Thr Trp Tyr Gln Gln Lys Pro Trp Lys Ser Pro Lys Thr Leu Ile
        35                  40                  45

Asn Tyr Ala Thr Ser Leu Ala Asp Gly Val Pro Ser Arg Phe Ser Gly
    50                  55                  60

Ser Gly Ser Gly Gln Asp Tyr Ser Leu Thr Ile Ser Ser Leu Glu Ser
65                  70                  75                  80

Asp Asp Thr Ala Thr Tyr Tyr Cys Leu Gln His Gly Gln Ser Pro Phe
                85                  90                  95
```

```
Thr Phe Gly Gly Gly Thr Arg Leu Glu Ile Lys Arg Ala Asp Ala Ala
                100                 105                 110

Pro Thr Val Ser Ile Phe Pro Pro Ser Ser Glu Gln Leu Thr Ser Gly
            115                 120                 125

Gly Ala Ser Val Val Cys Phe Leu Asn Asn Phe Tyr Pro Lys Asp Ile
        130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 57
<211> LENGTH: 1479
<212> TYPE: DNA
<213> ORGANISM: Artificial Sequence
<220> FEATURE:
<223> OTHER INFORMATION: Synthetic peptide.

<400> SEQUENCE: 57
atgagatcac tgttctcttt acagttactg agcacacagg acctcgccat gggatggagc      60
tgtatcatcc tcttcttggt agcaacagct acaggtgtcc actctcaggt ccaactgcag     120
cagcctgggg ctgagcttgt gaagcctggg gcttcagtga agctgtcctg caaggcttct     180
ggctacacct tcaccagtta ctggatgcag tgggtaaagc agaggcctgg acagggcctt     240
gagtggaccg gagagattga tccttctgat agctatacta actacaatca aaggttcaag     300
ggcaaggcca cattgactgt ggacacatcc tccagcacag cctacacaca gctcagcagc     360
ctgacgtctg aggactctgc ggtccatttc tgtgcaagac gctactatgg taactacgat     420
gggtttgctt actggggcca aggactctg gtcactgtct ctgcagccaa aacaacagcc     480
ccatcggtct atccactggc ccctgtgtgt ggaggtacaa ctggctcctc ggtgactcta     540
ggatgcctgg tcaagggtta tttccctgag ccagtgacct tgacctggaa ctctggatcc     600
ctgtccagtg gtgtgcacac cttcccagct ctcctgcagt ctggcctcta caccctcagc     660
agctcagtga ctgtaacctc gaacacctgg cccagccaga ccatcacctg caatgtggcc     720
cacccggcaa gcagcaccaa agtggacaag aaaattgagc ccagagtgcc cataacacag     780
aacccctgtc ctccactcaa agagtgtccc catgcgcag ctccagacct cttgggtgga     840
ccatccgtct tcatcttccc tccaaaggtc aaggatgtac tcatgatctc cctgagcccc     900
atggtcacat gtggtggt ggatgtgagc gaggatgacc cagacgtcca gatcagctgg     960
tttgtgaaca acgtggaagt acacacagct cagacacaaa cccatagaga ggattacaac    1020
agtactctcc gggtggtcag tgccctcccc atccagcacc aggactggat gagtggcaag    1080
gagttcaaat gcaaggtcaa caacagagcc ctcccatccc catcgagaa aaccatctca    1140 aaacccagag gccagtaag agctccacag gtatatgtct tgcctccacc agcagaagag    1200
atgactaaga aagagttcag tctgacctgc atgatcacag gcttcttacc tgccgaaatt    1260
gctgtggact ggaccagcaa tgggcgtaca gagcaaaact acaagaacac cgcaacagtc    1320
```

```
ctggactctg atggttctta cttcatgtac agcaagctca gagtacaaaa gagcacttgg   1380
gaaagaggaa gtctttttcgc ctgctcagtg gtccacgagg gtctgcacaa tcaccttacg   1440
actaagacca tctcccggtc tctgggtaaa gctagctga                          1479
```

<210> SEQ ID NO 58
<211> LENGTH: 457
<212> TYPE: PRT
<213> ORGANISM: Artificial Sequence
<220> FEATURE:
<223> OTHER INFORMATION: Synthetic peptide.

<400> SEQUENCE: 58

```
Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Trp Thr
        35                  40                  45

Gly Glu Ile Asp Pro Ser Asp Ser Tyr Thr Asn Tyr Asn Gln Arg Phe
    50                  55                  60

Lys Gly Lys Ala Thr Leu Thr Val Asp Thr Ser Ser Ser Thr Ala Tyr
65                  70                  75                  80

Thr Gln Leu Ser Ser Leu Thr Ser Glu Asp Ser Ala Val His Phe Cys
                85                  90                  95

Ala Arg Arg Tyr Tyr Gly Asn Tyr Asp Gly Phe Ala Tyr Trp Gly Gln
            100                 105                 110

Gly Thr Leu Val Thr Val Ser Ala Lys Thr Thr Ala Pro Ser Val
        115                 120                 125

Tyr Pro Leu Ala Pro Val Cys Gly Gly Thr Thr Gly Ser Ser Val Thr
    130                 135                 140

Leu Gly Cys Leu Val Lys Gly Tyr Phe Pro Glu Pro Val Thr Leu Thr
145                 150                 155                 160

Trp Asn Ser Gly Ser Leu Ser Ser Gly Val His Thr Phe Pro Ala Leu
                165                 170                 175

Leu Gln Ser Gly Leu Tyr Thr Leu Ser Ser Ser Val Thr Val Thr Ser
            180                 185                 190

Asn Thr Trp Pro Ser Gln Thr Ile Thr Cys Asn Val Ala His Pro Ala
        195                 200                 205

Ser Ser Thr Lys Val Asp Lys Lys Ile Glu Pro Arg Val Pro Ile Thr
    210                 215                 220

Gln Asn Pro Cys Pro Pro Leu Lys Glu Cys Pro Pro Cys Ala Ala Pro
225                 230                 235                 240

Asp Leu Leu Gly Gly Pro Ser Val Phe Ile Phe Pro Pro Lys Val Lys
                245                 250                 255

Asp Val Leu Met Ile Ser Leu Ser Pro Met Val Thr Cys Val Val Val
            260                 265                 270

Asp Val Ser Glu Asp Asp Pro Asp Val Gln Ile Ser Trp Phe Val Asn
        275                 280                 285

Asn Val Glu Val His Thr Ala Gln Thr Gln Thr His Arg Glu Asp Tyr
    290                 295                 300

Asn Ser Thr Leu Arg Val Val Ser Ala Leu Pro Ile Gln His Gln Asp
305                 310                 315                 320

Trp Met Ser Gly Lys Glu Phe Lys Cys Lys Val Asn Asn Arg Ala Leu
                325                 330                 335
```

```
Pro Ser Pro Ile Glu Lys Thr Ile Ser Lys Pro Arg Gly Pro Val Arg
            340                 345                 350

Ala Pro Gln Val Tyr Val Leu Pro Pro Ala Glu Glu Met Thr Lys
    355                 360                 365

Lys Glu Phe Ser Leu Thr Cys Met Ile Thr Gly Phe Leu Pro Ala Glu
370             375                 380

Ile Ala Val Asp Trp Thr Ser Asn Gly Arg Thr Glu Gln Asn Tyr Lys
385             390                 395                 400

Asn Thr Ala Thr Val Leu Asp Ser Asp Gly Ser Tyr Phe Met Tyr Ser
                405                 410                 415

Lys Leu Arg Val Gln Lys Ser Thr Trp Glu Arg Gly Ser Leu Phe Ala
            420                 425                 430

Cys Ser Val Val His Glu Gly Leu His Asn His Leu Thr Thr Lys Thr
            435                 440                 445

Ile Ser Arg Ser Leu Gly Lys Ala Ser
450                 455
```

<210> SEQ ID NO 59
<211> LENGTH: 2412
<212> TYPE: DNA
<213> ORGANISM: Artificial Sequence
<220> FEATURE:
<223> OTHER INFORMATION: Synthetic oligonucleotide.

<400> SEQUENCE: 59

```
atgacattga acatgctgtt ggggctgagg tgggttttct tgttgtttt tatcaaggt      60
gtgcattgtg aggtgcagct tgttgagtct ggtggaggat tggtgcagcc taaaggtca    120
ttgaaactct catgtgcagc ctctggatta accttcaata tctacgccat gaactgggtc   180
cgccaggctc caggaaaggg tttgaatgg gttgctcgca taagaaataa agtaataat    240
tatgcaacat attatgccga ttcagtgaaa gacaggttca ccatctccag agatgattca    300
caaagcttgc tctatctgca aatgaacaac ttgaaaactg aggacacagc catgtattac    360
tgtgtgggac gggactggtt tgattactgg ggccaaggga ctctggtcac tgtctctgca    420
gccaaaacga gggcccatc cgtcttcccc ctggcgccct gctccaggag cacctccgag    480
agcacagccg ccctgggctg cctggtcaag gactacttcc ccgaaccggt gacggtgtcg    540
tggaactcag gcgccctgac cagcggcgtg cacaccttcc cggctgtcct acagtcctca    600
ggactctact ccctcagcag cgtggtgacc gtgccctcca gcagcttggg cacgaagacc    660
tacacctgca acgtagatca caagcccagc aacaccaagg tggacaagag agttgagtcc    720
aaatatggtc ccccatgccc accctgccca gcacctgagt tcgaagggg accatcagtc    780
ttcctgttcc ccccaaaacc caaggacact ctcatgatct cccggaccc tgaggtcacg    840
tgcgtggtgg tggacgtgag ccaggaagac cccgaggtcc agttcaactg gtacgtggat    900
ggcgtggagg tgcataatgc caagacaaag ccgcgggagg agcagttcaa cagcacgtac    960
cgtgtggtca gcgtcctcac cgtcctgcac caggactggc tgaacggcaa ggagtacaag   1020
tgcaaggtct ccaacaaagg cctcccgtcc tccatcgaga aaaccatctc caaagccaaa   1080
gggcagcccc gagagccaca ggtgtacacc ctgcccccat cccaggagga gatgaccaag   1140
aaccaggtca gcctgacctg cctggtcaaa ggcttctacc ccagcgacat cgccgtggag   1200
tgggagagca atgggcagcc ggagaacaac tacaagacca cgcctcccgt gctggactcc   1260
gacggctcct tcttcctcta cagcaggcta accgtggaca gagcaggtg gcaggagggg   1320
aatgtcttct catgctccgt gatgcatgag gctctgcaca accactacac acagaagagc   1380
```

-continued

```
ctctccctgt ctctgggtaa agctagcgat acaacagaac ctgcaacacc tacaacacct    1440
gtaacaacag acacaatatg tataggctac catgcgaaca attcaaccga cactgttgac    1500
acagtactcg agaagaatgt gacagtgaca cactctgtta acctgctcga agacagccac    1560
aacggaaaac tatgtagatt aaaaggaata gccccactac aattggggaa atgtaacatc    1620
gccggatggc tcttgggaaa cccagaatgc gacccactgc ttccagtgag atcatggtcc    1680
tacattgtag aaacaccaaa ctctgagaat ggaatatgtt atccaggaga tttcatcgac    1740
tatgaggagc tgagggagca attgagctca gtgtcatcat tcgaaagatt cgaaatattt    1800
cccaaagaaa gctcatggcc caaccacaac acaaacggag taacggcagc atgctcccat    1860
gaggggaaaa gcagttttta cagaaatttg ctatggctga cggagaagga gggctcatac    1920
ccaaagctga aaaattctta tgtgaacaaa aagggaaag aagtccttgt actgtggggt    1980
attcatcacc cgcctaacag taaggaacaa cagaatctct atcagaatga aaatgcttat    2040
gtctctgtag tgacttcaaa ttataacagg agatttaccc cggaaatagc agaaagaccc    2100
aaagtaagag atcaagctgg gaggatgaac tattactgga ccttgctaaa acccggagac    2160
acaataatat ttgaggcaaa tggaaatcta atagcaccaa tgtatgcttt cgcactgagt    2220
agaggctttg ggtccggcat catcacctca aacgcatcaa tgcatgagtg taacacgaag    2280
tgtcaaacac ccctgggagc tataaacagc agtctcccct accagaatat acacccagtc    2340
acaataggag agtgcccaaa atacgtcagg agtgccaaat tgaggatggt tcaccatcac    2400
catcaccatt ga                                                        2412
```

<210> SEQ ID NO 60
<211> LENGTH: 780
<212> TYPE: PRT
<213> ORGANISM: Artificial Sequence
<220> FEATURE:
<223> OTHER INFORMATION: Synthetic peptide.

<400> SEQUENCE: 60

```
Glu Val Gln Leu Val Glu Ser Gly Gly Gly Leu Val Gln Pro Lys Gly
1               5                   10                  15

Ser Leu Lys Leu Ser Cys Ala Ala Ser Gly Leu Thr Phe Asn Ile Tyr
            20                  25                  30

Ala Met Asn Trp Val Arg Gln Ala Pro Gly Lys Gly Leu Glu Trp Val
        35                  40                  45

Ala Arg Ile Arg Asn Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Leu
65                  70                  75                  80

Leu Tyr Leu Gln Met Asn Asn Leu Lys Thr Glu Asp Thr Ala Met Tyr
                85                  90                  95

Tyr Cys Val Gly Arg Asp Trp Phe Asp Tyr Trp Gly Gln Gly Thr Leu
            100                 105                 110

Val Thr Val Ser Ala Ala Lys Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175
```

```
Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
            290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
            325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly Lys Ala Ser Asp Thr
            435                 440                 445

Thr Glu Pro Ala Thr Pro Thr Thr Pro Val Thr Thr Asp Thr Ile Cys
450                 455                 460

Ile Gly Tyr His Ala Asn Asn Ser Thr Asp Thr Val Asp Thr Val Leu
465                 470                 475                 480

Glu Lys Asn Val Thr Val Thr His Ser Val Asn Leu Leu Glu Asp Ser
                485                 490                 495

His Asn Gly Lys Leu Cys Arg Leu Lys Gly Ile Ala Pro Leu Gln Leu
            500                 505                 510

Gly Lys Cys Asn Ile Ala Gly Trp Leu Leu Gly Asn Pro Glu Cys Asp
            515                 520                 525

Pro Leu Leu Pro Val Arg Ser Trp Ser Tyr Ile Val Glu Thr Pro Asn
            530                 535                 540

Ser Glu Asn Gly Ile Cys Tyr Pro Gly Asp Phe Ile Asp Tyr Glu Glu
545                 550                 555                 560

Leu Arg Glu Gln Leu Ser Ser Val Ser Ser Phe Glu Arg Phe Glu Ile
                565                 570                 575

Phe Pro Lys Glu Ser Ser Trp Pro Asn His Asn Thr Asn Gly Val Thr
            580                 585                 590
```

```
Ala Ala Cys Ser His Glu Gly Lys Ser Ser Phe Tyr Arg Asn Leu Leu
        595                 600                 605

Trp Leu Thr Glu Lys Glu Gly Ser Tyr Pro Lys Leu Lys Asn Ser Tyr
    610                 615                 620

Val Asn Lys Lys Gly Lys Glu Val Leu Val Leu Trp Gly Ile His His
625                 630                 635                 640

Pro Pro Asn Ser Lys Glu Gln Gln Asn Leu Tyr Gln Asn Glu Asn Ala
                645                 650                 655

Tyr Val Ser Val Val Thr Ser Asn Tyr Asn Arg Arg Phe Thr Pro Glu
            660                 665                 670

Ile Ala Glu Arg Pro Lys Val Arg Asp Gln Ala Gly Arg Met Asn Tyr
        675                 680                 685

Tyr Trp Thr Leu Leu Lys Pro Gly Asp Thr Ile Ile Phe Glu Ala Asn
    690                 695                 700

Gly Asn Leu Ile Ala Pro Met Tyr Ala Phe Ala Leu Ser Arg Gly Phe
705                 710                 715                 720

Gly Ser Gly Ile Ile Thr Ser Asn Ala Ser Met His Glu Cys Asn Thr
                725                 730                 735

Lys Cys Gln Thr Pro Leu Gly Ala Ile Asn Ser Ser Leu Pro Tyr Gln
            740                 745                 750

Asn Ile His Pro Val Thr Ile Gly Glu Cys Pro Lys Tyr Val Arg Ser
        755                 760                 765

Ala Lys Leu Arg Met Val His His His His His
    770                 775                 780

<210> SEQ ID NO 61
<211> LENGTH: 2412
<212> TYPE: DNA
<213> ORGANISM: Artificial Sequence
<220> FEATURE:
<223> OTHER INFORMATION: Syntehtic oligonucleotide.

<400> SEQUENCE: 61
atgacattga acatgctgtt ggggctgagg tgggttttct tgttgttttt ttatcaaggt      60
gtgcattgtg aggtgcagct tgttgagtct ggtggaggat tggtgcagcc taaagggtca     120
ttgaaactct catgtgcagc ctctggatta accttcaata tctacgccat gaactgggtc     180
cgccaggctc caggaaaggg tttggaatgg gttgctcgca taagaaataa agtaataat      240 tatgcaacat attatgccga ttcagtgaaa gacaggttca ccatctccag agatgattca     300
caaagcttgc tctatctgca aatgaacaac ttgaaaactg aggacacagc catgtattac     360
tgtgtgggac gggactggtt tgattactgg ggccaaggga ctctggtcac tgtctctgca     420
gccaaaacga agggcccatc cgtcttcccc ctggcgccct gctccaggag cacctccgag     480
agcacagccg ccctgggctg cctggtcaag gactacttcc ccgaaccggt gacggtgtcg     540
tggaactcag gcgccctgac cagcggcgtg cacaccttcc cggctgtcct acagtcctca     600
ggactctact ccctcagcag cgtggtgacc gtgcccctcca gcagcttggg cacgaagacc     660
tacacctgca acgtagatca caagcccagc aacaccaagg tggacaagag agttgagtcc     720
aaatatggtc cccccatgccc acctgccca gcacctgagt tcgaagggg accatcagtc     780 ttcctgttcc ccccaaaacc caaggacact ctcatgatct cccggacccc tgaggtcacg     840
tgcgtggtgg tggacgtgag ccaggaagac cccgaggtcc agttcaactg gtacgtggat     900
ggcgtggagg tgcataatgc caagacaaag ccgcgggagg agcagttcaa cagcacgtac     960
cgtgtggtca gcgtcctcac cgtcctgcac caggactggc tgaacggcaa ggagtacaag    1020
```

```
tgcaaggtct ccaacaaagg cctcccgtcc tccatcgaga aaaccatctc caaagccaaa    1080
gggcagcccc gagagccaca ggtgtacacc ctgcccccat cccaggagga gatgaccaag    1140
aaccaggtca gcctgacctg cctggtcaaa ggcttctacc ccagcgacat cgccgtggag    1200
tgggagagca atgggcagcc ggagaacaac tacaagacca cgcctcccgt gctggactcc    1260
gacggctcct tcttcctcta cagcaggcta accgtggaca agagcaggtg gcaggagggg    1320
aatgtcttct catgctccgt gatgcatgag gctctgcaca accactacac acagaagagc    1380
ctctccctgt ctctgggtaa agctagcgat acaacagaac ctgcaacacc tacaacacct    1440
gtaacaacag atcagatttg cattggttac catgcaaaca actcgacaga gcaggttgac    1500
acaataatgg aaaagaacgt tactgttaca catgcccaag acatactgga aaagaaacac    1560
aacgggaagc tctgcgatct agatggagtg aagcctctaa ttttgagaga ttgtagcgta    1620
gctggatggc tcctcggaaa cccaatgtgt gacgaattca tcaatgtgcc ggaatggtct    1680
tacatagtgg agaaggccaa tccagtcaat gacctctgtt acccagggga tttcaatgac    1740
tatgaagaat tgaaacacct attgagcaga ataaaccatt ttgagaaaat tcagatcatc    1800
cccaaaagtt cttggtccag tcatgaagcc tcattagggg tgagctcagc atgtccatac    1860
cagggaaagt cctccttttt cagaaatgtg gtatggctta tcaaaaagaa cagtacatac    1920
ccaacaataa agaggagcta caataatacc aaccaagaag atcttttggt actgtggggg    1980
attcaccatc ctaatgatgc ggcagagcag acaaagctct atcaaaaccc aaccacctat    2040
atttccgttg gcacatcaac actaaaccag agattggtac caagaatagc tactagatcc    2100
aaagtaaacg ggcaaagtgg aaggatggag ttcttctgga caatttttaaa gccgaatgat    2160 gcaatcaact tcgagagtaa tggaaatttc attgctccag aatatgcata caaaattgtc    2220
aagaaagggg actcaacaat tatgaaaagt gaattggaat atggtaactg caacaccaag    2280
tgtcaaactc caatgggggc gataaactct agcatgccat tccacaatat acaccctctc    2340
accattgggg aatgccccaa atatgtgaaa tcaaacagat tagtccttgc gcaccatcac    2400
catcaccatt ga                                                        2412
```

<210> SEQ ID NO 62
<211> LENGTH: 780
<212> TYPE: PRT
<213> ORGANISM: Artificial Sequence
<220> FEATURE:
<223> OTHER INFORMATION: Syntehtic peptide.

<400> SEQUENCE: 62

```
Glu Val Gln Leu Val Glu Ser Gly Gly Gly Leu Val Gln Pro Lys Gly
1               5                   10                  15

Ser Leu Lys Leu Ser Cys Ala Ala Ser Gly Leu Thr Phe Asn Ile Tyr
            20                  25                  30

Ala Met Asn Trp Val Arg Gln Ala Pro Gly Lys Gly Leu Glu Trp Val
        35                  40                  45

Ala Arg Ile Arg Asn Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Leu
65                  70                  75                  80

Leu Tyr Leu Gln Met Asn Asn Leu Lys Thr Glu Asp Thr Ala Met Tyr
                85                  90                  95

Tyr Cys Val Gly Arg Asp Trp Phe Asp Tyr Trp Gly Gln Gly Thr Leu
            100                 105                 110
```

-continued

```
Val Thr Val Ser Ala Ala Lys Thr Lys Gly Pro Ser Val Phe Pro Leu
            115                 120                 125
Ala Pro Cys Ser Arg Ser Thr Ser Glu Ser Thr Ala Ala Leu Gly Cys
        130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Lys Thr Tyr Thr Cys Asn Val Asp His Lys Pro Ser Asn
        195                 200                 205
Thr Lys Val Asp Lys Arg Val Glu Ser Lys Tyr Gly Pro Pro Cys Pro
210                 215                 220
Pro Cys Pro Ala Pro Glu Phe Glu Gly Gly Pro Ser Val Phe Leu Phe
225                 230                 235                 240
Pro Pro Lys Pro Lys Asp Thr Leu Met Ile Ser Arg Thr Pro Glu Val
                245                 250                 255
Thr Cys Val Val Val Asp Val Ser Gln Glu Asp Pro Glu Val Gln Phe
            260                 265                 270
Asn Trp Tyr Val Asp Gly Val Glu Val His Asn Ala Lys Thr Lys Pro
        275                 280                 285
Arg Glu Glu Gln Phe Asn Ser Thr Tyr Arg Val Val Ser Val Leu Thr
290                 295                 300
Val Leu His Gln Asp Trp Leu Asn Gly Lys Glu Tyr Lys Cys Lys Val
305                 310                 315                 320
Ser Asn Lys Gly Leu Pro Ser Ser Ile Glu Lys Thr Ile Ser Lys Ala
                325                 330                 335
Lys Gly Gln Pro Arg Glu Pro Gln Val Tyr Thr Leu Pro Pro Ser Gln
            340                 345                 350
Glu Glu Met Thr Lys Asn Gln Val Ser Leu Thr Cys Leu Val Lys Gly
        355                 360                 365
Phe Tyr Pro Ser Asp Ile Ala Val Glu Trp Ser Asn Gly Gln Pro
370                 375                 380
Glu Asn Asn Tyr Lys Thr Thr Pro Pro Val Leu Asp Ser Asp Gly Ser
385                 390                 395                 400
Phe Phe Leu Tyr Ser Arg Leu Thr Val Asp Lys Ser Arg Trp Gln Glu
                405                 410                 415
Gly Asn Val Phe Ser Cys Ser Val Met His Glu Ala Leu His Asn His
            420                 425                 430
Tyr Thr Gln Lys Ser Leu Ser Leu Ser Leu Gly Lys Ala Ser Asp Thr
        435                 440                 445
Thr Glu Pro Ala Thr Pro Thr Thr Pro Val Thr Thr Asp Gln Ile Cys
450                 455                 460
Ile Gly Tyr His Ala Asn Asn Ser Thr Glu Gln Val Asp Thr Ile Met
465                 470                 475                 480
Glu Lys Asn Val Thr Val Thr His Ala Gln Asp Ile Leu Glu Lys Lys
                485                 490                 495
His Asn Gly Lys Leu Cys Asp Leu Asp Gly Val Lys Pro Leu Ile Leu
            500                 505                 510
Arg Asp Cys Ser Val Ala Gly Trp Leu Leu Gly Asn Pro Met Cys Asp
        515                 520                 525
```

```
Glu Phe Ile Asn Val Pro Glu Trp Ser Tyr Ile Val Glu Lys Ala Asn
                530                 535                 540

Pro Val Asn Asp Leu Cys Tyr Pro Gly Asp Phe Asn Asp Tyr Glu Glu
545                 550                 555                 560

Leu Lys His Leu Leu Ser Arg Ile Asn His Phe Glu Lys Ile Gln Ile
                565                 570                 575

Ile Pro Lys Ser Ser Trp Ser Ser His Glu Ala Ser Leu Gly Val Ser
                580                 585                 590

Ser Ala Cys Pro Tyr Gln Gly Lys Ser Ser Phe Phe Arg Asn Val Val
                595                 600                 605

Trp Leu Ile Lys Lys Asn Ser Thr Tyr Pro Thr Ile Lys Arg Ser Tyr
610                 615                 620

Asn Asn Thr Asn Gln Glu Asp Leu Leu Val Leu Trp Gly Ile His His
625                 630                 635                 640

Pro Asn Asp Ala Ala Glu Gln Thr Lys Leu Tyr Gln Asn Pro Thr Thr
                645                 650                 655

Tyr Ile Ser Val Gly Thr Ser Thr Leu Asn Gln Arg Leu Val Pro Arg
                660                 665                 670

Ile Ala Thr Arg Ser Lys Val Asn Gly Gln Ser Gly Arg Met Glu Phe
                675                 680                 685

Phe Trp Thr Ile Leu Lys Pro Asn Asp Ala Ile Asn Phe Glu Ser Asn
690                 695                 700

Gly Asn Phe Ile Ala Pro Glu Tyr Ala Tyr Lys Ile Val Lys Lys Gly
705                 710                 715                 720

Asp Ser Thr Ile Met Lys Ser Glu Leu Glu Tyr Gly Asn Cys Asn Thr
                725                 730                 735

Lys Cys Gln Thr Pro Met Gly Ala Ile Asn Ser Ser Met Pro Phe His
                740                 745                 750

Asn Ile His Pro Leu Thr Ile Gly Glu Cys Pro Lys Tyr Val Lys Ser
                755                 760                 765

Asn Arg Leu Val Leu Ala His His His His His
770                 775                 780

<210> SEQ ID NO 63
<211> LENGTH: 2202
<212> TYPE: DNA
<213> ORGANISM: Artificial Sequence
<220> FEATURE:
<223> OTHER INFORMATION: Synthetic oligonucleotide.

<400> SEQUENCE: 63
atgacattga acatgctgtt ggggctgaag tgggttttct tgttgttttt ttatcaaggt      60
gtgcattgtg aggtgcagct tgttgagtct ggtggaggat tggtgcagcc taaagggtca     120
ttgaaactct catgtgcagc ctctggatta accttcaata tctacgccat gaactgggtc     180
cgccaggctc caggaaaggg tttggaatgg gttgctcgca taagaaataa aagtaataat     240
tatgcaacat attatgccga ttcagtgaaa gacaggttca ccatctccag agatgattca     300
caaagcttgc tctatctgca aatgaacaac ttgaaaactg aggacacagc catgtattac     360
tgtgtgggac gggactggtt tgattactgg ggccaaggga ctctggtcac tgtctctgca     420
gccaaaacga agggcccatc cgtcttcccc ctggcgccct gctccaggag cacctccgag     480
agcacagccg ccctgggctg cctggtcaag gactacttcc ccgaaccggt gacggtgtcg     540
tggaactcag gcgccctgac cagcggcgtg cacaccttcc cggctgtcct acagtcctca     600
ggactctact ccctcagcag cgtggtgacc gtgccctcca gcagcttggg cacgaagacc     660
```

```
tacacctgca acgtagatca caagcccagc aacaccaagg tggacaagag agttgagtcc    720
aaatatggtc ccccatgccc accctgccca gcacctgagt cgaaggggg accatcagtc     780
ttcctgttcc ccccaaaacc caaggacact ctcatgatct cccggacccc tgaggtcacg    840
tgcgtggtgg tggacgtgag ccaggaagac cccgaggtcc agttcaactg gtacgtggat    900
ggcgtggagg tgcataatgc caagacaaag ccgcgggagg agcagttcaa cagcacgtac    960
cgtgtggtca gcgtcctcac cgtcctgcac caggactggc tgaacggcaa ggagtacaag   1020
tgcaaggtct ccaacaaagg cctcccgtcc tccatcgaga aaaccatctc caaagccaaa   1080
gggcagcccc gagagccaca ggtgtacacc ctgcccccat cccaggagga gatgaccaag   1140
aaccaggtca gcctgacctg cctggtcaaa ggcttctacc ccagcgacat cgccgtggag   1200
tgggagagca atgggcagcc ggagaacaac tacaagacca cgcctcccgt gctggactcc   1260
gacggctcct tcttcctcta cagcaggcta accgtggaca gagcaggtg gcaggagggg    1320
aatgtcttct catgctccgt gatgcatgag gctctgcaca accactacac acagaagagc   1380
ctctccctgt ctctgggtaa agctagcgat acaacagaac ctgcaacacc tacaacacct   1440
gtaacaacac cgacaacaac acttctagcg cccctcatcc tgtctcggat tgtgggaggc   1500
tgggagtgcg agaagcattc ccaaccctgg caggtgcttg tggcctctcg tggcagggca   1560
gtctgcggcg tgttctggt gcaccccag tgggtcctca cagctgccca ctgcatcagg    1620
aacaaaagcg tgatcttgct gggtcggcac agcctgtttc atcctgaaga cacaggccag   1680
gtatttcagg tcagccacag cttcccacac ccgctctacg atatgagcct cctgaagaat   1740
cgattcctca ggccaggtga tgactccagc cacgacctca tgctgctccg cctgtcagag   1800
cctgccgagc tcacggatgc tgtgaaggtc atggacctgc ccacccagga gccagcactg   1860
gggaccacct gctacgcctc aggctgggc agcattgaac cagaggagtt cttgacccca   1920
aagaaacttc agtgtgtgga cctccatgtt atttccaatg acgtgtgtgc gcaagttcac   1980
cctcagaagg tgaccaagtt catgctgtgt gctggacgct ggacaggggg caaaagcacc   2040
tgctcgggtg attctggggg cccacttgtc tgtaatggtg tgcttcaagg tatcacgtca   2100
tggggcagtg aaccatgtgc cctgcccgaa aggccttccc tgtacaccaa ggtggtgcat   2160
taccggaagt ggatcaagga caccatcgtg gccaacccct ga                      2202
```

<210> SEQ ID NO 64
<211> LENGTH: 710
<212> TYPE: PRT
<213> ORGANISM: Artificial Sequence
<220> FEATURE:
<223> OTHER INFORMATION: Synthetic peptide.

<400> SEQUENCE: 64

```
Glu Val Gln Leu Val Glu Ser Gly Gly Gly Leu Val Gln Pro Lys Gly
1               5                   10                  15

Ser Leu Lys Leu Ser Cys Ala Ala Ser Gly Leu Thr Phe Asn Ile Tyr
            20                  25                  30

Ala Met Asn Trp Val Arg Gln Ala Pro Gly Lys Gly Leu Glu Trp Val
        35                  40                  45

Ala Arg Ile Arg Asn Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Leu
65                  70                  75                  80

Leu Tyr Leu Gln Met Asn Asn Leu Lys Thr Glu Asp Thr Ala Met Tyr
```

```
            85                  90                  95
Tyr Cys Val Gly Arg Asp Trp Phe Asp Tyr Trp Gly Gln Gly Thr Leu
            100                 105                 110

Val Thr Val Ser Ala Ala Lys Thr Lys Gly Pro Ser Val Phe Pro Leu
            115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
            210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
            290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
            325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
            405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys Ala Ser Asp Thr
            435                 440                 445

Thr Glu Pro Ala Thr Pro Thr Thr Pro Val Thr Thr Pro Thr Thr Thr
450                 455                 460

Leu Leu Ala Pro Leu Ile Leu Ser Arg Ile Val Gly Gly Trp Glu Cys
465                 470                 475                 480

Glu Lys His Ser Gln Pro Trp Gln Val Leu Val Ala Ser Arg Gly Arg
            485                 490                 495

Ala Val Cys Gly Gly Val Leu Val His Pro Gln Trp Val Leu Thr Ala
            500                 505                 510
```

```
Ala His Cys Ile Arg Asn Lys Ser Val Ile Leu Leu Gly Arg His Ser
        515                 520                 525

Leu Phe His Pro Glu Asp Thr Gly Gln Val Phe Gln Val Ser His Ser
    530                 535                 540

Phe Pro His Pro Leu Tyr Asp Met Ser Leu Leu Lys Asn Arg Phe Leu
545                 550                 555                 560

Arg Pro Gly Asp Asp Ser Ser His Asp Leu Met Leu Leu Arg Leu Ser
                565                 570                 575

Glu Pro Ala Glu Leu Thr Asp Ala Val Lys Val Met Asp Leu Pro Thr
            580                 585                 590

Gln Glu Pro Ala Leu Gly Thr Thr Cys Tyr Ala Ser Gly Trp Gly Ser
        595                 600                 605

Ile Glu Pro Glu Glu Phe Leu Thr Pro Lys Lys Leu Gln Cys Val Asp
    610                 615                 620

Leu His Val Ile Ser Asn Asp Val Cys Ala Gln Val His Pro Gln Lys
625                 630                 635                 640

Val Thr Lys Phe Met Leu Cys Ala Gly Arg Trp Thr Gly Gly Lys Ser
                645                 650                 655

Thr Cys Ser Gly Asp Ser Gly Gly Pro Leu Val Cys Asn Gly Val Leu
            660                 665                 670

Gln Gly Ile Thr Ser Trp Gly Ser Glu Pro Cys Ala Leu Pro Glu Arg
        675                 680                 685

Pro Ser Leu Tyr Thr Lys Val Val His Tyr Arg Lys Trp Ile Lys Asp
    690                 695                 700

Thr Ile Val Ala Asn Pro
705                 710

<210> SEQ ID NO 65
<211> LENGTH: 2415
<212> TYPE: DNA
<213> ORGANISM: Artificial Sequence
<220> FEATURE:
<223> OTHER INFORMATION: Syntehtic oligonucleotide.

<400> SEQUENCE: 65
atggacccca aaggctccct tcctggaga atacttctgt ttctctccct ggcttttgag      60
ttgtcgtacg acaggttca gctgcggcag tctggacctg agctggtgaa gcctggggct     120
tcagtgaaga tgtcctgcaa ggcttctgga tacacattta ctgactatgt tataagttgg    180
gtgaagcaga gaactggaca gggccttgag tggattggag atatttatcc tggaagtggt    240
tattctttct acaatgagaa cttcaagggc aaggccacac tgactgcaga caaatcctcc    300
accacagcct acatgcagct cagcagcctg acatctgagg actctgcggt ctatttctgt    360
gcaacctact ataactaccc ttttgcttac tggggccaag ggactctggt cactgtctct    420
gcagccaaaa caacgggccc atccgtcttc cccctggcgc cctgctccag gagcacctcc    480
gagagcacag ccgccctggg ctgcctggtc aaggactact ccccgaacc ggtgacggtg    540
tcgtggaact caggcgccct gaccagcggc gtgcacacct tcccggctgt cctacagtcc    600
tcaggactct actccctcag cagcgtggtg accgtgccct ccagcagctt gggcacgaag    660
acctacacct gcaacgtaga tcacaagccc agcaacacca aggtggacaa gagagttgag    720
tccaaatatg gtccccatg cccaccctgc ccagcacctg agttcgaagg ggaccatca    780
gtcttcctgt tccccccaaa acccaaggac actctcatga tctcccggac ccctgaggtc    840
acgtgcgtgg tggtggacgt gagccaggaa gaccccgagg tccagttcaa ctggtacgtg    900
```

```
gatggcgtgg aggtgcataa tgccaagaca aagccgcggg aggagcagtt caacagcacg    960
taccgtgtgg tcagcgtcct caccgtcctg caccaggact ggctgaacgg caaggagtac   1020
aagtgcaagg tctccaacaa aggcctcccg tcctccatcg agaaaaccat ctccaaagcc   1080
aaagggcagc cccgagagcc acaggtgtac accctgcccc catcccagga ggagatgacc   1140
aagaaccagg tcagcctgac ctgcctggtc aaaggcttct accccagcga catcgccgtg   1200
gagtgggaga gcaatgggca gccggagaac aactacaaga ccacgcctcc cgtgctggac   1260
tccgacggct ccttcttcct ctacagcagg ctaaccgtgg acaagagcag gtggcaggag   1320
gggaatgtct tctcatgctc cgtgatgcat gaggctctgc acaaccacta cacacagaag   1380
agcctctccc tgtctctggg taaagctagc gatacaacag aacctgcaac acctacaaca   1440
cctgtaacaa cagatcagat ttgcattggt taccatgcaa acaactcgac agagcaggtt   1500
gacacaataa tggaaaagaa cgttactgtt acacatgccc aagacatact ggaaaagaaa   1560
cacaacggga agctctgcga tctagatgga gtgaagcctc taattttgag agattgtagc   1620
gtagctggat ggctcctcgg aaacccaatg tgtgacgaat tcatcaatgt gccggaatgg   1680
tcttacatag tggagaaggc caatccagtc aatgacctct gttacccagg ggatttcaat   1740
gactatgaag aattgaaaca cctattgagc agaataaacc attttgagaa aattcagatc   1800
atccccaaaa gttcttggtc cagtcatgaa gcctcattag gggtgagctc agcatgtcca   1860
taccagggaa agtcctcctt tttcagaaat gtggtatggc ttatcaaaaa gaacagtaca   1920
tacccaacaa taagaggag ctacaataat accaaccaag aagatctttt ggtactgtgg   1980
gggattcacc atcctaatga tgcggcagag cagacaaagc tctatcaaaa cccaaccacc   2040
tatatttccg ttgggacatc aacactaaac cagagattgg taccaagaat agctactaga   2100
tccaaagtaa acgggcaaag tggaaggatg gagttcttct ggacaatttt aaagccgaat   2160
gatgcaatca acttcgagag taatggaaat ttcattgctc cagaatatgc atacaaaatt   2220
gtcaagaaag gggactcaac aattatgaaa agtgaattgg aatatggtaa ctgcaacacc   2280
aagtgtcaaa ctccaatggg ggcgataaac tctagcatgc cattccacaa tatacaccct   2340
ctcaccattg gggaatgccc caaatatgtg aaatcaaaca gattagtcct tgcgcaccat   2400
caccatcacc attga                                                    2415
```

<210> SEQ ID NO 66
<211> LENGTH: 780
<212> TYPE: PRT
<213> ORGANISM: Artificial Sequence
<220> FEATURE:
<223> OTHER INFORMATION: Synthetic peptide.

<400> SEQUENCE: 66

Gln Val Gln Leu Arg Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Val Ile Ser Trp Val Lys Gln Arg Thr Gly Gln Gly Leu Glu Trp Ile
        35                  40                  45

Gly Asp Ile Tyr Pro Gly Ser Gly Tyr Ser Phe Tyr Asn Glu Asn Phe
    50                  55                  60

Lys Gly Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Phe Cys

```
                85                  90                  95
Ala Thr Tyr Tyr Asn Tyr Pro Phe Ala Tyr Trp Gly Gln Gly Thr Leu
                100                 105                 110

Val Thr Val Ser Ala Ala Lys Thr Thr Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Lys Thr Tyr Thr Cys Asn Val Asp His Lys Pro Ser Asn
                195                 200                 205

Thr Lys Val Asp Lys Arg Val Glu Ser Lys Tyr Gly Pro Pro Cys Pro
    210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
                260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
                340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly Lys Ala Ser Asp Thr
            435                 440                 445

Thr Glu Pro Ala Thr Pro Thr Thr Pro Val Thr Thr Asp Gln Ile Cys
    450                 455                 460

Ile Gly Tyr His Ala Asn Asn Ser Thr Glu Gln Val Asp Thr Ile Met
465                 470                 475                 480

Glu Lys Asn Val Thr Val Thr His Ala Gln Asp Ile Leu Glu Lys Lys
                485                 490                 495

His Asn Gly Lys Leu Cys Asp Leu Asp Gly Val Lys Pro Leu Ile Leu
                500                 505                 510
```

Arg Asp Cys Ser Val Ala Gly Trp Leu Leu Gly Asn Pro Met Cys Asp
    515                 520                 525

Glu Phe Ile Asn Val Pro Glu Trp Ser Tyr Ile Val Glu Lys Ala Asn
    530                 535                 540

Pro Val Asn Asp Leu Cys Tyr Pro Gly Asp Phe Asn Asp Tyr Glu Glu
545                 550                 555                 560

Leu Lys His Leu Leu Ser Arg Ile Asn His Phe Glu Lys Ile Gln Ile
                565                 570                 575

Ile Pro Lys Ser Ser Trp Ser Ser His Glu Ala Ser Leu Gly Val Ser
            580                 585                 590

Ser Ala Cys Pro Tyr Gln Gly Lys Ser Ser Phe Arg Asn Val Val
        595                 600                 605

Trp Leu Ile Lys Lys Asn Ser Thr Tyr Pro Thr Ile Lys Arg Ser Tyr
    610                 615                 620

Asn Asn Thr Asn Gln Glu Asp Leu Leu Val Leu Trp Gly Ile His His
625                 630                 635                 640

Pro Asn Asp Ala Ala Glu Gln Thr Lys Leu Tyr Gln Asn Pro Thr Thr
                645                 650                 655

Tyr Ile Ser Val Gly Thr Ser Thr Leu Asn Gln Arg Leu Val Pro Arg
            660                 665                 670

Ile Ala Thr Arg Ser Lys Val Asn Gly Gln Ser Gly Arg Met Glu Phe
        675                 680                 685

Phe Trp Thr Ile Leu Lys Pro Asn Asp Ala Ile Asn Phe Glu Ser Asn
    690                 695                 700

Gly Asn Phe Ile Ala Pro Glu Tyr Ala Tyr Lys Ile Val Lys Lys Gly
705                 710                 715                 720

Asp Ser Thr Ile Met Lys Ser Glu Leu Glu Tyr Gly Asn Cys Asn Thr
                725                 730                 735

Lys Cys Gln Thr Pro Met Gly Ala Ile Asn Ser Ser Met Pro Phe His
            740                 745                 750

Asn Ile His Pro Leu Thr Ile Gly Glu Cys Pro Lys Tyr Val Lys Ser
        755                 760                 765

Asn Arg Leu Val Leu Ala His His His His His His
    770                 775                 780

<210> SEQ ID NO 67
<211> LENGTH: 1638
<212> TYPE: DNA
<213> ORGANISM: Artificial Sequence
<220> FEATURE:
<223> OTHER INFORMATION: Syntehtic oligonucleotide.

<400> SEQUENCE: 67
atggacccca aaggctccct ttcctggaga atacttctgt ttctctccct ggcttttgag      60
ttgtcgtacg acaggttca gctgcggcag tctggacctg agctggtgaa gcctggggct     120
tcagtgaaga tgtcctgcaa ggcttctgga tacacattta ctgactatgt tataagttgg     180
gtgaagcaga gaactggaca gggccttgag tggattggag atatttatcc tggaagtggt     240
tattctttct acaatgagaa cttcaagggc aaggccacac tgactgcaga caaatcctcc     300
accacagcct acatgcagct cagcagcctg acatctgagg actctgcggt ctatttctgt     360
gcaacctact ataactaccc ttttgcttac tggggccaag ggactctggt cactgtctct     420
gcagccaaaa caacgggccc atccgtcttc cccctggcgc cctgctccag gagcacctcc     480
gagagcacag ccgccctggg ctgcctggtc aaggactact ccccgaacc ggtgacggtg     540

```
tcgtggaact caggcgccct gaccagcggc gtgcacacct tcccggctgt cctacagtcc      600
tcaggactct actccctcag cagcgtggtg accgtgcccc cagcagcttg ggcacgaag       660 acctacacct gcaacgtaga tcacaagccc agcaacacca aggtggacaa gagagttgag      720
tccaaatatg gtcccccatg cccacccctg ccagcacctg agttcgaagg gggaccatca      780
gtcttcctgt tccccccaaa acccaaggac actctcatga tctcccggac ccctgaggtc      840
acgtgcgtgt ggtggacgt gagccaggaa gaccccgagg tccagttcaa ctggtacgtg       900
gatggcgtgg aggtgcataa tgccaagaca aagccgcggg aggagcagtt caacagcacg      960
taccgtgtgg tcagcgtcct caccgtcctg caccaggact ggctgaacgg caaggagtac     1020
aagtgcaagg tctccaacaa aggcctcccg tcctccatcg agaaaaccat ctccaaagcc     1080
aaagggcagc cccgagagcc acaggtgtac accctgcccc catcccagga ggagatgacc     1140
aagaaccagg tcagcctgac ctgcctggtc aaaggcttct accccagcga catcgccgtg     1200
gagtgggaga gcaatgggca gccggagaac aactacaaga ccacgcctcc cgtgctggac     1260
tccgacggct ccttcttcct ctacagcagg ctaaccgtgg acaagagcag gtggcaggag     1320
gggaatgtct tctcatgctc cgtgatgcat gaggctctgc acaaccacta cacacagaag     1380
agcctctccc tgtctctggg taaagctagc aattctcctc aaaatgaagt actgtacgga     1440
gatgtgaatg atgacggaaa agtaaactcc actgacttga ctttgttaaa agatatgtt      1500 cttaaagccg tctcaactct cccttcttcc aaagctgaaa agaacgcaga tgtaaatcgt     1560
gacggaagag ttaattccag tgatgtcaca atactttcaa gatatttgat aagggtaatc     1620
gagaaattac caatataa                                                    1638
```

<210> SEQ ID NO 68
<211> LENGTH: 521
<212> TYPE: PRT
<213> ORGANISM: Artificial Sequence
<220> FEATURE:
<223> OTHER INFORMATION: Synthetic peptide.

<400> SEQUENCE: 68

```
Gln Val Gln Leu Arg Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Val Ile Ser Trp Val Lys Gln Arg Thr Gly Gln Gly Leu Glu Trp Ile
        35                  40                  45

Gly Asp Ile Tyr Pro Gly Ser Gly Tyr Ser Phe Tyr Asn Glu Asn Phe
    50                  55                  60

Lys Gly Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Phe Cys
                85                  90                  95

Ala Thr Tyr Tyr Asn Tyr Pro Phe Ala Tyr Trp Gly Gln Gly Thr Leu
            100                 105                 110

Val Thr Val Ser Ala Ala Lys Thr Thr Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160
```

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
        180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
                260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
        290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
                340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys Ala Ser Asn Ser
        435                 440                 445

Pro Gln Asn Glu Val Leu Tyr Gly Asp Val Asn Asp Asp Gly Lys Val
450                 455                 460

Asn Ser Thr Asp Leu Thr Leu Leu Lys Arg Tyr Val Leu Lys Ala Val
465                 470                 475                 480

Ser Thr Leu Pro Ser Ser Lys Ala Glu Lys Asn Ala Asp Val Asn Arg
                485                 490                 495

Asp Gly Arg Val Asn Ser Ser Asp Val Thr Ile Leu Ser Arg Tyr Leu
            500                 505                 510

Ile Arg Val Ile Glu Lys Leu Pro Ile
        515                 520

<210> SEQ ID NO 69
<211> LENGTH: 2415
<212> TYPE: DNA
<213> ORGANISM: Artificial Sequence
<220> FEATURE:
<223> OTHER INFORMATION: Syntehtic oligonucleotide.

<400> SEQUENCE: 69

```
atggacccca aaggctccct ttcctggaga atacttctgt ttctctccct ggcttttgag    60
ttgtcgtacg gacaggttca gctgcggcag tctggacctg agctggtgaa gcctggggct   120
tcagtgaaga tgtcctgcaa ggcttctgga tacacattta ctgactatgt tataagttgg   180
gtgaagcaga gaactggaca gggccttgag tggattggag atatttatcc tggaagtggt   240
tattctttct acaatgagaa cttcaagggc aaggccacac tgactgcaga caaatcctcc   300
accacagcct acatgcagct cagcagcctg acatctgagg actctgcggt ctatttctgt   360
gcaacctact ataactaccc ttttgcttac tggggccaag ggactctggt cactgtctct   420
gcagccaaaa caacgggccc atccgtcttc cccctggcgc cctgctccag gagcacctcc   480
gagagcacag ccgccctggg ctgcctggtc aaggactact tccccgaacc ggtgacggtg   540
tcgtggaact caggcgccct gaccagcggc gtgcacacct tcccggctgt cctacagtcc   600
tcaggactct actccctcag cagcgtggtg accgtgccct ccagcagctt gggcacgaag   660
acctacacct gcaacgtaga tcacaagccc agcaacacca aggtggacaa gagagttgag   720
tccaaatatg gtcccccatg cccacccctg ccagcacctg agttcgaagg ggaccatca   780
gtcttcctgt tccccccaaa acccaaggac actctcatga tctcccggac ccctgaggtc   840
acgtgcgtgg tggtggacgt gagccaggaa gaccccgagg tccagttcaa ctggtacgtg   900
gatggcgtgg aggtgcataa tgccaagaca aagccgcggg aggagcagtt caacagcacg   960
taccgtgtgt cagcgtcct caccgtcctg caccaggact ggctgaacgg caaggagtac  1020
aagtgcaagg tctccaacaa aggcctcccg tcctccatcg agaaaaccat ctccaaagcc  1080
aaagggcagc cccgagagcc acaggtgtac accctgcccc catcccagga ggagatgacc  1140
aagaaccagg tcagcctgac ctgcctggtc aaaggcttct accccagcga catcgccgtg  1200
gagtgggaga gcaatgggca gccggagaac aactacaaga ccacgcctcc cgtgctggac  1260
tccgacggct ccttcttcct ctacagcagg ctaaccgtgg acaagagcag gtggcaggag  1320
gggaatgtct tctcatgctc cgtgatgcat gaggctctgc acaaccacta cacacagaag  1380
agcctctccc tgtctctggg taaagctagc gatacaacag aacctgcaac acctacaaca  1440
cctgtaacaa cagacacaat atgtataggc taccatgcga acaattcaac cgacactgtt  1500
gacacagtac tcgagaagaa tgtgacagtg acacactctg ttaacctgct cgaagacagc  1560
cacaacggaa aactatgtag attaaaagga atagccccac tacaattggg gaaatgtaac  1620
atcgccggat ggctcttggg aaacccagaa tgcgaccac tgcttccagt gagatcatgg  1680
tcctacattg tagaaacacc aaactctgag aatggaatat gttatccagg agatttcatc  1740
gactatgagg agctgaggga gcaattgagc tcagtgtcat cattcgaaag attcgaaata  1800
tttcccaaag aaagctcatg gcccaaccac aacacaaacg gagtaacggc agcatgctcc  1860
catgagggga aaagcagttt ttacagaaat ttgctatggc tgacggagaa ggagggctca  1920
tacccaaagc tgaaaaattc ttatgtgaac aaaaaaggga agaagtcct tgtactgtgg  1980
ggtattcatc acccgcctaa cagtaaggaa caacagaatc tctatcagaa tgaaaatgct  2040
tatgtctctg tagtgacttc aaattataac aggagattta ccccggaaat agcagaaaga  2100
cccaaagtaa gagatcaagc tgggaggatg aactattact ggaccttgct aaaacccgga  2160
gacacaataa tatttgaggc aaatggaaat ctaatagcac caatgtatgc tttcgcactg  2220
agtagaggct ttgggtccgg catcatcacc tcaaacgcat caatgcatga gtgtaacacg  2280
aagtgtcaaa caccctggg agctataaac agcagtctcc cttaccagaa tatacaccca  2340
gtcacaatag gagagtgccc aaaatacgtc aggagtgcca aattgaggat ggttcaccat  2400
```
caccatcacc attga 2415

<210> SEQ ID NO 70
<211> LENGTH: 780
<212> TYPE: PRT
<213> ORGANISM: Artificial Sequence
<220> FEATURE:
<223> OTHER INFORMATION: Synthetic peptide.

<400> SEQUENCE: 70

```
Gln Val Gln Leu Arg Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Val Ile Ser Trp Val Lys Gln Arg Thr Gly Gln Gly Leu Glu Trp Ile
        35                  40                  45

Gly Asp Ile Tyr Pro Gly Ser Gly Tyr Ser Phe Tyr Asn Glu Asn Phe
    50                  55                  60

Lys Gly Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Phe Cys
                85                  90                  95

Ala Thr Tyr Tyr Asn Tyr Pro Phe Ala Tyr Trp Gly Gln Gly Thr Leu
            100                 105                 110

Val Thr Val Ser Ala Ala Lys Thr Thr Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350
```

```
Glu Glu Met Thr Lys Asn Gln Val Ser Leu Thr Cys Leu Val Lys Gly
            355                 360                 365
Phe Tyr Pro Ser Asp Ile Ala Val Glu Trp Glu Ser Asn Gly Gln Pro
    370                 375                 380
Glu Asn Asn Tyr Lys Thr Thr Pro Pro Val Leu Asp Ser Asp Gly Ser
385                 390                 395                 400
Phe Phe Leu Tyr Ser Arg Leu Thr Val Asp Lys Ser Arg Trp Gln Glu
                405                 410                 415
Gly Asn Val Phe Ser Cys Ser Val Met His Glu Ala Leu His Asn His
            420                 425                 430
Tyr Thr Gln Lys Ser Leu Ser Leu Ser Leu Gly Lys Ala Ser Asp Thr
        435                 440                 445
Thr Glu Pro Ala Thr Pro Thr Thr Pro Val Thr Thr Asp Thr Ile Cys
    450                 455                 460
Ile Gly Tyr His Ala Asn Asn Ser Thr Asp Thr Val Asp Thr Val Leu
465                 470                 475                 480
Glu Lys Asn Val Thr Val Thr His Ser Val Asn Leu Leu Glu Asp Ser
                485                 490                 495
His Asn Gly Lys Leu Cys Arg Leu Lys Gly Ile Ala Pro Leu Gln Leu
            500                 505                 510
Gly Lys Cys Asn Ile Ala Gly Trp Leu Leu Gly Asn Pro Glu Cys Asp
        515                 520                 525
Pro Leu Leu Pro Val Arg Ser Trp Ser Tyr Ile Val Glu Thr Pro Asn
    530                 535                 540
Ser Glu Asn Gly Ile Cys Tyr Pro Gly Asp Phe Ile Asp Tyr Glu Glu
545                 550                 555                 560
Leu Arg Glu Gln Leu Ser Ser Val Ser Ser Phe Glu Arg Phe Glu Ile
                565                 570                 575
Phe Pro Lys Glu Ser Ser Trp Pro Asn His Asn Thr Asn Gly Val Thr
            580                 585                 590
Ala Ala Cys Ser His Glu Gly Lys Ser Ser Phe Tyr Arg Asn Leu Leu
        595                 600                 605
Trp Leu Thr Glu Lys Glu Gly Ser Tyr Pro Lys Leu Lys Asn Ser Tyr
    610                 615                 620
Val Asn Lys Lys Gly Lys Glu Val Leu Val Leu Trp Gly Ile His His
625                 630                 635                 640
Pro Pro Asn Ser Lys Glu Gln Gln Asn Leu Tyr Gln Asn Glu Asn Ala
                645                 650                 655
Tyr Val Ser Val Val Thr Ser Asn Tyr Asn Arg Arg Phe Thr Pro Glu
            660                 665                 670
Ile Ala Glu Arg Pro Lys Val Arg Asp Gln Ala Gly Arg Met Asn Tyr
        675                 680                 685
Tyr Trp Thr Leu Leu Lys Pro Gly Asp Thr Ile Ile Phe Glu Ala Asn
    690                 695                 700
Gly Asn Leu Ile Ala Pro Met Tyr Ala Phe Ala Leu Ser Arg Gly Phe
705                 710                 715                 720
Gly Ser Gly Ile Ile Thr Ser Asn Ala Ser Met His Glu Cys Asn Thr
                725                 730                 735
Lys Cys Gln Thr Pro Leu Gly Ala Ile Asn Ser Ser Leu Pro Tyr Gln
            740                 745                 750
Asn Ile His Pro Val Thr Ile Gly Glu Cys Pro Lys Tyr Val Arg Ser
        755                 760                 765
Ala Lys Leu Arg Met Val His His His His His His
```

<210> SEQ ID NO 71
<211> LENGTH: 2154
<212> TYPE: DNA
<213> ORGANISM: Artificial Sequence
<220> FEATURE:
<223> OTHER INFORMATION: Syntehtic oligonucleotide.

<400> SEQUENCE: 71

```
atggacccca aaggctccct ttcctggaga atacttctgt ttctctccct ggcttttgag     60
ttgtcgtacg acaggttca gctgcggcag tctggacctg agctggtgaa gcctggggct    120
tcagtgaaga tgtcctgcaa ggcttctgga tacacattta ctgactatgt tataagttgg    180
gtgaagcaga gaactggaca gggccttgag tggattggag atatttatcc tggaagtggt    240
tattctttct acaatgagaa cttcaagggc aaggccacac tgactgcaga caaatcctcc    300
accacagcct acatgcagct cagcagcctg acatctgagg actctgcggt ctatttctgt    360
gcaacctact ataactaccc ttttgcttac tggggccaag gactctggt cactgtctct    420
gcagccaaaa caacgggccc atccgtcttc cccctggcgc cctgctccag gagcacctcc    480
gagagcacag ccgccctggg ctgcctggtc aaggactact ccccgaacc ggtgacggtg    540
tcgtggaact caggcgccct gaccagcggc gtgcacacct tcccggctgt cctacagtcc    600
tcaggactct actccctcag cagcgtggtg accgtgccct ccagcagctt gggcacgaag    660
acctacacct gcaacgtaga tcacaagccc agcaacacca aggtggacaa gagagttgag    720
tccaaatatg gtcccccatg cccacccctgc ccagcacctg agttcgaagg ggaccatca    780
gtcttcctgt tccccccaaa acccaaggac actctcatga tctcccggac ccctgaggtc    840
acgtgcgtgt ggtggacgt gagccaggaa gaccccgagg tccagttcaa ctggtacgtg    900
gatggcgtgg aggtgcataa tgccaagaca aagccgcggg aggagcagtt caacagcacg    960
taccgtgtgt tcagcgtcct caccgtcctg caccaggact ggctgaacgg caaggagtac   1020
aagtgcaagg tctccaacaa aggcctcccg tcctccatcg agaaaaccat ctccaaagcc   1080
aaagggcagc cccgagagcc acaggtgtac accctgcccc catcccagga ggagatgacc   1140
aagaaccagg tcagcctgac ctgcctggtc aaaggcttct accccagcga catcgccgtg   1200
gagtgggaga gcaatgggca gccggagaac aactacaaga ccacgcctcc cgtgctggac   1260
tccgacggct ccttcttcct ctacagcagg ctaaccgtgg acaagagcag gtggcaggag   1320
gggaatgtct tctcatgctc cgtgatgcat gaggctctgc acaaccacta cacacagaag   1380
agcctctccc tgtctctggg taaagctagc gacatggcca agaaggagac agtctggagg   1440
ctcgaggagt tcggtaggcc tatagtgcag aacatccagg ggcaaatggt acatcaggcc   1500
atatcaccta gaacttaaa tgcatgggta aaagtagtag aagagaaggc tttcagccca   1560
gaagtaatac ccatgttttc agcattatca gaaggagcca ccccacaaga tttaaacacc   1620
atgctaaaca cagtgggggg acatcaagca gccatgcaaa tgttaaaaga gaccatcaat   1680
gaggaagctg cagaatggga tagagtacat ccagtgcatg cagggcctat tgcaccaggc   1740
cagatgagag aaccaagggg aagtgacata gcaggaacta ctagtaccct tcaggaacaa   1800
ataggatgga tgacaaataa tccacctatc ccagtaggag aaatttataa aagatggata   1860
atcctgggat taaataaaat agtaagaatg tatagcccta ccagcattct ggacataaga   1920
caaggaccaa agaaccctttt tagagactat gtagaccggt tctataaaac tctaagagcc   1980
gagcaagctt cacaggaggt aaaaaattgg atgacagaaa ccttgttggt ccaaaatgcg   2040
```

```
aacccagatt gtaagactat tttaaaagca ttgggaccag cggctacact agaagaaatg    2100
atgacagcat gtcagggagt aggaggaccc ggccataagg caagagtttt gtga          2154
```

<210> SEQ ID NO 72
<211> LENGTH: 693
<212> TYPE: PRT
<213> ORGANISM: Artificial Sequence
<220> FEATURE:
<223> OTHER INFORMATION: Synthetic peptide.

<400> SEQUENCE: 72

```
Gln Val Gln Leu Arg Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Val Ile Ser Trp Val Lys Gln Arg Thr Gly Gln Gly Leu Glu Trp Ile
        35                  40                  45

Gly Asp Ile Tyr Pro Gly Ser Gly Tyr Ser Phe Tyr Asn Glu Asn Phe
    50                  55                  60

Lys Gly Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Phe Cys
                85                  90                  95

Ala Thr Tyr Tyr Asn Tyr Pro Phe Ala Tyr Trp Gly Gln Gly Thr Leu
            100                 105                 110

Val Thr Val Ser Ala Ala Lys Thr Thr Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
```

```
            340             345             350
Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys Ala Ser Asp Met
        435                 440                 445

Ala Lys Lys Glu Thr Val Trp Arg Leu Glu Glu Phe Gly Arg Pro Ile
    450                 455                 460

Val Gln Asn Ile Gln Gly Gln Met Val His Gln Ala Ile Ser Pro Arg
465                 470                 475                 480

Thr Leu Asn Ala Trp Val Lys Val Val Glu Glu Lys Ala Phe Ser Pro
                485                 490                 495

Glu Val Ile Pro Met Phe Ser Ala Leu Ser Glu Gly Ala Thr Pro Gln
            500                 505                 510

Asp Leu Asn Thr Met Leu Asn Thr Val Gly Gly His Gln Ala Ala Met
        515                 520                 525

Gln Met Leu Lys Glu Thr Ile Asn Glu Glu Ala Ala Glu Trp Asp Arg
    530                 535                 540

Val His Pro Val His Ala Gly Pro Ile Ala Pro Gly Gln Met Arg Glu
545                 550                 555                 560

Pro Arg Gly Ser Asp Ile Ala Gly Thr Thr Ser Thr Leu Gln Glu Gln
                565                 570                 575

Ile Gly Trp Met Thr Asn Asn Pro Pro Ile Pro Val Gly Glu Ile Tyr
            580                 585                 590

Lys Arg Trp Ile Ile Leu Gly Leu Asn Lys Ile Val Arg Met Tyr Ser
        595                 600                 605

Pro Thr Ser Ile Leu Asp Ile Arg Gln Gly Pro Lys Glu Pro Phe Arg
    610                 615                 620

Asp Tyr Val Asp Arg Phe Tyr Lys Thr Leu Arg Ala Glu Gln Ala Ser
625                 630                 635                 640

Gln Glu Val Lys Asn Trp Met Thr Glu Thr Leu Leu Val Gln Asn Ala
                645                 650                 655

Asn Pro Asp Cys Lys Thr Ile Leu Lys Ala Leu Gly Pro Ala Ala Thr
            660                 665                 670

Leu Glu Glu Met Met Thr Ala Cys Gln Gly Val Gly Gly Pro Gly His
        675                 680                 685

Lys Ala Arg Val Leu
    690

<210> SEQ ID NO 73
<211> LENGTH: 2187
<212> TYPE: DNA
<213> ORGANISM: Artificial Sequence
<220> FEATURE:
<223> OTHER INFORMATION: Syntehtic oligonucleotide.

<400> SEQUENCE: 73
atggaatgga ggatctttct cttcatcctg tcaggaactg caggtgtcca ctcccaggtt      60
```

```
cagctgcggc agtctggacc tgagctggtg aagcctgggg cttcagtgaa gatgtcctgc      120
aaggcttctg gatacacatt tactgactat gttataagtt gggtgaagca gagaactgga      180
cagggccttg agtggattgg agatatttat cctggaagtg gttattcttt ctacaatgag      240
aacttcaagg gcaaggccac actgactgca gacaaatcct ccaccacagc ctacatgcag      300
ctcagcagcc tgacatctga ggactctgcg gtctatttct gtgcaaccta ctataactac      360 cctttttgctt actggggcca agggactctg gtcactgtct ctgcagccaa aacaacgggc      420
ccatccgtct tcccctggc gccctgctcc aggagcacct ccgagagcac agccgccctg       480
ggctgcctgg tcaaggacta cttccccgaa ccggtgacgg tgtcgtggaa ctcaggcgcc      540
ctgaccagcg gcgtgcacac cttcccggct gtcctacagt cctcaggact ctactccctc      600
agcagcgtgt gaccgtgcc ctccagcagc ttgggcacga agacctacac ctgcaacgta       660
gatcacaagc ccagcaacac caaggtggac aagagagttg agtccaaata tggtccccca     720
tgcccaccct gcccagcacc tgagttcgaa ggggggaccat cagtcttcct gttccccccca    780 aaacccaagg acactctcat gatctcccgg acccctgagg tcacgtgcgt ggtggtggac      840
gtgagccagg aagaccccga ggtccagttc aactggtacg tggatggcgt ggaggtgcat      900
aatgccaaga caaagccgcg ggaggagcag ttcaacagca cgtaccgtgt ggtcagcgtc      960
ctcaccgtcc tgcaccagga ctggctgaac ggcaaggagt acaagtgcaa ggtctccaac    1020
aaaggcctcc cgtcctccat cgagaaaacc atctccaaag ccaaagggca gccccgagag    1080
ccacaggtgt acaccctgcc cccatcccag gaggagatga ccaagaacca ggtcagcctg    1140
acctgcctgg tcaaaggctt ctaccccagc gacatcgccg tggagtggga gagcaatggg    1200
cagccggaga caactacaa gaccacgcct cccgtgctgg actccgacgg ctccttcttc     1260
ctctacagca ggctaaccgt ggacaagagc aggtggcagg aggggaatgt cttctcatgc    1320
tccgtgatgc atgaggctct gcacaaccac tacacacaga gagcctctc cctgtctctg     1380 ggtaaagcta gcgatacaac agaacctgca acacctacaa cacctgtaac aacaccgaca    1440
acaacacttc tagcgcccct catcctgtct cggattgtgg aggctggga gtgcgagaag     1500 cattcccaac cctggcaggt gcttgtggcc tctcgtggca gggcagtctg cggcggtgtt    1560
ctggtgcacc cccagtgggt cctcacagct gcccactgca tcaggaacaa aagcgtgatc    1620
ttgctgggtc ggcacagcct gtttcatcct gaagacacag gccaggtatt tcaggtcagc    1680
cacagcttcc cacacccgct ctacgatatg agcctcctga gaatcgatt cctcaggcca     1740 ggtgatgact ccagccacga cctcatgctg ctccgcctgt cagagcctgc cgagctcacg    1800
gatgctgtga aggtcatgga cctgcccacc caggagccag cactggggac cacctgctac    1860
gcctcaggct gggcagcat tgaaccagag gagttcttga ccccaaagaa acttcagtgt    1920
gtggacctcc atgttatttc caatgacgtg tgtgcgcaag ttcaccctca gaaggtgacc    1980
aagttcatgt gtgtgctgg acgctggaca ggggcaaaa gcacctgctc gggtgattct     2040
gggggcccac ttgtctgtaa tggtgtgctt caaggtatca cgtcatgggg cagtgaacca    2100
tgtgccctgc ccgaaaggcc ttccctgtac accaaggtgg tgcattaccg gaagtggatc    2160
aaggacacca tcgtggccaa ccccctga                                       2187
```

<210> SEQ ID NO 74
<211> LENGTH: 710
<212> TYPE: PRT
<213> ORGANISM: Artificial Sequence
<220> FEATURE:

-continued

```
<223> OTHER INFORMATION: Synthetic peptide.

<400> SEQUENCE: 74

Gln Val Gln Leu Arg Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Val Ile Ser Trp Val Lys Gln Arg Thr Gly Gln Gly Leu Glu Trp Ile
        35                  40                  45

Gly Asp Ile Tyr Pro Gly Ser Gly Tyr Ser Phe Tyr Asn Glu Asn Phe
    50                  55                  60

Lys Gly Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Phe Cys
                85                  90                  95

Ala Thr Tyr Tyr Asn Tyr Pro Phe Ala Tyr Trp Gly Gln Gly Thr Leu
            100                 105                 110

Val Thr Val Ser Ala Ala Lys Thr Thr Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400
```

```
Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys Ala Ser Asp Thr
        435                 440                 445

Thr Glu Pro Ala Thr Pro Thr Thr Pro Val Thr Thr Pro Thr Thr Thr
450                 455                 460

Leu Leu Ala Pro Leu Ile Leu Ser Arg Ile Val Gly Gly Trp Glu Cys
465                 470                 475                 480

Glu Lys His Ser Gln Pro Trp Gln Val Leu Val Ala Ser Arg Gly Arg
                485                 490                 495

Ala Val Cys Gly Gly Val Leu Val His Pro Gln Trp Val Leu Thr Ala
            500                 505                 510

Ala His Cys Ile Arg Asn Lys Ser Val Ile Leu Leu Gly Arg His Ser
        515                 520                 525

Leu Phe His Pro Glu Asp Thr Gly Gln Val Phe Gln Val Ser His Ser
530                 535                 540

Phe Pro His Pro Leu Tyr Asp Met Ser Leu Leu Lys Asn Arg Phe Leu
545                 550                 555                 560

Arg Pro Gly Asp Asp Ser Ser His Asp Leu Met Leu Leu Arg Leu Ser
                565                 570                 575

Glu Pro Ala Glu Leu Thr Asp Ala Val Lys Val Met Asp Leu Pro Thr
            580                 585                 590

Gln Glu Pro Ala Leu Gly Thr Thr Cys Tyr Ala Ser Gly Trp Gly Ser
        595                 600                 605

Ile Glu Pro Glu Glu Phe Leu Thr Pro Lys Lys Leu Gln Cys Val Asp
610                 615                 620

Leu His Val Ile Ser Asn Asp Val Cys Ala Gln Val His Pro Gln Lys
625                 630                 635                 640

Val Thr Lys Phe Met Leu Cys Ala Gly Arg Trp Thr Gly Gly Lys Ser
                645                 650                 655

Thr Cys Ser Gly Asp Ser Gly Gly Pro Leu Val Cys Asn Gly Val Leu
            660                 665                 670

Gln Gly Ile Thr Ser Trp Gly Ser Glu Pro Cys Ala Leu Pro Glu Arg
        675                 680                 685

Pro Ser Leu Tyr Thr Lys Val Val His Tyr Arg Lys Trp Ile Lys Asp
690                 695                 700

Thr Ile Val Ala Asn Pro
705                 710
```

<210> SEQ ID NO 75
<211> LENGTH: 2268
<212> TYPE: DNA
<213> ORGANISM: Artificial Sequence
<220> FEATURE:
<223> OTHER INFORMATION: Syntehtic oligonucleotide.

<400> SEQUENCE: 75

```
atggaatgga ggatctttct cttcatcctg tcaggaactg caggtgtcca ctcccaggtt      60
cagctgcggc agtctggacc tgagctggtg aagcctgggg cttcagtgaa gatgtcctgc     120
aaggcttctg gatacacatt tactgactat gttataagtt gggtgaagca gagaactgga     180
cagggccttg agtggattgg agatatttat cctggaagtg gtattctttt ctacaatgag     240
aacttcaagg gcaaggccac actgactgca gacaaatcct ccaccacagc ctacatgcag     300
```

```
ctcagcagcc tgacatctga ggactctgcg gtctatttct gtgcaaccta ctataactac    360 cctttttgctt actggggcca agggactctg gtcactgtct ctgcagccaa acaacgggc    420 ccatccgtct tcccccctggc gccctgctcc aggagcacct ccgagagcac agccgccctg    480
ggctgcctgg tcaaggacta cttccccgaa ccggtgacgg tgtcgtggaa ctcaggcgcc    540
ctgaccagcg gcgtgcacac cttcccggct gtcctacagt cctcaggact ctactccctc    600
agcagcgtgg tgaccgtgcc ctccagcagc ttgggcacga gacctacac ctgcaacgta    660 gatcacaagc ccagcaacac caaggtggac aagagagttg agtccaaata tggtccccca    720
tgcccaccct gcccagcacc tgagttcgaa ggggggaccat cagtcttcct gttccccccca    780 aaacccaagg acactctcat gatctcccgg acccctgagg tcacgtgcgt ggtggtggac    840
gtgagccagg aagaccccga ggtccagttc aactggtacg tggatggcgt ggaggtgcat    900
aatgccaaga caaagccgcg ggaggagcag ttcaacagca cgtaccgtgt ggtcagcgtc    960
ctcaccgtcc tgcaccagga ctggctgaac ggcaaggagt acaagtgcaa ggtctccaac    1020
aaaggcctcc cgtcctccat cgagaaaacc atctccaaag ccaaagggca gccccgagag    1080
ccacaggtgt acaccctgcc cccatcccag gaggagatga ccaagaacca ggtcagcctg    1140
acctgcctgg tcaaaggctt ctaccccagc gacatcgccg tggagtggga gagcaatggg    1200
cagccggaga caactacaa gaccacgcct cccgtgctgg actccgacgg ctccttcttc    1260
ctctacagca ggctaaccgt ggacaagagc aggtggcagg aggggaatgt cttctcatgc    1320
tccgtgatgc atgaggctct gcacaaccac tacacacaga gagcctctc cctgtctctg    1380 ggtaaagcta gtcagacccc caccaacacc atcagcgtga cccccaccaa caacagcacc    1440
cccaccaaca cagcaaccc caagcccaac cccgctagtg agaagatccg gctgcggccc    1500
ggcggcaaga agaagtacaa gctgaagcac atcgtggcta gtagcagcgt gagccccacc    1560
accagcgtgc accccacccc caccagcgtg ccccccaccc ccaccaagag cagccccgct    1620
agtaaccccc ccatcccgt gggcgagatc tacaagcggt ggatcatcct gggcctgaac    1680
aagatcgtgc ggatgtacag ccccaccagc atcctggacg ctagtcccac cagcaccccc    1740
gccgacagca gcaccatcac ccccaccgcc accccaccg ccaccccac catcaagggc    1800 gctagtcaca cccagggcta cttccccgac tggcagaact acaccccgg ccccggcgtg    1860 cggtaccccc tgaccttcgg ctggctgtac aagctggcta gtaccgtgac ccccaccgcc    1920
accgccaccc ccagcgccat cgtgaccacc atcacccccca ccgccaccac caagcccgct    1980
agtgtgggct tccccgtgac ccccaggtg ccctgcggc ccatgaccta caaggccgcc    2040
gtggacctga gccacttcct gaaggagaag ggcggcctgg ctagtaccaa cggcagcatc    2100
accgtggccg ccaccgcccc caccgtgacc ccaccgtga cgccacccc cagcgccgcc    2160 gctagtgcca tcttccagag cagcatgacc aagatcctgg agcccttccg gaagcagaac    2220
cccgacatcg tgatctacca gtacatggac gacctgtacg ctagctga                2268
```

<210> SEQ ID NO 76
<211> LENGTH: 737
<212> TYPE: PRT
<213> ORGANISM: Artificial Sequence
<220> FEATURE:
<223> OTHER INFORMATION: Synthetic peptide.

<400> SEQUENCE: 76

```
Gln Val Gln Leu Arg Gln Ser Gly Pro Glu Leu Val Lys Pro Gly Ala
1               5                   10                  15
```

-continued

```
Ser Val Lys Met Ser Cys Lys Ala Ser Gly Tyr Thr Phe Thr Asp Tyr
             20                  25                  30
Val Ile Ser Trp Val Lys Gln Arg Thr Gly Gln Gly Leu Glu Trp Ile
         35                  40                  45
Gly Asp Ile Tyr Pro Gly Ser Gly Tyr Ser Phe Tyr Asn Glu Asn Phe
     50                  55                  60
Lys Gly Lys Ala Thr Leu Thr Ala Asp Lys Ser Ser Thr Thr Ala Tyr
65                  70                  75                  80
Met Gln Leu Ser Ser Leu Thr Ser Glu Asp Ser Ala Val Tyr Phe Cys
             85                  90                  95
Ala Thr Tyr Tyr Asn Tyr Pro Phe Ala Tyr Trp Gly Gln Gly Thr Leu
            100                 105                 110
Val Thr Val Ser Ala Ala Lys Thr Thr Gly Pro Ser Val Phe Pro Leu
        115                 120                 125
Ala Pro Cys Ser Arg Ser Thr Ser Glu Ser Thr Ala Ala Leu Gly Cys
    130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
            165                 170                 175
Ser Gly Leu Tyr Ser Leu Ser Ser Val Val Thr Val Pro Ser Ser Ser
        180                 185                 190
Leu Gly Thr Lys Thr Tyr Thr Cys Asn Val Asp His Lys Pro Ser Asn
    195                 200                 205
Thr Lys Val Asp Lys Arg Val Glu Ser Lys Tyr Gly Pro Pro Cys Pro
210                 215                 220
Pro Cys Pro Ala Pro Glu Phe Glu Gly Gly Pro Ser Val Phe Leu Phe
225                 230                 235                 240
Pro Pro Lys Pro Lys Asp Thr Leu Met Ile Ser Arg Thr Pro Glu Val
            245                 250                 255
Thr Cys Val Val Val Asp Val Ser Gln Glu Asp Pro Glu Val Gln Phe
        260                 265                 270
Asn Trp Tyr Val Asp Gly Val Glu Val His Asn Ala Lys Thr Lys Pro
    275                 280                 285
Arg Glu Glu Gln Phe Asn Ser Thr Tyr Arg Val Val Ser Val Leu Thr
290                 295                 300
Val Leu His Gln Asp Trp Leu Asn Gly Lys Glu Tyr Lys Cys Lys Val
305                 310                 315                 320
Ser Asn Lys Gly Leu Pro Ser Ser Ile Glu Lys Thr Ile Ser Lys Ala
            325                 330                 335
Lys Gly Gln Pro Arg Glu Pro Gln Val Tyr Thr Leu Pro Pro Ser Gln
        340                 345                 350
Glu Glu Met Thr Lys Asn Gln Val Ser Leu Thr Cys Leu Val Lys Gly
    355                 360                 365
Phe Tyr Pro Ser Asp Ile Ala Val Glu Trp Glu Ser Asn Gly Gln Pro
370                 375                 380
Glu Asn Asn Tyr Lys Thr Thr Pro Pro Val Leu Asp Ser Asp Gly Ser
385                 390                 395                 400
Phe Phe Leu Tyr Ser Arg Leu Thr Val Asp Lys Ser Arg Trp Gln Glu
            405                 410                 415
Gly Asn Val Phe Ser Cys Ser Val Met His Glu Ala Leu His Asn His
        420                 425                 430
```

```
Tyr Thr Gln Lys Ser Leu Ser Leu Ser Leu Gly Lys Ala Ser Gln Thr
            435                 440                 445

Pro Thr Asn Thr Ile Ser Val Thr Pro Thr Asn Asn Ser Thr Pro Thr
    450                 455                 460

Asn Asn Ser Asn Pro Lys Pro Asn Pro Ala Ser Glu Lys Ile Arg Leu
465                 470                 475                 480

Arg Pro Gly Gly Lys Lys Tyr Lys Leu Lys His Ile Val Ala Ser
                485                 490                 495

Ser Ser Val Ser Pro Thr Ser Val His Pro Thr Pro Thr Ser Val
            500                 505                 510

Pro Pro Thr Pro Thr Lys Ser Ser Pro Ala Ser Asn Pro Pro Ile Pro
        515                 520                 525

Val Gly Glu Ile Tyr Lys Arg Trp Ile Ile Leu Gly Leu Asn Lys Ile
    530                 535                 540

Val Arg Met Tyr Ser Pro Thr Ser Ile Leu Asp Ala Ser Pro Thr Ser
545                 550                 555                 560

Thr Pro Ala Asp Ser Ser Thr Ile Thr Pro Thr Ala Thr Pro Thr Ala
                565                 570                 575

Thr Pro Thr Ile Lys Gly Ala Ser His Thr Gln Gly Tyr Phe Pro Asp
                580                 585                 590

Trp Gln Asn Tyr Thr Pro Gly Pro Gly Val Arg Tyr Pro Leu Thr Phe
        595                 600                 605

Gly Trp Leu Tyr Lys Leu Ala Ser Thr Val Thr Pro Thr Ala Thr Ala
    610                 615                 620

Thr Pro Ser Ala Ile Val Thr Thr Ile Thr Pro Thr Ala Thr Thr Lys
625                 630                 635                 640

Pro Ala Ser Val Gly Phe Pro Val Thr Pro Gln Val Pro Leu Arg Pro
                645                 650                 655

Met Thr Tyr Lys Ala Ala Val Asp Leu Ser His Phe Leu Lys Glu Lys
                660                 665                 670

Gly Gly Leu Ala Ser Thr Asn Gly Ser Ile Thr Val Ala Ala Thr Ala
            675                 680                 685

Pro Thr Val Thr Pro Thr Val Asn Ala Thr Pro Ser Ala Ala Ala Ser
        690                 695                 700

Ala Ile Phe Gln Ser Ser Met Thr Lys Ile Leu Glu Pro Phe Arg Lys
705                 710                 715                 720

Gln Asn Pro Asp Ile Val Ile Tyr Gln Tyr Met Asp Asp Leu Tyr Ala
                725                 730                 735

Ser

<210> SEQ ID NO 77
<211> LENGTH: 708
<212> TYPE: DNA
<213> ORGANISM: Artificial Sequence
<220> FEATURE:
<223> OTHER INFORMATION: Synthetic oligonucleotide.

<400> SEQUENCE: 77 atggatttc aagtgcagat tttcagcttc ctgctaatca gtgcttcagt cataatgtcc     60
agaggacaaa ttgttctctc ccagtctcca gcaatcctgt ctgcatctcc aggggagaag   120
gtcacaatga cttgcagggc cagctcaagt gtaagttaca tgcactggta ccagcggaag   180
ccaggatcct cccccaaacc ctggatttat gccacatcca acctggcttc tggagtccct   240
gctcgcttca gtggcagtgg gtctgggacc tcttattctc tcacaatcag cagagtggag   300
```

```
gctgaagatg ctgccactta ttactgccag cagtggagta gtaacccgct cacgttcggt    360
gctgggacca agctggagct gaaacgggct gatgctgcac caactgtatc catcttccca    420
ccatccagtg agcagttaac atctggaggt gcctcagtcg tgtgcttctt gaacaacttc    480
taccccaaag acatcaatgt caagtggaag attgatggca gtgaacgaca aaatggcgtc    540
ctgaacagtt ggactgatca ggacagcaaa gacagcacct acagcatgag cagcaccctc    600
acgttgacca aggacgagta tgaacgacat aacagctata cctgtgaggc cactcacaag    660
acatcaactt cacccatcgt caagagcttc aacaggaatg agtgttag              708
```

<210> SEQ ID NO 78
<211> LENGTH: 213
<212> TYPE: PRT
<213> ORGANISM: Artificial Sequence
<220> FEATURE:
<223> OTHER INFORMATION: Synthetic peptide.

<400> SEQUENCE: 78

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Arg Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys Arg Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210

<210> SEQ ID NO 79
<211> LENGTH: 1428
<212> TYPE: DNA
<213> ORGANISM: Artificial Sequence
<220> FEATURE:
<223> OTHER INFORMATION: Synthetic oligonucleotide.

<400> SEQUENCE: 79

```
atggaatgga gctgggtctt tctcttcctc ctgtcagtaa ttgcaggtgt ccaatcccag    60
gttcagctgc agcagtctgg ggctgagctg gtgaggcctg ggcttcagt gacgctgtcc    120
```

```
tgcaaggctt cgggctacac atttattgac catgatatgc actgggtgca gcagacacct    180
gtgtatggcc tggaatggat cggagctatt gatcctgaaa ctggtgatac tggctacaat    240
cagaagttca agggcaaggc catactgact gcagacaaat cctccaggac agcctacatg    300
gaactccgca gcctgacatc tgaggactct gccgtctatt actgtacaat ccccttctac    360
tatagtaact acagcccgtt tgcttactgg ggccaagggg ctctggtcac tgtctctgca    420
gccaaaacaa cagccccatc ggtctatcca ctggcccctg tgtgtggagg tacaactggc    480
tcctcggtga ctctaggatg cctggtcaag ggttatttcc ctgagccagt gaccttgacc    540
tggaactctg gatccctgtc cagtggtgtg cacaccttcc cagctctcct gcagtctggc    600
ctctacaccc tcagcagctc agtgactgta acctcgaaca cctggcccag ccagaccatc    660
acctgcaatg tggcccaccc ggcaagcagc accaaagtgg acaagaaaat tgagcccaga    720
gtgcccataa cacagaaccc ctgtcctcca ctcaaagagt gtccccatg cgcagacctc    780 ttgggtggac catccgtctt catcttccct ccaaagatca aggatgtact catgatctcc    840
ctgagcccca tggtcacatg tgtggtggtg gatgtgagcg aggatgaccc agacgcccag    900
atcagctggt ttgtgaacaa cgtggaagta cacacagctc agacacaaac ccatagagag    960
gattacaaca gtactctccg ggtggtcagt gccctcccca tccagcacca ggactggatg   1020
agtggcaagg agttcaaatg caaggtcaac aacagagccc tcccatcccc catcgagaaa   1080
accatctcaa aacccagagg gccagtaaga gctccacagg tatatgtctt gcctccacca   1140
gcagaagaga tgactaagaa agagttcagt ctgacctgca tgatcacagg cttcttacct   1200
gccgaaattg ctgtggactg gaccagcaat gggcgtacag agcaaaacta caagaacacc   1260
gcaacagtcc tggactctga tggttcttac ttcatgtaca gcaagctcag agtacaaaag   1320
agcacttggg aaagaggaag tctttcgcc tgctcagtgg tccacgaggg tctgcacaat   1380
caccttacga ctaagaccat ctcccggtct ctgggtaaag ctagctga              1428
```

<210> SEQ ID NO 80
<211> LENGTH: 456
<212> TYPE: PRT
<213> ORGANISM: Artificial Sequence
<220> FEATURE:
<223> OTHER INFORMATION: Synthetic peptide.

<400> SEQUENCE: 80

```
Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Ile Asp His
            20                  25                  30

Asp Met His Trp Val Gln Gln Thr Pro Val Tyr Gly Leu Glu Trp Ile
        35                  40                  45

Gly Ala Ile Asp Pro Glu Thr Gly Asp Thr Gly Tyr Asn Gln Lys Phe
    50                  55                  60

Lys Gly Lys Ala Ile Leu Thr Ala Asp Lys Ser Ser Arg Thr Ala Tyr
65                  70                  75                  80

Met Glu Leu Arg Ser Leu Thr Ser Glu Asp Ser Ala Val Tyr Tyr Cys
                85                  90                  95

Thr Ile Pro Phe Tyr Tyr Ser Asn Tyr Ser Pro Phe Ala Tyr Trp Gly
            100                 105                 110

Gln Gly Ala Leu Val Thr Val Ser Ala Ala Lys Thr Thr Ala Pro Ser
        115                 120                 125
```

```
Val Tyr Pro Leu Ala Pro Val Cys Gly Gly Thr Thr Gly Ser Ser Val
    130                 135                 140
Thr Leu Gly Cys Leu Val Lys Gly Tyr Phe Pro Glu Pro Val Thr Leu
145                 150                 155                 160
Thr Trp Asn Ser Gly Ser Leu Ser Ser Gly Val His Thr Phe Pro Ala
                165                 170                 175
Leu Leu Gln Ser Gly Leu Tyr Thr Leu Ser Ser Ser Val Thr Val Thr
            180                 185                 190
Ser Asn Thr Trp Pro Ser Gln Thr Ile Thr Cys Asn Val Ala His Pro
        195                 200                 205
Ala Ser Ser Thr Lys Val Asp Lys Lys Ile Glu Pro Arg Val Pro Ile
    210                 215                 220
Thr Gln Asn Pro Cys Pro Pro Leu Lys Glu Cys Pro Pro Cys Ala Asp
225                 230                 235                 240
Leu Leu Gly Gly Pro Ser Val Phe Ile Phe Pro Pro Lys Ile Lys Asp
                245                 250                 255
Val Leu Met Ile Ser Leu Ser Pro Met Val Thr Cys Val Val Val Asp
            260                 265                 270
Val Ser Glu Asp Asp Pro Asp Ala Gln Ile Ser Trp Phe Val Asn Asn
        275                 280                 285
Val Glu Val His Thr Ala Gln Thr Gln Thr His Arg Glu Asp Tyr Asn
    290                 295                 300
Ser Thr Leu Arg Val Val Ser Ala Leu Pro Ile Gln His Gln Asp Trp
305                 310                 315                 320
Met Ser Gly Lys Glu Phe Lys Cys Lys Val Asn Asn Arg Ala Leu Pro
                325                 330                 335
Ser Pro Ile Glu Lys Thr Ile Ser Lys Pro Arg Gly Pro Val Arg Ala
            340                 345                 350
Pro Gln Val Tyr Val Leu Pro Pro Ala Glu Glu Met Thr Lys Lys
        355                 360                 365
Glu Phe Ser Leu Thr Cys Met Ile Thr Gly Phe Leu Pro Ala Glu Ile
370                 375                 380
Ala Val Asp Trp Thr Ser Asn Gly Arg Thr Glu Gln Asn Tyr Lys Asn
385                 390                 395                 400
Thr Ala Thr Val Leu Asp Ser Asp Gly Ser Tyr Phe Met Tyr Ser Lys
                405                 410                 415
Leu Arg Val Gln Lys Ser Thr Trp Glu Arg Gly Ser Leu Phe Ala Cys
            420                 425                 430
Ser Val Val His Glu Gly Leu His Asn His Leu Thr Thr Lys Thr Ile
        435                 440                 445
Ser Arg Ser Leu Gly Lys Ala Ser
    450                 455

<210> SEQ ID NO 81
<211> LENGTH: 1635
<212> TYPE: DNA
<213> ORGANISM: Artificial Sequence
<220> FEATURE:
<223> OTHER INFORMATION: Synthetic sequence

<400> SEQUENCE: 81
atgacattga acatgctgtt ggggctgagg tgggtttttct tgttgtttt ttatcaaggt      60 gtgcattgtg aggtgcagct tgttgagtct ggtggaggat tggtgcagcc taaagggtca    120
ttgaaactct catgtgcagc ctctggatta accttcaata tctacgccat gaactgggtc    180
```

```
cgccaggctc caggaaaggg tttggaatgg gttgctcgca taagaaataa agtaataat      240 tatgcaacat attatgccga ttcagtgaaa gacaggttca ccatctccag agatgattca      300
caaagcttgc tctatctgca aatgaacaac ttgaaaactg aggacacagc catgtattac      360
tgtgtgggac gggactggtt tgattactgg ggccaaggga ctctggtcac tgtctctgca      420
gccaaaacga agggcccatc cgtcttcccc ctggcgccct gctccaggag cacctccgag      480
agcacagccg ccctgggctg cctggtcaag gactacttcc ccgaaccggt gacggtgtcg      540
tggaactcag gcgccctgac cagcggcgtg cacaccttcc cggctgtcct acagtcctca      600
ggactctact ccctcagcag cgtggtgacc gtgccctcca gcagcttggg cacgaagacc      660
tacacctgca acgtagatca caagcccagc aacaccaagg tggacaagag agttgagtcc      720
aaatatggtc ccccatgccc accctgccca gcacctgagt tcgaaggggg accatcagtc      780
ttcctgttcc ccccaaaacc caaggacact ctcatgatct cccggacccc tgaggtcacg      840
tgcgtggtgg tggacgtgag ccaggaagac cccgaggtcc agttcaactg gtacgtggat      900
ggcgtggagg tgcataatgc caagacaaag ccgcgggagg agcagttcaa cagcacgtac      960
cgtgtggtca gcgtcctcac cgtcctgcac caggactggc tgaacggcaa ggagtacaag     1020
tgcaaggtct ccaacaaagg cctcccgtcc tccatcgaga aaaccatctc caaagccaaa     1080
gggcagcccc gagagccaca ggtgtacacc ctgcccccat cccaggagga gatgaccaag     1140
aaccaggtca gcctgacctg cctggtcaaa ggcttctacc ccagcgacat cgccgtggag     1200
tgggagagca atgggcagcc ggagaacaac tacaagacca cgcctcccgt gctggactcc     1260
gacggctcct tcttcctcta cagcaggcta accgtggaca agagcaggtg gcaggagggg     1320
aatgtcttct catgctccgt gatgcatgag gctctgcaca accactacac acagaagagc     1380 ctctcccctgt ctctgggtaa agctagcaat tctcctcaaa atgaagtact gtacggagat     1440
gtgaatgatg acggaaaagt aaactccact gacttgactt tgttaaaaag atatgttctt     1500
aaagccgtct caactctccc ttcttccaaa gctgaaaaga acgcagatgt aaatcgtgac     1560
ggaagagtta attccagtga tgtcacaata ctttcaagat atttgataag ggtaatcgag     1620
aaattaccaa tataa                                                      1635
```

<210> SEQ ID NO 82
<211> LENGTH: 521
<212> TYPE: PRT
<213> ORGANISM: Artificial Sequence
<220> FEATURE:
<223> OTHER INFORMATION: Synthetic peptide

<400> SEQUENCE: 82

```
Glu Val Gln Leu Val Glu Ser Gly Gly Gly Leu Val Gln Pro Lys Gly
1               5                   10                  15

Ser Leu Lys Leu Ser Cys Ala Ala Ser Gly Leu Thr Phe Asn Ile Tyr
            20                  25                  30

Ala Met Asn Trp Val Arg Gln Ala Pro Gly Lys Gly Leu Glu Trp Val
        35                  40                  45

Ala Arg Ile Arg Asn Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Leu
65                  70                  75                  80

Leu Tyr Leu Gln Met Asn Asn Leu Lys Thr Glu Asp Thr Ala Met Tyr
                85                  90                  95

Tyr Cys Val Gly Arg Asp Trp Phe Asp Tyr Trp Gly Gln Gly Thr Leu
            100                 105                 110
```

-continued

```
Val Thr Val Ser Ala Ala Lys Thr Lys Gly Pro Ser Val Phe Pro Leu
            115                 120                 125
Ala Pro Cys Ser Arg Ser Thr Ser Glu Ser Thr Ala Ala Leu Gly Cys
130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
                180                 185                 190
Leu Gly Thr Lys Thr Tyr Thr Cys Asn Val Asp His Lys Pro Ser Asn
            195                 200                 205
Thr Lys Val Asp Lys Arg Val Glu Ser Lys Tyr Gly Pro Pro Cys Pro
        210                 215                 220
Pro Cys Pro Ala Pro Glu Phe Glu Gly Gly Pro Ser Val Phe Leu Phe
225                 230                 235                 240
Pro Pro Lys Pro Lys Asp Thr Leu Met Ile Ser Arg Thr Pro Glu Val
                245                 250                 255
Thr Cys Val Val Val Asp Val Ser Gln Glu Asp Pro Glu Val Gln Phe
                260                 265                 270
Asn Trp Tyr Val Asp Gly Val Glu Val His Asn Ala Lys Thr Lys Pro
            275                 280                 285
Arg Glu Glu Gln Phe Asn Ser Thr Tyr Arg Val Val Ser Val Leu Thr
        290                 295                 300
Val Leu His Gln Asp Trp Leu Asn Gly Lys Glu Tyr Lys Cys Lys Val
305                 310                 315                 320
Ser Asn Lys Gly Leu Pro Ser Ser Ile Glu Lys Thr Ile Ser Lys Ala
                325                 330                 335
Lys Gly Gln Pro Arg Glu Pro Gln Val Tyr Thr Leu Pro Pro Ser Gln
            340                 345                 350
Glu Glu Met Thr Lys Asn Gln Val Ser Leu Thr Cys Leu Val Lys Gly
        355                 360                 365
Phe Tyr Pro Ser Asp Ile Ala Val Glu Trp Glu Ser Asn Gly Gln Pro
    370                 375                 380
Glu Asn Asn Tyr Lys Thr Thr Pro Pro Val Leu Asp Ser Asp Gly Ser
385                 390                 395                 400
Phe Phe Leu Tyr Ser Arg Leu Thr Val Asp Lys Ser Arg Trp Gln Glu
                405                 410                 415
Gly Asn Val Phe Ser Cys Ser Val Met His Glu Ala Leu His Asn His
            420                 425                 430
Tyr Thr Gln Lys Ser Leu Ser Leu Ser Leu Gly Lys Ala Ser Asn Ser
        435                 440                 445
Pro Gln Asn Glu Val Leu Tyr Gly Asp Val Asn Asp Asp Gly Lys Val
    450                 455                 460
Asn Ser Thr Asp Leu Thr Leu Leu Lys Arg Tyr Val Leu Lys Ala Val
465                 470                 475                 480
Ser Thr Leu Pro Ser Ser Lys Ala Glu Lys Asn Ala Asp Val Asn Arg
                485                 490                 495
Asp Gly Arg Val Asn Ser Ser Asp Val Thr Ile Leu Ser Arg Tyr Leu
            500                 505                 510
Ile Arg Val Ile Glu Lys Leu Pro Ile
        515                 520
```

VACCINES DIRECTED TO LANGERHANS CELLS

CROSS-REFERENCE TO RELATED APPLICATIONS

This application is a continuation of U.S. patent application Ser. No. 12/882,052 now abandoned, which claims priority to U.S. Provisional Application Ser. No. 61/242,283, filed Sep. 14, 2009, the entire contents of which are incorporated herein by reference.

STATEMENT OF FEDERALLY FUNDED RESEARCH

This invention was made with U.S. Government support under Contract No. 1U19AI057234-0100003 awarded by the NIH. The government has certain rights in this invention.

TECHNICAL FIELD OF THE INVENTION

The present invention relates in general to the field of vaccines, and more particularly, to compositions and methods for targeting and delivering antigens to Langerhans cells for antigen presentation using high affinity anti-Langerin monoclonal antibodies and fusion proteins therewith.

INCORPORATION-BY-REFERENCE OF MATERIALS FILED ON COMPACT DISC

None.

BACKGROUND OF THE INVENTION

Without limiting the scope of the invention, its background is described in connection with antigen presentation.

Dendritic Cells (DCs) are professional antigen-presenting cells (APCs) that induce and sustain immune responses and are fundamental in establishing both tolerance and immunity. DCs capture and present antigens to CD4+ T cells, which then determine the quantity and quality of antigen-specific CD8+ T cells. There are subsets of DCs[1,2], including both myeloid and plasmacytoid DCs (mDCs and pDCs, respectively).

Prior Langerin related agents include those taught in U.S. Pat. No. 6,878,528, issued to Duvert-Frances, et al., which include polynucleotides encoding a mammalian Langerhans cell antigen, including purified mammalian DC cell surface protein, designated Langerin, nucleic acids encoding Langerin, and antibodies which specifically bind Langerin.

Other anti-DC related agents are taught in, e.g., United States Patent Application Publication No. 20060257412, filed by Bowdish, et al., which includes a method of treating autoimmune disease by inducing antigen presentation by tolerance inducing antigen presenting cells. Briefly, this application teaches that antibodies to antigen presenting cells may be utilized to interfere with the interaction of the antigen presenting cell and immune cells, including T cells. Peptides may be linked to the antibodies thereby generating an immune response to such peptides, e.g., those peptides associated with autoimmunity.

SUMMARY OF THE INVENTION

In one embodiment, the present invention includes compositions and methods for activating T and B cell responses by targeting antigens to antigen presenting cells along with the proper activation of the APC to activate T cell and B cells responses. One embodiment is a vaccine comprising an isolated anti-Langerin antibody or binding fragment thereof and one or more antigenic peptides at the carboxy-terminus of the anti-Langerin antibody, wherein when two or more antigens are present, they are separated by one or more linker peptides that comprise at least one glycosylation site. In one aspect, the antibody binding fragment is selected from an Fv, Fab, Fab', F(ab')2, Fc, or a ScFv fragment. In another aspect, the antibody comprises one or more complementarity determining regions selected from:

(SEQ ID NO.: 45)
ASISCRSSQSLVHSNGNTYLHWYLQKPGQSPKLLIYKVSNRFSGVPDRFSG

SGSGTNFTLKISRVEAEDLGLYFCS;

(SEQ ID NO.: 46)
SVKMSCKASGYTFTDYVISWVKQRTGQGLEWIGDIYPGSGYSFYNENFKGK

ATLTADKSSTTAYMQLSSLTSEDSAVYFCA;

(SEQ ID NO.: 47)
VTLTCRSSTGAVTTSNYANWVQEKPDHLFTGLIGGTNNRVSGVPARFSGSL

IGDKAALTITGAQTEDEAIYFCA;

(SEQ ID NO.: 48)
SLKLSCAASGLTFNIYAMNWVRQAPGKGLEWVARIRNKSNNYATYYADSVK

DRFTISRDDSQSLLYLQMNNLKTEDTAMYYC;

or a direct equivalent thereof. In another aspect, the antigenic peptide is a cancer antigen selected from:

(SEQ ID NO.: 9)
MWVPVVFLTLSVTWIGAAPLILSRIVGGWECEKHSQPWQVLVASRGRAVCG

GVLVHPQWV;

(SEQ ID NO.: 10)
LTAAHCIRNKSVILLGRHSLFHPEDTGQVFQVSHSFPHPLYDMSLLKNRFL

RPGDDSSHD;

(SEQ ID NO.: 11)
LMLLRLSEPAELTDAVKVMDLPTQEPALGTTCYASGWGSIEPEEFLTPKKL

QCVDLHVIS;

(SEQ ID NO.: 12)
NDVCAQVHPQKVTKFMLCAGRWTGGKSTCSGDSGGPLVCNGVLQGITSWGS

EPCALPERP;

(SEQ ID NO.: 13)
SLYTKVVHYRKWIKDTIVANP;

(SEQ ID NO.: 14)
IMDQVPFSV;

(SEQ ID NO.: 15)
ITDQVPFSV;

(SEQ ID NO.: 16)
YLEPGPVTV;

(SEQ ID NO.: 17)
YLEPGPVTA;

(SEQ ID NO.: 18)
KTWGQYWQV;

(SEQ ID NO.: 19)
APLILSRIVGGWECEKHSQPWQVLVASRGRAVCGGVLVHPQWVLTAAHCIR

NKSVILLGRHSLFHPEDTGQVFQVSHSFPHPLYDMSLLKNRFLRPGDDSSH

-continued

DLMLLRLSEPAELTDAVKVMDLPTQEPALGTTCYASGWGSIEPEEFLTPKK

LQCVDLHVISNDVCAQVHPQKVTKFMLCAGRWTGGKSTCSGDSGGPLVCNG

VLQGITSWGSEPCALPERPSLYTKVVHYRKWIKDTIVANP;

(SEQ ID NO.: 20)
DTTEPATPTTPVTTPTTTKVPRNQDWLGVSRQLRTKAWNRQLYPEWTEAQR

LDCWRGGQVSLKVSNDGPTLIGANASFSIALNFPGSQKVLPDGQVIWVNNT

IINGSQVWGGQPVYPQETDDACIFPDGGPCPSGSWSQKRSFVYVWKTWGQY

WQVLGGPVSGLSIGTGRAMLGTHTMEVTVYHRRGSQSYVPLAHSSSAFTIT

DQVPFSVSVSQLRALDGGNKHFLRNQ;

(SEQ ID NO.: 21)
PLTFALQLHDPSGYLAEADLSYTWDFGDSSGTLISRAXVVTHTYLEPGPVT

AQVVLQAAIPLTSCGSSPVPAS;

(SEQ ID NO.: 22)
GTTDGHRPTAEAPNTTAGQVPTTEVVGTTPGQAPTAEPSGTTSVQVPTTEV

ISTAPVQMPTAESTGMTPEKVPVSEVMGTTLAEMSTPEATGMTPAEVSIVV

LSGTTAA;

(SEQ ID NO.: 23)
QVTTTEWVETTARELPIPEPEGPDASSIMSTESITGSLGPLLDGTATLRLV

KRQVPLDCVLYRYGSFSVTLDIVQ;

(SEQ ID NO.: 24)
GIESAEILQAVPSGEGDAFELTVSCQGGLPKEACMEISSPGCQPPAQRLCQ

PVLPSPACQLVLHQILKGGSGTYCLNVSLADTNSLAVVSTQLIVPGILLTG

QEAGLGQ;

(SEQ ID NO.: 25)
MEMKILRALNFGLGRPLPLHFLRRASKIGEVDVEQHTLAKYLMELTMLDY;

(SEQ ID NO.: 26)
DWLVQVQMKFRLLQETMYMTVSIIDRFMQNNCVPKK;

(SEQ ID NO.: 27)
MEHQLLCCEVETIRRAYPDANLLNDRVLRAMLKAEETCAPSVSYFKCV;

(SEQ ID NO.: 28)
QKEVLPSMRKIVATWMLEVCEEQKCEEEVFPLAMNYLDRFLSLEPVKKSRL

QLLGATCMFVASKMKETIPLTAEKLCIYTDNSIRPEELLQMELL;

(SEQ ID NO.: 29)
LVNKLKWNLAAMTPHDFIEHFLSKMPEAEENKQIIRKHAQTFVALCATDVK

FISNPPSMV;
or (SEQ ID NO.: 30)
AAGSVVAAVQGLNLRSPNNFLSYYRLTRFLSRVIKCDPDCLRACQEQIEAL

LESSLRQAQQNMDPKAAEEEEEEEEEVDLACTPTDVRDVDI, or binding fragments thereof. In another aspect, the antigenic peptide is a viral antigen selected from:

(SEQ ID NO.: 31)
VGFPVTPQVPLRPMTYKAAVDLSHFLKEKGGL;

(SEQ ID NO.: 32)
HTQGYFPDWQNYTPGPGVRYPLTFGWLYKL;

(SEQ ID NO.: 33)
EKIRLRPGGKKKYKLKHIV;

(SEQ ID NO.: 34)
NPPIPVGEIYKRWIILGLNKIVRMYSPTSILD;

(SEQ ID NO.: 35)
AIFQSSMTKILEPFRKQNPDIVIYQYMDDLY;

(SEQ ID NO.: 36)
DTICIGYHANNSTDTVDTVLEKNVTVTHSVNLLEDSHNGKLCRLKGIAPLQ

LGKCNIAGWLLGNPECDPLLPVRSWSYIVETPNSENGICYPGDFIDYEELR

EQLSSVSSFERFEIFPKESSWPNHNTNGVTAACSHEGKSSFYRNLLWLTEK

EGSYPKLKNSYVNKKGKEVLVLWGIHHPPNSKEQQNLYQNENAYVSVVTSN

YNRRFTPEIAERPKVRDQAGRMNYYWTLLKPGDTIIFEANGNLIAPMYAFA

LSRGFGSGIITSNASMHECNTKCQTPLGAINSSLPYQNIHPVTIGECPKYV

RSAKLRMV;

(SEQ ID NO.: 37)
DQICIGYHANNSTEQVDTIMEKNVTVTHAQDILEKKHNGKLCDLDGVKPLI

LRDCSVAGWLLGNPMCDEFINVPEWSYIVEKANPVNDLCYPGDFNDYEELK

HLLSRINHFEKIQIIPKSSWSSHEASLGVSSACPYQGKSSFFRNVVWLIKK

NSTYPTIKRSYNNTNQEDLLVLWGIHHPNDAAEQTKLYQNPTTYISVGTST

LNQRLVPRIATRSKVNGQSGRMEFFWTILKPNDAINFESNGNFIAPEYAYK

IVKKGDSTIMKSELEYGNCNTKCQTPMGAINSSMPFHNIHPLTIGECPKYV

KSNRLVLA;
or (SEQ ID NO.: 38)
PIVQNIQGQMVHQAISPRTLNAWVKVVEEKAFSPEVIPMFSALSEGATPQD

LNTMLNTVGGHQAAMQMLKETINEEAAEWDRVHPVHAGPIAPGQMREPRGS

DIAGTTSTLQEQIGWMTNNPPIPVGEIYKRWIILGLNKIVRMYSPTSILDI

RQGPKEPFRDYVDRFYKTLRAEQASQEVKNWMTETLLVQNANPDCKTILKA

LGPAATLEEMMTACQGVGGPGHKARVL.

In another aspect, when two or more antigens are present, the antigens are separated by one or more peptide linkers are selected from:

(SEQ ID NO.: 39)
SSVSPTTSVHPTPTSVPPTPTKSSP;

(SEQ ID NO.: 40)
PTSTPADSSTITPTATPTATPTIKG;

(SEQ ID NO.: 41)
TVTPTATATPSAIVTTITPTATTKP;
or (SEQ ID NO.: 42)
TNGSITVAATAPTVTPTVNATPSAA.

In another aspect, the anti-Langerin antibody is selected from the following pairs of amino acid sequences SEQ ID NOS.: 2 and 4; 6 and 7; 52 and 54; 56 and 58; and 78 and 80 or binding fragments thereof. In another aspect, the anti-Langerin antibody is the expression product of the following pairs of nucleic acid sequences SEQ ID NOS.: 1 and 3; 5 and 6; 51 and 53; 55 and 57; and 77 and 79. In another aspect, the anti-Langerin antibody or binding fragment thereof is at least one of 15B10 having ATCC Accession No. PTA-9852, 2G3 having ATCC Accession No. PTA-9853, 91E7, 37C1, or 4C7 and humanized derivatives thereof. In another aspect, the anti-Langerin antibody or binding fragment thereof and the antigenic peptide are a fusion protein.

Another embodiment of the present invention includes an isolated nucleic acid vector that expresses an anti-Langerin antibody or binding fragment thereof and two or more antigenic peptides at the carboxy-terminus of the light chain, the heavy chain or both the light and heavy chains of the anti-Langerin antibody, wherein when two or more antigenic peptides are present, the antigenic peptides are separated by the one or more peptide linkers that comprise at least one glycosylation site. In one aspect, the antigenic peptides are cancer peptides selected from tumor associated antigens selected from CEA, prostate specific antigen (PSA), HER-2/neu, BAGE, GAGE, MAGE 1-4, 6 and 12, MUC (Mucin) (e.g., MUC-1, MUC-2, etc.), GM2 and GD2 gangliosides, ras, myc, tyrosinase, MART (melanoma antigen), MARCO-MART, cyclin B1, cyclin D, Pmel 17(gp100), GnT-V intron V sequence (N-acetylglucoaminyltransferase V intron V sequence), Prostate Ca psm, prostate serum antigen (PSA), PRAME (melanoma antigen), β-catenin, MUM-1-B (melanoma ubiquitous mutated gene product), GAGE (melanoma antigen) 1, BAGE (melanoma antigen) 2-10, c-ERB2 (Her2/neu), EBNA (Epstein-Barr Virus nuclear antigen) 1-6, gp75, human papilloma virus (HPV) E6 and E7, p53, lung resistance protein (LRP), Bcl-2, and Ki-67. In another aspect, the antigenic peptides are cancer peptides selected from tumor associated antigens comprising antigens from leukemias and lymphomas, neurological tumors such as astrocytomas or glioblastomas, melanoma, breast cancer, lung cancer, head and neck cancer, gastrointestinal tumors, gastric cancer, colon cancer, liver cancer, pancreatic cancer, genitourinary tumors such cervix, uterus, ovarian cancer, vaginal cancer, testicular cancer, prostate cancer or penile cancer, bone tumors, vascular tumors, or cancers of the lip, nasopharynx, pharynx and oral cavity, esophagus, rectum, gall bladder, biliary tree, larynx, lung and bronchus, bladder, kidney, brain and other parts of the nervous system, thyroid, Hodgkin's disease, non-Hodgkin's lymphoma, multiple myeloma and leukemia. In another aspect, the antigenic peptides are selected from Influenza A Hemagglutinin HA-1 from a H1N1 Flu strain, HLA-A201-FluMP (58-66) peptide (GILGFVFTL (SEQ ID NO. 43)) tetramer, Avian Flu (HA5-1), Influenza A Hemagglutinin HA-1 from a H1N1 Flu strain (HA1-1), dockerin domain from *C. thermocellum* (doc), HIV gag p24 (gag), or a string of HIV peptides (LipoS), PSA (KLQCVDLHV (SEQ ID NO. 44))-tetramer, or an HIVgag-derived p24-PLA. In another aspect, the anti-Langerin antibody is selected from the following pairs of amino acid sequences SEQ ID NOS.: 2 and 4; 6 and 8; 52 and 54; 56 and 58; and 78 and 80 or binding fragments thereof. In another aspect, the anti-Langerin antibody is the expression product of the following pairs of nucleic acid sequences SEQ ID NOS.: 1 and 3; 5 and 7; 51 and 53; 55 and 57; and 77 and 79. In another aspect, the anti-Langerin antibody or binding fragment thereof is at least one of 15B10 having ATCC Accession No. PTA-9852, 2G3 having ATCC Accession No. PTA-9853, 91E7, 37C1, or 4C7 and humanized derivatives thereof. In another aspect, the anti-Langerin antibody or binding fragment thereof and the antigenic peptide are a fusion protein.

Yet another embodiment of the present invention includes a method of enhancing T and B cell responses comprising: immunizing a subject in need of vaccination with an effective amount of a vaccine comprising an isolated fusion protein comprising an anti-Langerin antibody or binding portion thereof and one or more antigenic peptides linked to the carboxy-terminus of the anti-Langerin antibody. In one aspect, the antigenic peptides are cancer peptides selected from tumor associated antigens selected from CEA, prostate specific antigen (PSA), HER-2/neu, BAGE, GAGE, MAGE 1-4, 6 and 12, MUC (Mucin) (e.g., MUC-1, MUC-2, etc.), GM2 and GD2 gangliosides, ras, myc, tyrosinase, MART (melanoma antigen), MARCO-MART, cyclin B1, cyclin D, Pmel 17(gp100), GnT-V intron V sequence (N-acetylglucoaminyltransferase V intron V sequence), Prostate Ca psm, prostate serum antigen (PSA), PRAME (melanoma antigen), β-catenin, MUM-1-B (melanoma ubiquitous mutated gene product), GAGE (melanoma antigen) 1, BAGE (melanoma antigen) 2-10, c-ERB2 (Her2/neu), EBNA (Epstein-Ban Virus nuclear antigen) 1-6, gp75, human papilloma virus (HPV) E6 and E7, p53, lung resistance protein (LRP), Bcl-2, and Ki-67. In another aspect, the antigenic peptides are cancer peptides selected from tumor associated antigens comprising antigens from leukemias, lymphomas, neurological tumors such as astrocytomas or glioblastomas, melanoma, breast cancer, lung cancer, head and neck cancer, gastrointestinal tumors, gastric cancer, colon cancer, liver cancer, pancreatic cancer, genitourinary tumors such cervix, uterus, ovarian cancer, vaginal cancer, testicular cancer, prostate cancer or penile cancer, bone tumors, vascular tumors, or cancers of the lip, nasopharynx, pharynx and oral cavity, esophagus, rectum, gall bladder, biliary tree, larynx, lung and bronchus, bladder, kidney, brain and other parts of the nervous system, thyroid, Hodgkin's disease, non-Hodgkin's lymphoma, multiple myeloma and leukemia. In another aspect, the antigenic peptides are selected from Influenza A Hemagglutinin HA-1 from a H1N1 Flu strain, HLA-A201-FluMP (58-66) peptide (GILGFVFTL (SEQ ID NO. 43)) tetramer, Avian Flu (HA5-1), Influenza A Hemagglutinin HA-1 from a H1N1 Flu strain (HA1-1), dockerin domain from *C. thermocellum* (doc), HIV gag p24 (gag), or a string of HIV peptides (Hipo5), PSA (KLQCVDLHV (SEQ ID NO. 44))-tetramer, or an HIVgag-derived p24-PLA.

Yet another embodiment is a method of making an anti-Langerin-antigen fusion protein comprising: expressing an isolated fusion protein comprising an anti-Langerin antibody or binding fragment thereof in a host cell, the fusion protein comprising one or more antigenic peptides at the carboxy-terminus of the anti-Langerin antibody or binding fragment thereof, wherein when two or more cancer peptides are present, the cancer peptides are separated by one or more linkers, at least one linker comprising a glycosylation site; and isolating the fusion protein. In one aspect, fusion protein expressed in the host is further isolated and purified. In another aspect, the host is a eukaryotic cell. In another aspect, the antigenic peptides are cancer peptides selected from tumor associated antigens selected from CEA, prostate specific antigen (PSA), HER-2/neu, BAGE, GAGE, MAGE 1-4, 6 and 12, MUC-related protein (Mucin) (MUC-1, MUC-2, etc.), GM2 and GD2 gangliosides, ras, myc, tyrosinase, MART (melanoma antigen), MARCO-MART, cyclin B1, cyclin D, Pmel 17 (gp100), GnT-V intron V sequence (N-acetylglucoaminyltransferase V intron V sequence), Prostate Ca psm, prostate serum antigen (PSA), PRAME (melanoma antigen), β-catenin, MUM-1-B (melanoma ubiquitous mutated gene product), GAGE (melanoma antigen) 1, BAGE (melanoma antigen) 2-10, c-ERB2 (Her2/neu), EBNA (Epstein-Barr Virus nuclear antigen) 1-6, gp75, human papilloma virus (HPV) E6 and E7, p53, lung resistance protein (LRP), Bcl-2, and Ki-67. In another aspect, the antigenic peptides are cancer peptides selected from tumor associated antigens comprising antigens from leukemias and lymphomas, neurological tumors such as astrocytomas or glioblastomas, melanoma, breast cancer, lung cancer, head and neck cancer, gastrointestinal tumors, gastric cancer, colon cancer, liver cancer, pancreatic cancer, genitourinary tumors such cervix, uterus, ovarian cancer, vaginal cancer, testicular cancer, prostate cancer or penile cancer, bone tumors, vascular tumors, or cancers of the lip, nasopharynx, pharynx and oral cavity, esophagus, rectum, gall bladder, biliary tree, larynx, lung and bronchus, bladder, kidney, brain and other parts of the nervous system, thyroid, Hodgkin's disease, non-Hodgkin's lymphoma, multiple myeloma and leukemia. In another aspect, the cancer peptides are selected from at least one of:

(SEQ ID NO.: 9)
MWVPVVFLTLSVTWIGAAPLILSRIVGGWECEKHSQPWQVLVASRGRAVCG

GVLVHPQWV;

(SEQ ID NO.: 10)
LTAAHCIRNKSVILLGRHSLFHPEDTGQVFQVSHSFPHPLYDMSLLKNRFL

RPGDDSSHD;

(SEQ ID NO.: 11)
LMLLRLSEPAELTDAVKVMDLPTQEPALGTTCYASGWGSIEPEEFLTPKKL

QCVDLHVIS;

(SEQ ID NO.: 12)
NDVCAQVHPQKVTKFMLCAGRWTGGKSTCSGDSGGPLVCNGVLQGITSWGS

EPCALPERP;

(SEQ ID NO.: 13)
SLYTKVVHYRKWIKDTIVANP;

(SEQ ID NO.: 14)
IMDQVPFSV;

(SEQ ID NO.: 15)
ITDQVPFSV;

(SEQ ID NO.: 16)
YLEPGPVTV;

(SEQ ID NO.: 17)
YLEPGPVTA;

(SEQ ID NO.: 18)
KTWGQYWQV;

(SEQ ID NO.: 19)
APLILSRIVGGWECEKHSQPWQVLVASRGRAVCGGVLVHPQWVLTAAHCIR

NKSVILLGRHSLFHPEDTGQVFQVSHSFPHPLYDMSLLKNRFLRPGDDSSH

DLMLLRLSEPAELTDAVKVMDLPTQEPALGTTCYASGWGSIEPEEFLTPKK

LQCVDLHVISNDVCAQVHPQKVTKFMLCAGRWTGGKSTCSGDSGGPLVCNG

VLQGITSWGSEPCALPERPSLYTKVVHYRKWIKDTIVANP;

(SEQ ID NO.: 20)
DTTEPATPTTPVTTPTTTKVPRNQDWLGVSRQLRTKAWNRQLYPEWTEAQR

LDCWRGGQVSLKVSNDGPTLIGANASFSIALNFPGSQKVLPDGQVIWVNNT

IINGSQVWGGQPVYPQETDDACIFPDGGPCPSGSWSQKRSFVYVWKTWGQY

WQVLGGPVSGLSIGTGRAMLGTHTMEVTVYHRRGSQSYVPLAHSSSAFTIT

DQVPFSVSVSQLRALDGGNKHFLRNQ;

(SEQ ID NO.: 21)
PLTFALQLHDPSGYLAEADLSYTWDFGDSSGTLISRAXVVTHTYLEPGPVT

AQVVLQAAIPLTSCGSSPVPAS;

(SEQ ID NO.: 22)
GTTDGHRPTAEAPNTTAGQVPTTEVVGTTPGQAPTAEPSGTTSVQVPTTEV

ISTAPVQMPTAESTGMTPEKVPVSEVMGTTLAEMSTPEATGMTPAEVSIVV

LSGTTAA;

(SEQ ID NO.: 23)
QVTTTEWVETTARELPIPEPEGPDASSIMSTESITGSLGPLLDGTATLRLV

KRQVPLDCVLYRYGSFSVTLDIVQ;

(SEQ ID NO.: 24)
GIESAEILQAVPSGEGDAFELTVSCQGGLPKEACMEISSPGCQPPAQRLCQ

PVLPSPACQLVLHQILKGGSGTYCLNVSLADTNSLAVVSTQLIVPGILLTG

QEAGLGQ;

(SEQ ID NO.: 25)
MEMKILRALNFGLGRPLPLHFLRRASKIGEVDVEQHTLAKYLMELTMLDY;

(SEQ ID NO.: 26)
DWLVQVQMKFRLLQETMYMTVSIIDRFMQNNCVPKK;

(SEQ ID NO.: 27)
MEHQLLCCEVETIRRAYPDANLLNDRVLRAMLKAEETCAPSVSYFKCV;

(SEQ ID NO.: 28)
QKEVLPSMRKIVATWMLEVCEEQKCEEEVFPLAMNYLDRFLSLEPVKKSRL

QLLGATCMFVASKMKETIPLTAEKLCIYTDNSIRPEELLQMELL;

(SEQ ID NO.: 29)
LVNKLKWNLAAMTPHDFIEHFLSKMPEAEENKQIIRKHAQTFVALCATDVK

FISNPPSMV;
or (SEQ ID NO.: 30)
AAGSVVAAVQGLNLRSPNNFLSYYRLTRFLSRVIKCDPDCLRACQEQIEAL

LESSLRQAQQNMDPKAAEEEEEEEEEVDLACTPTDVRDVDI, or immunogenic fragments thereof.

In another embodiment, the invention includes a method of expanding antigen-specific T cells or B cells in vitro comprising: isolating peripheral blood mononuclear cells (PBMCs) from a cancer patient; incubating the isolated PBMCs with an immunogenic amount of an isolated anti-Langerin-(PL-Ag)x or anti-Langerin-(Ag-PL)x vaccine, wherein Ag is a tumor associated antigen and x is an integer 1 to 20; expanding the PBMCs in the presence of an effective amount of IL-2; harvesting the cells; and assessing the cytokine production by the cells to determine the presence of anti-cancer specific T cells or B cells.

In yet another embodiment, the invention includes a tumor associated antigen-specific T cell or B cell made by the method comprising: isolating peripheral blood mononuclear cells (PBMCs) from a cancer patient; incubating the isolated PBMCs with an immunogenic amount of an anti-Langerin-(PL-Ag)x or anti-Langerin-(Ag-PL)x vaccine, wherein Ag is a tumor associated antigen and x is an integer 1 to 20; expanding the PBMCs in the presence of an effective amount of IL-2; harvesting the cells; and assessing the cytokine production by the cells to determine the presence of tumor associated antigen-specific T cells or B cells.

Another embodiment of the invention includes a therapeutic vaccine comprising an isolated fusion protein comprising the formula: Ab-(PL-Ag)x; Ab-(Ag-PL)x; Ab-(PL-Ag-PL)x; Ab-(Ag-PL-Ag)x; Ab-(PL-Ag)x-PL; or Ab-(Ag-PL)x-Ag; wherein Ab is an anti-Langerin monoclonal antibody or binding fragment thereof; PL is at least one peptide linker comprising at least one glycosylation site; Ag is at least one infectious disease antigen; and x is an integer from 1 to 20.

Yet another embodiment includes a method of expanding antigen-specific T cells or B cells in vitro comprising: isolating peripheral blood mononuclear cells (PBMCs) from a patient suspected of having an infection; incubating the isolated PBMCs with an immunogenic amount of an isolated anti-Langerin-(PL-Ag)x or αLangerin-(Ag-PL)x vaccine, wherein Ag is an antigen of the infectious agent and x is an integer 1 to 20; expanding the PBMCs in the presence of an effective amount of one or more cytokines; harvesting the cells; and assessing the cytokine production by the cells to determine the presence of anti-infections agent specific T cells or B cells. Another embodiment is a viral associated antigen-specific T cell or B cell made by the method comprising: isolating peripheral blood mononuclear cells (PBMCs) from a patient suspected of having a viral infection; incubating the isolated PBMCs with an immunogenic amount of an isolated anti-Langerin-(PL-Ag)x or anti-Langerin-(Ag-PL)x vaccine, wherein Ag is a viral associated antigen and x is an integer 1 to 20; expanding the PBMCs in the presence of an effective amount of one or more cytokines; harvesting the cells; and assessing the cytokine production by the cells to determine the presence of viral associated antigen-specific T cells or B cells.

Another embodiment is a therapeutic vaccine comprising an isolated fusion protein comprising the formula: Ab-(PL-Ag)x; Ab-(Ag-PL)x; Ab-(PL-Ag-PL)x; Ab-(Ag-PL-Ag)x; Ab-(PL-Ag)x-PL; or Ab-(Ag-PL)x-Ag; wherein Ab is an anti-Langerin monoclonal antibody or binding fragment thereof; PL is at least one peptide linker comprising at least one glycosylation site; Ag is at least one viral antigen; and x is an integer from 1 to 20. In one example, the isolated antibody comprising one or more of complementarity determining regions selected from:

(SEQ ID NO.: 45)
ASISCRSSQSLVHSNGNTYLHWYLQKPGQSPKLLIYKVSNRFSGVPDRFSG

SGSGTNFTLKISRVEAEDLGLYFCS;

(SEQ ID NO.: 46)
SVKMSCKASGYTFTDYVISWVKQRTGQGLEWIGDIYPGSGYSFYNENFKGK

ATLTADKSSTTAYMQLSSLTSEDSAVYFCA;

(SEQ ID NO.: 47)
VTLTCRSSTGAVTTSNYANWVQEKPDHLFTGLIGGTNNRVSGVPARFSGSL

IGDKAALTITGAQTEDEAIYFCA;

(SEQ ID NO.: 48)
SLKLSCAASGLTFNIYAMNWVRQAPGKGLEWVARIRNKSNNYATYYADSVK

DRFTISRDDSQSLLYLQMNNLKTEDTAMYYC;

or a direct equivalent thereof. In one aspect, the antibody is humanized. In another aspect, the antibody is 15B10 having ATCC Accession No. PTA-9852 and humanized derivatives thereof. In another aspect, the antibody is 2G3 having ATCC Accession No. PTA-9853, 91E7, 37C1, or 4C7, and humanized derivatives thereof.

Yet another embodiment is an isolated nucleic acid that encodes a 15B10, 2G3, 91E7, 37C1, or 4C7 antibody, antibody binding fragment or a humanized derivative thereof. In one aspect, the anti-Langerin antibody is selected from the following pairs of amino acid sequences SEQ ID NOS.: 2 and 4; 6 and 7; 52 and 54; 56 and 58; and 78 and 80; or binding fragments thereof respectively. In another aspect, the anti-Langerin antibody is the expression product from the following pairs of nucleic acid sequences SEQ ID NOS.: 1 and 3; 5 and 6; 51 and 53; 55 and 57; and 77 and 79; or binding fragments thereof, which are the 15B10, 2G3, 91E7, 37C1, or 4C7 antibodies, respectively.

Yet another embodiment of the present invention is a pharmaceutical composition comprising an isolated anti-Langerin antibody or binding fragment thereof and one or more antigenic peptides attached to the anti-Langerin antibody, wherein when two or more antigens are present, they are separated by one or more linker peptides that comprise at least one glycosylation site. In one aspect, the antibody binding fragment is selected from an Fv, Fab, Fab', F(ab')2, Fc, or a ScFv fragment. In another aspect, the anti-Langerin antibody is selected from the following pairs of amino acid sequences SEQ ID NOS.: 2 and 4; 6 and 7; 52 and 54; 56 and 58; and 78 and 80 or binding fragments thereof. In another aspect, the anti-Langerin antibody is the expression product of the following pairs of nucleic acid sequences SEQ ID NOS.: 1 and 3; 5 and 6; 51 and 53; 55 and 57; and 77 and 79. In another aspect, the anti-Langerin antibody or binding fragment thereof is at least one of 15B10 having ATCC Accession No. PTA-9852, 2G3 having ATCC Accession No. PTA-9853, 91E7, 37C1, or 4C7 and humanized derivatives thereof. In another aspect, the anti-Langerin antibody or binding fragment thereof and the antigenic peptide are a fusion protein. In another aspect, the composition further comprises an adjuvant. In another aspect, the composition further comprises one or more pharmaceutical excipients.

Yet another embodiment of the present invention is a therapeutic vaccine comprising a fusion protein comprising the formula: Ab-(PL-Ag)x; Ab-(Ag-PL)x; Ab-(PL-Ag-PL)x; Ab-(Ag-PL-Ag)x; Ab-(PL-Ag)x-PL; or Ab-(Ag-PL)x-Ag; wherein Ab is an anti-Langerin monoclonal antibody or binding fragment thereof; PL is at least one peptide linker comprising at least one glycosylation site; Ag is at least one viral antigen; and x is an integer from 1 to 20.

The invention provides a Langerin binding antibody (15B10) that comprises at least one immunoglobulin light chain variable domain (VL) which comprises the amino acid and nucleic acid sequence encoding:

(SEQ ID NO.: 45)
ASISCRSSQSLVHSNGNTYLHWYLQKPGQSPKLLIYKVSNRFSGVPDRFSG

SGSGTNFTLKISRVEAEDLGLYFCS;

or and direct equivalent thereof.

Accordingly the invention provides a Langerin binding antibody (15B10) that comprises an antigen binding site comprising at least one immunoglobulin heavy chain variable domain (VH) which comprises the amino acid and nucleic acid sequence encoding:

(SEQ ID NO.: 46)
SVKMSCKASGYTFTDYVISWVKQRTGQGLEWIGDIYPGSGYSFYNENFKGK

ATLTADKSSTTAYMQLSSLTSEDSAVYFCA;

and direct equivalents thereof.

The invention provides a Langerin binding antibody (2G3) that comprises at least one immunoglobulin light chain variable domain (VL) which comprises the amino acid and nucleic acid sequence encoding:

(SEQ ID NO.: 47)
VTLTCRSSTGAVTTSNYANWVQEKPDHLFTGLIGGTNNRVSGVPARFSGSL

IGDKAALTITGAQTEDEAIYFCA;

or and direct equivalent thereof.

Accordingly the invention provides a Langerin binding antibody (2G3) that comprises an antigen binding site comprising at least one immunoglobulin heavy chain variable domain (VH) which comprises the amino acid and nucleic acid sequence encoding:

(SEQ ID NO.: 48)
SLKLSCAASGLTFNIYAMNWVRQAPGKGLEWVARIRNKSNNYATYYADSVK

DRFTISRDDSQSLLYLQMNNLKTEDTAMYYC;

and direct equivalents thereof.

In one aspect the invention provides a single domain Langerin antibody comprising an isolated immunoglobulin light chain comprising a heavy chain variable domain (VL) as defined above. In another aspect the invention provides a single domain Langrin binding molecule comprising an isolated immunoglobulin heavy chain comprising a heavy chain variable domain (VH) as defined above.

In another aspect the invention also provides a Langerin binding antibody comprising a light chain (VL) variable domains in which the Langerin binding antibody comprises at least one antigen binding site comprising: an antibody light chain variable domain (VL) which comprises in sequence hypervariable regions obtained from the amino acid and nucleic acid sequences encoding:

(SEQ ID NO.: 45)
ASISCRSSQSLVHSNGNTYLHWYLQKPGQSPKLLIYKVSNRFSGVPDRFSG

SGSGTNFTLKISRVEAEDLGLYFCS;
or
(SEQ ID NO.: 47)
VTLTCRSSTGAVTTSNYANWVQEKPDHLFTGLIGGTNNRVSGVPARFSGSL

IGDKAALTITGAQTEDEAIYFCA;

and direct equivalents thereof.

In another aspect the invention also provides a Langerin binding antibody comprising, the amino acid and nucleic acid sequences of heavy chain variable domain (VH) which comprises in sequence hypervariable regions obtained from:

(SEQ ID NO.: 46)
SVKMSCKASGYTFTDYVISWVKQRTGQGLEWIGDIYPGSGYSFYNENFKGK

ATLTADKSSTTAYMQLSSLTSEDSAVYFCA;
or
(SEQ ID NO.: 48)
SLKLSCAASGLTFNIYAMNWVRQAPGKGLEWVARIRNKSNNYATYYADSVK

DRFTISRDDSQSLLYLQMNNLKTEDTAMYYC;

and direct equivalents thereof.

mAnti-Langerin15B10K—Nucleotide and mature protein amino acid sequence of the light chain of the mouse anti-Langerin 15B10 antibody cDNA, respectively. The variable region residues are underlined.

(SEQ ID NO. 49)
ATGAAGTTGCCTGTTAGGCTGTTGGTGCTGATGTTCTGGATTCCTGC
TTCCAGCAGTGATGTTGTGATGACCCAAACTCCACTCTCCCTGCCTG
TCCGTCTTGGAGATCAAGCCTCCATCTCTTGCAGATCTAGTCAGAGC
CTTGTACACAGTAATGGAAACACCTATTTACATTGGTACCTGCAGAA
GCCAGGCCAGTCTCCAAAGCTCCTGATCTACAAAGTTTCCAACCGAT
TTTCTGGGGTCCCAGACAGGTTCAGTGGCAGTGGATCAGGGACAAAT
TTCACACTCAAGATCAGCAGAGTGGAGGCTGAGGATCTGGGACTTTA
TTTCTGCTCTCAAAGTACACATGTTCCGTACACGTTCGGAGGGGGGA
CCAAGCTGGAAATAAAACGGGCTGATGCTGCACCAACTGTATCCATC
TTCCCACCATCCAGTGAGCAGTTAACATCTGGAGGTGCCTCAGTCGT
GTGCTTCTTGAACAACTTCTACCCCAAAGACATCAATGTCAAGTGGA
AGATTGATGGCAGTGAACGACAAAATGGCGTCCTGAACAGTTGGACT
GATCAGGACAGCAAAGACAGCACCTACAGCATGAACAGCACCCTCAC
GTTGACCAAGGACGAGTATGAACGACATAACAGCTATACCTGTGAGG
CCACTCACAAGACATCAACTTCACCCATCGTCAAGAGCTTCAACAGG
AATGAGTGTTAG

(SEQ ID NO. 50)
DVVMTQTPLSLPVRLGDQ<u>ASISCRSSQSLVHSNGNTYLHWYLQKPGQ</u>
<u>SPKLLIYKVSNRFSGVPDRFSGSGSGTNFTLKISRVEAEDLGLYFCS</u>
<u>QSTHVPYT</u>FGGGTKLEIKRADAAPTVSIFPPSSEQLTSGGASVVCFL
NNFYPKDINVKWKIDGSERQNGVLNSWTDQDSKDSTYSMNSTLTLTK
DEYERHNSYTCEATHKTSTSPIVKSFNRNEC mAnti-Langerin15B10H-LV-hIgG4H-C—Nucleotide and mature protein amino acid sequence of the heavy chain variable region of the mouse anti-Langerin 15B10 antibody fused to human IgG4, respectively. The variable region residues are underlined.

(SEQ ID NO. 51)
ATGGAATGGAGGATCTTTCTCTTCATCCTGTCAGGAACTGCAGGTG
TCCACTCCCAGGTTCAGCTGCGGCAGTCTGGACCTGAGCTGGTGAA
GCCTGGGGCTTCAGTGAAGATGTCCTGCAAGGCTTCTGGATACACA
TTTACTGACTATGTTATAAGTTGGGTGAAGCAGAGAACTGGACAGG
GCCTTGAGTGGATTGGAGATATTTATCCTGGAAGTGGTTATTCTTT
CTACAATGAGAACTTCAAGGGCAAGGCCACACTGACTGCAGACAAA
TCCTCCACCACAGCCTACATGCAGCTCAGCAGCCTGACATCTGAGG
ACTCTGCGGTCTATTTCTGTGCAACCTACTATAACTACCCTTTTGC
TTACTGGGGCCAAGGGACTCTGGTCACTGTCTCTGCAGCCAAAACA
ACGGGCCCATCCGTCTTCCCCCTGGCGCCCTGCTCCAGGAGCACCT
CCGAGAGCACAGCCGCCCTGGGCTGCCTGGTCAAGGACTACTTCCC
CGAACCGGTGACGGTGTCGTGGAACTCAGGCGCCCTGACCAGCGGC
GTGCACACCTTCCCGGCTGTCCTACAGTCCTCAGGACTCTACTCCC
TCAGCAGCGTGGTGACCGTGCCCTCCAGCAGCTTGGGCACGAAGAC
CTACACCTGCAACGTAGATCACAAGCCCAGCAACACCAAGGTGGAC
AAGAGAGTTGAGTCCAAATATGGTCCCCCATGCCCACCCTGCCCAG
CACCTGAGTTCGAAGGGGGACCATCAGTCTTCCTGTTCCCCCCAAA
ACCCAAGGACACTCTCATGATCTCCCGGACCCCTGAGGTCACGTGC
GTGGTGGTGGACGTGAGCCAGGAAGACCCCGAGGTCCAGTTCAACT
GGTACGTGGATGGCGTGGAGGTGCATAATGCCAAGACAAAGCCGCG
GGAGGAGCAGTTCAACAGCACGTACCGTGTGGTCAGCGTCCTCACC
GTCCTGCACCAGGACTGGCTGAACGGCAAGGAGTACAAGTGCAAGG
TCTCCAACAAAGGCCTCCCGTCCTCCATCGAGAAAACCATCTCCAA
AGCCAAAGGGCAGCCCCGAGAGCCACAGGTGTACACCCTGCCCCCA
TCCCAGGAGGAGATGACCAAGAACCAGGTCAGCCTGACCTGCCTGG
TCAAAGGCTTCTACCCCAGCGACATCGCCGTGGAGTGGGAGAGCAA
TGGGCAGCCGGAGAACAACTACAAGACCACGCCTCCCGTGCTGGAC
TCCGACGGCTCCTTCTTCCTCTACAGCAGGCTAACCGTGGACAAGA
GCAGGTGGCAGGAGGGGAATGTCTTCTCATGCTCCGTGATGCATGA
GGCTCTGCACAACCACTACACACAGAAGAGCCTCTCCCTGTCTCTG
GGTAAAGCTAGCTGA

(SEQ ID NO. 52)
QVQLRQSGPELVKPGA<u>SVKMSCKASGYTFTDYVISWVKQRTGQGLE</u>
<u>WIGDIYPGSGYSFYNENFKGKATLTADKSSTTAYMQLSSLTSEDSA</u>
<u>VYFCA</u>TYYNYPFAYWGQGTLVTVSAAKTTGPSVFPLAPCSRSTSES
TAALGCLVKDYFPEPVTVSWNSGALTSGVHTFPAVLQSSGLYSLSS
VVTVPSSSLGTKTYTCNVDHKPSNTKVDKRVESKYGPPCPPCPAPE
FEGGPSVFLFPPKPKDTLMISRTPEVTCVVVDVSQEDPEVQFNWYV
DGVEVHNAKTKPREEQFNSTYRVVSVLTVLHQDWLNGKEYKCKVSN
KGLPSSIEKTISKAKGQPREPQVYTLPPSQEEMTKNQVSLTCLVKG
FYPSDIAVEWESNGQPENNYKTTPPVLDSDGSFFLYSRLTVDKSRW
QEGNVFSCSVMHEALHNHYTQKSLSLSLGKAS mAnti-Langerin2G3L—Nucleotide and mature protein amino acid sequence of the light chain of the mouse anti-Langerin 2G3 antibody cDNA, respectively. The variable region residues are underlined.

(SEQ ID NO. 53)
ATGGCCTGGATTTCACTTATACTCTCTCCTGGCTCTCAGCTCAG
GGGCCATTTCCCAGGCTGTTGTGACTCAGGAATCTGCACTCACCAC
ATCACCTGGTGAAACAGTCACACTCACTTGTCGCTCAAGTACTGGG
GCTGTTACAACTAGTAACTATGCCAACTGGGTCCAAGAAAAACCAG
ATCATTTATTCACTGGTCTAATAGGTGGTACCAACAACCGAGTTTC
AGGTGTTCCTGCCAGATTCTCAGGCTCCCTGATTGGAGACAAGGCT
GCCCTCACCATCACAGGGGCACAGACTGAGGATGAGGCAATATATT
TCTGTGCTCTATGGTACAGCAACCATTGGGTGTTCGGTGGAGGAAC
CAAACTGACTGTCCTAGGCCAGCCCAAGTCTTCGCCATCAGTCACC
CTGTTTCCACCTTCCTCTGAAGAGCTCGAGACTAACAAGGCCACAC
TGGTGTGTACGATCACTGATTTCTACCCAGGTGTGGTGACAGTGGA

-continued
CTGGAAGGTAGATGGTACCCCTGTCACTCAGGGTATGGAGACAACC
CAGCCTTCCAAACAGAGCAACAACAAGTACATGGCTAGCAGCTACC
TGACCCTGACAGCAAGAGCATGGGAAAGGCATAGCAGTTACAGCTG
CCAGGTCACTCATGAAGGTCACACTGTGGAGAAGAGTTTGTCCCGT
GCTGACTGTTCCTAG

(SEQ ID NO. 54)
QAVVTQESALTTSPGET<u>VTLTCRSSTGAVTTSNYANWVQEKPDHLF
TGLIGGTNNRVSGVPARFSGSLIGDKAALTITGAQTEDEAIYFCAL
WYSNHWVFGGGTKLTVLGQPKSSPSVTLFPPSSEELETNKATLVCT
ITDFYPGVVTVDWKVDGTPVTQGMETTQPSKQSNNKYMASSYLTLT
ARAWERHSSYSCQVTHEGHTVEKSLSRADCS</u> mAnti-Langerin2G3H—Nucleotide and mature protein amino acid sequence of the heavy chain of the mouse anti-Langerin 2G3 antibody cDNA, respectively. The variable region residues are underlined.

(SEQ ID NO. 55)
ATGACATTGAACATGCTGTTGGGGCTGAAGTGGGTTTTCTTTGTTGT
TTTTTATCAAGGTGTGCATTGTGAGGTGCAGCTTGTTGAGTCTGGTG
GAGGATTGGTGCAGCCTAAAGGGTCATTGAAACTCTCATGTGCAGCC
TCTGGATTAACCTTCAATATCTACGCCATGAACTGGGTCCGCCAGGC
TCCAGGAAAGGGTTTGGAATGGGTTGCTCGCATAAGAAATAAAAGTA
ATAATTATGCAACATATTATGCCGATTCAGTGAAAGACAGGTTCACC
ATCTCCAGAGATGATTCACAAAGCTTGCTCTATCTGCAAATGAACAA
CTTGAAAACTGAGGACACAGCCATGTATTACTGTGTGGGACGGGACT
GGTTTGATTACTGGGGCCAAGGGACTCTGGTCACTGTCTCTGCAGCC
AAAACGACACCCCCATCTGTCTATCCACTGGCCCTGGATCTGCTGC
CCAAACTAACTCCATGGTGACCCTGGGATGCCTGGTCAAGGGCTATT
TCCCTGAGCCAGTGACAGTGACCTGGAACTCTGGATCCCTGTCCAGC
GGTGTGCACACCTTCCCAGCTGTCCTGCAGTCTGACCTCTACACTCT
GAGCAGCTCAGTGACTGTCCCCTCCAGCACCTGGCCCAGCGAGACCG
TCACCTGCAACGTTGCCCACCCGGCCAGCAGCACCAAGGTGGACAAG
AAAATTGTGCCCAGGGATTGTGGTTGTAAGCCTTGCATATGTACAGT
CCCAGAAGTATCATCTGTCTTCATCTTCCCCCCAAAGCCCAAGGATG
TGCTCACCATTACTCTGACTCCTAAGGTCACGTGTGTTGTGGTAGAC
ATCAGCAAGGATGATCCCGAGGTCCAGTTCAGCTGGTTTGTAGATGA
TGTGGAGGTGCACACAGCTCAGACGCAACCCCGGGAGGAGCAGTTCA
ACAGCACTTTCCGCTCAGTCAGTGAACTTCCCATCATGCACCAGGAC
TGGCTCAATGGCAAGGAGTTCAAATGCAGGGTCAACAGTGCAGCTTT
CCCTGCCCCCATCGAGAAAACCATCTCCAAAACCAAAGGCAGACCGA
AGGCTCCACAGGTGTACACCATTCCACCTCCCAAGGAGCAGATGGCC
AAGGATAAAGTCAGTCTGACCTGCATGATAACAGACTTCTTCCCTGA
AGACATTACTGTGGAGTGGCAGTGGAATGGGCAGCCAGCGGAGAACT
ACAAGAACACTCAGCCCATCATGGACACAGATGGCTCTTACTTCGTC
TACAGCAAGCTCAATGTGCAGAAGAGCAACTGGGAGGCAGGAAATAC
TTTCACCTGCTCTGTGTTACATGAGGGCCTGCACAACCACCATACTG
AGAAGAGCCTCTCCCACTCTCCTGGTAAAGCTAGCTGA

(SEQ ID NO. 56)
EVQLVESGGGLVQPKGS<u>LKLSCAASGLTFNIYAMNWVRQAPGKGLEW
VARIRNKSNNYATYYADSVKDRFTISRDDSQSLLYLQMNNLKTEDTA
MYYC</u>VGRDWFDYWGQGTLVTVSAAKTTPPSVYPLAPGSAAQTNSMVT
LGCLVKGYFPEPVTVTWNSGSLSSGVHTFPAVLQSDLYTLSSSVTVP
SSTWPSETVTCNVAHPASSTKVDKKIVPRDCGCKPCICTVPEVSSVF
IFPPKPKDVLTITLTPKVTCVVVDISKDDPEVQFSWFVDDVEVHTAQ
TQPREEQFNSTFRSVSELPIMHQDWLNGKEFKCRVNSAAFPAPIEKT
ISKTKGRPKAPQVYTIPPPKEQMAKDKVSLTCMITDFFPEDITVEWQ
WNGQPAENYKNTQPIMDTDGSYFVYSKLNVQKSNWEAGNTFTCSVLH
EGLHNHHTEKSLSHSPGKAS

In another embodiment the invention includes an antibody comprising one or more of the complementarity determining regions selected from: ASISCRSSQSLVHSNGNTYLHW-YLQKPGQSPKLLIYKVSNRFSGVPDRF-SGSGSGTNFTLKISRVEAEDLGLYFCS (SEQ ID NO.: 45); SVKMSCKASGYTFTDYVISWVKQRTGQ-GLEWIGDIYPGSGYSFYNENFKGKATL-TADKSSTTAYMQLSSLTSEDSAVYFCA (SEQ ID NO.: 46); VTLTCRSSTGAVTTSNYANWVQEKP-DHLFTGLIGGTNNRVSGVPARFSGS-LIGDKAALTITGAQTEDEAIYFCA (SEQ ID NO.: 47); SLKLSCAASGLTFNIYAMNWVRQAPGK-GLEWVARIRNKSNNYATYYADSVKDRFT-ISRDDSQSLLYLQMNNLKTEDTAMYYC (SEQ ID NO.: 48); or a direct equivalent thereof. In one aspect, the antibody is humanized. In another aspect, the antibody is 15B10, 2G3 or humanized derivatives thereof. In another aspect, the invention includes nucleic acids that encode the 15B10, the 2G3 antibody or humanized derivatives thereof.

BRIEF DESCRIPTION OF THE DRAWINGS

For a more complete understanding of the features and advantages of the present invention, reference is now made to the detailed description of the invention along with the accompanying figures and in which:

FIG. 6 (A-C) shows the differential expression of Langerin by human skin DCs.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Figure 1:
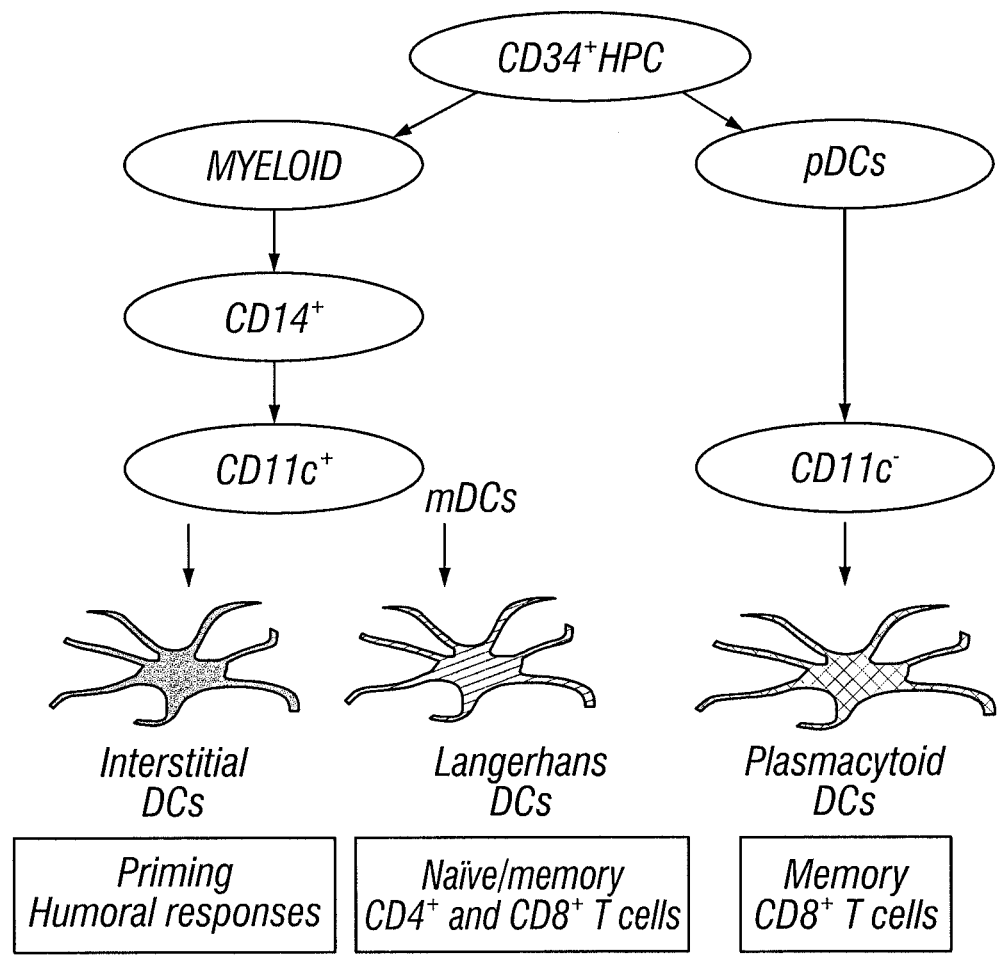
FIG. 1 shows that two main DC differentiation pathways exist. A myeloid pathway generates two subsets: Langerhans cells (LCs) found in stratified epithelia such as the skin, and interstitial DCs (intDCs) found in all other tissues.

Subsets of Dendritic Cells (DCs). The present inventors have discovered that two main DC differentiation pathways exist. A myeloid pathway generates two subsets: Langerhans cells (LCs) found in stratified epithelia such as the skin, and interstitial DCs (intDCs) found in all other tissues. A plasmacytoid pathway generates plasmacytoid DCs (pDCs), which secrete large amounts of IFNαβ after viral infection[3] and efficiently present viral antigens in a novel mechanism[4] (FIG. 1). DCs and their precursors show remarkable functional plasticity. For example, pDCs form a first barrier to the expansion of intruding viruses, thereby acting, through the release of interferon, as part of the innate immune response[5,6]. Monocytes can differentiate into either macrophages, which act as scavengers, or DCs that induce specific immune responses[7,8]. Different cytokines skew the in vitro differentiation of monocytes into DCs with different phenotypes and functions. Thus, when activated (e.g., by GM-CSF) monocytes encounter IL-4, they yield IL-4DCs[9-11]. By contrast, after encountering IFNα, TNFα, or IL-15, activated monocytes will differentiate into IFNDCs[12-15], TNFDCs[8], or IL-15DCs[16]. Each of these DC subsets has common as well as unique biological functions, determined by a unique combination of cell-surface molecules and cytokines. For example, whereas IL-4DCs are a homologous population of immature cells devoid of LCs, large portions of IFNDCs express CD1a and Langerin[8].

The invention includes also variants and other modification of an antibody (or "Ab") of fragments thereof, e.g., anti-Langerin fusion protein (antibody is used interchangeably with the term "immunoglobulin"). As used herein, the term "antibodies or binding fragments thereof," includes whole antibodies or binding fragments of an antibody, e.g., Fv, Fab, Fab', F(ab')$_2$, Fc, and single chain Fv fragments (ScFv) or any biologically effective fragments of an immunoglobulins that binds specifically to, e.g., Langerin. Antibodies from human origin or humanized antibodies have lowered or no immunogenicity in humans and have a lower number or no immunogenic epitopes compared to non-human antibodies. Antibodies and their fragments will generally be selected to have a reduced level or no antigenicity in humans.

As used herein, the terms "Ag" or "antigen" refer to a substance capable of either binding to an antigen binding region of an immunoglobulin molecule or of eliciting an immune response, e.g., a T cell-mediated immune response by the presentation of the antigen on Major Histocompatibility Antigen (MHC) cellular proteins. As used herein, "antigen" includes, but is not limited to, antigenic determinants, haptens, and immunogens, which may be peptides, small molecules, carbohydrates, lipids, nucleic acids or combinations thereof. The skilled immunologist will recognize that when discussing antigens that are processed for presentation to T cells, the term "antigen" refers to those portions of the antigen (e.g., a peptide fragment) that is a T cell epitope presented by MHC to the T cell receptor. When used in the context of a B cell mediated immune response in the form of an antibody that is specific for an "antigen", the portion of the antigen that binds to the complementarity determining regions of the variable domains of the antibody (light and heavy) the bound portion may be a linear or three-dimensional epitope. In the context of the present invention, the term antigen is used on both contexts, that is, the antibody is specific for a protein antigen (Langerin), but also carries one or more peptide epitopes for presentation by MHC to T cells. In certain cases, the antigens delivered by the vaccine or fusion protein of the present invention are internalized and processed by antigen presenting cells prior to presentation, e.g., by cleavage of one or more portions of the antibody or fusion protein.

As used herein, the term "antigenic peptide" refers to that portion of a polypeptide antigen that is specifically recognized by either B-cells or T-cells. B-cells respond to foreign antigenic determinants via antibody production, whereas T-lymphocytes are the mediate cellular immunity. Thus, antigenic peptides are those parts of an antigen that are recognized by antibodies, or in the context of an MHC, by T-cell receptors.

As used herein, the term "epitope" refers to any protein determinant capable of specific binding to an immunoglobulin or of being presented by a Major Histocompatibility Complex (MHC) protein (e.g., Class I or Class II) to a T-cell receptor. Epitopic determinants are generally short peptides 5-30 amino acids long that fit within the groove of the MHC molecule that presents certain amino acid side groups toward the T cell receptor and has certain other residues in the groove, e.g., due to specific charge characteristics of the groove, the peptide side groups and the T cell receptor. Generally, an antibody specifically binds to an antigen when the dissociation constant is 1 mM, 100 nM or even 10 nM.

As used herein, the term "vector" is used in two different contexts. When using the term "vector" with reference to a vaccine, a vector is used to describe a non-antigenic portion that is used to direct or deliver the antigenic portion of the vaccine. For example, an antibody or binding fragments thereof may be bound to or form a fusion protein with the antigen that elicits the immune response. For cellular vaccines, the vector for delivery and/or presentation of the antigen is the antigen presenting cell, which is delivered by the cell that is loaded with antigen. In certain cases, the cellular vector itself may also process and present the antigen(s) to T cells and activate an antigen-specific immune response. When used in the context of nucleic acids, a "vector" refers a construct that is capable of delivering, and preferably expressing, one or more genes or polynucleotide sequences of interest in a host cell. Examples of vectors include, but are not limited to, viral vectors, naked DNA or RNA expression vectors, DNA or RNA expression vectors associated with cationic condensing agents, DNA or RNA expression vectors encapsulated in liposomes, and certain eukaryotic cells, such as producer cells.

The compositions and methods of the present invention can be used with a wide variety of peptides and/or protein in which the antibody or binding fragment thereof and the peptide linker or "PL" create a protein that is stable and/or soluble.

As used herein, the compositions and methods use an anti-Langerin antigen delivery vector comprising the formula:

Ab-(PL-Ag)x or Ab-(Ag-PL)x;

wherein Ab is an anti-Langerin antibody or binding fragment thereof;
PL is at least one Peptide Linker comprising at least one glycosylation site;
Ag is at least one antigen; and
x is an integer from 1 to 20.

As used herein, the terms "stable" and "unstable" when referring to proteins is used to describe a peptide or protein that maintains its three-dimensional structure and/or activity (stable) or that loses immediately or over time its three-dimensional structure and/or activity (unstable). As used herein, the term "insoluble" refers to those proteins that when produced in a cell (e.g., a recombinant protein expressed in a eukaryotic or prokaryotic cell or in vitro) are not soluble in solution absent the use of denaturing conditions or agents (e.g., heat or chemical denaturants, respectively). The antibody or binding fragment thereof and the linkers taught herein have been found to convert antibody fusion proteins with the peptides from insoluble and/or unstable into proteins that are stable and/or soluble. Another example of stability versus instability is when the domain of the protein with a stable conformation has a higher melting temperature ($T_m$) than the unstable domain of the protein when measured in the same solution. A domain is stable compared to another domain when the difference in the $T_m$ is at least about 2° C., more preferably about 4° C., still more preferably about 7° C., yet more preferably about 10° C., even more preferably about 15° C., still more preferably about 20° C., even still more preferably about 25° C., and most preferably about 30° C., when measured in the same solution.

As used herein, "polynucleotide" or "nucleic acid" refers to a strand of deoxyribonucleotides or ribonucleotides in either a single- or a double-stranded form (including known analogs of natural nucleotides). A double-stranded nucleic acid sequence will include the complementary sequence. The polynucleotide sequence may encode variable and/or constant region domains of immunoglobulin that are formed into a fusion protein with one or more linkers. For use with the present invention, multiple cloning sites (MCS) may be engineered into the locations at the carboxy-terminal end of the heavy and/or light chains of the antibodies to allow for in-frame insertion of peptide for expression between the linkers. As used herein, the term "isolated polynucleotide" refers to a polynucleotide of genomic, cDNA, or synthetic origin or some combination thereof. By virtue of its origin the "isolated polynucleotide" (1) is not associated with all or a portion of a polynucleotide in which the "isolated polynucleotides" are found in nature, (2) is operably linked to a polynucleotide which it is not linked to in nature, or (3) does not occur in nature as part of a larger sequence. The skilled artisan will recognize that to design and implement a vector having the formula Ab-(PL-Ag)x or Ab-(Ag-PL)x, can be manipulated at the nucleic acid level by using techniques known in the art, such as those taught in Current Protocols in Molecular Biology, 2007 by John Wiley and Sons, relevant portions incorporated herein by reference. Briefly, the Ab, Ag and PL encoding nucleic acid sequences can be inserted using polymerase chain reaction, enzymatic insertion of oligonucleotides or polymerase chain reaction fragments in a vector, which may be an expression vector. To facilitate the insertion of (PL-Ag)x or (Ag-PL)x at the carboxy terminus of the antibody light chain, the heavy chain, or both, a multiple cloning site (MCS) may be engineered in sequence with the antibody sequences.

As used herein, the term "polypeptide" refers to a polymer of amino acids and does not refer to a specific length of the product; thus, peptides, oligopeptides, and proteins are included within the definition of polypeptide. This term also does not refer to or exclude post expression modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring. The term "domain," or "polypeptide domain" refers to that sequence of a polypeptide that folds into a single globular region in its native conformation, and that may exhibit discrete binding or functional properties. As used herein, the term "fusion protein" refers to a hybrid protein expressed by a nucleic acid molecule comprising nucleotide sequences of at least two genes into a protein. For example, a fusion protein can comprise at least part of anti-Langerin antibody or binding fragment thereof fused with one or more antigen and/or one or more linkers if more than one antigen is fused with the antibody or fragment thereof.

A polypeptide or amino acid sequence "derived from" a designated nucleic acid sequence refers to a polypeptide having an amino acid sequence identical to that of a polypeptide encoded in the sequence, or a portion thereof wherein the portion consists of at least 3-5 amino acids, preferably at least 4-7 amino acids, more preferably at least 8-10 amino acids, and even more preferably at least 11-15 amino acids, or which is immunologically identifiable with a polypeptide encoded in the sequence. This terminology also includes a polypeptide expressed from a designated nucleic acid sequence.

As used herein, "pharmaceutically acceptable carrier" refers to any material that when combined with an immunoglobulin (Ig) fusion protein of the present invention allows the Ig to retain biological activity and is generally non-reactive with the subject's immune system. Examples include, but are not limited to, standard pharmaceutical carriers such as a phosphate buffered saline solution, water, emulsions such as an oil/water emulsion, and various types of wetting agents. Certain diluents may be used with the present invention, e.g., for aerosol or parenteral administration, that may be phosphate buffered saline or normal (0.85%) saline.

The invention provides a Langerin binding antibody (15B10) that comprises at least one immunoglobulin light chain variable domain (VL) which comprises the amino acid and nucleic acid sequence encoding: ASISCRSSQSLVH-SNGNTYLHWYLQKPGQSPKLLIYKVSN-RFSGVPDRFSGSGSGTNFTLKISRVEAEDLGLYFCS (SEQ ID NO.: 45); or and direct equivalent thereof.

Accordingly the invention provides a Langerin binding antibody (15B10) that comprises an antigen binding site comprising at least one immunoglobulin heavy chain variable domain (VH) which comprises the amino acid and nucleic acid sequence encoding: SVKMSCKASGYTFT-DYVISWVKQRTGQGLEWIGDIYPGSGYS-FYNENFKGKATLTADKSSTTAYMQLSS-LTSEDSAVYFCA (SEQ ID NO.: 46); and direct equivalents thereof.

The invention provides a Langerin binding antibody (2G3) that comprises at least one immunoglobulin light chain variable domain (VL) which comprises the amino acid and nucleic acid sequence encoding: VTLTCRSSTGAVTTSN-YANWVQEKPDHLFTGLIGGTNNRVSGV-PARFSGSLIGDKAALTITGAQTEDEAIYFCA (SEQ ID NO.: 47); or and direct equivalent thereof.

Accordingly the invention provides a Langerin binding antibody (2G3) that comprises an antigen binding site comprising at least one immunoglobulin heavy chain variable domain (VH) which comprises the amino acid and nucleic acid sequence encoding: SLKLSCAASGLTFNIYAMN-WVRQAPGKGLEWVARIRNKSNNYATYY-ADSVKDRFTISRDDSQSLLYLQMNNLKTEDTAMYYC (SEQ ID NO.: 48); and direct equivalents thereof.

In one aspect the invention provides a single domain Langerin antibody comprising an isolated immunoglobulin light chain comprising a heavy chain variable domain (VL) as defined above. In another aspect the invention provides a single domain Langerin binding molecule comprising an isolated immunoglobulin heavy chain comprising a heavy chain variable domain (VH) as defined above.

In another aspect the invention also provides a Langerin binding antibody comprising a light chain (VL) variable domains in which the Langerin binding antibody comprises at least one antigen binding site comprising: an antibody light chain variable domain (VL) which comprises in sequence hypervariable regions obtained from the amino acid and nucleic acid sequences encoding: ASISCRSSQSLVHSNGNTYLHWYLQKPGQSPKLLIYKVSNRFSGVPDRFSGSGSGTNFTLKISRVEAEDLGLYFCS (SEQ ID NO.: 45); or VTLTCRSSTGAVTTSNYANWVQEKPDHLFTGLIGGTNNRVSGVPARFSGSLIGDKAALTITGAQTEDEAIYFCA (SEQ ID NO.: 47); and direct equivalents thereof.

In another aspect the invention also provides a Langerin binding antibody comprising, the amino acid and nucleic acid sequences of heavy chain variable domain (VH) which comprises in sequence hypervariable regions obtained from: SVKMSCKASGYTFTDYVISWVKQRTGQGLEWIGDIYPGSGYSFYNENFKGKATLTADKSSTTAYMQLSSLTSEDSAVYFCA (SEQ ID NO.: 46); or SLKLSCAASGLTFNIYAMNWVRQAPGKGLEWVARIRNKSNNYATYYADSVKDRFTISRDDSQSLLYLQMNNLKTEDTAMYYC (SEQ ID NO.: 48); and direct equivalents thereof.

Unless otherwise indicated, any polypeptide chain is herein described as having an amino acid sequence starting at the N-terminal end and ending at the C-terminal end. When the antigen binding site comprises both the VH and VL domains, these may be located on the same polypeptide molecule or, preferably, each domain may be on a different chain, the VH domain being part of an immunoglobulin heavy chain or binding fragment thereof and the VL being part of an immunoglobulin light chain or binding fragment thereof.

As used herein, the term "Langerin binding molecule" or "Langerin binding antibody" refer to any molecule capable of binding to the Langerin antigen either alone or associated with other molecules having one or more the VL and VH CDRs taught herein, in some cases 2, 3, 4, 5, or all 6 CDRs. The binding reaction may be shown by standard methods (qualitative assays) including, for example, a bioassay for determining by blocking the binding of other molecules to Langerin or any kind of binding or activity assays (e.g., activation, reduction or modulation of an immune response), with reference to a negative control test in which an antibody of unrelated specificity but of the same isotype, e.g., an anti-CD25 or anti-CD80 antibody, is used.

The present invention may also be made into a single chain antibody having the variable domains of the heavy and light chains of an antibody covalently bound by a peptide linker usually including from 10 to 30 amino acids, preferably from 15 to 25 amino acids. Therefore, such a structure does not include the constant part of the heavy and light chains and it is believed that the small peptide spacer should be less antigenic than a whole constant part.

As used herein, the term "chimeric antibody" refers to an antibody in which the constant regions of heavy or light chains or both are of human origin while the variable domains of both heavy and light chains are of non-human (e.g., mouse, hamster or rat) origin or of human origin but derived from a different human antibody.

As used herein, the term "CDR-grafted antibody" refers to an antibody in which the hypervariable complementarity determining regions (CDRs) are derived from a donor antibody, such as a non-human (e.g., mouse) antibody or a different human antibody, while all or substantially all the other parts of the immunoglobulin (e.g., the conserved regions of the variable domains, i.e., framework regions), are derived from an acceptor antibody (in the case of a humanized antibody—an antibody of human origin). A CDR-grafted antibody may include a few amino acids of the donor sequence in the framework regions, for instance in the parts of the framework regions adjacent to the hypervariable regions.

As used herein, the term "human antibody" refers to an antibody in which the constant and variable regions of both the heavy and light chains are all of human origin, or substantially identical to sequences of human origin, not necessarily from the same antibody and includes antibodies produced by mice in which the mouse, hamster or rat immunoglobulin variable and constant part genes have been replaced by their human counterparts, e.g. as described in general terms in EP 0546073 B1, U.S. Pat. No. 5,545,806, U.S. Pat. No. 5,569,825, U.S. Pat. No. 5,625,126, U.S. Pat. No. 5,633,425, U.S. Pat. No. 5,661,016, U.S. Pat. No. 5,770,429, EP Patent No. 0 438474 B1 and EP Patent No. 0 463151 B1, relevant portions incorporated herein by reference.

The Langerin binding antibodies of the invention include humanized antibodies that comprise the CDRs obtained from the anti-Langerin 15B10 or 2G3 antibody. One example of a chimeric antibody includes the variable domains of both heavy and light chains are of human origin, for instance those of the anti-Langerin 15B10 or 2G3 antibody. The constant region domains preferably also comprise suitable human constant region domains, for instance as described in "Sequences of Proteins of Immunological Interest", Kabat E. A. et al, US Department of Health and Human Services, Public Health Service, National Institute of Health.

Hypervariable regions may be associated with any kind of framework regions, e.g., of human origin. Suitable framework regions were described Kabat E. A. One heavy chain framework is a heavy chain framework, for instance those of the anti-Langerin 15B10 or 2G3 antibody, includes sequences for the light chain framework regions: FR1L, FR2L, FR3L and FR4L regions. In a similar manner, the anti-Langerin 15B10 or 2G3 heavy chain framework that includes the sequence of FR1H, FR2H, FR3H and FR4H regions. The CDRs may be added to a human antibody framework, such as those described in U.S. Pat. No. 7,456,260, issued to Rybak, et al., which teach new human variable chain framework regions and humanized antibodies comprising the framework regions, relevant portions and framework sequences incorporated herein by reference. To accomplish the engraftment at a genetic level, the present invention also includes the underlying nucleic acid sequences for the VL AND VH regions as well as the complete antibodies and the humanized versions thereof. The nucleic acid sequences of the present invention include the anti-Langerin antibody light and the heavy chains, respectively, as well as those nucleic acid sequences that include variable codon usage for the same amino acid sequences and conservative variations thereof having 85, 90, 95 or 100% sequence identity at the nucleic or amino acid level. Likewise, the CDRs may have 85, 90, 95 or 100% sequence identity at the nucleic or amino acid level, individually, in groups or 2, 3, 4 or 5 or all together.

Monoclonal antibodies raised against a protein naturally found in all humans are typically developed in a non-human system e.g. in mice, and as such are typically non-human proteins. As a direct consequence of this, a xenogenic antibody as produced by a hybridoma, when administered to humans, elicits an undesirable immune response that is predominantly mediated by the constant part of the xenogenic immunoglobulin. Xenogeneic antibodies tend to elicit a host immune response, thereby limiting the use of such antibodies as they cannot be administered over a prolonged period of time. Therefore, it is particularly useful to use single chain, single domain, chimeric, CDR-grafted, or especially human antibodies that are not likely to elicit a substantial allogenic response when administered to humans. The present invention includes antibodies with minor changes in an amino acid sequence such as deletion, addition or substitution of one, a few or even several amino acids which are merely allelic forms of the original protein having substantially identical properties.

The inhibition of the binding of Langerin to its receptor may be conveniently tested in various assays including such assays are described hereinafter in the text. By the term "to the same extent" is meant that the reference and the equivalent molecules exhibit, on a statistical basis, essentially identical Langerin binding inhibition curves in one of the assays referred to above. For example, the assay used may be an assay of competitive inhibition of binding of Langerin by the binding molecules of the invention.

Generally, the human anti-Langerin antibody comprises at least: (a) one light chain which comprises a variable domain having an amino acid sequence substantially identical to the 15B10 or 2G3 antibody starting with the amino acid at position 1 and ending with the amino acid at position 107 and the constant part of a human light chain; and (b) one heavy chain which comprises a variable domain having an amino acid sequence substantially identical to the 15B10 or 2G3 antibody and the constant part of a human heavy chain. The constant part of a human heavy chain may be of the γ1, γ2, γ3, μ, β2, or δ or ϵ type, preferably of the γ-type, whereas the constant part of a human light chain may be of the κ or λ type (which includes the λ1, λ2 and λ3 subtypes) but is preferably of the κ type. The amino acid sequences of the general locations of the variable and constant domains are well known in the art and generally follow the Kabat nomenclature.

A Langerin binding molecule of the invention may be produced by recombinant DNA techniques. In view of this, one or more DNA molecules encoding the binding molecule must be constructed, placed under appropriate control sequences and transferred into a suitable host organism for expression.

In a very general manner, there are accordingly provided: (i) DNA molecules encoding a single domain Langerin binding molecule of the invention, a single chain Langerin binding molecule of the invention, a heavy or light chain or binding fragments thereof of a Langerin binding molecule of the invention; and (ii) the use of the DNA molecules of the invention for the production of a Langerin binding molecule of the invention by recombinant methods.

The present state of the art is such that the skilled worker in the art can synthesize the DNA molecules of the invention given the information provided herein, i.e., the amino acid sequences of the hypervariable regions and the DNA sequences coding for them. A method for constructing a variable domain gene is for example described in EPA 239 400, relevant portions incorporated herein by reference. Briefly, a gene encoding a variable domain of a MAb is cloned. The DNA segments encoding the framework and hypervariable regions are determined and the DNA segments encoding the hypervariable regions are removed so that the DNA segments encoding the framework regions are fused together with suitable restriction sites at the junctions. The restriction sites may be generated at the appropriate positions by mutagenesis of the DNA molecule by standard procedures. Double stranded synthetic CDR cassettes are prepared by DNA synthesis according to the sequences given in for 15B10 or 2G3 (amino acid and nucleic acid sequences, respectively). These cassettes are often provided with sticky ends so that they can be ligated at the junctions of the framework.

It is not necessary to have access to the mRNA from a producing hybridoma cell line in order to obtain a DNA construct coding for the Langerin binding molecules of the invention. For example, PCT application WO 90/07861 gives full instructions for the production of an antibody by recombinant DNA techniques given only written information as to the nucleotide sequence of the gene, relevant portions incorporated herein by reference. Briefly, the method comprises the synthesis of a number of oligonucleotides, their amplification by the PCR method, and their splicing to give the desired DNA sequence.

Expression vectors comprising a suitable promoter or genes encoding heavy and light chain constant parts are publicly available. Thus, once a DNA molecule of the invention is prepared it may be conveniently transferred in an appropriate expression vector. DNA molecules encoding single chain antibodies may also be prepared by standard methods, for example, as described in WO 88/1649. In view of the foregoing, no hybridoma or cell line deposit is necessary to comply with the criteria of sufficiency of description.

For example, first and second DNA constructs are made that bind specifically to Langerin. Briefly, a first DNA construct encodes a light chain of an antibody, CDRs or binding fragments thereof and comprises a) a first part which encodes a variable domain comprising alternatively framework and hypervariable regions, the hypervariable regions being in sequence CDR1L, CDR2L and CDR3L the amino acid sequences of which are found in SEQ ID NOs. 45-48; this first part starting with a codon encoding the first amino acid of the variable domain and ending with a codon encoding the last amino acid of the variable domain, and b) a second part encoding a light chain constant part or binding fragment thereof which starts with a codon encoding the first amino acid of the constant part of the heavy chain and ends with a codon encoding the last amino acid of the constant part or binding fragment thereof, followed by a stop codon.

The first part encodes a variable domain having an amino acid sequence substantially identical to the amino acid sequences of 15B10 or 2G3. A second part encodes the constant part of a human heavy chain, more preferably the constant part of the human γ1 chain. This second part may be a DNA fragment of genomic origin (comprising introns) or a cDNA fragment (without introns).

The second DNA construct encodes a heavy chain or binding fragment thereof and comprises a) a first part which encodes a variable domain comprising alternatively framework and hypervariable regions; the hypervariable regions being CDR1H and optionally CDR2H and CDR3H, the amino acid sequences of 15B10 or 2G3; this first part starting with a codon encoding the first amino acid of the variable domain and ending with a codon encoding the last amino acid of the variable domain, and b) a second part encoding a heavy chain constant part or binding fragment thereof which starts with a codon encoding the first amino acid of the constant part of the light chain and ends with a codon encoding the last amino acid of the constant part or binding fragment thereof followed by a stop codon.

The first part encodes a variable domain having an amino acid sequence substantially identical to the amino acid sequence of 15B10 or 2G3. The first part has the nucleotide sequence of the 15B10 or 2G3 antibodies starting with the nucleotide at position 1 and ending with the nucleotide at position 321. Also preferably the second part encodes the constant part of a human light chain, more preferably the constant part of the human κ chain.

The invention also includes Langerin binding molecules in which one or more of the residues of CDR1L, CDR2L, CDR3L, CDR1H, CDR2H or CDR3H or the frameworks, typically only a few (e.g. FR1-4L or H), are changed from the residues of the 15B10 or 2G3 antibodies; by, e.g., site directed mutagenesis of the corresponding DNA sequences. The invention includes the DNA sequences coding for such changed Langerin binding molecules. In particular the invention includes a Langerin binding molecules in which one or more residues of CDR1L, CDR2L and/or CDR3L have been changed from the residues of the 15B10 or 2G3 antibodies and one or more residues of CDR1H, CDR2H and/or CDR3H have been changed from the residues of the 15B10 or 2G3 antibodies.

Each of the DNA constructs are placed under the control of suitable control sequences, in particular under the control of a suitable promoter. Any kind of promoter may be used, provided that it is adapted to the host organism in which the DNA constructs will be transferred for expression. However, if expression is to take place in a mammalian cell, an immunoglobulin gene promoter may be used in B cells. The first and second parts may be separated by an intron, and, an enhancer may be conveniently located in the intron between the first and second parts. The presence of such an enhancer that is transcribed but not translated, may assist in efficient transcription. In particular embodiments the first and second DNA constructs comprise the enhancer of, e.g., a heavy chain human gene.

The antibody or binding fragments thereof can be isolated, purified, and stored using any method known in the art. The binding fragments retain the specific binding activity of the intact antibody, and can be used for any application that employs the intact antibody (e.g., therapeutics, diagnostic assays, competitive binding assays, etc.).

In another aspect, the invention provides an antibody or binding fragment generated by the above-described method, and may further include a half-life extending vehicle, such as those known to those skilled in the art. Such vehicles include, but are not limited to, linear polymers (e.g., polyethylene glycol (PEG), polylysine, dextran, etc.); branched-chain polymers (See, e.g., U.S. Pat. No. 4,289,872; U.S. Pat. No. 5,229,490; WO 93/21259); a lipid; a cholesterol group (such as a steroid); a carbohydrate or polysaccharide; or any natural or synthetic protein, polypeptide or peptide. Additionally, it will be appreciated that one or more Fc regions, can also be employed with the invention to increase half-life. It will be appreciated that the vehicle can be linked to the antibody or binding fragment by way of various techniques known in the art including, for example, covalent linkage.

The desired antibody may be produced in an animal as an ascites, in cell culture or in a transgenic animal. A suitable transgenic animal may be obtained according to standard methods that include micro injecting into eggs the first and second DNA constructs placed under suitable control sequences transferring the so prepared eggs into appropriate pseudo-pregnant females and selecting a descendant expressing the desired antibody.

The invention also provides an expression vector able to replicate in a prokaryotic or eukaryotic cell line, which comprises at least one of the DNA constructs above described. Each expression vector containing a DNA construct is then transferred into a suitable host organism. When the DNA constructs are separately inserted on two expression vectors, they may be transferred separately, i.e. one type of vector per cell, or co-transferred, this latter possibility being preferred. A suitable host organism may be a bacterium, a yeast or a mammalian cell line, this latter being preferred. More preferably, the mammalian cell line is of lymphoid origin, e.g., a myeloma, hybridoma or a normal immortalized B-cell, which conveniently does not express any endogenous antibody heavy or light chain.

When the antibody chains are produced in a cell culture, the DNA constructs must first be inserted into either a single expression vector or into two separate but compatible expression vectors, the latter possibility being preferred. For expression in mammalian cells it is preferred that the coding sequence of the Langerin binding molecule is integrated into the host cell DNA within a locus which permits or favors high level expression of the Langerin binding molecule.

In a further aspect of the invention there is provided a process for the product of a Langerin binding molecule that comprises: (i) culturing an organism which is transformed with an expression vector as defined above; and (ii) recovering the Langerin binding molecule from the culture.

In accordance with the present invention it has been found that the anti-Langerin antibodies 15B10, 2G3, 91E7, 37C1, or 4C7 and humanized derivatives thereof, appear to have binding specificity for the antigenic epitope of human Langerin. It is therefore most surprising that antibodies to this epitope, e.g. the anti-Langerin 15B10, 2G3, 91E7, 37C1, or 4C7 and humanized derivatives thereof, are capable of delivering antigen efficiently into dendritic cells (DCs). Antibodies, in particular chimeric and CDR-grafted antibodies and especially human antibodies, which have binding specificity for the antigenic epitope of mature human Langerin; and use of such antibodies for DC antigen loading are novel and are included within the scope of the present invention.

To use the anti-Langerin antibody of the present invention for treatment indications, the appropriate dosage will, of course, vary depending upon, for example, the antibody disclosed herein to be employed, the host, the mode of administration and the nature and severity of the condition being treated. However, in prophylactic use, satisfactory results are generally found at dosages from about 0.05 mg to about 10 mg per kilogram body weight more usually from about 0.1 mg to about 5 mg per kilogram body weight. The frequency of dosing for prophylactic uses will normally be in the range from about once per week up to about once every 3 months, more usually in the range from about once every 2 weeks up to about once every 10 weeks, e.g., once every 4 to 8 weeks. The anti-Langerin antibody of the present can be administered parenterally, intravenously, e.g., into the antecubital or other peripheral vein, intramuscularly, or subcutaneously.

Pharmaceutical compositions of the invention may be manufactured in conventional manner, e.g., in a lyophilized form. For immediate administration it is dissolved in a suitable aqueous carrier, for example sterile water for injection or sterile buffered physiological saline. If it is considered desirable to make up a solution of larger volume for administration by infusion rather as a bolus injection, it is advantageous to incorporate human serum albumin or the patient's own heparinized blood into the saline at the time of formulation. The presence of an excess of such physiologically inert protein prevents loss of antibody by adsorption onto the walls of the container and tubing used with the infusion solution. If albumin is used, a suitable concentration is from 0.5 to 4.5% by weight of the saline solution.

One embodiment of the present invention provides an immunoconjugate comprising a humanized antibody of the invention, e.g., a humanized anti-Langerin antibody, linked to one or more effector molecules, antigen(s) and/or a detectable label(s). Preferably, the effector molecule is a therapeutic molecule such as, for example, one or more peptides that comprise one or more T cell epitopes, a toxin, a small molecule, a cytokine or a chemokine, an enzyme, or a radiolabel.

Exemplary toxins include, but are not limited to, *Pseudomonas* exotoxin or diphtheria toxin. Examples of small molecules include, but are not limited to, chemotherapeutic compounds such as taxol, doxorubicin, etoposide, and bleiomycin. Exemplary cytokines include, but are not limited to, IL-1, IL-2, IL-4, IL-5, IL-6, and IL-12, IL-17, and IL-25. Exemplary enzymes include, but are not limited to, RNAses, DNAses, proteases, kinases, and caspases. Exemplary radioisotopes include, but are not limited to, 32P and 125I.

As used herein, the term "epitope" refers to a molecule or substance capable of stimulating an immune response. In one example, epitopes include but are not limited to a polypeptide and a nucleic acid encoding a polypeptide, wherein expression of the nucleic acid into a polypeptide is capable of stimulating an immune response when the polypeptide is processed and presented on a Major Histocompatibility Complex (MHC) molecule. Generally, epitopes include peptides presented on the surface of cells non-covalently bound to the binding groove of Class I or Class II MHC, such that they can interact with T cell receptors and the respective T cell accessory molecules.

Proteolytic Processing of Antigens. Epitopes that are displayed by MHC on antigen presenting cells are cleavage peptides or products of larger peptide or protein antigen precursors. For MHC I epitopes, protein antigens are often digested by proteasomes resident in the cell. Intracellular proteasomal digestion produces peptide fragments of about 3 to 23 amino acids in length that are then loaded onto the MHC protein. Additional proteolytic activities within the cell, or in the extracellular milieu, can trim and process these fragments further. Processing of MHC Class II epitopes generally occurs via intracellular proteases from the lysosomal/endosomal compartment. The present invention includes, in one embodiment, pre-processed peptides that are attached to the anti-Langerin antibody (or binding fragment thereof) that directs the peptides against which an enhanced immune response is sought directly to antigen presenting cells.

To identify epitopes potentially effective as immunogenic compounds, predictions of MHC binding alone are useful but often insufficient. The present invention includes methods for specifically identifying the epitopes within antigens most likely to lead to the immune response sought for the specific sources of antigen presenting cells and responder T cells.

The present invention allows for a rapid and easy assay for the identification of those epitopes that are most likely to produce the desired immune response using the patient's own antigen presenting cells and T cell repertoire. The compositions and methods of the present invention are applicable to any protein sequence, allowing the user to identify the epitopes that are capable of binding to MHC and are properly presented to T cells that will respond to the antigen. Accordingly, the invention is not limited to any particular target or medical condition, but instead encompasses and MHC epitope(s) from any useful source.

As used herein, the term "veneered" refers to a humanized antibody framework onto which antigen-binding sites or CDRs obtained from non-human antibodies (e.g., mouse, rat or hamster), are placed into human heavy and light chain conserved structural framework regions (FRs), for example, in a light chain or heavy chain polynucleotide to "graft" the specificity of the non-human antibody into a human framework from, e.g., SEQ ID NOS: 45-48 or the nucleic acids that encode those sequences, as will be readily apparent to the skilled artisan. The polynucleotide expression vector or vectors that express the veneered antibodies can be transfected mammalian cells for the expression of recombinant human antibodies which exhibit the antigen specificity of the non-human antibody and will undergo posttranslational modifications that will enhance their expression, stability, solubility, or combinations thereof.

Antigens.

Examples of viral antigens for use with the present invention include, but are not limited to, e.g., HIV, HCV, CMV, adenoviruses, retroviruses, picornaviruses, etc. Non-limiting example of retroviral antigens such as retroviral antigens from the human immunodeficiency virus (HIV) antigens such as gene products of the gag, pol, and env genes, the Nef protein, reverse transcriptase, and other HIV components; hepatitis viral antigens such as the S, M, and L proteins of hepatitis B virus, the pre-S antigen of hepatitis B virus, and other hepatitis, e.g., hepatitis A, B, and C, viral components such as hepatitis C viral RNA; influenza viral antigens such as hemagglutinin and neuraminidase and other influenza viral components; measles viral antigens such as the measles virus fusion protein and other measles virus components; rubella viral antigens such as proteins E1 and E2 and other rubella virus components; rotaviral antigens such as VP7sc and other rotaviral components; cytomegaloviral antigens such as envelope glycoprotein B and other cytomegaloviral antigen components; respiratory syncytial viral antigens such as the RSV fusion protein, the M2 protein and other respiratory syncytial viral antigen components; herpes simplex viral antigens such as immediate early proteins, glycoprotein D, and other herpes simplex viral antigen components; varicella zoster viral antigens such as gpI, gpII, and other varicella zoster viral antigen components; Japanese encephalitis viral antigens such as proteins E, M-E, M-E-NS1, NS1, NS1-NS2A, 80% E, and other Japanese encephalitis viral antigen components; rabies viral antigens such as rabies glycoprotein, rabies nucleoprotein and other rabies viral antigen components. See Fundamental Virology, Second Edition, eds. Fields, B. N. and Knipe, D. M. (Raven Press, New York, 1991) for additional examples of viral antigens. The at least one viral antigen may be peptides from an adenovirus, retrovirus, picornavirus, herpesvirus, rotaviruses, hantaviruses, coronavirus, togavirus, flavirvirus, rhabdovirus, paramyxovirus, orthomyxovirus, bunyavirus, arenavirus, reovirus, papilomavirus, parvovirus, poxvirus, hepadnavirus, or spongiform virus. In certain specific, non-limiting examples, the at least one viral antigen are peptides obtained from at least one of HIV, CMV, hepatitis A, B, and C, influenza, measles, polio, smallpox, rubella; respiratory syncytial, herpes simplex, varicella zoster, Epstein-Barr, Japanese encephalitis, rabies, flu, and/or cold viruses.

In one aspect, the one or more of the antigenic peptides are selected from at least one of: Nef (66-97): VGFPVTPQVPL-RPMTYKAAVDLSHFLKEKGGL (SEQ ID NO.: 31); Nef (116-145): HTQGYFPDWQNYTPGPGVRYPLTFGW-LYKL (SEQ ID NO.: 32); Gag p17 (17-35): EKIRLRPG-GKKKYKLKHIV (SEQ ID NO.: 33); Gag p17-p24 (253-284): NPPIPVGEIYKRWIILGLNKIVRMYSPTSILD (SEQ ID NO.: 34); or Pol 325-355 (RT 158-188) is: AIFQSSMTKILEPFRKQNPDIVIYQYMDDLY (SEQ ID NO.: 35). In one aspect, the fusion protein peptides are separated by one or more linkers selected from:

SSVSPTTSVHPTPTPTSVPPTPTKSSP;                    (SEQ ID NO.: 39)

PTSTPADSSTITPTATPTATPTIKG;                      (SEQ ID NO.: 40)

TVTPTATATPSAIVTTITPTATTKP;                      (SEQ ID NO.: 41)
or

TNGSITVAATAPTVTPTVNATPSAA.                      (SEQ ID NO.: 42)

Antigenic targets that may be delivered using the anti-Langerin-antigen vaccines of the present invention include genes encoding antigens such as viral antigens, bacterial antigens, fungal antigens or parasitic antigens. Pathogens include trypanosomes, tapeworms, roundworms, helminthes, malaria. Tumor markers, such as fetal antigen or prostate specific antigen, may be targeted in this manner. Other examples include: HIV env proteins and hepatitis B surface antigen. Administration of a vector according to the present invention for vaccination purposes would require that the vector-associated antigens be sufficiently non-immunogenic to enable long-term expression of the transgene, for which a strong immune response would be desired. In some cases, vaccination of an individual may only be required infrequently, such as yearly or biennially, and provide long-term immunologic protection against the infectious agent. Specific examples of organisms, allergens and nucleic and amino sequences for use in vectors and ultimately as antigens with the present invention may be found in U.S. Pat. No. 6,541, 011, relevant portions incorporated herein by reference, in particular, the tables that match organisms and specific sequences that may be used with the present invention.

Bacterial antigens for use with the anti-Langerin-antigen vaccines disclosed herein include, but are not limited to, e.g., bacterial antigens such as pertussis toxin, filamentous hemagglutinin, pertactin, FIM2, FIM3, adenylate cyclase and other pertussis bacterial antigen components; diptheria bacterial antigens such as diptheria toxin or toxoid and other diptheria bacterial antigen components; tetanus bacterial antigens such as tetanus toxin or toxoid and other tetanus bacterial antigen components; streptococcal bacterial antigens such as M proteins and other streptococcal bacterial antigen components; gram-negative bacilli bacterial antigens such as lipopolysaccharides and other gram-negative bacterial antigen components, *Mycobacterium tuberculosis* bacterial antigens such as mycolic acid, heat shock protein 65 (HSP65), the 30 kDa major secreted protein, antigen 85A and other mycobacterial antigen components; *Helicobacter pylori* bacterial antigen components; pneumococcal bacterial antigens such as pneumolysin, pneumococcal capsular polysaccharides and other pneumococcal bacterial antigen components; *haemophilus influenza* bacterial antigens such as capsular polysaccharides and other *haemophilus influenza* bacterial antigen components; anthrax bacterial antigens such as anthrax protective antigen and other anthrax bacterial antigen components; rickettsiae bacterial antigens such as rompA and other rickettsiae bacterial antigen component. Also included with the bacterial antigens described herein are any other bacterial, mycobacterial, mycoplasmal, rickettsial, or chlamydial antigens. Partial or whole pathogens may also be: *haemophilus influenza; Plasmodium falciparum; neisseria meningitidis; streptococcus pneumoniae; neisseria gonorrhoeae; salmonella* serotype *typhi; shigella; vibrio cholerae*; Dengue Fever; Encephalitides; Japanese Encephalitis; lyme disease; *Yersinia pestis*; west nile virus; yellow fever; tularemia; hepatitis (viral; bacterial); RSV (respiratory syncytial virus); HPIV 1 and HPIV 3; adenovirus; small pox; allergies and cancers.

Fungal antigens for use with compositions and methods of the invention include, but are not limited to, e.g., candida fungal antigen components; histoplasma fungal antigens such as heat shock protein 60 (HSP60) and other histoplasma fungal antigen components; cryptococcal fungal antigens such as capsular polysaccharides and other cryptococcal fungal antigen components; coccidiodes fungal antigens such as spherule antigens and other coccidiodes fungal antigen components; and tinea fungal antigens such as trichophytin and other coccidiodes fungal antigen components.

Examples of protozoal and other parasitic antigens include, but are not limited to, e.g., *plasmodium falciparum* antigens such as merozoite surface antigens, sporozoite surface antigens, circumsporozoite antigens, gametocyte/gamete surface antigens, blood-stage antigen pf 155/RESA and other plasmodial antigen components; toxoplasma antigens such as SAG-1, p30 and other toxoplasmal antigen components; schistosomae antigens such as glutathione-S-transferase, paramyosin, and other schistosomal antigen components; *leishmania major* and other leishmaniae antigens such as gp63, lipophosphoglycan and its associated protein and other leishmanial antigen components; and *trypanosoma cruzi* antigens such as the 75-77 kDa antigen, the 56 kDa antigen and other trypanosomal antigen components.

Antigen that can be targeted using the anti-Langerin-antigen vaccines of the present invention will generally be selected based on a number of factors, including: likelihood of internalization, level of immune cell specificity, type of immune cell targeted, level of immune cell maturity and/or activation and the like. In this embodiment, the antibodies may be mono- or bi-specific antibodies that include one anti-Langerin binding domain and one binding domain against a second antigen, e.g., cell surface markers for dendritic cells such as, MHC class I, MHC Class II, B7-2, CD18, CD29, CD31, CD43, CD44, CD45, CD54, CD58, CD83, CD86, CMRF-44, CMRF-56, DCIR and/or Dectin-1 and the like; while in some cases also having the absence of CD2, CD3, CD4, CD8, CD14, CD15, CD16, CD 19, CD20, CD56, and/or CD57. Examples of cell surface markers for antigen presenting cells include, but are not limited to, MHC class I, MHC Class I, CD45, B7-1, B7-2, IFN-γ receptor and IL-2 receptor, ICAM-1 and/or Fcγ receptor. Examples of cell surface markers for T cells include, but are not limited to, CD3, CD4, CD8, CD 14, CD20, CD11b, CD16, CD45 and HLA-DR.

Target antigens on cell surfaces for delivery include those characteristic of tumor antigens typically will be derived from the cell surface, cytoplasm, nucleus, organelles and the like of cells of tumor tissue. Examples of tumor targets for the antibody portion of the present invention include, without limitation, hematological cancers such as leukemias and lymphomas, neurological tumors such as astrocytomas or glioblastomas, melanoma, breast cancer, lung cancer, head and neck cancer, gastrointestinal tumors such as gastric or colon cancer, liver cancer, pancreatic cancer, genitourinary tumors such cervix, uterus, ovarian cancer, vaginal cancer, testicular cancer, prostate cancer or penile cancer, bone tumors, vascular tumors, or cancers of the lip, nasopharynx, pharynx and oral cavity, esophagus, rectum, gall bladder, biliary tree, larynx, lung and bronchus, bladder, kidney, brain and other parts of the nervous system, thyroid, Hodgkin's disease, non-Hodgkin's lymphoma, multiple myeloma and leukemia.

Examples of antigens that may be delivered alone or in combination to immune cells for antigen presentation using the present invention includes tumor proteins, e.g., mutated oncogenes; viral proteins associated with tumors; and tumor mucins and glycolipids. The antigens may be viral proteins associated with tumors would be those from the classes of viruses noted above. Certain antigens may be characteristic of tumors (one subset being proteins not usually expressed by a tumor precursor cell), or may be a protein that is normally expressed in a tumor precursor cell, but having a mutation characteristic of a tumor. Other antigens include mutant variant(s) of the normal protein having an altered activity or subcellular distribution, e.g., mutations of genes giving rise to tumor antigens.

Specific non-limiting examples of tumor antigens for use in an anti-Langerin-fusion protein vaccine include, e.g., CEA, prostate specific antigen (PSA), HER-2/neu, BAGE, GAGE, MAGE 1-4, 6 and 12, MUC (Mucin) (e.g., MUC-1, MUC-2, etc.), GM2 and GD2 gangliosides, ras, myc, tyrosinase, MART (melanoma antigen), Pmel 17 (gp100), GnT-V intron V sequence (N-acetylglucoaminyltransferase V intron V sequence), Prostate Ca psm, PRAME (melanoma antigen), β-catenin, MUM-1-B (melanoma ubiquitous mutated gene product), GAGE (melanoma antigen) 1, MAGE, BAGE (melanoma antigen) 2-10, c-ERB2 (Her2/neu), DAGE, EBNA (Epstein-Barr Virus nuclear antigen) 1-6, gp75, human papilloma virus (HPV) E6 and E7, p53, lung resistance protein (LRP), Bcl-2, Ki-67, Cyclin B1, gp100, Survivin, and NYESO-1.

In addition, the immunogenic molecule can be an autoantigen involved in the initiation and/or propagation of an autoimmune disease, the pathology of which is largely due to the activity of antibodies specific for a molecule expressed by the relevant target organ, tissue, or cells, e.g., SLE or MG. In such diseases, it can be desirable to direct an ongoing antibody-mediated (i.e., a Th2-type) immune response to the relevant autoantigen towards a cellular (i.e., a Th1-type) immune response. Alternatively, it can be desirable to prevent onset of or decrease the level of a Th2 response to the autoantigen in a subject not having, but who is suspected of being susceptible to, the relevant autoimmune disease by prophylactically inducing a Th1 response to the appropriate autoantigen. Autoantigens of interest include, without limitation: (a) with respect to SLE, the Smith protein, RNP ribonucleoprotein, and the SS-A and SS-B proteins; and (b) with respect to MG, the acetylcholine receptor. Examples of other miscellaneous antigens involved in one or more types of autoimmune response include, e.g., endogenous hormones such as luteinizing hormone, follicular stimulating hormone, testosterone, growth hormone, prolactin, and other hormones.

Antigens involved in autoimmune diseases, allergy, and graft rejection can be used in the compositions and methods of the invention. For example, an antigen involved in any one or more of the following autoimmune diseases or disorders can be used in the present invention: diabetes, diabetes mellitus, arthritis (including rheumatoid arthritis, juvenile rheumatoid arthritis, osteoarthritis, psoriatic arthritis), multiple sclerosis, myasthenia gravis, systemic lupus erythematosis, autoimmune thyroiditis, dermatitis (including atopic dermatitis and eczematous dermatitis), psoriasis, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Crohn's disease, Graves ophthalmopathy, sarcoidosis, primary biliary cirrhosis, uveitis posterior, and interstitial lung fibrosis. Examples of antigens involved in autoimmune disease include glutamic acid decarboxylase 65 (GAD 65), native DNA, myelin basic protein, myelin proteolipid protein, acetylcholine receptor components, thyroglobulin, and the thyroid stimulating hormone (TSH) receptor.

Examples of antigens involved in allergy include pollen antigens such as Japanese cedar pollen antigens, ragweed pollen antigens, rye grass pollen antigens, animal derived antigens such as dust mite antigens and feline antigens, histocompatiblity antigens, and penicillin and other therapeutic drugs. Examples of antigens involved in graft rejection include antigenic components of the graft to be transplanted into the graft recipient such as heart, lung, liver, pancreas, kidney, and neural graft components. The antigen may be an altered peptide ligand useful in treating an autoimmune disease.

It will be appreciated by those of skill in the art that the sequence of any protein effector molecule may be altered in a manner that does not substantially affect the functional advantages of the effector protein. For example, glycine and alanine are typically considered to be interchangeable as are aspartic acid and glutamic acid and asparagine and glutamine. One of skill in the art will recognize that many different variations of effector sequences will encode effectors with roughly the same activity as the native effector. The effector molecule and the antibody may be conjugated by chemical or by recombinant means as described above. Chemical modifications include, for example, derivitization for the purpose of linking the effector molecule and the antibody to each other, either directly or through a linking compound, by methods that are well known in the art of protein chemistry. Both covalent and noncovalent attachment methods may be used with the humanized antibodies of the present invention.

The procedure for attaching an effector molecule to an antibody will vary according to the chemical structure of the moiety to be attached to the antibody. Polypeptides typically contain a variety of functional groups; e.g., carboxylic acid (COOH), free amine (—$NH_2$) or sulfhydryl (—SH) groups, which are available for reaction with a suitable functional group on an antibody to result in the binding of the effector molecule. Alternatively, the antibody can be derivatized to expose or to attach additional reactive functional groups, e.g., by attachment of any of a number of linker molecules such as those available from Pierce Chemical Company, Rockford Ill.

The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (e.g., through a disulfide linkage to cysteine). However, in a preferred embodiment, the linkers will be joined to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages that are cleavable in the vicinity of the target site. Cleavage of the linker to release the effector molecule from the antibody may be prompted by enzymatic activity or conditions to which the immunoconjugate is subjected either inside the target cell or in the vicinity of the target site. When the target site is a tumor, a linker that is cleavable under conditions present at the tumor site (e.g. when exposed to tumor-associated enzymes or acidic pH) may be used.

Exemplary chemical modifications of the effector molecule and the antibody of the present invention also include derivitization with polyethylene glycol (PEG) to extend time of residence in the circulatory system and reduce immunogenicity, according to well known methods (See for example, Lisi, et al., Applied Biochem. 4:19 (1982); Beauchamp, et al., Anal Biochem. 131:25 (1982); and Goodson, et al., Bio/Technology 8:343 (1990)).

The present invention contemplates vaccines for use in both active and passive immunization embodiments. Immunogenic compositions, proposed to be suitable for use as a vaccine, may be prepared most readily directly from immunogenic T-cell stimulating peptides prepared in a manner disclosed herein. The final vaccination material is dialyzed extensively to remove undesired small molecular weight molecules and/or lyophilized for more ready formulation into a desired vehicle. In certain embodiment of the present invention, the compositions and methods of the present invention are used to manufacture a cellular vaccine, e.g., the antigen-delivering anti-Langerin binding portion of the antibody is used to direct the antigen(s) to an antigen presenting cell, which then "loads" the antigen onto MHC proteins for presentation. The cellular vaccine is, therefore, the antigen presenting cell that has been loaded using the compositions of the present invention to generate antigen-loaded antigen presenting cells.

When the vaccine is the anti-Langerin binding protein itself, e.g., a complete antibody or binding fragments thereof, then these "active ingredients" can be made into vaccines using methods understood in the art, e.g., U.S. Pat. Nos. 4,608,251; 4,601,903; 4,599,231; 4,599,230; and 4,578,770, relevant portions incorporated herein by reference. Typically, such vaccines are prepared as injectables, e.g., as liquid solutions or suspensions or solid forms suitable for re-suspension in liquid prior to injection. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants that enhance the effectiveness of the vaccines.

The vaccines are administered in a manner compatible with the dosage formulation, and in such amount as will be therapeutically effective and immunogenic. The quantity to be administered depends on the subject to be treated, including, e.g., the capacity of the individual's immune system to generate an immune response. Precise amounts of cells or active ingredient required to be administered depend on the judgment of the practitioner. However, suitable dosage ranges are of the order of a few thousand cells (to millions of cells) for cellular vaccines. For standard epitope or epitope delivery vaccines then the vaccine may be several hundred micrograms active ingredient per vaccination. Suitable regimes for initial administration and booster shots are also variable, but are typified by an initial administration followed by subsequent inoculations or other administrations.

The manner of application may vary widely, however, certain embodiments herein will most likely be delivered intravenously or at the site of a tumor or infection directly. Regardless, any of the conventional methods for administration of a vaccine are applicable. The dosage of the vaccine will depend on the route of administration and will vary according to the size of the host.

In many instances, it will be desirable to have multiple administrations of the vaccine, e.g., four to six vaccinations provided weekly or every other week. A normal vaccination regimen will often occur in two to twelve week intervals or from three to six week intervals. Periodic boosters at intervals of 1-5 years, usually three years, may be desirable to maintain protective levels of the immune response or upon a likelihood of a remission or re-infection. The course of the immunization may be followed by assays for, e.g., T cell activation, cytokine secretion or even antibody production, most commonly conducted in vitro. These immune response assays are well known and may be found in a wide variety of patents and as taught herein.

The vaccine of the present invention may be provided in one or more "unit doses" depending on whether the nucleic acid vectors are used, the final purified proteins, or the final vaccine form is used. Unit dose is defined as containing a predetermined-quantity of the therapeutic composition calculated to produce the desired responses in association with its administration, i.e., the appropriate route and treatment regimen. The quantity to be administered, and the particular route and formulation, are within the skill of those in the clinical arts. The subject to be treated may also be evaluated, in particular, the state of the subject's immune system and the protection desired. A unit dose need not be administered as a single injection but may include continuous infusion over a set period of time. Unit dose of the present invention may conveniently be described in terms of DNA/kg (or protein/Kg) body weight, with ranges between about 0.05, 0.10, 0.15, 0.20, 0.25, 0.5, 1, 10, 50, 100, 1,000 or more mg/DNA or protein/kg body weight are administered.

Likewise, the amount of anti-Langerin-antigen vaccine delivered can vary from about 0.2 to about 8.0 mg/kg body weight. Thus, in particular embodiments, 0.4 mg, 0.5 mg, 0.8 mg, 1.0 mg, 1.5 mg, 2.0 mg, 2.5 mg, 3.0 mg, 4.0 mg, 5.0 mg, 5.5 mg, 6.0 mg, 6.5 mg, 7.0 mg and 7.5 mg of the vaccine may be delivered to an individual in vivo. The dosage of vaccine to be administered depends to a great extent on the weight and physical condition of the subject being treated as well as the route of administration and the frequency of treatment. A pharmaceutical composition that includes a naked polynucleotide prebound to a liposomal or viral delivery vector may be administered in amounts ranging from 1 µg to 1 mg polynucleotide to 1 µg to 100 mg protein. Thus, particular compositions may include between about 1 µg, 5 µg, 10 µg, 20 µg, 30 µg, 40 µg, 50 µg, 60 µg, 70 µg, 80 µg, 100 µg, 150 µg, 200 µg, 250 µg, 500 µg, 600 µg, 700 µg, 800 µg, 900 µg or 1,000 µg polynucleotide or protein that is bound independently to 1 µg, 5 µg, 10 µg, 20 µg, 3.0 µg, 40 µg 50 µg, 60 µg, 70 µg, 80 µg, 100 µg, 150 µg, 200 µg, 250 µg, 500 µg, 600 µg, 700 µg, 800 µg, 900 µg, 1 mg, 1.5 mg, 5 mg, 10 mg, 20 mg, 30 mg, 40 mg, 50 mg, 60 mg, 70 mg, 80 mg, 90 mg or 100 mg vector.

Antibodies of the present invention may optionally be covalently or non-covalently linked to a detectable label. Detectable labels suitable for such use include any composition detectable by spectroscopic, photochemical, biochemical, immunochemical, electrical, optical or chemical methods. Useful labels in the present invention include magnetic beads (e.g. DYNABEADS™), fluorescent dyes (e.g., fluorescein isothiocyanate, Texas red, rhodamine, green fluorescent protein, and the like), radiolabels (e.g., $^{3}H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic (e.g. polystyrene, polypropylene, latex, etc.) beads.

Methods of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

The antibody and/or immunoconjugate compositions of this invention are particularly useful for parenteral administration, such as intravenous administration or administration into a body cavity. The compositions for administration will commonly comprise a solution of the antibody and/or immunoconjugate dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well-known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of fusion protein in these formulations can vary widely, and will be selected primarily based on fluid volumes, viscosities, body weight and the like in accordance with the particular mode of administration selected and the patient's needs.

Thus, a typical pharmaceutical immunoconjugate composition of the present invention for intravenous administration would be about 0.1 to 10 mg per patient per day. Dosages from 0.1 up to about 100 mg per patient per day may be used. Actual methods for preparing administrable compositions will be known or apparent to those skilled in the art and are described in more detail in such publications as REMINGTON'S PHARMACEUTICAL SCIENCE, 19TH ED., Mack Publishing Company, Easton, Pa. (1995).

The compositions of the present invention can be administered for therapeutic treatments. In therapeutic applications, compositions are administered to a patient suffering from a disease, in an amount sufficient to cure or at least partially arrest the disease and its complications. An amount adequate to accomplish this is defined as a "therapeutically effective dose." Amounts effective for this use will depend upon the severity of the disease and the general state of the patient's health. An effective amount of the compound is that which provides either subjective relief of a symptom(s) or an objectively identifiable improvement as noted by the clinician or other qualified observer.

Single or multiple administrations of the compositions are administered depending on the dosage and frequency as required and tolerated by the patient. In any event, the composition should provide a sufficient quantity of the proteins of this invention to effectively treat the patient. Preferably, the dosage is administered once but may be applied periodically until either a therapeutic result is achieved or until side effects warrant discontinuation of therapy. Generally, the dose is sufficient to treat or ameliorate symptoms or signs of disease without producing unacceptable toxicity to the patient.

Controlled release parenteral formulations of the immunoconjugate compositions of the present invention can be made as implants, oily injections, or as particulate systems. For a broad overview of protein delivery systems see, Banga, A. J., THERAPEUTIC PEPTIDES AND PROTEINS: FORMULATION, PROCESSING, AND DELIVERY SYSTEMS, Technomic Publishing Company, Inc., Lancaster, Pa., (1995) incorporated herein by reference. Particulate systems include microspheres, microparticles, microcapsules, nanocapsules, nanospheres, and nanoparticles. Microcapsules contain the therapeutic protein as a central core. In microspheres the therapeutic is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly.

Polymers can be used for ion-controlled release of immunoconjugate compositions of the present invention. Various degradable and non-degradable polymeric matrices for use in controlled drug delivery are known in the art (Langer, R., Accounts Chem. Res. 26:537-542 (1993)). For example, the block copolymer, poloxamer 407® exists as a viscous yet mobile liquid at low temperatures but forms a semisolid gel at body temperature, hydroxyapatite has been used as a microcarrier for controlled release of proteins, and/or liposomes may be used for controlled release as well as drug targeting of the lipid-capsulated drug. Numerous additional systems for controlled delivery of therapeutic proteins are known. See, e.g., U.S. Pat. Nos. 5,055,303, 5,188,837, 4,235,871, 4,501,728, 4,837,028 4,957,735 and 5,019,369, 5,055,303; 5,514,670; 5,413,797; 5,268,164; 5,004,697; 4,902,505; 5,506,206, 5,271,961; 5,254,342 and 5,534,496, relevant portions of each of which are incorporated herein by reference.

Among various uses of the immunoconjugates of the invention are included a variety of disease conditions caused by specific human cells that may be eliminated by the toxic action of the fusion protein. For example, for the humanized Anti-Langerin antibodies, e.g., 15B10 having ATCC Accession No. PTA-9852, 2G3 having ATCC Accession No. PTA-9853, 91E7, 37C1, or 4C7 and binding fragments thereof, disclosed herein. For example, one application for immunoconjugates is the treatment of malignant cells expressing Langerin. Exemplary malignant cells include those of chronic lymphocytic leukemia and hairy cell leukemia.

In another embodiment, this invention provides kits for the delivery of antigens, e.g., Langerin or an immunoreactive fragment thereof, conjugated or in the form of a fusion protein with one or more T cell or B cell epitopes. A "biological sample" as used herein is a sample of biological tissue or fluid that contains the antigen. Such samples include, but are not limited to, tissue from biopsy, blood, and blood cells (e.g., white cells). Preferably, the cells are lymphocytes, e.g., dendritic cells. Biological samples also include sections of tissues, such as frozen sections taken for histological purposes. A biological sample is typically obtained from a multicellular eukaryote, preferably a mammal such as rat, mouse, cow, dog, guinea pig, or rabbit, and more preferably a primate, such as a macaque, chimpanzee, or human. Most preferably, the sample is from a human. The antibodies of the invention may also be used in vivo, for example, as a diagnostic tool for in vivo imaging.

Kits will typically comprise a nucleic acid sequence that encodes an antibody of the present invention (or binding fragment thereof) with one or more framework portions or multiple cloning sites at the carboxy-terminal end into which the coding sequences for one or more antigens may be inserted. In some embodiments, the antibody will be a humanized anti-Langerin Fv fragment, such as an scFv or dsFv fragment. In addition the kits will typically include instructional materials disclosing methods of use of an antibody of the present invention (e.g. for loading into dendritic cells prior to immunization with the dendritic cells, which can be autologous dendritic cells). The kits may also include additional components to facilitate the particular application for which the kit is designed. Thus, for example, the kit may additionally contain methods of detecting the label (e.g. enzyme substrates for enzymatic labels, filter sets to detect fluorescent labels, appropriate secondary labels such as a sheep anti-mouse-HRP, or the like). The kits may additionally include buffers and other reagents routinely used for the practice of a particular method. Such kits and appropriate contents are well known to those of skill in the art.

In another set of uses for the invention, immunoconjugates targeted by antibodies of the invention can be used to purge targeted cells from a population of cells in a culture. For example, if a specific population of T cells is preferred, the immunoconjugates of the present invention may be used to enrich a population of T cells having the opposite effect of the on-going immune response. Thus, for example, cells cultured from a patient having a cancer can be purged of cancer cells by providing the patient with dendritic cells that were antigen loaded using the antibodies of the invention as a targeting moiety for the antigens that will trigger an immune response against the cancer, virus or other pathogen. Likewise, the immunoconjugates can be used to increase the population of regulatory T cells or drive the immune response toward or away from a cytotoxic T cell response or even drive a B cell response.

Differential functions of DC subsets: The present inventors have demonstrated that LCs and intDCs derived from CD34+ hematopoietic progenitor cells differ in their capacity to activate lymphocytes (FIG. 1). IntDCs induce the differentiation of naïve B cells into immunoglobulin-secreting plasma cells and differentiation of CD4+ T cells into follicular helper T cells (TFH)[17,18], while LCs are particularly efficient activators of cytotoxic CD8+ lymphocytes (CTLs). In addition, only interstitial DCs produce IL-10 and their enzymatic activity, which might be fundamental for the selection of peptides that will be presented to T cells, is not the same. Indeed, different enzymes are likely to degrade a antigen into different peptide repertoires, as shown for HIV nef protein[19]. This will lead to different sets of MHC/peptide complexes being presented and to a distinct antigen-specific T-cell repertoire. Dudziak, et al.[20] have shown that antigens delivered to DCs through the subset-specific lectin Dectin-1 were presented differentially on MHC class II, while those presented through DEC-205 were mostly on MHC Class I and this difference was intrinsic to the DC subsets.

DC subsets play an important role in determining CD4+ T cell responses. Either polarized DCs or distinct DC subsets provide T cells with different signals that determine the types of immune response (Type 1 versus Type 2)[21]. Thus, in mice, splenic CD8+ DCs prime naïve CD4+ T cells to make Th1 cytokines in a process involving IL-12, whereas splenic CD8+DCs prime naïve CD4+ T cells to make Th2 cytokines[22,23]. Furthermore, different signals from the same DCs can induce different T-cell polarization, as shown by the induction of IL-12 production and Th1-cell polarization when DCs are activated with *Escherichia coli* lipopolysaccharide (LPS), but no IL-12 production and Th2-cell polarization when DCs are exposed to LPS from *Porphyromonas gingivalis*[24]. CD40-ligand (CD40L)-activated DCs prime Th1 responses through an IL-12-dependent mechanism, whereas pDCs activated with IL-3 and CD40L have been shown to secrete negligible amounts of IL-12 and prime Th2 responses[25]. Soares, et al. also reported that two DC subsets that express different lectins have innate propensities to differentially affect the Th1/Th2 balance in vivo by distinct mechanisms. More interestingly, we have found that delivering the same antigens to the same type of DCs, but through different DC-receptors, induces a different quality of CD4+ T cell responses (see preliminary data). Thus, both DC subsets and activation signals to which DCs are exposed are important factors determining the nature of immune outcome.

Figure 2:
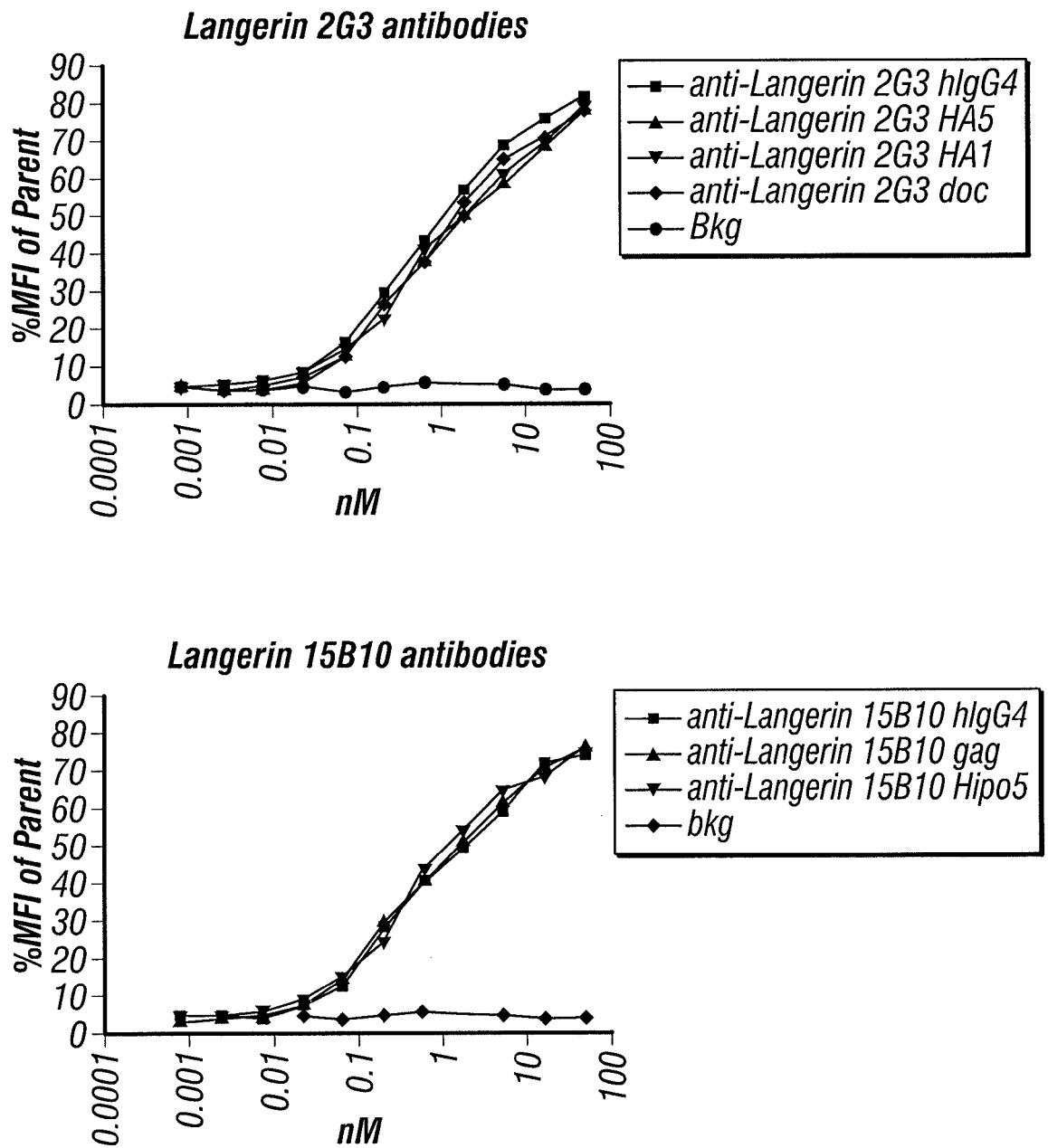
FIG. 2 shows that recombinant anti-Langerin antibodies fused to antigens retain their ability to bind to cell surface Langerin.

FIG. 2—Recombinant anti-Langerin antibodies fused to antigens retain their ability to bind to cell surface Langerin. CHO-S cells were stably transfected with a plasmid directing the expression of full-length human Langerin. Pure recombinant anti-Langerin 2G3 or 15B10 mouse V region-human IgG4 chimeric antibodies or the same antibodies with C-terminal fusions to Influenza A Hemagglutinin HA-1 domain from Avian Flu (HA5-1), Influenza A Hemagglutinin HA-1 from a H1N1 Flu strain (HA1-1), dockerin domain from *C. thermocellum* (doc), HIV gag p24 (gag), or a string of HIV peptides (Hipo5), were titrated against the Langerin-CHO cells. After incubation on ice, the cells were washed and treated with an anti-human Fc-PE reagent. After further incubation on ice, the cells were washed and analyzed on a FACS Array instrument to determine the amount of cell-bound florescence (expressed as % MFI compared to untransfected CHO-S cells).

This data shows that addition of antigen to the H-chain C-termini does not affect the binding of the antibody to cell surface Langerin and also demonstrates that these anti-Langerin antibodies serve as effective vehicles to bring antigen to the surface of cells bearing human Langerin.

Figure 3A:
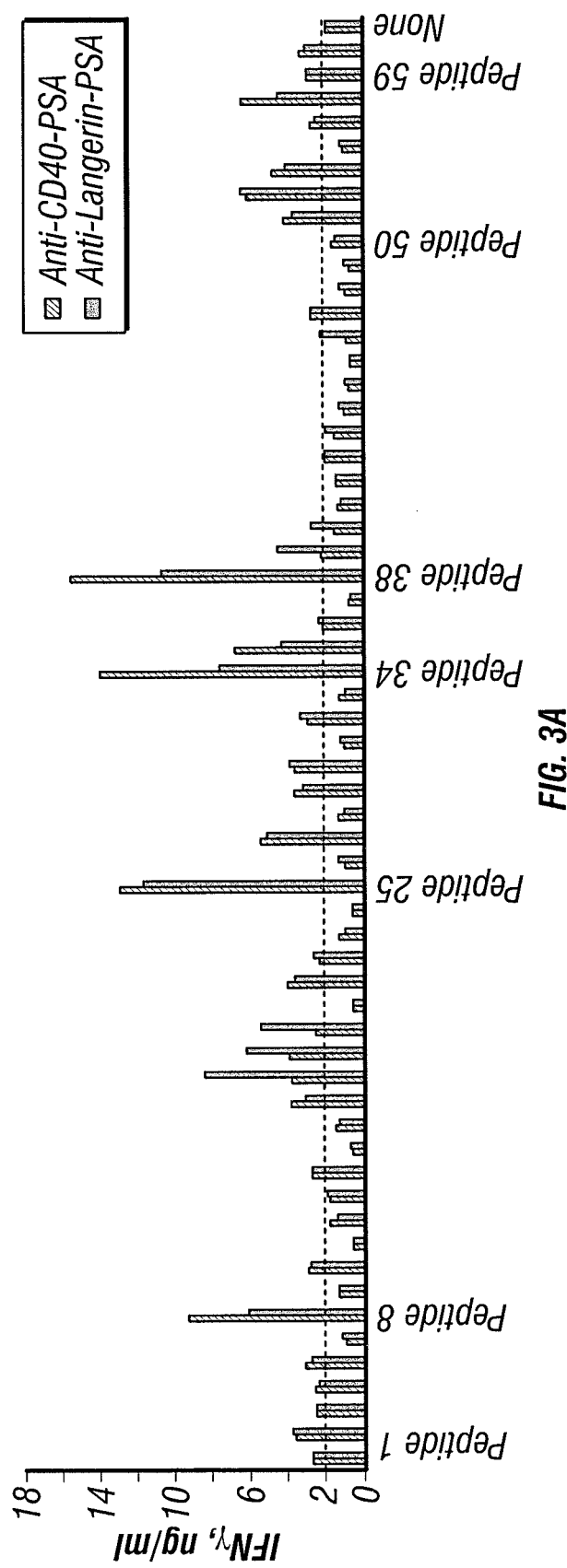
FIG. 3(A-B) is a demonstration of the ability of recombinant anti-Langerin antibody fused to the human prostate specific cancer antigen to elicit the expansion of antigen-specific CD4+ T cells from a health donor.
Figure 3B:
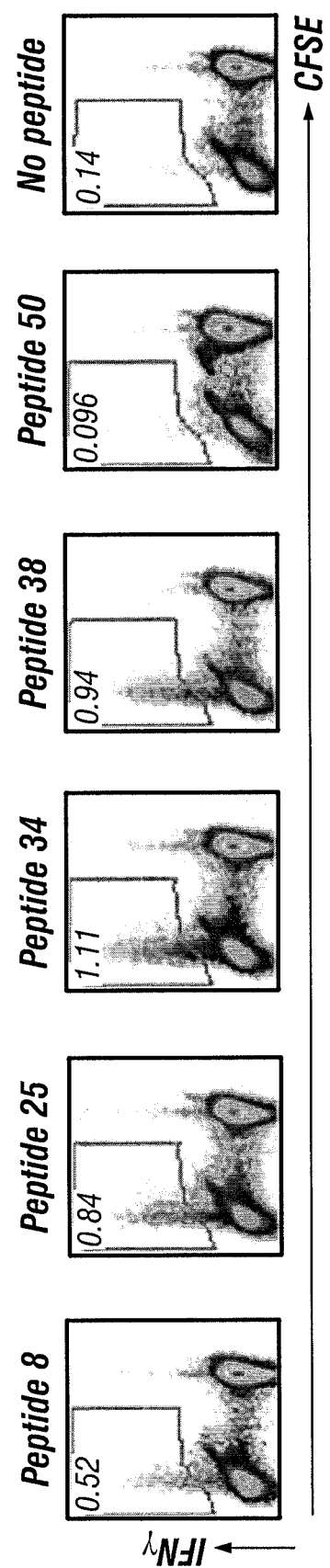

FIG. 3—demonstration of the ability of recombinant anti-Langerin antibody fused to the human prostate specific cancer antigen to elicit the expansion of antigen-specific CD4+ T cells from a health donor. FIG. 3a compares delivering PSA to DCs through CD40 and Langerin induces IFNγ-producing PSA-specific CD4+ T cells. CD4+ T cells from healthy donors were co-cultured with IFNDCs targeted with anti-CD40-PSA or anti-Langerin-PSA for 8 days. Cells were stimulated with individual peptides (59 peptides of 15-mers) of PSA (5 µM). After 2 days, culture supernatants were analyzed for measuring IFNγ. Dotted lines represent upper limits of average±SD for no peptides and responses above this line are considered significant. FIG. 3b shows that CD4+ T cells were stained for measuring the frequency of peptide-specific intracellular IFNγ+ cells.

These data show that an anti-Langerin vaccine bearing a cancer antigen can prime a potent antigen-specific anti-CD4+ T cell response in vitro using immune cells from a normal individual. In this in vitro culture system this agent is as potent as an anti-CD40 based vaccine—these DCs express both receptors. In vivo, an anti-Langerin-based vaccine would target antigen only to Langerhans cells (LCs), and based on recent research [Immunity, Volume 29, Issue 3, 497-510, 19 Sep. 2008] LCs preferentially induce the differentiation of CD4+ T cells secreting T helper 2 (Th2) cell cytokines and are particularly efficient at priming and cross priming naive CD8+ T cells—the latter characteristic is particularly desirable for evoking anti-cancer CTL responses. In contrast, anti-CD40 targeting agents would deliver antigen to a much broader array of APC in vivo.

Figure 4:
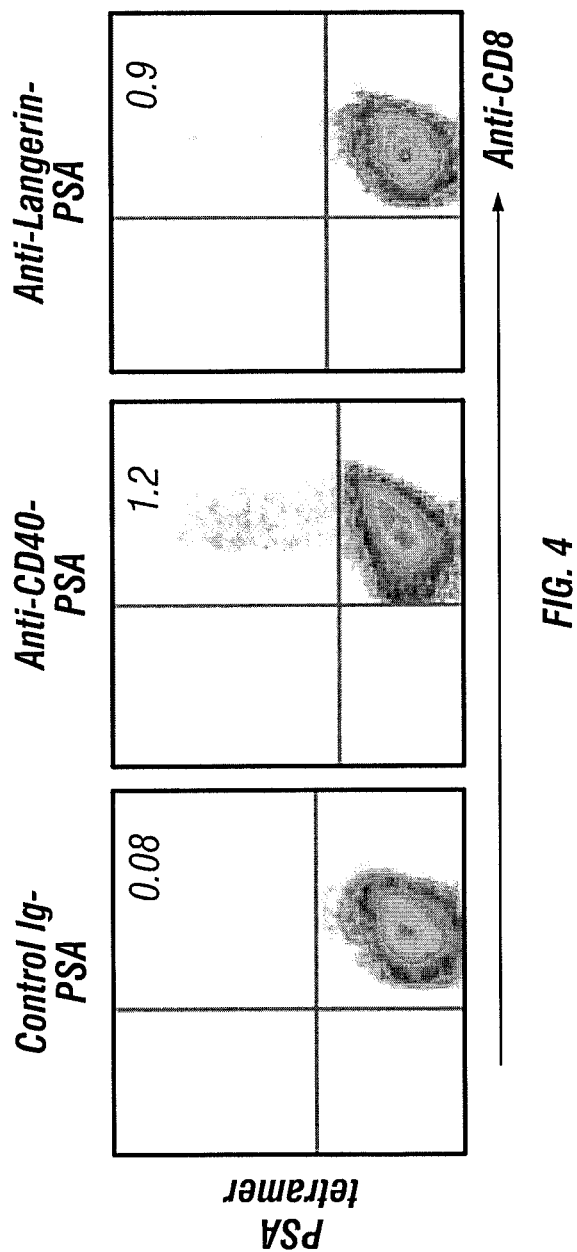
FIG. 4 is a demonstration of the ability of recombinant anti-Langerin antibody fused to the human prostate specific cancer antigen to elicit the expansion of antigen-specific CD8+ T cells from a prostate cancer patient.

FIG. 4—demonstration of the ability of recombinant anti-Langerin antibody fused to the human prostate specific cancer antigen to elicit the expansion of antigen-specific CD8+ T cells from a prostate cancer patient. DCs targeted with anti-CD40-PSA and anti-Langerin-PSA targeted to DCs induces PSA-specific CD8+ T cell responses. (a) IFNDCs were targeted with 1 mg mAb fusion proteins with PSA. Purified autologous CD8+ T cells were co-cultured for 10 days. Cells were stained with anti-CD8 and PSA (KLQCVDLHV (SEQ ID NO. 44))-tetramer. Cells are from HLA-A*0201 positive prostate cancer patients. The PSA tetramer reagent identified T cells bearing T cell receptors specifically reactive with HLA-A*0201 complexes bearing the PSA KLQCVDLHV (SEQ ID NO. 44) peptide.

These data show that an anti-Langerin vaccine bearing a cancer antigen can prime a potent antigen-specific anti-CD8+ T cell response in vitro using immune cells from a prostate cancer. In this in vitro culture system this agent is as potent as a anti-CD40 based vaccine—these DCs express both receptors. In vivo, an anti-Langerin-based vaccine would target antigen only to Langerhans cells (LCs), and based on recent research [Immunity, Volume 29, Issue 3, 497-510, 19 Sep. 2008] LCs preferentially induce the differentiation of CD4+ T cells secreting T helper 2 (Th2) cell cytokines and are particularly efficient at priming and cross priming naive CD8+ T cells—the latter characteristic is particularly desirable for evoking anti-cancer CTL responses. In contrast, anti-CD40 targeting agents would deliver antigen to a much broader array of APC in vivo.

FIG. 5—Anti-Langerin preferentially targets epidermal LCs. Purified skin DC subsets (Epidermal LCs, dermal CD1a+ DCs and CD14+ DCs) from HLA-A201 donor were cultured with 8 nM anti-Langerin, IgG4 conjugates mAbs, free FluMP or without antigen for 3 h. Syngeneic purified CD8+ T cells were cultured with the antigen-pulsed DCs at a DC/T ratio 1:20. CD40L (100 ng/ml; R&D) was added to the culture after 24 h. CD40-ligation enhances crosspresentation by DCs. The cocultures were incubated at 37° C. for 8-10 days. IL-2 (10 U/ml) was added at day 3. The response of FluMP-specific CD8+ T cells was evaluated using HLA-A201-FluMP (58-66) peptide (GILGFVFTL (SEQ ID NO. 43)) tetramer.

Figure 5A:
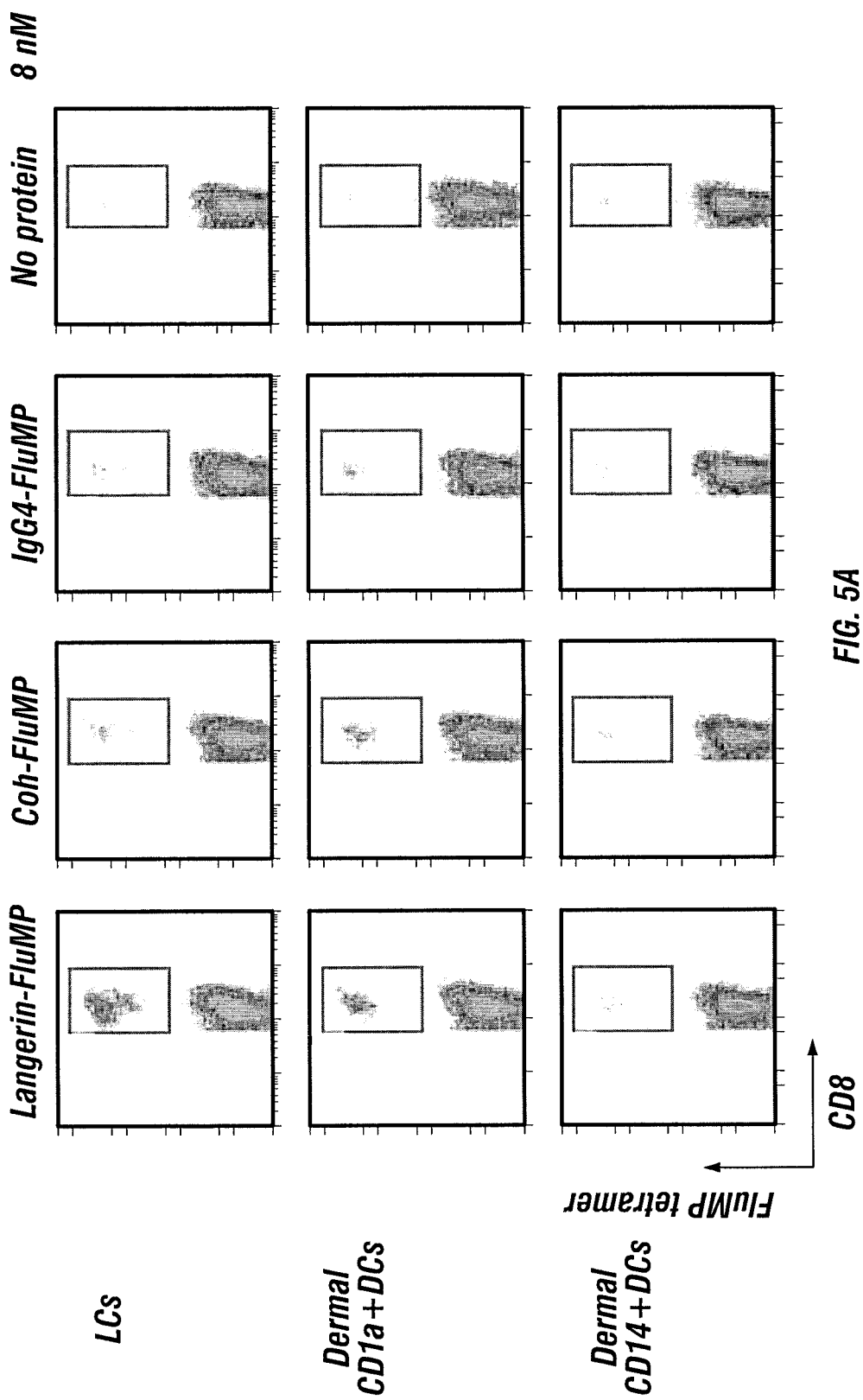
FIG. 5 (A-C) shows that anti-Langerin preferentially targets epidermal LCs.
Figure 5B:
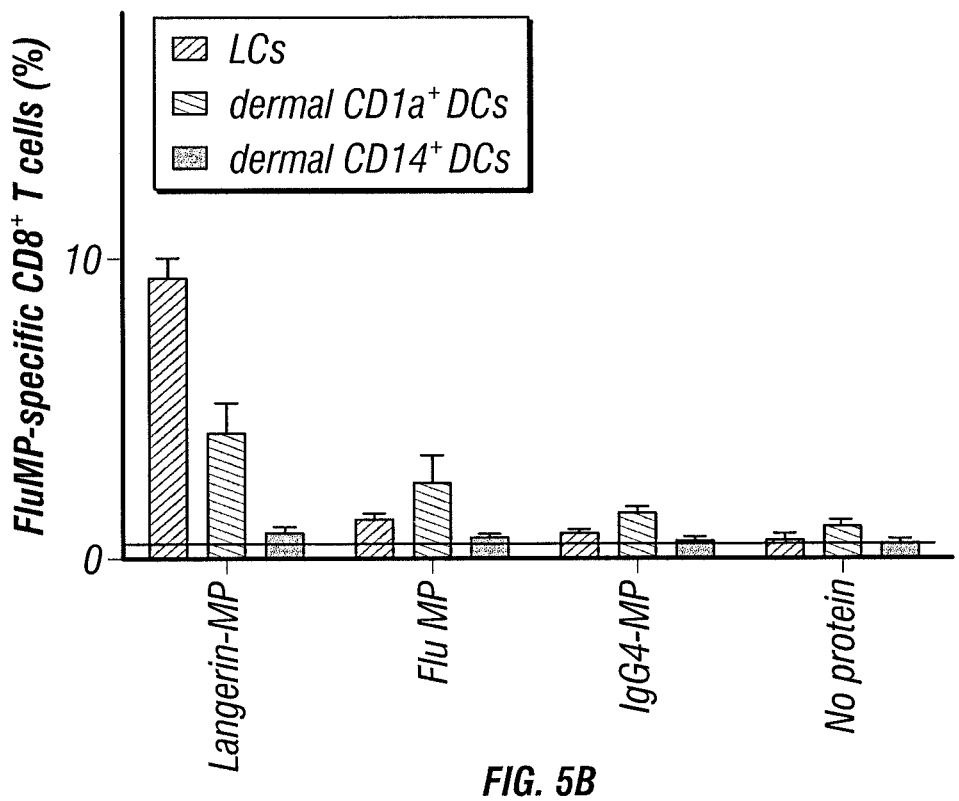
Figure 5C:
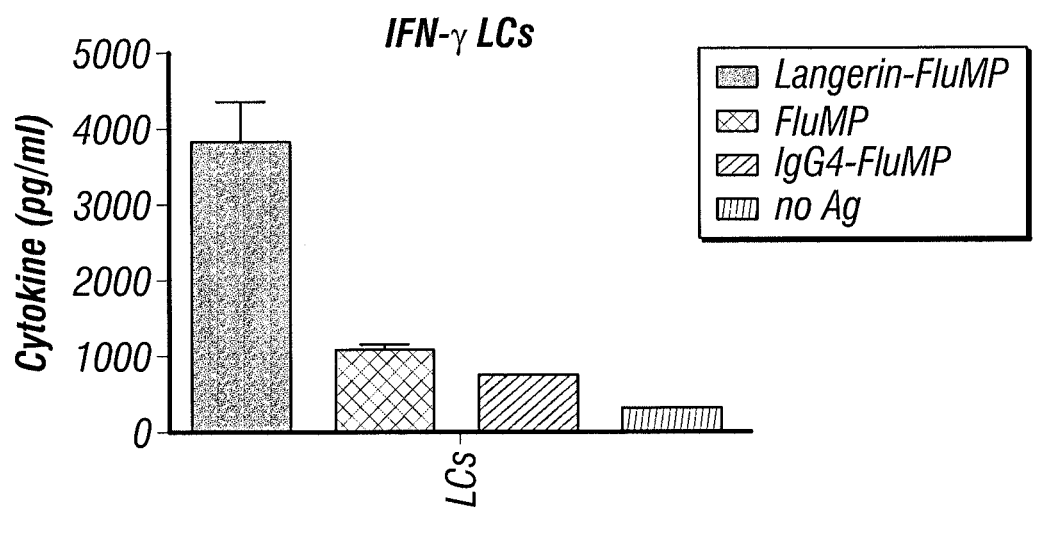

The data in panel FIG. 5A: 2D FACs-plots showing FluMP-specific CD8+ T cell expansion as evaluated by specific HLA-A201-FluMP (58-66) tetramer staining demonstrating that targeting antigen via anti-Langerin elicits antigen-specific CD8+ T cell expansion only through LCs, which is more robust than other methods of antigen delivery such as free FluMP. Some response is induced by the dermal CD1a+ DCs, in concordance with the ability of these cells to upregulate Langerin in culture. FIG. 5B summarizes the data in a graph shows mean±sd, N=3. FIG. 5C. IFN-γ levels in the culture supernatants of human LCs that were culture for 8 days with either Langerin-FluMP, control IgG4-FluMP, free FluMP or no antigen after 8 days.

FIG. 6 shows the differential expression of Langerin by human skin DCs. FIG. 6A shows the expression of Langerin on isolated human skin DC subsets. Data show restricted expression of Langerin on human LCs, but not on dermal CD1a+ or CD14+ DCs. FIG. 6B show a gene expression analysis of Langerin by skin DCs isolated from 3 different specimens. RNA was prepared from sorted migrated skin mDC subsets: epidermal LCs, dermal CD1a+ DCs and CD14+ DCs. FIG. 6C shows the immunofluorescent staining of normal human skin using Langerin and HLA-DR mAbs.

Figure 7:
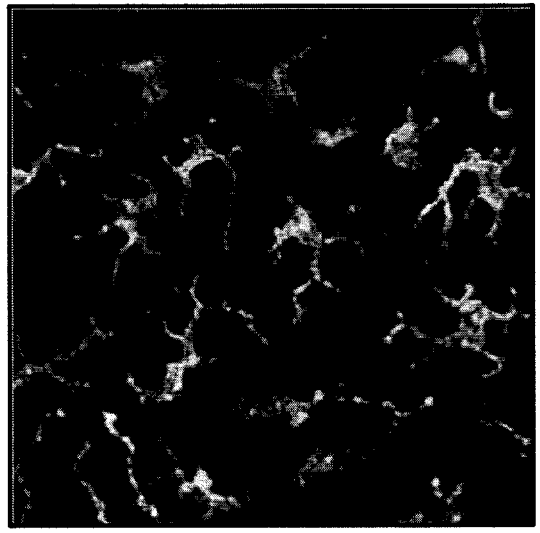
FIG. 7 shows that the anti-Langerin antibody (15B10) specifically stains human Langerhans cells.
Figure 7:
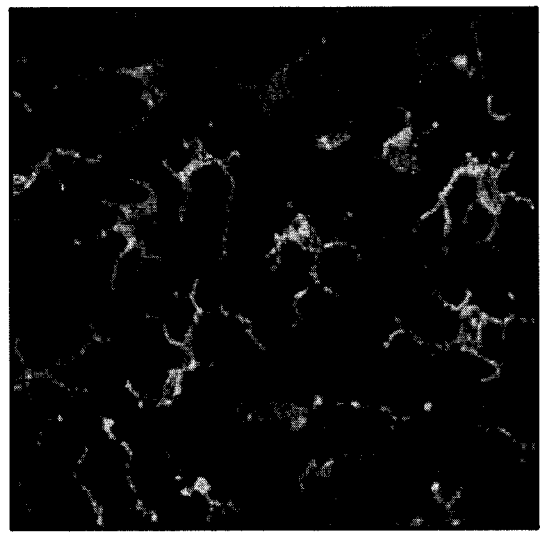
Figure 7:
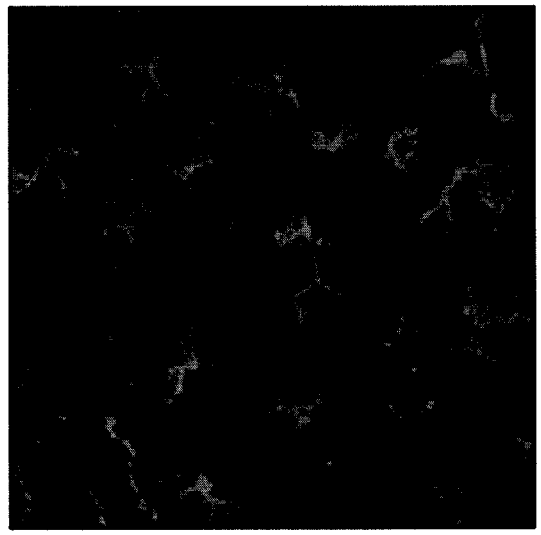

FIG. 7—Anti-Langerin 15B10 antibody (produced by hybridoma ATCC Accession No. PTA-9852) specifically stains human Langerhans cells. Human epithelial sheet was prepared and stained with Alexa568 [red]-labeled anti-Langerin 15B10 and a commercial anti-HLA antibody labeled green. The top image shows the red and green image superimposed highlighting the co-localization of these two markers.

Constructs.

mAnti-Langerin15B10K—Nucleotide and mature protein amino acid sequence of the light chain of the mouse anti-Langerin 15B10 antibody cDNA, respectively. The variable region residues are underlined.

```
                                            (SEQ ID NO. 1)
ATGAAGTTGCCTGTTAGGCTGTTGGTGCTGATGTTCTGGATTCCTG
CTTCCAGCAGTGATGTTGTGATGACCCAAACTCCACTCTCCCTGCC
TGTCCGTCTTGGAGATCAAGCCTCCATCTCTTGCAGATCTAGTCAG
AGCCTTGTACACAGTAATGGAAACACCTATTTACATTGGTACCTGC
AGAAGCCAGGCCAGTCTCCAAAGCTCCTGATCTACAAAGTTTCCAA
CCGATTTTCTGGGGTCCCAGACAGGTTCAGTGGCAGTGGATCAGGG
ACAAATTTCACACTCAAGATCAGCAGAGTGGAGGCTGAGGATCTGG
GACTTTATTTCTGCTCTCAAAGTACACATGTTCCGTACACGTTCGG
AGGGGGGACCAAGCTGGAAATAAAACGGGCTGATGCTGCACCAACT
GTATCCATCTTCCCACCATCCAGTGAGCAGTTAACATCTGGAGGTG
CCTCAGTCGTGTGCTTCTTGAACAACTTCTACCCCAAAGACATCAA
TGTCAAGTGGAAGATTGATGGCAGTGAACGACAAAATGGCGTCCTG
AACAGTTGGACTGATCAGGACAGCAAAGACAGCACCTACAGCATGA
ACAGCACCCTCACGTTGACCAAGGACGAGTATGAACGACATAACAG
CTATACCTGTGAGGCCACTCACAAGACATCAACTTCACCCATCGTC
AAGAGCTTCAACAGGAATGAGTGTTAG
```

```
                                            (SEQ ID NO. 2)
DVVMTQTPLSLPVRLGDQASISCRSSQSLVHSNGNTYLHWYLQKPG
QSPKLLIYKVSNRFSGVPDRFSGSGSGTNFTLKISRVEAEDLGLYF
CSQSTHVPYTFGGGTKLEIKRADAAPTVSIFPPSSEQLTSGGASVV
CFLNNFYPKDINVKWKIDGSERQNGVLNSWTDQDSKDSTYSMNSTL
TLTKDEYERHNSYTCEATHKTSTSPIVKSFNRNEC
``` mAnti-Langerin15B10H-LV-hIgG4H-C—Nucleotide and mature protein amino acid sequence of the heavy chain variable region of the mouse anti-Langerin 15B10 antibody fused to human IgG4, respectively. The variable region residues are underlined.

```
                                            (SEQ ID NO. 3)
ATGGAATGGAGGATCTTTCTCTTCATCCTGTCAGGAACTGCAGGTGT
CCACTCCCAGGTTCAGCTGCGGCAGTCTGGACCTGAGCTGGTGAAGC
CTGGGGCTTCAGTGAAGATGTCCTGCAAGGCTTCTGGATACACATTT
ACTGACTATGTTATAAGTTGGGTGAAGCAGAGAACTGGACAGGGCCT
TGAGTGGATTGGAGATATTTATCCTGGAAGTGGTTATTCTTTCTACA
ATGAGAACTTCAAGGGCAAGGCCACACTGACTGCAGACAAATCCTCC
ACCACAGCCTACATGCAGCTCAGCAGCCTGACATCTGAGGACTCTGC
GGTCTATTTCTGTGCAACCTACTATAACTACCCTTTTGCTTACTGGG
GCCAAGGGACTCTGGTCACTGTCTCTGCAGCCAAAACAACGGGCCCA
TCCGTCTTCCCCCTGGCGCCCTGCTCCAGGAGCACCTCCGAGAGCAC
AGCCGCCCTGGGCTGCCTGGTCAAGGACTACTTCCCCGAACCGGTGA
CGGTGTCGTGGAACTCAGGCGCCCTGACCAGCGGCGTGCACACCTTC
CCGGCTGTCCTACAGTCCTCAGGACTCTACTCCCTCAGCAGCGTGGT
GACCGTGCCCTCCAGCAGCTTGGGCACGAAGACCTACACCTGCAACG
TAGATCACAAGCCCAGCAACACCAAGGTGGACAAGAGAGTTGAGTCC
AAATATGGTCCCCCATGCCCACCCTGCCCAGCACCTGAGTTCGAAGG
GGGACCATCAGTCTTCCTGTTCCCCCCAAAACCCAAGGACACTCTCA
TGATCTCCCGGACCCCTGAGGTCACGTGCGTGGTGGTGGACGTGAGC
CAGGAAGACCCCGAGGTCCAGTTCAACTGGTACGTGGATGGCGTGGA
GGTGCATAATGCCAAGACAAAGCCGCGGGAGGAGCAGTTCAACAGCA
CGTACCGTGTGGTCAGCGTCCTCACCGTCCTGCACCAGGACTGGCTG
AACGGCAAGGAGTACAAGTGCAAGGTCTCCAACAAAGGCCTCCCGTC
CTCCATCGAGAAAACCATCTCCAAAGCCAAAGGGCAGCCCCGAGAGC
CACAGGTGTACACCCTGCCCCCATCCCAGGAGGAGATGACCAAGAAC
CAGGTCAGCCTGACCTGCCTGGTCAAAGGCTTCTACCCCAGCGACAT
CGCCGTGGAGTGGGAGAGCAATGGGCAGCCGGAGAACAACTACAAGA
CCACGCCTCCCGTGCTGGACTCCGACGGCTCCTTCTTCCTCTACAGC
AGGCTAACCGTGGACAAGAGCAGGTGGCAGGAGGGGAATGTCTTCTC
ATGCTCCGTGATGCATGAGGCTCTGCACAACCACTACACACAGAAGA
GCCTCTCCCTGTCTCTGGGTAAAGCTAGCTGA
```

```
                                            (SEQ ID NO. 4)
QVQLRQSGPELVKPGASVKMSCKASGYTFTDYVISWVKQRTGQGLEW
IGDIYPGSGYSFYNENFKGKATLTADKSSTTAYMQLSSLTSEDSAVY
FCATYYNYPFAYWGQGTLVTVSAAKTTGPSVFPLAPCSRSTSESTAA
LGCLVKDYFPEPVTVSVVNSGALTSGVHTFPAVLQSSGLYSLSSVVT
VPSSSLGTKTYTCNVDHKPSNTKVDKRVESKYGPPCPPCPAPEFEGG
PSVFLFPPKYKDTLMISRTPEVTCVVVDVSQEDPEVQFNWYVDGVEV
HNAKTKPREEQFNSTYRVVSVLTVLHQDWLNGKEYKCKVSNKGLPSS
```

IEKTISKAKGQPREPQVYTLPPSQEEMTKNQVSLTCLVKGFYPSDIA
VEWESNGQPENNYKTTPPVLDSDGSFFLYSRLTVDKSRWQEGNVFSC
SVMHEALHNHYTQKSLSLSLGKAS mAnti-Langerin2G3L (produced by hybridoma ATCC Accession No. PTA-9853)—Nucleotide and mature protein amino acid sequence of the light chain of the mouse anti-Langerin 2G3 antibody cDNA, respectively. The variable region residues are underlined.

(SEQ ID NO. 5)
ATGGCCTGGATTTCACTTATACTCTCTCTCCTGGCTCTCAGCTCAG
GGGCCATTTCCCAGGCTGTTGTGACTCAGGAATCTGCACTCACCAC
ATCACCTGGTGAAACAGTCACACTCACTTGTCGCTCAAGTACTGGG
GCTGTTACAACTAGTAACTATGCCAACTGGGTCCAAGAAAAACCAG
ATCATTTATTCACTGGTCTAATAGGTGGTACCAACAACCGAGTTTC
AGGTGTTCCTGCCAGATTCTCAGGCTCCCTGATTGGAGACAAGGCT
GCCCTCACCATCACAGGGGCACAGACTGAGGATGAGGCAATATATT
TCTGTGCTCTATGGTACAGCAACCATTGGGTGTTCGGTGGAGGAAC
CAAACTGACTGTCCTAGGCCAGCCCAAGTCTTCGCCATCAGTCACC
CTGTTTCCACCTTCCTCTGAAGAGCTCGAGACTAACAAGGCCACAC
TGGTCTGTACGATCACTGATTTCTACCCAGGTGTGGTGACAGTGGA
CTGGAAGGTAGATGGTACCCCTGTCACTCAGGGTATGGAGACAACC
CAGCCTTCCAAACAGAGCAACAACAAGTACATGGCTAGCAGCTACC
TGACCCTGACAGCAAGAGCATGGGAAAGGCATAGCAGTTACAGCTG
CCAGGTCACTCATGAAGGTCACACTGTGGAGAAGAGTTTGTCCCGT
GCTGACTGTTCCTAG

(SEQ ID NO. 6)
QAVVTQESALTTSPGET<u>VTLTCRSSTGAVTTSNYANWVQEKPDHLFT
GLIGGTNNRVSGVPARFSGSLIGDKAALTITGAQTEDEAIYFCALWY
SNHWVFGGGTKLTVLG</u>QPKSSPSVTLFPPSSEELETNKATLVCTITD
FYPGVVTVDWKVDGTPVTQGMETTQPSKQSNNKYMASSYLTLTARAW
ERHSSYSCQVTHEGHTVEKSLSRADCS mAnti-Langerin2G3H—Nucleotide and mature protein amino acid sequence of the heavy chain of the mouse anti-Langerin 2G3 antibody cDNA, respectively. The variable region residues are underlined.

(SEQ ID NO. 7)
ATGACATTGAACATGCTGTTGGGGCTGAAGTGGGTTTTCTTTGTTGT
TTTTTATCAAGGTGTGCATTGTGAGGTGCAGCTTGTTGAGTCTGGTG
GAGGATTGGTGCAGCCTAAAGGGTCATTGAAACTCTCATGTGCAGCC
TCTGGATTAACCTTCAATATCTACGCCATGAACTGGGTCCGCCAGGC
TCCAGGAAAGGGTTTGGAATGGGTTGCTCGCATAAGAAATAAAAGTA
ATAATTATGCAACATATTATGCCGATTCAGTGAAAGACAGGTTCACC
ATCTCCAGAGATGATTCACAAAGCTTGCTCTATCTGCAAATGAACAA
CTTGAAAACTGAGGACACAGCCATGTATTACTGTGTGGGACGGGACT
GGTTTGATTACTGGGGCCAAGGGACTCTGGTCACTGTCTCTGCAGCC
AAAACGACACCCCCATCTGTCTATCCACTGGCCCCTGGATCTGCTGC
CCAAACTAACTCCATGGTGACCCTGGGATGCCTGGTCAAGGGCTATT
TCCCTGAGCCAGTGACAGTGACCTGGAACTCTGGATCCCTGTCCAGC
GGTGTGCACACCTTCCCAGCTGTCCTGCAGTCTGACCTCTACACTCT
GAGCAGCTCAGTGACTGTCCCCTCCAGCACCTGGCCCAGCGAGACCG
TCACCTGCAACGTTGCCCACCCGGCCAGCAGCACCAAGGTGGACAAG
AAAATTGTGCCCAGGGATTGTGGTTGTAAGCCTTGCATATGTACAGT
CCCAGAAGTATCATCTGTCTTCATCTTCCCCCAAAGCCCAAGGATG
TGCTCACCATTACTCTGACTCCTAAGGTCACGTGTGTTGTGTAGAC
ATCAGCAAGGATGATCCCGAGGTCCAGTTCAGCTGGTTTGTAGATGA
TGTGGAAGGTGCACACAGCTCAGACGCAACCCCGGGAGGAGCAGTTCA
ACAGCACTTTCCGCTCAGTCAGTGAACTTCCCATCATGCACCAGGAC
TGGCTCAATGGCAAGGAGTTCAAATGCAGGGTCAACAGTGCAGCTTT
CCCTGCCCCCATCGAGAAAACCATCTCCAAAACCAAAGGCAGACCGA
AGGCTCCACAGGTGTACACCATTCCACCTCCCAAGGAGCAGATGGCC
AAGGATAAAGTCAGTCTGACCTGCATGATAACAGACTTCTTCCCTGA
AGACATTACTGTGGAGTGGCAGTGGAATGGGCAGCCAGCGAGGAACT
ACAAGAACACTCAGCCCATCATGGACACAGATGGCTCTTACTTCGTC
TACAGCAAGCTCAATGTGCAGAAGAGCAACTGGGAGGCAGGAAATAC
TTTCACCTGCTCTGTGTTACATGAGGGCCTGCACAACCACCATACTG
AGAAGAGCCTCTCCCACTCTCCTGGTAAAGCTAGCTGA

(SEQ ID NO. 8)
EVQLVESGGGLVQPKG<u>SLKLSCAASGLTFNIYAMNWVRQAPGKGLEW
VARIRNKSNNYATYYADSVKDRFTISRDDSQSLLYLQMNNLKTEDTA
MYYCVGRDWFDYWGQGTLVTVSA</u>AKTTPPSVYPLAPGSAAQTNSMVT

LGCLVKGYFPEPVTVTWNSGSLSSGVHTFPAVLQSDLYTLSSSVTVP
SSTWPSETVTCNVAHPASSTKVDKKIVPRDCGCKPCICTVPEVSSVF
IFPPKPKDVLTITLTPKVTCVVVDISKDDPEVQFSWFVDDVEVHTAQ
TQPREEQFNSTFRSVSELPIMHQDWLNGKEFKCRVNSAAFPAPIEKT
ISKTKGRPKAPQVYTIPPPKEQMAKDKVSLTCMITDFFPEDITVEWQ
WNGQPAENYKNTQPIMDTDGSYFVYSKLNVQKSNWEAGNTFTCSVLH
EGLHNHHTEKSLSHSPGKAS

C84 rAB-pIRES2 [mAnti-Langerin2G3H-LV-hIgG4H-C-Dockerin] The coding region for this H chain-dockerin fusion protein is shown below. Start and stop codons are in bold, as is the joining GCTAGC restriction site.

(SEQ ID NO. 57)
ATGACATTGAACATGCTGTTGGGGCTGAGGTGGGTTTTCTTTGTTGTTTT

TTATCAAGGTGTGCATTGTGAGGTGCAGCTTGTTGAGTCTGGTGGAGGAT

TGGTGCAGCCTAAAGGGTCATTGAAACTCTCATGTGCAGCCTCTGGATTA

ACCTTCAATATCTACGCCATGAACTGGGTCCGCCAGGCTCCAGGAAAGGG

TTTGGAATGGGTTGCTCGCATAAGAAATAAAAGTAATAATTATGCAACAT

ATTATGCCGATTCAGTGAAAGACAGGTTCACCATCTCCAGAGATGATTCA

CAAAGCTTGCTCTATCTGCAAATGAACAACTTGAAAACTGAGGACACAGC

CATGTATTACTGTGTGGGACGGGACTGGTTTGATTACTGGGGCCAAGGGA

CTCTGGTCACTGTCTCTGCAGCCAAAACGAAGGGCCCATCCGTCTTCCCC

CTGGCGCCCTGCTCCAGGAGCACCTCCGAGAGCACAGCCGCCCTGGGCTG

CCTGGTCAAGGACTACTTCCCCGAACCGGTGACGGTGTCGTGGAACTCAG

GCGCCCTGACCAGCGGCGTGCACACCTTCCCGGCTGTCCTACAGTCCTCA

GGACTCTACTCCCTCAGCAGCGTGGTGACCGTGCCCTCCAGCAGCTTGGG

CACGAAGACCTACACCTGCAACGTAGATCACAAGCCCAGCAACACCAAGG

TGGACAAGAGAGTTGAGTCCAAATATGGTCCCCCATGCCCACCCTGCCCA

GCACCTGAGTTCGAAGGGGGACCATCAGTCTTCCTGTTCCCCCCAAAACC

CAAGGACACTCTCATGATCTCCCGGACCCCTGAGGTCACGTGCGTGGTGG

TGGACGTGAGCCAGGAAGACCCCGAGGTCCAGTTCAACTGGTACGTGGAT

GGCGTGGAGGTGCATAATGCCAAGACAAAGCCGCGGGAGGAGCAGTTCAA

CAGCACGTACCGTGTGGTCAGCGTCCTCACCGTCCTGCACCAGGACTGGC

TGAACGGCAAGGAGTACAAGTGCAAGGTCTCCAACAAAGGCCTCCCGTCC

TCCATCGAGAAAACCATCTCCAAAGCCAAAGGGCAGCCCCGAGAGCCACA

GGTGTACACCCTGCCCCCATCCCAGGAGGAGATGACCAAGAACCAGGTCA

GCCTGACCTGCCTGGTCAAAGGCTTCTACCCCAGCGACATCGCCGTGGAG

TGGGAGAGCAATGGGCAGCCGGAGAACAACTACAAGACCACGCCTCCCGT

GCTGGACTCCGACGGCTCCTTCTTCCTCTACAGCAGGCTAACCGTGGACA

AGAGCAGGTGGCAGGAGGGGAATGTCTTCTCATGCTCCGTGATGCATGAG

GCTCTGCACAACCACTACACACAGAAGAGCCTCTCCCTGTCTCTGGGTAA

AGCTAGCAATTCTCCTCAAAATGAAGTACTGTACGGAGATGTGAATGATG

ACGGAAAAGTAAACTCCACTGACTTGACTTTGTTAAAAAGATATGTTCTT

AAAGCCGTCTCAACTCTCCCTTCTTCCAAAGCTGAAAAGAACGCAGATGT

AAATCGTGACGGAAGAGTTAATTCCAGTGATGTCACAATACTTTCAAGAT

The mature H chain sequence for C84 heavy chain is shown below. Joining sequence AS is bold and dockerin is underlined.

(SEQ ID NO. 58)
EVQLVESGGGLVQPKGSLKLSCAASGLTFNIYAMNWVRQAPGKGLEWVARIRNKSNN

YATYYADSVKDRFTISRDDSQSLLYLQMNNLKTEDTAMYYCVGRDWFDYWGQGTLV

TVSAAKTKGPSVFPLAPCSRSTSESTAALGCLVKDYFPEPVTVSWNSGALTSGVHTFPA

VLQSSGLYSLSSVVTVPSSSLGTKTYTCNVDHKPSNTKVDKRVESKYGPPCPPCPAPEFE

GGPSVFLFPPKPKDTLMISRTPEVTCVVVDVSQEDPEVQFNWYVDGVEVHNAKTKPRE

EQFNSTYRVVSVLTVLHQDWLNGKEYKCKVSNKGLPSSIEKTISKAKGQPREPQVYTLP

PSQEEMTKNQVSLTCLVKGFYPSDIAVEWESNGQPENNYKTTPPVLDSDGSFFLYSRLT

VDKSRWQEGNVFSCSVMHEALHNHYTQKSLSLSLGKAS<u>NSPQNEVLYGDVNDDGKV

NSTDLTLLKRYVLKAVSTLPSSKAEKNADVNRDGRVNSSDVTILSRYLIRVIEKLPI</u>

C85 rAB-pIRES2 [mAnti-Langerin2G3H-LV-hIgG4H-C-Flex-FluHA1-1-6×His] The coding region for this H chain-Flu HA1-1 fusion protein is shown below. Start and stop codons are in bold, as is the joining GCTAGC restriction site.

(SEQ ID NO. 59)
ATGACATTGAACATGCTGTTGGGGCTGAGGTGGGTTTTCTTTGTTTT

TTATCAAGGTGTGCATTGTGAGGTGCAGCTTGTTGAGTCTGGTGGAGGAT

TGGTGCAGCCTAAAGGGTCATTGAAACTCTCATGTGCAGCCTCTGGATTA

ACCTTCAATATCTACGCCATGAACTGGGTCCGCCAGGCTCCAGGAAAGGG

TTTGGAATGGGTTGCTCGCATAAGAAATAAAAGTAATAATTATGCAACAT

ATTATGCCGATTCAGTGAAAGACAGGTTCACCATCTCCAGAGATGATTCA

CAAAGCTTGCTCTATCTGCAAATGAACAACTTGAAAACTGAGGACACAGC

CATGTATTACTGTGTGGGACGGGACTGGTTTGATTACTGGGGCCAAGGGA

CTCTGGTCACTGTCTCTGCAGCCAAAACGAAGGGCCCATCCGTCTTCCCC

CTGGCGCCCTGCTCCAGGAGCACCTCCGAGAGCACAGCCGCCCTGGGCTG

CCTGGTCAAGGACTACTTCCCCGAACCGGTGACGGTGTCGTGGAACTCAG

GCGCCCTGACCAGCGGCGTGCACACCTTCCCGGCTGTCCTACAGTCCTCA

GGACTCTACTCCCTCAGCAGCGTGGTGACCGTGCCCTCCAGCAGCTTGGG

CACGAAGACCTACACCTGCAACGTAGATCACAAGCCCAGCAACACCAAGG

TGGACAAGAGAGTTGAGTCCAAATATGGTCCCCCATGCCCACCCTGCCCA

GCACCTGAGTTCGAAGGGGGACCATCAGTCTTCCTGTTCCCCCCAAAACC

CAAGGACACTCTCATGATCTCCCGGACCCCTGAGGTCACGTGCGTGGTGG

TGGACGTGAGCCAGGAAGACCCCGAGGTCCAGTTCAACTGGTACGTGGAT

GGCGTGGAGGTGCATAATGCCAAGACAAAGCCGCGGGAGGAGCAGTTCAA

CAGCACGTACCGTGTGGTCAGCGTCCTCACCGTCCTGCACCAGGACTGGC

TGAACGGCAAGGAGTACAAGTGCAAGGTCTCCAACAAAGGCCTCCCGTCC

TCCATCGAGAAAACCATCTCCAAAGCCAAAGGGCAGCCCCGAGAGCCACA

GGTGTACACCCTGCCCCCATCCCAGGAGGAGATGACCAAGAACCAGGTCA

GCCTGACCTGCCTGGTCAAAGGCTTCTACCCCAGCGACATCGCCGTGGAG

TGGGAGAGCAATGGGCAGCCGGAGAACAACTACAAGACCACGCCTCCCGT

GCTGGACTCCGACGGCTCCTTCTTCCTCTACAGCAGGCTAACCGTGGACA

AGAGCAGGTGGCAGGAGGGGAATGTCTTCTCATGCTCCGTGATGCATGAG

GCTCTGCACAACCACTACACACAGAAGAGCCTCTCCCTGTCTCTGGGTAA

AGCTAGC<u>GATACAACAGAACCTGCAACACCTACAACACCTGTAACAACAG

ACACAATATGTATAGGCTACCATGCGAACAATTCAACCGACACTGTTGAC

ACAGTACTCGAGAAGAATGTGACAGTGACACACTCTGTTAACCTGCTCGA

AGACAGCCACAACGGAAAACTATGTAGATTAAAAGGAATAGCCCCACTAC

AATTGGGGAAATGTAACATCGCCGGATGGCTCTTGGGAAACCCAGAATGC

GACCCACTGCTTCCAGTGAGATCATGGTCCTACATTGTAGAAACACCAAA

CTCTGAGAATGGAATATGTTATCCAGGAGATTTCATCGACTATGAGGAGC

TGAGGGAGCAATTGAGCTCAGTGTCATCATTCGAAAGATTCGAAATATTT

CCCAAAGAAAGCTCATGGCCCAACCACAACACAAACGGAGTAACGGCAGC

ATGCTCCCATGAGGGGAAAAGCAGTTTTTACAGAAATTTGCTATGGCTGA

CGGAGAAGGAGGGCTCATACCCAAAGCTGAAAAATTCTTATGTGAACAAA

AAAGGGAAAGAAGTCCTTGTACTGTGGGGTATTCATCACCCGCCTAACAG

TAAGGAACAACAGAATCTCTATCAGAATGAAAATGCTTATGTCTCTGTAG

TGACTTCAAATTATAACAGGAGATTTACCCCGGAAATAGCAGAAAGACCC

AAAGTAAGAGATCAAGCTGGGAGGATGAACTATTACTGGACCTTGCTAAA

ACCCGGAGACACAATAATATTTGAGGCAAATGGAAATCTAATAGCACCAA

TGTATGCTTTCGCACTGAGTAGAGGCTTTGGGTCCGGCATCATCACCTCA

AACGCATCAATGCATGAGTGTAACACGAAGTGTCAAACACCCCTGGGAGC

TATAAACAGCAGTCTCCCTTACCAGAATATACACCCAGTCACAATAGGAG

AGTGCCCAAAATACGTCAGGAGTGCCAAATTGAGGATGGTTCACCATCAC

CATCACCAT</u>TGA

The mature H chain sequence for C85 heavy chain is shown below. Joining sequence AS is bold and Flu HA1-1 is underlined. A flexible linker joining sequence is italicized.

(SEQ ID NO. 60)
EVQLVESGGGLVQPKGSLKLSCAASGLTFNIYAMNWVRQAPGKGLEWVARIRNKSNN
YATYYADSVKDRFTISRDDSQSLLYLQMNNLKTEDTAMYYCVGRDWFDYWGQGTLV
TVSAAKTKGPSVFPLAPCSRSTSESTAALGCLVKDYFPEPVTVSWNSGALTSGVHTFPA
VLQSSGLYSLSSVVTVPSSSLGTKTYTCNVDHKPSNTKVDKRVESKYGPPCPPCPAPEFE
GGPSVFLFPPKPKDTLMISRTPEVTCVVVDVSQEDPEVQFNWYVDGVEVHNAKTKPRE
EQFNSTYRVVSVLTVLHQDWLNGKEYKCKVSNKGLPSSIEKTISKAKGQPREPQVYTLP
PSQEEMTKNQVSLTCLVKGFYPSDIAVEWESNGQPENNYKTTPPVLDSDGSFFLYSRLT
VDKSRWQEGNVFSCSVMHEALHNHYTQKSLSLSLGKAS*DTTEPATPTTPVTT*DTICIGY
HANNSTDTVDTVLEKNVTVTHSVNLLEDSHNGKLCRLKGIAPLQLGKCNIAGWLLGNP
ECDPLLPVRSWSYIVETPNSENGICYPGDFIDYEELREQLSSVSSFERFEIFPKESSWPNHN
TNGVTAACSHEGKSSFYRNLLWLTEKEGSYPKLKNSYVNKKGKEVLVLWGIHHPPNS
KEQQNLYQNENAYVSVVTSNYNRRFTPEIAERPKVRDQAGRMNYYWTLLKPGDTIIFE
ANGNLIAPMYAFALSRGFGSGIITSNASMHECNTKCQTPLGAINSSLPYQNIHPVTIGECP
KYVRSAKLRMVHHHHHH

C86 rAB-pIRES2 [mAnti-Langerin2G3H-LV-hIgG4H-C-Flex-FluHA5-1-6×His] The coding region for this H chain-Flu HA5-1 fusion protein is shown below. Start and stop codons are in bold, as is the joining GCTAGC restriction site.

(SEQ ID NO. 61)

ATGACATTGAACATGCTGTTGGGGCTGAGGTGGGTTTTCTTTGTTGTTTT

TTATCAAGGTGTGCATTGTGAGGTGCAGCTTGTTGAGTCTGGTGGAGGAT

TGGTGCAGCCTAAAGGGTCATTGAAACTCTCATGTGCAGCCTCTGGATTA

ACCTTCAATATCTACGCCATGAACTGGGTCCGCCAGGCTCCAGGAAAGGG

TTTGGAATGGGTTGCTCGCATAAGAAATAAAAGTAATAATTATGCAACAT

ATTATGCCGATTCAGTGAAAGACAGGTTCACCATCTCCAGAGATGATTCA

CAAAGCTTGCTCTATCTGCAAATGAACAACTTGAAAACTGAGGACACAGC

CATGTATTACTGTGTGGGACGGGACTGGTTTGATTACTGGGGCCAAGGGA

CTCTGGTCACTGTCTCTGCAGCCAAAACGAAGGGCCCATCCGTCTTCCCC

CTGGCGCCCTGCTCCAGGAGCACCTCCGAGAGCACAGCCGCCCTGGGCTG

CCTGGTCAAGGACTACTTCCCCGAACCGGTGACGGTGTCGTGGAACTCAG

GCGCCCTGACCAGCGGCGTGCACACCTTCCCGGCTGTCCTACAGTCCTCA

GGACTCTACTCCCTCAGCAGCGTGGTGACCGTGCCCTCCAGCAGCTTGGG

CACGAAGACCTACACCTGCAACGTAGATCACAAGCCCAGCAACACCAAGG

TGGACAAGAGAGTTGAGTCCAAATATGGTCCCCCATGCCCACCCTGCCCA

GCACCTGAGTTCGAAGGGGGACCATCAGTCTTCCTGTTCCCCCCAAAACC

CAAGGACACTCTCATGATCTCCCGGACCCCTGAGGTCACGTGCGTGGTGG

TGGACGTGAGCCAGGAAGACCCCGAGGTCCAGTTCAACTGGTACGTGGAT

GGCGTGGAGGTGCATAATGCCAAGACAAAGCCGCGGGAGGAGCAGTTCAA

CAGCACGTACCGTGTGGTCAGCGTCCTCACCGTCCTGCACCAGGACTGGC

TGAACGGCAAGGAGTACAAGTGCAAGGTCTCCAACAAAGGCCTCCCGTCC

-continued

TCCATCGAGAAAACCATCTCCAAAGCCAAAGGGCAGCCCCGAGAGCCACA

GGTGTACACCCTGCCCCCATCCCAGGAGGAGATGACCAAGAACCAGGTCA

GCCTGACCTGCCTGGTCAAAGGCTTCTACCCCAGCGACATCGCCGTGGAG

TGGGAGAGCAATGGGCAGCCGGAGAACAACTACAAGACCACGCCTCCCGT

GCTGGACTCCGACGGCTCCTTCTTCCTCTACAGCAGGCTAACCGTGGACA

AGAGCAGGTGGCAGGAGGGGAATGTCTTCTCATGCTCCGTGATGCATGAG

GCTCTGCACAACCACTACACACAGAAGAGCCTCTCCCTGTCTCTGGGTAA

AGCTAGCGATACAACAGAACCTGCAACACCTACAACACCTGTAACAACAG

ATCAGATTTGCATTGGTTACCATGCAAACAACTCGACAGAGCAGGTTGAC

ACAATAATGGAAAAGAACGTTACTGTTACACATGCCCAAGACATACTGGA

AAAGAAACACAACGGGAAGCTCTGCGATCTAGATGGAGTGAAGCCTCTAA

TTTTGAGAGATTGTAGCGTAGCTGGATGGCTCCTCGGAAACCCAATGTGT

GACGAATTCATCAATGTGCCGGAATGGTCTTACATAGTGGAGAAGGCCAA

TCCAGTCAATGACCTCTGTTACCCAGGGGATTTCAATGACTATGAAGAAT

TGAAACACCTATTGAGCAGAATAAACCATTTTGAGAAAATTCAGATCATC

CCCAAAAGTTCTTGGTCCAGTCATGAAGCCTCATTAGGGGTGAGCTCAGC

ATGTCCATACCAGGGAAAGTCCTCCTTTTTCAGAAATGTGGTATGGCTTA

TCAAAAAGAACAGTACATACCCAACAATAAAGAGGAGCTACAATAATACC

AACCAAGAAGATCTTTTGGTACTGTGGGGGATTCACCATCCTAATGATGC

GGCAGAGCAGACAAAGCTCTATCAAAACCCAACCACCTATATTTCCGTTG

GGACATCAACACTAAACCAGAGATTGGTACCAAGAATAGCTACTAGATCC

AAAGTAAACGGGCAAAGTGGAAGGATGGAGTTCTTCTGGACAATTTTAAA

GCCGAATGATGCAATCAACTTCGAGAGTAATGGAAATTTCATTGCTCCAG

AATATGCATACAAAATTGTCAAGAAAGGGGACTCAACAATTATGAAAAGT

GAATTGGAATATGGTAACTGCAACACCAAGTGTCAAACTCCAATGGGGGC

```
GATAAACTCTAGCATGCCATTCCACAATATACACCCTCTCACCATTGGGG

AATGCCCCAAATATGTGAAATCAAACAGATTAGTCCTTGCGCACCATCAC

CATCACCATTGA
```

The mature H chain sequence for C86 heavy chain is shown below. Joining sequence AS is bold and Flu HA5-1 is underlined. A flexible linker joining sequence is italicized.

```
                                          (SEQ ID NO. 62)
EVQLVESGGGLVQPKGSLKLSCAASGLTFNIYAMNWVRQAPGKGLEWVARIRNKSNN

YATYYADSVKDRFTISRDDSQSLLYLQMNNLKTEDTAMYYCVGRDWFDYWGQGTLV

TVSAAKTKGPSVFPLAPCSRSTSESTAALGCLVKDYFPEPVTVSWNSGALTSGVHTFPA

VLQSSGLYSLSSVVTVPSSSLGTKTYTCNVDHKPSNTKVDKRVESKYGPPCPPCPAPEFE

GGPSVFLFPPKPKDTLMISRTPEVTCVVVDVSQEDPEVQFNWYVDGVEVHNAKTKPRE

EQFNSTYRVVSVLTVLHQDWLNGKEYKCKVSNKGLPSSIEKTISKAKGQPREPQVYTLP

PSQEEMTKNQVSLTCLVKGFYPSDIAVEWESNGQPENNYKTTPPVLDSDGSFFLYSRLT

VDKSRWQEGNVFSCSVMHEALHNHYTQKSLSLSLGKASDTTEPATPTTPVTTDQICIGY

HANNSTEQVDTIMEKNVTVTHAQDILEKKHNGKLCDLDGVKPLILRDCSVAGWLLGN

PMCDEFINVPEWSYIVEKANPVNDLCYPGDFNDYEELKHLLSRINHFEKIQIIPKSSWSS

HEASLGVSSACPYQGKSSFFRNVVWLIKKNSTYPTIKRSYNNTNQEDLLVLWGIHHPND

AAEQTKLYQNPTTYISVGTSTLNQRLVPRIATRSKVNGQSGRMEFFWTILKPNDAINFES

NGNFIAPEYAYKIVKKGDSTIMKSELEYGNCNTKCQTPMGAINSSMPFHNIHPLTIGECP

KYVKSNRLVLAHHHHHH
```

C804 rAB-cetHS-puro [mAnti-Langerin2G3H-LV-hIgGK-C-Flex-hPSA] The coding region for this H chain-PSA fusion protein is shown below. Start and stop codons are in bold, as is the joining GCTAGC restriction site.

```
                                          (SEQ ID NO. 63)
ATGACATTGAACATGCTGTTGGGGCTGAAGTGGGTTTTCTTTGTTGTTTT

TTATCAAGGTGTGCATTGTGAGGTGCAGCTTGTTGAGTCTGGTGGAGGAT

TGGTGCAGCCTAAAGGGTCATTGAAACTCTCATGTGCAGCCTCTGGATTA

ACCTTCAATATCTACGCCATGAACTGGGTCCGCCAGGCTCCAGGAAAGGG

TTTGGAATGGGTTGCTCGCATAAGAAATAAAAGTAATAATTATGCAACAT

ATTATGCCGATTCAGTGAAAGACAGGTTCACCATCTCCAGAGATGATTCA

CAAAGCTTGCTCTATCTGCAAATGAACAACTTGAAAACTGAGGACACAGC

CATGTATTACTGTGTGGGACGGGACTGGTTTGATTACTGGGGCCAAGGGA

CTCTGGTCACTGTCTCTGCAGCCAAAACGAAGGGCCCATCCGTCTTCCCC

CTGGCGCCCTGCTCCAGGAGCACCTCCGAGAGCACAGCCGCCCTGGGCTG

CCTGGTCAAGGACTACTTCCCCGAACCGGTGACGGTGTCGTGGAACTCAG

GCGCCCTGACCAGCGGCGTGCACACCTTCCCGGCTGTCCTACAGTCCTCA

GGACTCTACTCCCTCAGCAGCGTGGTGACCGTGCCCTCCAGCAGCTTGGG

CACGAAGACCTACACCTGCAACGTAGATCACAAGCCCAGCAACACCAAGG

TGGACAAGAGAGTTGAGTCCAAATATGGTCCCCCATGCCCACCCTGCCCA

GCACCTGAGTTCGAAGGGGGACCATCAGTCTTCCTGTTCCCCCCAAAACC

CAAGGACACTCTCATGATCTCCCGGACCCCTGAGGTCACGTGCGTGGTGG

TGGACGTGAGCCAGGAAGACCCCGAGGTCCAGTTCAACTGGTACGTGGAT

GGCGTGGAGGTGCATAATGCCAAGACAAAGCCGCGGGAGGAGCAGTTCAA

CAGCACGTACCGTGTGGTCAGCGTCCTCACCGTCCTGCACCAGGACTGGC

TGAACGGCAAGGAGTACAAGTGCAAGGTCTCCAACAAAGGCCTCCCGTCC

TCCATCGAGAAACCATCTCCAAAGCCAAAGGGCAGCCCCGAGAGCCACA

GGTGTACACCCTGCCCCCATCCCAGGAGGAGATGACCAAGAACCAGGTCA

GCCTGACCTGCCTGGTCAAAGGCTTCTACCCCAGCGACATCGCCGTGGAG

TGGGAGAGCAATGGGCAGCCGGAGAACAACTACAAGACCACGCCTCCCGT

GCTGGACTCCGACGGCTCCTTCTTCCTCTACAGCAGGCTAACCGTGGACA

AGAGCAGGTGGCAGGAGGGGAATGTCTTCTCATGCTCCGTGATGCATGAG

GCTCTGCACAACCACTACACACAGAAGAGCCTCTCCCTGTCTCTGGGTAA

AGCTAGCGATACAACAGAACCTGCAACACCTACAACACCTGTAACAACAC

CGACAACAACACTTCTAGCGCCCCTCATCCTGTCTCGGATTGTGGGAGGC

TGGGAGTGCGAGAAGCATTCCCAACCCTGGCAGGTGCTTGTGGCCTCTCG

TGGCAGGGCAGTCTGCGGCGGTGTTCTGGTGCACCCCCAGTGGGTCCTCA

CAGCTGCCCACTGCATCAGGAACAAAAGCGTGATCTTGCTGGGTCGGCAC

AGCCTGTTTCATCCTGAAGACACAGGCCAGGTATTTCAGGTCAGCCACAG

CTTCCCACACCCGCTCTACGATATGAGCCTCCTGAAGAATCGATTCCTCA

GGCCAGGTGATGACTCCAGCCACGACCTCATGCTGCTCCGCCTGTCAGAG

CCTGCCGAGCTCACGGATGCTGTGAAGGTCATGGACCTGCCCACCCAGGA

GCCAGCACTGGGGACCACCTGCTACGCCTCAGGCTGGGGCAGCATTGAAC
```

```
CAGAGGAGTTCTTGACCCCAAAGAAACTTCAGTGTGTGGACCTCCATGTT

ATTTCCAATGACGTGTGTGCGCAAGTTCACCCTCAGAAGGTGACCAAGTT

CATGCTGTGTGCTGGACGCTGGACAGGGGGCAAAAGCACCTGCTCGGGTG

ATTCTGGGGGCCCACTTGTCTGTAATGGTGTGCTTCAAGGTATCACGTCA

TGGGGCAGTGAACCATGTGCCCTGCCCGAAAGGCCTTCCCTGTACACCAA

GGTGGTGCATTACCGGAAGTGGATCAAGGACACCATCGTGGCCAACCCCT

GA
```

The mature H chain sequence for C804 heavy chain is shown below. Joining sequence AS is bold and PSA is underlined. A flexible linker joining sequence is italicized.

(SEQ ID NO. 64)
```
EVQLVESGGGLVQPKGSLKLSCAASGLTFNIYAMNWVRQAPGKGLEWVARIRNKSNN

YATYYADSVKDRFTISRDDSQSLLYLQMNNLKTEDTAMYYCVGRDWFDYWGQGTLV

TVSAAKTKGPSVFPLAPCSRSTSESTAALGCLVKDYFPEPVTVSWNSGALTSGVHTFPA

VLQSSGLYSLSSVVTVPSSSLGTKTYTCNVDHKPSNTKVDKRVESKYGPPCPPCPAPEFE

GGPSVFLFPPKPKDTLMISRTPEVTCVVVDVSQEDPEVQFNWYVDGVEVHNAKTKPRE

EQFNSTYRVVSVLTVLHQDWLNGKEYKCKVSNKGLPSSIEKTISKAKGQPREPQVYTLP

PSQEEMTKNQVSLTCLVKGFYPSDIAVEWESNGQPENNYKTTPPVLDSDGSFFLYSRLT

VDKSRWQEGNVFSCSVMHEALHNHYTQKSLSLSLGKAS_DTTEPATPTTPVTTPTTTLL_AP

LILSRIVGGWECEKHSQPWQVLVASRGRAVCGGVLVHPQWVLTAAHCIRNKSVILLGR

HSLFHPEDTGQVFQVSHSFPHPLYDMSLLKNRFLRPGDDSSHDLMLLRLSEPAELTDAV

KVMDLPTQEPALGTTCYASGWGSIEPEEFLTPKKLQCVDLHVISNDVCAQVHPQKVTK

FMLCAGRWTGGKSTCSGDSGGPLVCNGVLQGITSWGSEPCALPERPSLYTKVVHYRK

WIKDTIVANP
```

C87 rAB-pIRES2 [mAnti-Langerin15B10H-SLAML-V-hIgG4H-Flex-FluHA5-1-6×His] The coding region for this H chain-Flu HA5-1 fusion protein is shown below. Start and stop codons are in bold, as is the joining GCTAGC restriction site.

(SEQ ID NO. 65)
```
ATGGACCCCAAAGGCTCCCTTTCCTGGAGAATACTTCTGTTTCTCTCCCT

GGCTTTTGAGTTGTCGTACGGACAGGTTCAGCTGCGGCAGTCTGGACCTG

AGCTGGTGAAGCCTGGGGCTTCAGTGAAGATGTCCTGCAAGGCTTCTGGA

TACACATTTACTGACTATGTTATAAGTTGGGTGAAGCAGAGAACTGGACA

GGGCCTTGAGTGGATTGGAGATATTTATCCTGGAAGTGGTTATTCTTTCT

ACAATGAGAACTTCAAGGGCAAGGCCACACTGACTGCAGACAAATCCTCC

ACCACAGCCTACATGCAGCTCAGCAGCCTGACATCTGAGGACTCTGCGGT

CTATTTCTGTGCAACCTACTATAACTACCCTTTTGCTTACTGGGGCCAAG

GGACTCTGGTCACTGTCTCTGCAGCCAAAACAACGGGCCCATCCGTCTTC

CCCCTGGCGCCCTGCTCCAGGAGCACCTCCGAGAGCACAGCCGCCCTGGG

CTGCCTGGTCAAGGACTACTTCCCCGAACCGGTGACGGTGTCGTGGAACT

CAGGCGCCCTGACCAGCGGCGTGCACACCTTCCCGGCTGTCCTACAGTCC

TCAGGACTCTACTCCCTCAGCAGCGTGGTGACCGTGCCCTCCAGCAGCTT

GGGCACGAAGACCTACACCTGCAACGTAGATCACAAGCCCAGCAACACCA

AGGTGGACAAGAGAGTTGAGTCCAAATATGGTCCCCCATGCCCACCCTGC

CCAGCACCTGAGTTCGAAGGGGGACCATCAGTCTTCCTGTTCCCCCCAAA

ACCCAAGGACACTCTCATGATCTCCCGGACCCCTGAGGTCACGTGCGTGG

TGGTGGACGTGAGCCAGGAAGACCCCGAGGTCCAGTTCAACTGGTACGTG

GATGGCGTGGAGGTGCATAATGCCAAGACAAAGCCGCGGGAGGAGCAGTT

CAACAGCACGTACCGTGTGGTCAGCGTCCTCACCGTCCTGCACCAGGACT

GGCTGAACGGCAAGGAGTACAAGTGCAAGGTCTCCAACAAAGGCCTCCCG

TCCTCCATCGAGAAAACCATCTCCAAAGCCAAAGGGCAGCCCCGAGAGCC

ACAGGTGTACACCCTGCCCCCATCCCAGGAGGAGATGACCAAGAACCAGG

TCAGCCTGACCTGCCTGGTCAAAGGCTTCTACCCCAGCGACATCGCCGTG

GAGTGGGAGAGCAATGGGCAGCCGGAGAACAACTACAAGACCACGCCTCC

CGTGCTGGACTCCGACGGCTCCTTCTTCCTCTACAGCAGGCTAACCGTGG

ACAAGAGCAGGTGGCAGGAGGGGAATGTCTTCTCATGCTCCGTGATGCAT

GAGGCTCTGCACAACCACTACACACAGAAGAGCCTCTCCCTGTCTCTGGG

TAAAGCTAGCGATACAACAGAACCTGCAACACCTACAACACCTGTAACAA

CAGATCAGATTTGCATTGGTTACCATGCAAACAACTCGACAGAGCAGGTT

GACACAATAATGGAAAAGAACGTTACTGTTACACATGCCCAAGACATACT

GGAAAAGAAACACAACGGGAAGCTCTGCGATCTAGATGGAGTGAAGCCTC

TAATTTTGAGAGATTGTAGCGTAGCTGGATGGCTCCTCGGAAACCCAATG

TGTGACGAATTCATCAATGTGCCGGAATGGTCTTACATAGTGGAGAAGGC

CAATCCAGTCAATGACCTCTGTTACCCAGGGGATTTCAATGACTATGAAG

AATTGAAACACCTATTGAGCAGAATAAACCATTTTGAGAAAATTCAGATC
```

```
ATCCCCAAAAGTTCTTGGTCCAGTCATGAAGCCTCATTAGGGGTGAGCTC

AGCATGTCCATACCAGGGAAAGTCCTCCTTTTTCAGAAATGTGGTATGGC

TTATCAAAAGAACAGTACATACCCAACAATAAAGAGGAGCTACAATAAT

ACCAACCAAGAAGATCTTTTGGTACTGTGGGGGATTCACCATCCTAATGA

TGCGGCAGAGCAGACAAAGCTCTATCAAAACCCAACCACCTATATTTCCG

TTGGGACATCAACACTAAACCAGAGATTGGTACCAAGAATAGCTACTAGA

TCCAAAGTAAACGGGCAAAGTGGAAGGATGGAGTTCTTCTGGACAATTTT

AAAGCCAATGATGCAATCAACTTCGAGAGTAATGGAAATTTCATTGCTC

CAGAATATGCATACAAAATTGTCAAGAAGGGGACTCAACAATTATGAAA

AGTGAATTGGAATATGGTAACTGCAACACCAAGTGTCAAACTCCAATGGG

GGCGATAAACTCTAGCATGCCATTCCACAATATACACCCTCTCACCATTG

GGGAATGCCCCAAATATGTGAAATCAAACAGATTAGTCCTTGCGCACCAT

CACCATCACCATTGA
```

The mature H chain sequence for C87 heavy chain is shown below. Joining sequence AS is bold and Flu HA5-1 is underlined.

(SEQ ID NO. 66)

QVQLRQSGPELVKPGASVKMSCKASGYTFTDYVISWVKQRTGQGLEWIGDIYPGSGYS

FYNENFKGKATLTADKSSTTAYMQLSSLTSEDSAVYFCATYYNYPFAYWGQGTLVTVS

AAKTTGPSVFPLAPCSRSTSESTAALGCLVKDYFPEPVTVSWNSGALTSGVHTFPAVLQ

SSGLYSLSSVVTVPSSSLGTKTYTCNVDHKPSNTKVDKRVESKYGPPCPPCPAPEFEGGP

SVFLFPPKPKDTLMISRTPEVTCVVVDVSQEDPEVQFNWYVDGVEVHNAKTKPREEQF

NSTYRVVSVLTVLHQDWLNGKEYKCKVSNKGLPSSIEKTISKAKGQPREPQVYTLPPSQ

EEMTKNQVSLTCLVKGFYPSDIAVEWESNGQPENNYKTTPPVLDSDGSFFLYSRLTVDK

SRWQEGNVFSCSVMHEALHNHYTQKSLSLSLGKASDTTEPATPTTPVTT<u>DQICIGYHAN

NSTEQVDTIMEKNVTVTHAQDILEKKHNGKLCDLDGVKPLILRDCSVAGWLLGNPMC

DEFINVPEWSYIVEKANPVNDLCYPGDFNDYEELKHLLSRINHFEKIQIIPKSSWSSHEAS

LGVSSACPYQGKSSFFRNVVWLIKKNSTYPTIKRSYNNTNQEDLLVLWGIHHPNDAAE

QTKLYQNPTTYISVGTSTLNQRLVPRIATRSKVNGQSGRMEFFWTILKPNDAINFESNGN

FIAPEYAYKIVKKGDSTIMKSELEYGNCNTKCQTPMGAINSSMPFHNIHPLTIGECPKYV

KSNRLVLAHHHHHH</u>

C88 rAB-pIRES2 [mAnti-Langerin15B10H-SLAML-V-hIgG4H-C-Dockerin] The coding region for this H chain-dockerin fusion protein is shown below. Start and stop codons are in bold, as is the joining GCTAGC restriction site.

(SEQ ID NO. 67)
```
ATGGACCCCAAAGGCTCCCTTTCCTGGAGAATACTTCTGTTTCTCTCCCT

GGCTTTTGAGTTGTCGTACGGACAGGTTCAGCTGCGGCAGTCTGGACCTG

AGCTGGTGAAGCCTGGGGCTTCAGTGAAGATGTCCTGCAAGGCTTCTGGA

TACACATTTACTGACTATGTTATAAGTTGGGTGAAGCAGAGAACTGGACA

GGGCCTTGAGTGGATTGGAGATATTTATCCTGGAAGTGGTTATTCTTTCT

ACAATGAGAACTTCAAGGGCAAGGCCACACTGACTGCAGACAAATCCTCC

ACCACAGCCTACATGCAGCTCAGCAGCCTGACATCTGAGGACTCTGCGGT

CTATTTCTGTGCAACCTACTATAACTACCCTTTTGCTTACTGGGGCCAAG

GGACTCTGGTCACTGTCTCTGCAGCCAAAACAACGGGCCCATCCGTCTTC

CCCCTGGCGCCCTGCTCCAGGAGCACCTCCGAGAGCACAGCCGCCCTGGG

CTGCCTGGTCAAGGACTACTTCCCCGAACCGGTGACGGTGTCGTGGAACT

CAGGCGCCCTGACCAGCGGCGTGCACACCTTCCCGGCTGTCCTACAGTCC

TCAGGACTCTACTCCCTCAGCAGCGTGGTGACCGTGCCCTCCAGCAGCTT

GGGCACGAAGACCTACACCTGCAACGTAGATCACAAGCCCAGCAACACCA

AGGTGGACAAGAGAGTTGAGTCCAAATATGGTCCCCCATGCCCACCCTGC

CCAGCACCTGAGTTCGAAGGGGGACCATCAGTCTTCCTGTTCCCCCCAAA

ACCCAAGGACACTCTCATGATCTCCCGGACCCCTGAGGTCACGTGCGTGG

TGGTGGACGTGAGCCAGGAAGACCCCGAGGTCCAGTTCAACTGGTACGTG

GATGGCGTGGAGGTGCATAATGCCAAGACAAAGCCGCGGGAGGAGCAGTT

CAACAGCACGTACCGTGTGGTCAGCGTCCTCACCGTCCTGCACCAGGACT

GGCTGAACGGCAAGGAGTACAAGTGCAAGGTCTCCAACAAAGGCCTCCCG

TCCTCCATCGAGAAAACCATCTCCAAAGCCAAAGGGCAGCCCCGAGAGCC

ACAGGTGTACACCCTGCCCCCATCCCAGGAGGAGATGACCAAGAACCAGG

TCAGCCTGACCTGCCTGGTCAAAGGCTTCTACCCCAGCGACATCGCCGTG

GAGTGGGAGAGCAATGGGCAGCCGGAGAACAACTACAAGACCACGCCTCC

CGTGCTGGACTCCGACGGCTCCTTCTTCCTCTACAGCAGGCTAACCGTGG

ACAAGAGCAGGTGGCAGGAGGGGAATGTCTTCTCATGCTCCGTGATGCAT

GAGGCTCTGCACAACCACTACACACAGAAGAGCCTCTCCCTGTCTCTGGG

TAAAGCTAGC<u>AATTCTCCTCAAAATGAAGTACTGTACGGAGATGTGAATG
```

-continued

```
ATGACGGAAAAGTAAACTCCACTGACTTGACTTTGTTAAAAAGATATGTT

CTTAAAGCCGTCTCAACTCTCCCTTCTTCCAAAGCTGAAAAGAACGCAGA

TGTAAATCGTGACGGAAGAGTTAATTCCAGTGATGTCACAATACTTTCAA

GATATTTGATAAGGGTAATCGAGAAATTACCAATATAA
```

The mature H chain sequence for C88 heavy chain is shown below. Joining sequence AS is bold and dockerin is shaded grey. A flexible linker joining sequence is underlined.

(SEQ ID NO. 68)
QVQLRQSGPELVKPGASVKMSCKASGYTFTDYVISWVKQRTGQGLEWIGDIYPGSGYS

FYNENFKGKATLTADKSSTTAYMQLSSLTSEDSAVYFCATYYNYPFAYWGQGTLVTVS

AAKTTGPSVFPLAPCSRSTSESTAALGCLVKDYFPEPVTVSWNSGALTSGVHTFPAVLQ

SSGLYSLSSVVTVPSSSLGTKTYTCNVDHKPSNTKVDKRVESKYGPPCPPCPAPEFEGGP

SVFLFPPKPKDTLMISRTPEVTCVVVDVSQEDPEVQFNWYVDGVEVHNAKTKPREEQF

NSTYRVVSVLTVLHQDWLNGKEYKCKVSNKGLPSSIEKTISKAKGQPREPQVYTLPPSQ

EEMTKNQVSLTCLVKGFYPSDIAVEWESNGQPENNYKTTPPVLDSDGSFFLYSRLTVDK

SRWQEGNVFSCSVMHEALHNHYTQKSLSLSLGKASNSPQNEVLYGDVNDDGKVNSTD

LTLLKRYVLKAVSTLPSSKAEKNADVNRDGRVNSSDVTILSRYLIRVIEKLPI

C89 rAB-pIRES2[mAnti-Langerin15B10H-SLAML-V-hIgG4H-Flex-FluHA1-1-6×His] The coding region for this H chain-Flu HA1-1 fusion protein is shown below. Start and stop codons are in bold, as is the joining GCTAGC restriction site.

(SEQ ID NO. 69)
ATGGACCCCAAAGGCTCCCTTTCCTGGAGAATACTTCTGTTTCTCTCCCT
GGCTTTTGAGTTGTCGTACGGACAGGTTCAGCTGCGGCAGTCTGGACCTG
AGCTGGTGAAGCCTGGGGCTTCAGTGAAGATGTCCTGCAAGGCTTCTGGA
TACACATTTACTGACTATGTTATAAGTTGGGTGAAGCAGAGAACTGGACA
GGGCCTTGAGTGGATTGGAGATATTTATCCTGGAAGTGGTTATTCTTTCT
ACAATGAGAACTTCAAGGGCAAGGCCACACTGACTGCAGACAAATCCTCC
ACCACAGCCTACATGCAGCTCAGCAGCCTGACATCTGAGGACTCTGCGGT
CTATTTCTGTGCAACCTACTATAACTACCCTTTTGCTTACTGGGGCCAAG
GGACTCTGGTCACTGTCTCTGCAGCCAAAACAACGGGCCCATCCGTCTTC
CCCCTGGCGCCCTGCTCCAGGAGCACCTCCGAGAGCACAGCCGCCCTGGG
CTGCCTGGTCAAGGACTACTTCCCCGAACCGGTGACGGTGTCGTGGAACT
CAGGCGCCCTGACCAGCGGCGTGCACACCTTCCCGGCTGTCCTACAGTCC
TCAGGACTCTACTCCCTCAGCAGCGTGGTGACCGTGCCCTCCAGCAGCTT
GGGCACGAAGACCTACACCTGCAACGTAGATCACAAGCCCAGCAACACCA
AGGTGGACAAGAGAGTTGAGTCCAAATATGGTCCCCCATGCCCACCCTGC
CCAGCACCTGAGTTCGAAGGGGGACCATCAGTCTTCCTGTTCCCCCCAAA
ACCCAAGGACACTCTCATGATCTCCCGGACCCCTGAGGTCACGTGCGTGG
TGGTGGACGTGAGCCAGGAAGACCCCGAGGTCCAGTTCAACTGGTACGTG
GATGGCGTGGAGGTGCATAATGCCAAGACAAAGCCGCGGGAGGAGCAGTT

-continued

GAGTGGGAGAGCAATGGGCAGCCGGAGAACAACTACAAGACCACGCCTCC
CGTGCTGGACTCCGACGGCTCCTTCTTCCTCTACAGCAGGCTAACCGTGG
ACAAGAGCAGGTGGCAGGAGGGGAATGTCTTCTCATGCTCCGTGATGCAT
GAGGCTCTGCACAACCACTACACACAGAAGAGCCTCTCCCTGTCTCTGGG
TAAAGCTAGCGATACAACAGAACCTGCAACACCTACAACACCTGTAACAA
CAGACACAATATGTATAGGCTACCATGCGAACAATTCAACCGACACTGTT
GACACAGTACTCGAGAAGAATGTGACAGTGACACACTCTGTTAACCTGCT
CGAAGACAGCCACAACGGAAAACTATGTAGATTAAAAGGAATAGCCCCAC
TACAATTGGGGAAATGTAACATCGCCGGATGGCTCTTGGGAAACCCAGAA
TGCGACCCACTGCTTCCAGTGAGATCATGGTCCTACATTGTAGAAACACC
AAACTCTGAGAATGGAATATGTTATCCAGGAGATTTCATCGACTATGAGG
AGCTGAGGGAGCAATTGAGCTCAGTGTCATCATTCGAAAGATTCGAAATA
TTTCCCAAAGAAAGCTCATGGCCCAACCACAACACAAACGGAGTAACGGC
AGCATGCTCCCATGAGGGGAAAAGCAGTTTTTACAGAAATTTGCTATGGC
TGACGGAGAAGGAGGGCTCATACCCAAAGCTGAAAAATTCTTATGTGAAC
AAAAAAGGGAAAGAAGTCCTTGTACTGTGGGGTATTCATCACCCGCCTAA
CAGTAAGGAACAACAGAATCTCTATCAGAATGAAAATGCTTATGTCTCTG
TAGTGACTTCAAATTATAACAGGAGATTTACCCCGGAAATAGCAGAAAGA
CCCAAAGTAAGAGATCAAGCTGGGAGGATGAACTATTACTGGACCTTGCT
AAAACCCGGAGACACAATAATATTTGAGGCAAATGGAAATCTAATAGCAC
CAATGTATGCTTTCGCACTGAGTAGAGGCTTTGGGTCCGGCATCATCACC
TCAAACGCATCAATGCATGAGTGTAACACGAAGTGTCAAACACCCCTGGG
AGCTATAAACAGCAGTCTCCCTTACCAGAATATACACCCAGTCACAATAG

GAGAGTGCCCAAAATACGTCAGGAGTGCCAAATTGAGGATGGTTCACCAT

CACCATCACCATTGA

The mature H chain sequence for C89 heavy chain is shown below. Joining sequence AS is bold and Flu HA1-1 is underlined. A flexible linker joining sequence is italicized.

(SEQ ID NO. 70)
QVQLRQSGPELVKPGASVKMSCKASGYTFTDYVISWVKQRTGQGLEWIGDIYPGSGYS

FYNENFKGKATLTADKSSTTAYMQLSSLTSEDSAVYFCATYYNYPFAYWGQGTLVTVS

AAKTTGPSVFPLAPCSRSTSESTAALGCLVKDYFPEPVTVSWNSGALTSGVHTFPAVLQ

SSGLYSLSSVVTVPSSSLGTKTYTCNVDHKPSNTKVDKRVESKYGPPCPPCPAPEFEGGP

SVFLFPPKPKDTLMISRTPEVTCVVVDVSQEDPEVQFNWYVDGVEVHNAKTKPREEQF

NSTYRVVSVLTVLHQDWLNGKEYKCKVSNKGLPSSIEKTISKAKGQPREPQVYTLPPSQ

EEMTKNQVSLTCLVKGFYPSDIAVEWESNGQPENNYKTTPPVLDSDGSFFLYSRLTVDK

SRWQEGNVFSCSVMHEALHNHYTQKSLSLSLGKAS*DTTEPATPTTPVTT*DTICIGYHAN

NSTDTVDTVLEKNVTVTHSVNLLEDSHNGKLCRLKGIAPLQLGKCNIAGWLLGNPECD

PLLPVRSWSYIVETPNSENGICYPGDFIDYEELREQLSSVSSFERFEIFPKESSWPNHNTN

GVTAACSHEGKSSFYRNLLWLTEKEGSYPKLKNSYVNKKGKEVLVLWGIHHPPNSKE

QQNLYQNENAYVSVVTSNYNRRFTPEIAERPKVRDQAGRMNYYWTLLKPGDTIIFEAN

GNLIAPMYAFALSRGEGSGIITSNASMHECNTKCQTPLGAINSSLPYQNIHPVTIGECPKY

VRSAKLRMVHHHHHH

C246 rAB-pIRES2[mAnti-Langerin15B10H-SLAML-V-hIgG4H-Viralgag] The coding region for this H chain-gag fusion protein is shown below. Start and stop codons are in bold, as is the joining GCTAGC restriction site.

(SEQ ID NO. 71)
ATGGACCCCAAAGGCTCCCTTTCCTGGAGAATACTTCTGTTTCTCTCCCT

GGCTTTTGAGTTGTCGTACGGACAGGTTCAGCTGCGGCAGTCTGGACCTG

AGCTGGTGAAGCCTGGGGCTTCAGTGAAGATGTCCTGCAAGGCTTCTGGA

TACACATTTACTGACTATGTTATAAGTTGGGTGAAGCAGAGAACTGGACA

GGGCCTTGAGTGGATTGGAGATATTTATCCTGGAAGTGGTTATTCTTTCT

ACAATGAGAACTTCAAGGGCAAGGCCACACTGACTGCAGACAAATCCTCC

ACCACAGCCTACATGCAGCTCAGCAGCCTGACATCTGAGGACTCTGCGGT

CTATTTCTGTGCAACCTACTATAACTACCCTTTTGCTTACTGGGGCCAAG

GGACTCTGGTCACTGTCTCTGCAGCCAAAACAACGGGCCCATCCGTCTTC

CCCCTGGCGCCCTGCTCCAGGAGCACCTCCGAGAGCACAGCCGCCCTGGG

CTGCCTGGTCAAGGACTACTTCCCCGAACCGGTGACGGTGTCGTGGAACT

CAGGCGCCCTGACCAGCGGCGTGCACACCTTCCCGGCTGTCCTACAGTCC

TCAGGACTCTACTCCCTCAGCAGCGTGGTGACCGTGCCCTCCAGCAGCTT

GGGCACGAAGACCTACACCTGCAACGTAGATCACAAGCCCAGCAACACCA

AGGTGGACAAGAGAGTTGAGTCCAAATATGGTCCCCCATGCCCACCCTGC

CCAGCACCTGAGTTCGAAGGGGGACCATCAGTCTTCCTGTTCCCCCCAAA

ACCCAAGGACACTCTCATGATCTCCCGGACCCCTGAGGTCACGTGCGTGG

TGGTGGACGTGAGCCAGGAAGACCCCGAGGTCCAGTTCAACTGGTACGTG

GATGGCGTGGAGGTGCATAATGCCAAGACAAAGCCGCGGGAGGAGCAGTT

CAACAGCACGTACCGTGTGGTCAGCGTCCTCACCGTCCTGCACCAGGACT

GGCTGAACGGCAAGGAGTACAAGTGCAAGGTCTCCAACAAAGGCCTCCCG

TCCTCCATCGAGAAAACCATCTCCAAAGCCAAAGGGCAGCCCCGAGAGCC

ACAGGTGTACACCCTGCCCCCATCCCAGGAGGAGATGACCAAGAACCAGG

TCAGCCTGACCTGCCTGGTCAAAGGCTTCTACCCCAGCGACATCGCCGTG

GAGTGGGAGAGCAATGGGCAGCCGGAGAACAACTACAAGACCACGCCTCC

CGTGCTGGACTCCGACGGCTCCTTCTTCCTCTACAGCAGGCTAACCGTGG

ACAAGAGCAGGTGGCAGGAGGGGAATGTCTTCTCATGCTCCGTGATGCAT

GAGGCTCTGCACAACCACTACACACAGAAGCCTCTCCCTGTCTCTGGG

TAAAGCTAGCGACATGGCCAAGAAGGAGACAGTCTGGAGGCTCGAGGAGT

TCGGTAGGCCTATAGTGCAGAACATCCAGGGGCAAATGGTACATCAGGCC

ATATCACCTAGAACTTTAAATGCATGGGTAAAAGTAGTAGAAGAGAAGGC

TTTCAGCCCAGAAGTAATACCCATGTTTTCAGCATTATCAGAAGGAGCCA

CCCCACAAGATTTAAACACCATGCTAAACACAGTGGGGGACATCAAGCA

GCCATGCAAATGTTAAAAGAGACCATCAATGAGGAAGCTGCAGAATGGGA

TAGAGTACATCCAGTGCATGCAGGGCCTATTGCACCAGGCCAGATGAGAG

AACCAAGGGGAAGTGACATAGCAGGAACTACTAGTACCCTTCAGGAACAA

ATAGGATGGATGACAAATAATCCACCTATCCCAGTAGGAGAAATTTATAA

AAGATGGATAATCCTGGGATTAAATAAAATAGTAAGAATGTATAGCCCTA

CCAGCATTCTGGACATAAGACAAGGACCAAAAGAACCTTTTAGAGACTAT

GTAGACCGGTTCTATAAAACTCTAAGAGCCGAGCAAGCTTCACAGGAGGT

AAAAAATTGGATGACAGAAACCTTGTTGGTCCAAAATGCGAACCCAGATT

GTAAGACTATTTTAAAAGCATTGGGACCAGCGGCTACACTAGAAGAAATG

ATGACAGCATGTCAGGGAGTAGGAGGACCCGGCCATAAGGCAAGAGTTTT

GTGA

The mature H chain sequence for C89 heavy chain is shown below. Joining sequence AS is bold and Gag p24 is underlined. A flexible linker joining sequence is italicized.

(SEQ ID NO. 72)

QVQLRQSGPELVKPGASVKMSCKASGYTFTDYVISWVKQRTGQGLEWIGDIYPGSGYS

FYNENFKGKATLTADKSSTTAYMQLSSLTSEDSAVYFCATYYNYPFAYWGQGTLVTVS

AAKTTGPSVFPLAPCSRSTSESTAALGCLVKDYFPEPVTVSWNSGALTSGVHTFPAVLQ

SSGLYSLSSVVTVPSSSLGTKTYTCNVDHKPSNTKVDKRVESKYGPPCPPCPAPEFEGGP

SVFLFPPKPKDTLMISRTPEVTCVVVDVSQEDPEVQFNWYVDGVEVHNAKTKPREEQF

NSTYRVVSVLTVLHQDWLNGKEYKCKVSNKGLPSSIEKTISKAKGQPREPQVYTLPPSQ

EEMTKNQVSLTCLVKGFYPSDIAVEWESNGQPENNYKTTPPVLDSDGSFFLYSRLTVDK

SRWQEGNVFSCSVMHEALHNHYTQKSLSLSLGKASDMAKKETVWRLEEFGRPIVQNIQ

GQMVHQAISPRTLNAWVKVVEEKAFSPEVIPMFSALSEGATPQDLNTMLNTVGGHQA

AMQMLKETINEEAAEWDRVHPVHAGPIAPGQMREPRGSDIAGTTSTLQEQIGWMTNNP

PIPVGEIYKRWIILGLNKIVRMYSPTSILDIRQGPKEPFRDYVDRFYKTLRAEQASQEVKN

WMTETLLVQNANPDCKTILKALGPAATLEEMMTACQGVGGPGHKARVL

C742 rAB-cetHS-puro [mAnti-Langerin15B10H-LV-hIgG4H-C-Flex-hPSA] The coding region for this H chain-PSA fusion protein is shown below. Start and stop codons are in bold, as is the joining GCTAGC restriction site.

(SEQ ID NO. 73)
ATGGAATGGAGGATCTTTCTCTTCATCCTGTCAGGAACTGCAGGTGTCCA

CTCCCAGGTTCAGCTGCGGCAGTCTGGACCTGAGCTGGTGAAGCCTGGGG

CTTCAGTGAAGATGTCCTGCAAGGCTTCTGGATACACATTTACTGACTAT

GTTATAAGTTGGGTGAAGCAGAGAACTGGACAGGGCCTTGAGTGGATTGG

AGATATTTATCCTGGAAGTGGTTATTCTTTCTACAATGAGAACTTCAAGG

GCAAGGCCACACTGACTGCAGACAAATCCTCCACCACAGCCTACATGCAG

CTCAGCAGCCTGACATCTGAGGACTCTGCGGTCTATTTCTGTGCAACCTA

CTATAACTACCCTTTTGCTTACTGGGGCCAAGGGACTCTGGTCACTGTCT

CTGCAGCCAAAACAACGGGCCCATCCGTCTTCCCCCTGGCGCCCTGCTCC

AGGAGCACCTCCGAGAGCACAGCCGCCCTGGGCTGCCTGGTCAAGGACTA

CTTCCCCGAACCGGTGACGGTGTCGTGGAACTCAGGCGCCCTGACCAGCG

GCGTGCACACCTTCCCGGCTGTCCTACAGTCCTCAGGACTCTACTCCCTC

AGCAGCGTGGTGACCGTGCCCTCCAGCAGCTTGGGCACGAAGACCTACAC

CTGCAACGTAGATCACAAGCCCAGCAACACCAAGGTGGACAAGAGAGTTG

AGTCCAAATATGGTCCCCCATGCCCACCCTGCCCAGCACCTGAGTTCGAA

GGGGGACCATCAGTCTTCCTGTTCCCCCCAAAACCCAAGGACACTCTCAT

GATCTCCCGGACCCCTGAGGTCACGTGCGTGGTGGTGGACGTGAGCCAGG

AAGACCCCGAGGTCCAGTTCAACTGGTACGTGGATGGCGTGGAGGTGCAT

AATGCCAAGACAAAGCCGCGGGAGGAGCAGTTCAACAGCACGTACCGTGT

GGTCAGCGTCCTCACCGTCCTGCACCAGGACTGGCTGAACGGCAAGGAGT

ACAAGTGCAAGGTCTCCAACAAAGGCCTCCCGTCCTCCATCGAGAAAACC

ATCTCCAAAGCCAAAGGGCAGCCCCGAGAGCCACAGGTGTACACCCTGCC

CCCATCCCAGGAGGAGATGACCAAGAACCAGGTCAGCCTGACCTGCCTGG

TCAAAGGCTTCTACCCCAGCGACATCGCCGTGGAGTGGGAGAGCAATGGG

CAGCCGGAGAACAACTACAAGACCACGCCTCCCGTGCTGGACTCCGACGG

CTCCTTCTTCCTCTACAGCAGGCTAACCGTGGACAAGAGCAGGTGGCAGG

AGGGGAATGTCTTCTCATGCTCCGTGATGCATGAGGCTCTGCACAACCAC

TACACACAGAAGAGCCTCTCCCTGTCTCTGGGTAAAGCTAGCGATACAAC

AGAACCTGCAACACCTACAACACCTGTAACAACACCGACAACAACACTTC

TAGCGCCCCTCATCCTGTCTCGGATTGTGGGAGGCTGGGAGTGCGAGAAG

CATTCCCAACCCTGGCAGGTGCTTGTGGCCTCTCGTGGCAGGGCAGTCTG

CGGCGGTGTTCTGGTGCACCCCCAGTGGGTCCTCACAGCTGCCCACTGCA

TCAGGAACAAAAGCGTGATCTTGCTGGGTCGGCACAGCCTGTTTCATCCT

GAAGACACAGGCCAGGTATTTCAGGTCAGCCACAGCTTCCCACACCCGCT

CTACGATATGAGCCTCCTGAAGAATCGATTCCTCAGGCCAGGTGATGACT

CCAGCCACGACCTCATGCTGCTCCGCCTGTCAGAGCCTGCCGAGCTCACG

GATGCTGTGAAGGTCATGGACCTGCCCACCCAGGAGCCAGCACTGGGGAC

CACCTGCTACGCCTCAGGCTGGGGCAGCATTGAACCAGAGGAGTTCTTGA

CCCCAAAGAAACTTCAGTGTGTGGACCTCCATGTTATTTCCAATGACGTG

TGTGCGCAAGTTCACCCTCAGAAGGTGACCAAGTTCATGCTGTGTGCTGG

ACGCTGGACAGGGGGCAAAAGCACCTGCTCGGGTGATTCTGGGGGCCCAC

-continued

TTGTCTGTAATGGTGTGCTTCAAGGTATCACGTCATGGGGCAGTGAACCA

TGTGCCCTGCCCGAAAGGCCTTCCCTGTACACCAAGGTGGTGCATTACCG

GAAGTGGATCAAGGACACCATCGTGGCCAACCCCTGA

The mature H chain sequence for C742 heavy chain is shown below. Joining sequence AS is bold and PSA is underlined. A flexible linker joining sequence is italicized.

(SEQ ID NO. 74)
QVQLRQSGPELVKPGASVKMSCKASGYTFTDYVISWVKQRTGQGLEWIGDIYPGSGYS

FYNENFKGKATLTADKSSTTAYMQLSSLTSEDSAVYFCATYYNYPFAYWGQGTLVTVS

AAKTTGPSVFPLAPCSRSTSESTAALGCLVKDYFPEPVTVSWNSGALTSGVHTFPAVLQ

SSGLYSLSSVVTVPSSSLGTKTYTCNVDHKPSNTKVDKRVESKYGPPCPPCPAPEFEGGP

SVFLFPPKPKDTLMISRTPEVTCVVVDVSQEDPEVQFNWYVDGVEVHNAKTKPREEQF

NSTYRVVSVLTVLHQDWLNGKEYKCKVSNKGLPSSIEKTISKAKGQPREPQVYTLPPSQ

EEMTKNQVSLTCLVKGFYPSDIAVEWESNGQPENNYKTTPPVLDSDGSFFLYSRLTVDK

SRWQEGNVFSCSVMHEALHNHYTQKSLSLSLGKAS_DTTEPATPTTPVTTPTTTLL_APLILS

RIVGGWECEKHSQPWQVLVASRGRAVCGGVLVHPQWVLTAAHCIRNKSVILLGRHSL

FHPEDTGQVFQVSHSFPHPLYDMSLLKNRFLRPGDDSSHDLMLLRLSEPAELTDAVKV

MDLPTQEPALGTTCYASGWGSIEPEEFLTPKKLQCVDLHVISNDVCAQVHPQKVTKFM

LCAGRWTGGKSTCSGDSGGPLVCNGVLQGITSWGSEPCALPERPSLYTKVVHYRKWIK

DTIVANP

C1011 rAB-cetHS-puro [mAnti-Langerin15B10H-LV-hIgG4H-C-Flex-v1-Pep-gag17-f1-gag253-2-nef116-f3-nef66-f4-pol158] a.k.a. Anti-Langerin15B10H-HIPO5. The coding region for this H chain-HIV peptides fusion protein is shown below. Start and stop codons are in bold, as is the joining GCTAGT restriction site.

(SEQ ID NO. 75)
ATGGAATGGAGGATCTTTCTCTTCATCCTGTCAGGAACTGCAGGTGTCCA

CTCCCAGGTTCAGCTGCGGCAGTCTGGACCTGAGCTGGTGAAGCCTGGGG

CTTCAGTGAAGATGTCCTGCAAGGCTTCTGGATACACATTTACTGACTAT

GTTATAAGTTGGGTGAAGCAGAGAACTGGACAGGGCCTTGAGTGGATTGG

AGATATTTATCCTGGAAGTGGTTATTCTTTCTACAATGAGAACTTCAAGG

GCAAGGCCACACTGACTGCAGACAAATCCTCCACCACAGCCTACATGCAG

CTCAGCAGCCTGACATCTGAGGACTCTGCGGTCTATTTCTGTGCAACCTA

CTATAACTACCCTTTTGCTTACTGGGGCCAAGGGACTCTGGTCACTGTCT

CTGCAGCCAAAACAACGGGCCCATCCGTCTTCCCCCTGGCGCCCTGCTCC

AGGAGCACCTCCGAGAGCACAGCCGCCCTGGGCTGCCTGGTCAAGGACTA

CTTCCCCGAACCGGTGACGGTGTCGTGGAACTCAGGCGCCCTGACCAGCG

GCGTGCACACCTTCCCGGCTGTCCTACAGTCCTCAGGACTCTACTCCCTC

AGCAGCGTGGTGACCGTGCCCTCCAGCAGCTTGGGCACGAAGACCTACAC

CTGCAACGTAGATCACAAGCCCAGCAACACCAAGGTGGACAAGAGAGTTG

AGTCCAAATATGGTCCCCCATGCCCACCCTGCCCAGCACCTGAGTTCGAA

-continued

GGGGGACCATCAGTCTTCCTGTTCCCCCCAAAACCCAAGGACACTCTCAT

GATCTCCCGGACCCCTGAGGTCACGTGCGTGGTGGTGGACGTGAGCCAGG

AAGACCCCGAGGTCCAGTTCAACTGGTACGTGGATGGCGTGGAGGTGCAT

AATGCCAAGACAAAGCCGCGGGAGGAGCAGTTCAACAGCACGTACCGTGT

GGTCAGCGTCCTCACCGTCCTGCACCAGGACTGGCTGAACGGCAAGGAGT

ACAAGTGCAAGGTCTCCAACAAAGGCCTCCCGTCCTCCATCGAGAAAACC

ATCTCCAAAGCCAAAGGGCAGCCCCGAGAGCCACAGGTGTACACCCTGCC

CCCATCCCAGGAGGAGATGACCAAGAACCAGGTCAGCCTGACCTGCCTGG

TCAAAGGCTTCTACCCCAGCGACATCGCCGTGGAGTGGGAGAGCAATGGG

CAGCCGGAGAACAACTACAAGACCACGCCTCCCGTGCTGGACTCCGACGG

CTCCTTCTTCCTCTACAGCAGGCTAACCGTGGACAAGAGCAGGTGGCAGG

AGGGGAATGTCTTCTCATGCTCCGTGATGCATGAGGCTCTGCACAACCAC

TACACACAGAAGAGCCTCTCCCTGTCTCTGGGTAAAGCTAGTCAGACCCC

CACCAACACCATCAGCGTGACCCCCACCAACAACAGCACCCCCACCAACA

ACAGCAACCCCAAGCCCAACCCCGCTAGTGAGAAGATCCGGCTGCGGCCC

GGCGGCAAGAAGAAGTACAAGCTGAAGCACATCGTGGCTAGTAGCAGCGT

GAGCCCCACCACCAGCGTGCACCCCACCCCCACCAGCGTGCCCCCCACCC

CCACCAAGAGCAGCCCCGCTAGTAACCCCCCCATCCCCGTGGGCGAGATC

TACAAGCGGTGGATCATCCTGGGCCTGAACAAGATCGTGCGGATGTACAG

CCCCACCAGCATCCTGGACGCTAGTCCCACCAGCACCCCGCCGACAGCA

GCACCATCACCCCCACCGCCACCCCCACCGCCACCCCCACCATCAAGGGC

GCTAGTCACACCCAGGGCTACTTCCCCGACTGGCAGAACTACACCCCCGG

CCCCGGCGTGCGGTACCCCCTGACCTTCGGCTGGCTGTACAAGCTGGCTA

GTACCGTGACCCCCACCGCCACCGCCACCCCCAGCGCCATCGTGACCACC

-continued

ATCACCCCCACCGCCACCACCAAGCCCGCTAGTGTGGGCTTCCCCGTGAC

CCCCCAGGTGCCCCTGCGGCCCATGACCTACAAGGCCGCCGTGGACCTGA

GCCACTTCCTGAAGGAGAAGGGCGGCCTGGCTAGTACCAACGGCAGCATC

ACCGTGGCCGCCACCGCCCCCACCGTGACCCCCACCGTGAACGCCACCCC

CAGCGCCGCCGCTAGTGCCATCTTCCAGAGCAGCATGACCAAGATCCTGG

AGCCCTTCCGGAAGCAGAACCCCGACATCGTGATCTACCAGTACATGGAC

GACCTGTACGCTAGCTGA

The mature H chain sequence for C1011 heavy chain is shown below. Joining sequences AS are bold and HIV peptides are underlined. A flexible linker joining sequence is italicized.

(SEQ ID NO. 76)
QVQLRQSGPELVKPGASVKMSCKASGYTFTDYVISWVKQRTGQGLEWIGDIYPGSGYS

FYNENFKGKATLTADKSSTTAYMQLSSLTSEDSAVYFCATYYNYPFAYWGQGTLVTVS

AAKTTGPSVFPLAPCSRSTSESTAALGCLVKDYFPEPVTVSWNSGALTSGVHTFPAVLQ

SSGLYSLSSVVTVPSSSLGTKTYTCNVDHKPSNTKVDKRVESKYGPPCPPCPAPEFEGGP

SVFLFPPKPKDTLMISRTPEVTCVVVDVSQEDPEVQFNWYVDGVEVHNAKTKPREEQF

NSTYRVVSVLTVLHQDWLNGKEYKCKVSNKGLPSSIEKTISKAKGQPREPQVYTLPPSQ

EEMTKNQVSLTCLVKGFYPSDIAVEWESNGQPENNYKTTPPVLDSDGSFFLYSRLTVDK

SRWQEGNVFSCSVMHEALHNHYTQKSLSLSLGKAS*QTPTNTISVTPTNNSTPTNNSNPKP*

*NPAS*EKIRLRPGGKKKYKLKHIVASSSSVSPTTSVHPTPTSVPPTPTKSSPASNPPIPVGEIYK

RWIILGLNKIVRMYSPTSILDAS*PTSTPADSSTITPTATPTATPTIKG*ASHTQGYFPDWQNY

TPGPGVRYPLTFGWLYKLAS*TVTPTATATPSAIVTTITPTATTKP*ASVGFPVTPQVPLRPMT

YKAAVDLSHFLKEKGGLAS*TNGSITVAATAPTVTPTVNATPSAA*ASAIFQSSMTKILEPFRK

QNPDIVIYQYMDDLYAS

Figure 8:
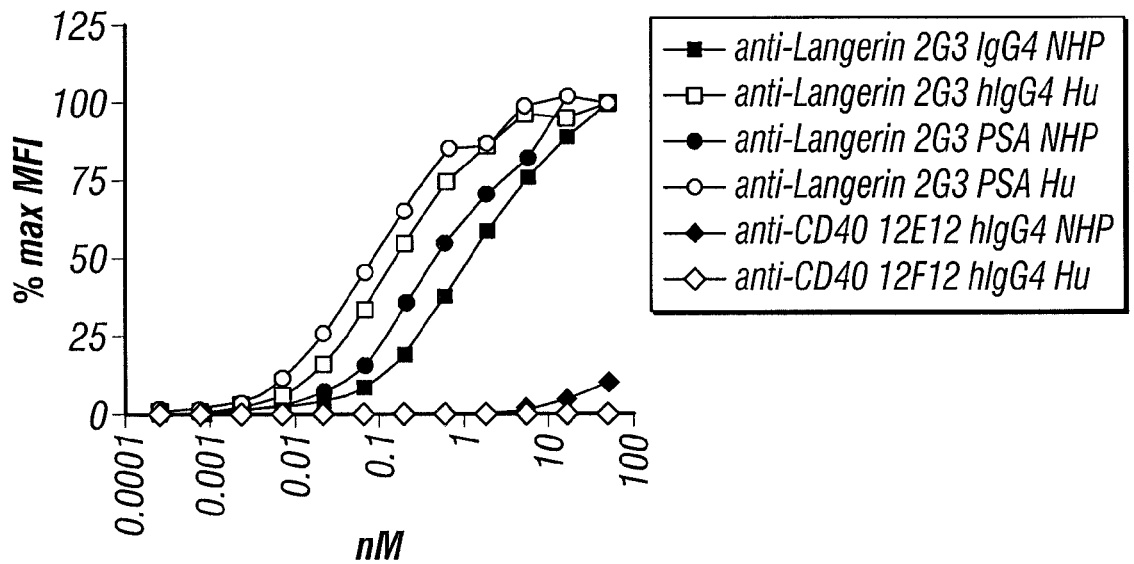
FIG. 8 shows the binding results of the anti-Langerin antibodies against a non-human primate target.
Figure 8:
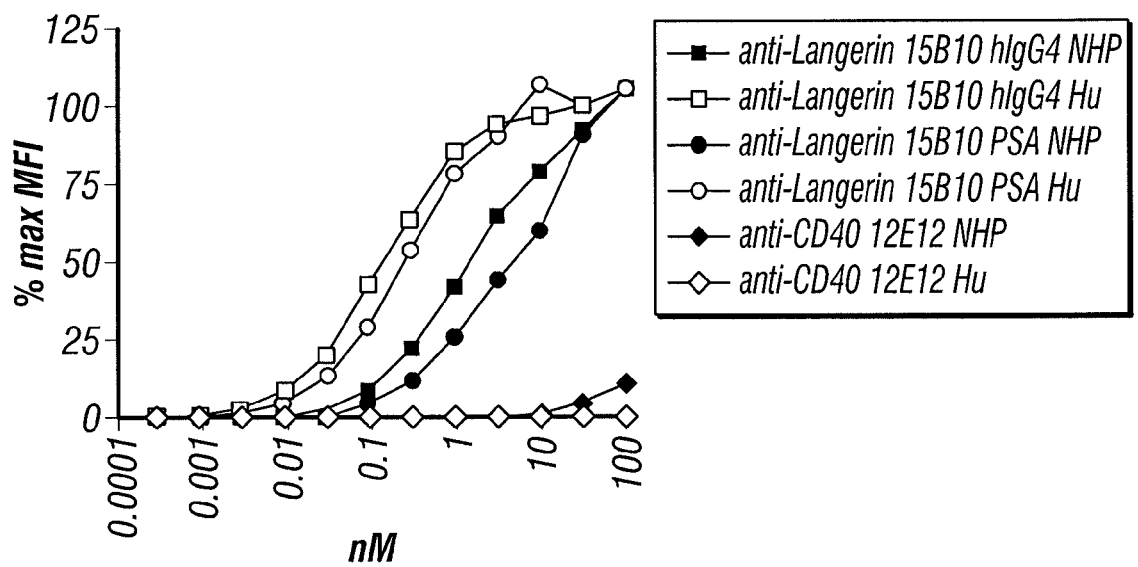

FIG. 8 shows the binding of recombinant anti-Langerin antibodies fused to antigens retain their ability to bind to beads decorated with human and non-human primate (NHP) Langerin ectodomain proteins. Luminex beads of different colors were covalently linked to cellulose binding protein fused to dockerin. The beads were then mixed with either human Langerin ectodomain fused to cohesin, or with NHP (Rhesus macaque) Langerin ectodomain fused to cohesin. The beads were washed and mixed, then incubated with serial dilutions of various pure recombinant anti-Langerin 2G3 or 15B10 mouse V region-human IgG4 chimeric antibodies or the same antibodies with C-terminal fusions to human prostate specific antigen (PSA), or control pure recombinant anti-CD40 12E12 mouse V region-human IgG4 chimeric antibody. After washing, the beads were incubated with an anti-human Fc-PE reagent, washed again, and then read on a BioPlex instrument to detect florescence bound to the different colored beads (expressed as % MFI relative to the maximal signal seen on each bead type.

Figure 9:
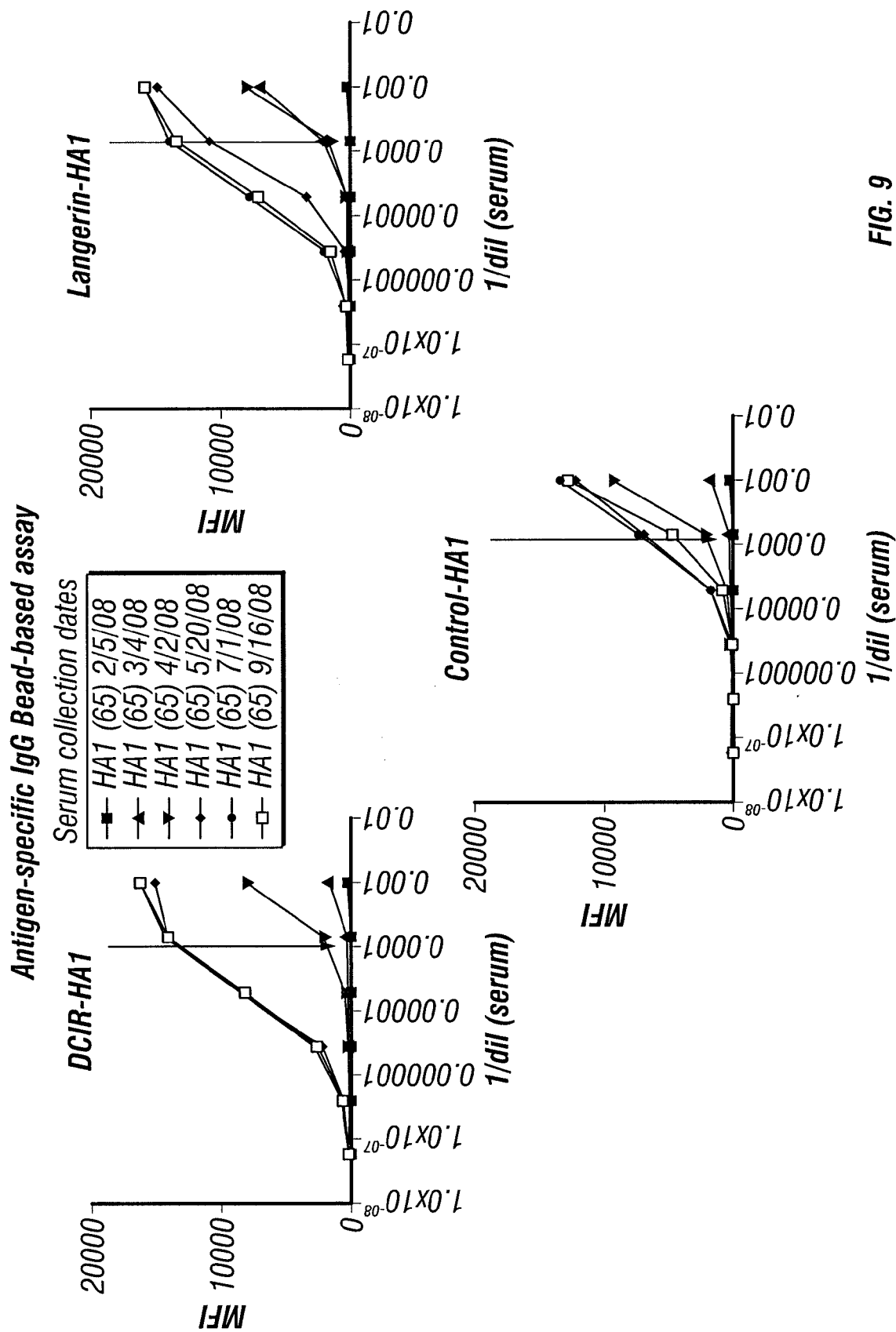
FIG. 9 shows the ability of recombinant anti-Langerin 15B10 antibody fused to Influenza A Hemagglutinin HA-1 from a H1N1 Flu strain to evoke potent antigen-specific antibody production in NHP.

FIG. 9 shows the ability of recombinant anti-Langerin 15B10 antibody fused to Influenza A Hemagglutinin HA-1 from a H1N1 Flu strain to evoke potent antigen-specific antibody production in NHP. NHP were injected intramuscularly (im) with 10E6 pr8 Flu virus and subcutaneously (sc) HIV gag p24 protein (First boost); ~2 months later the NHP were again injected with HIV gag p24 protein (Second boost); about 6 weeks and 4 months later, the NHP were injected intradermal (id) with 100 µg anti-Langerin 15B10 HA1-1 fusion protein with poly IC as adjuvant, or with anti-DCIR HA1-1 fusion protein with poly IC, or with a standard dose of commercial Vaccigrip Flu vaccine and 10E6 pr8 Flu virus. At the indicated dates, serum samples were taken and pooled (4 NHP per group) and serial dilutions were tested for HA1-1 specific IgG antibodies by a baed-based assay. The data shows that the anti-Langerin-HA1-1 vaccine raises potent high titer anti-HA1-1 antibody responses in NHP—the titers observed were 1-2 logs higher than observed with the Vaccigrip control group.

These data show that both anti-Langerin 15B10 and 2G3 recombinant antibodies or such antibodies linked to a cancer antigen retain significant binding to NHP Langerin—a very desirable property for commercial development of these antibodies as antigen-targeting vaccines [this enables mechanism-based preclinical testing of safety and efficacy in NHP models].

Figure 10:
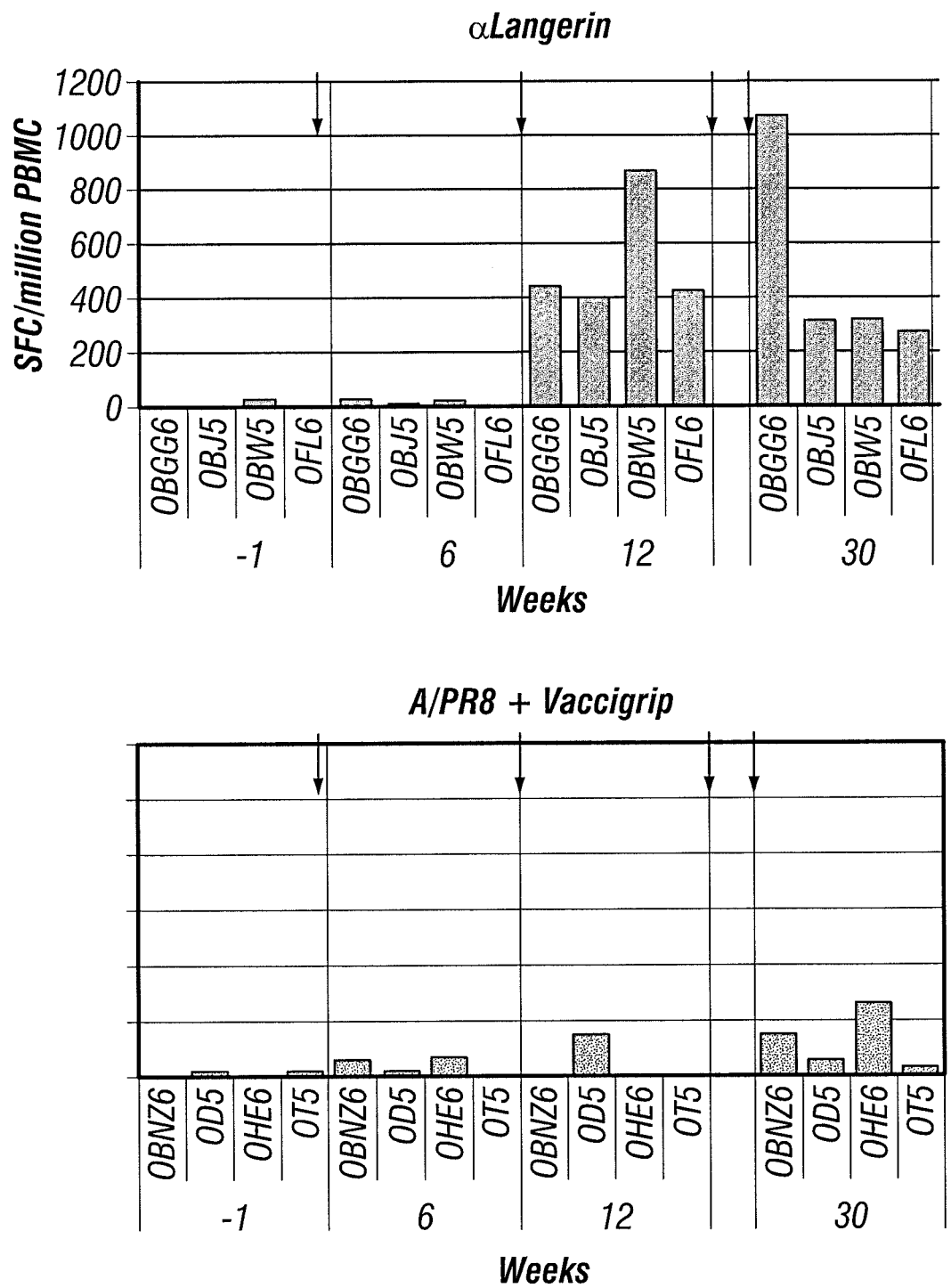
FIG. 10 shows that recombinant fusion proteins of anti-human DC receptors and antigens induce antigen-specific immune responses in NHP.

FIG. 10 shows that recombinant fusion proteins of anti-human DC receptors and antigens induce antigen-specific immune responses in NHP: Rhesus macaques (4 animals in each group) immunized i.m. with live influenza virus (A/PR8, H1N1) and HIVgag-derived p24-PLA on day 0. On day 28, animals were boosted with p24-PLA alone. On day 77 and day 119, each group of animals was immunized as described in FIG. 18 (below). Anti-Langerin-HA1 response in Rhesus macaque—IFN-γ response measured by ELISPOT after ex vivo stimulation with HA peptides. Red arrows indicate priming injections with live influenza virus (A/PR8, H1N1). Blue arrows indicate boost injections. Control group (4 animals) were immunized i.m. with live influenza virus and commercial flu vaccine, VACCIGRIP, with 100 ug poly I:C per animal. Experimental group (4 animals) were boosted i.d. with anti-DCIR-HA1 (100 µg/animals) with 100 µg of poly I:C per animal. The data above show that anti-Langerin-HA1 elicited potent HA1-specific T cells responses as measured by IFNγ ELISPOT.

Figure 11:
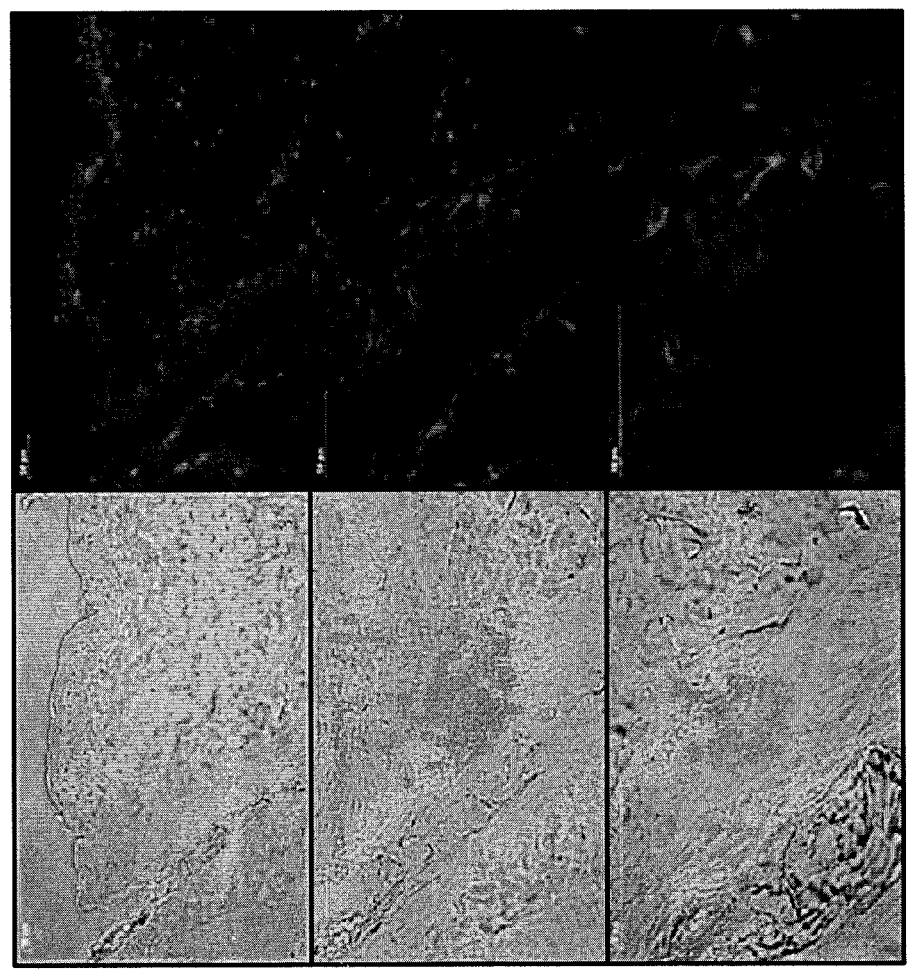
FIG. 11 shows that the Anti-Langerin G3 antibody specifically stains NHP Langerhans cells.

FIG. 11 shows that the Anti-Langerin G3 antibody specifically stains NHP Langerhans cells. Rhesus macaque skin sections were prepared and stained with anti-Langerin 2G3 and then Texas Red-labeled goat ant-mouse reagent. Cell nuclei were stained with DAPI [blue]. This shows specific staining of NHP LC demonstrating the specific cross-reactivity of this anti-human Langerin antibody with NHP Langerin.

The 15B10.3 hydridoma has been deposited under the Budapest Treaty with the U.S. American Type Culture Collection and received Deposit No. PTA-9852; and the 2G3.6 hybridoma received Deposit No. PTA-9853.

Figure 12:
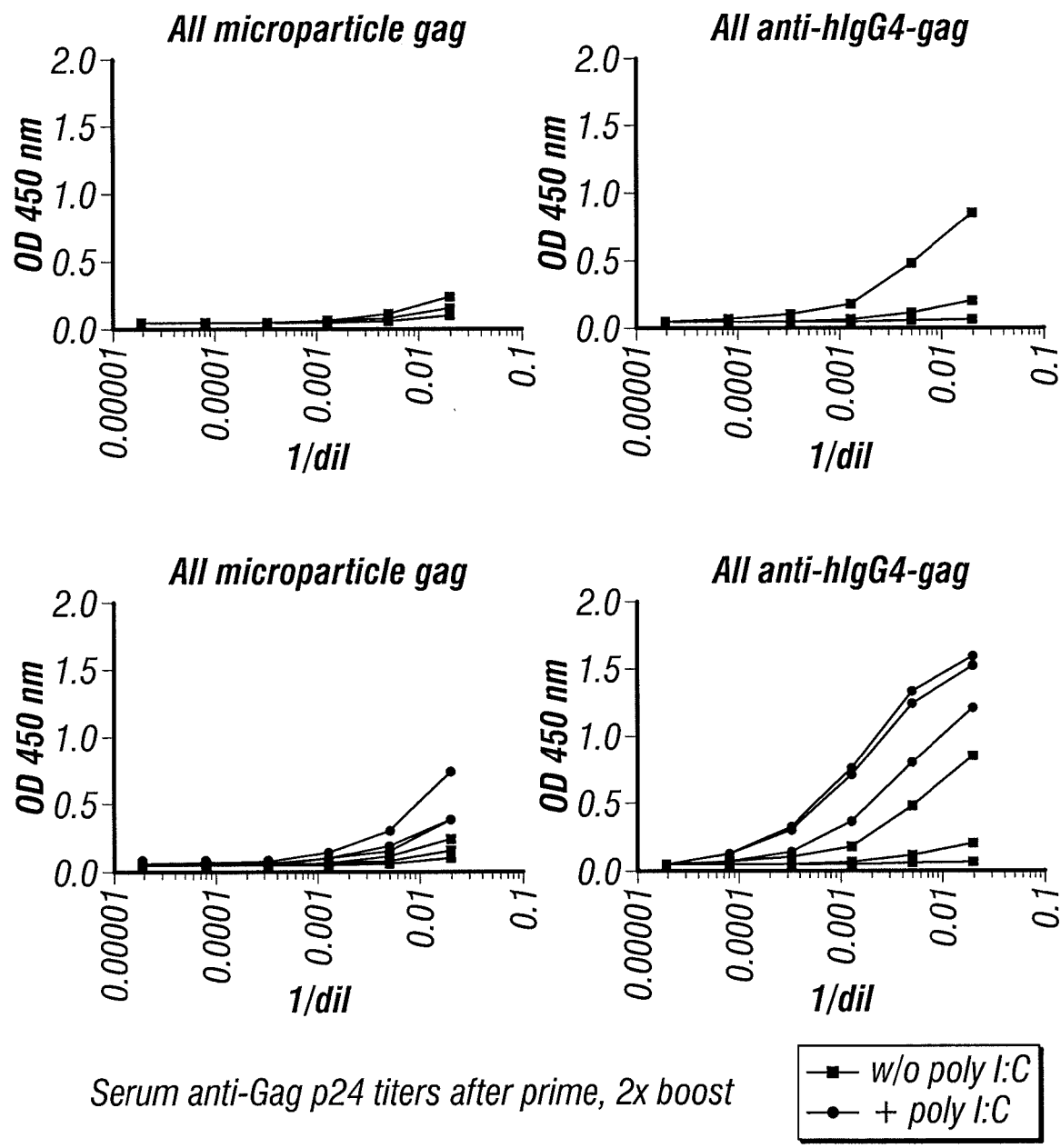
FIG. 12 shows the antibody titers for anti-HIV-gag antibodies in NHP vaccination with a gag-microparticle, an anti-hIGG4-gag antibody, an anti-DCIR-gag vaccine and an anti-Langerin-gag-p24 vaccine, all with or without poly I:C as an adjuvant.
Figure 12:
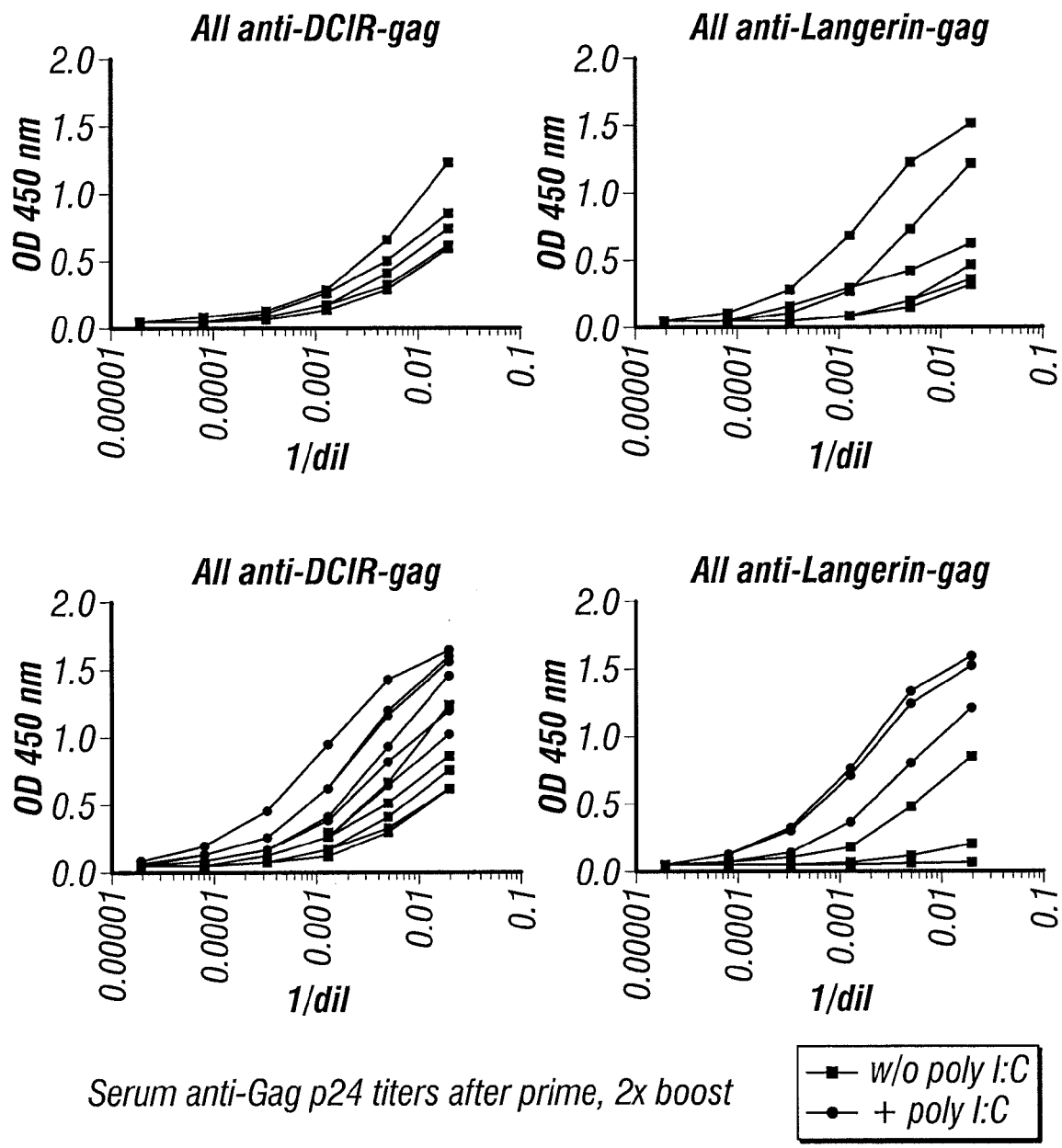

FIG. 12 shows the antibody titers for anti-HIV-gag antibodies in NHP vaccination with a gag-microparticle, an anti-hIGG4-gag antibody, an anti-DCIR-gag vaccine and an anti-Langerin-gag-p24 vaccine, all with or without poly I:C as an adjuvant. Briefly, non-human primates (NHP) were immunized and anti-Langerin-gag24 antibody responses were determined. It was found that more potent were possible with the anti-Langerin-gag p24 constructs than with gag p24 on a microcarrier or control antibody-p24. Unlike anti-DCIR targeting, it was found that anti-Langerin-Ag vaccination is relatively independent of poly I:C adjuvant. Each curve is an individual monkey, the assay is serum dilutions tested for antibodies against p24. Cynomolgus macaques were injected i.d. with 250 ug of each antibody-HIV gag p24 vaccine or gag p24 attached to a microcarrier (p24 amount was normalized to correspond to the actual amount of p24 mass injected). The animals were then injected twice more at 6 week intervals. The FIG. 12 graph shows represents ELISA assay for antigen-specific anti-gag p24 titers of serum samples taken 2 weeks after the third injection. FIG. 12 shows serial dilutions of the sera graphed for each individual monkey [graph lines shown in blue]. A parallel group of monkeys were co-injected with the p24 proteins and poly I:C adjuvant [graph lines shown in red].

Figure 13:
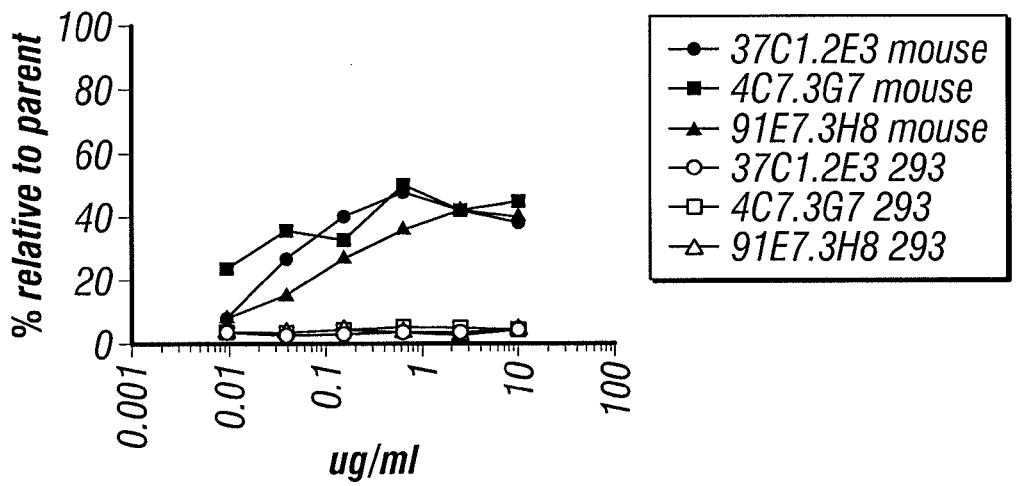
FIG. 13 shows FACS analysis on Langerin clones: 293F cells were transiently transfected with vectors directing the expression of full-length (cell surface) Langerin from human, Rhesus macaque, and mouse.
Figure 13:
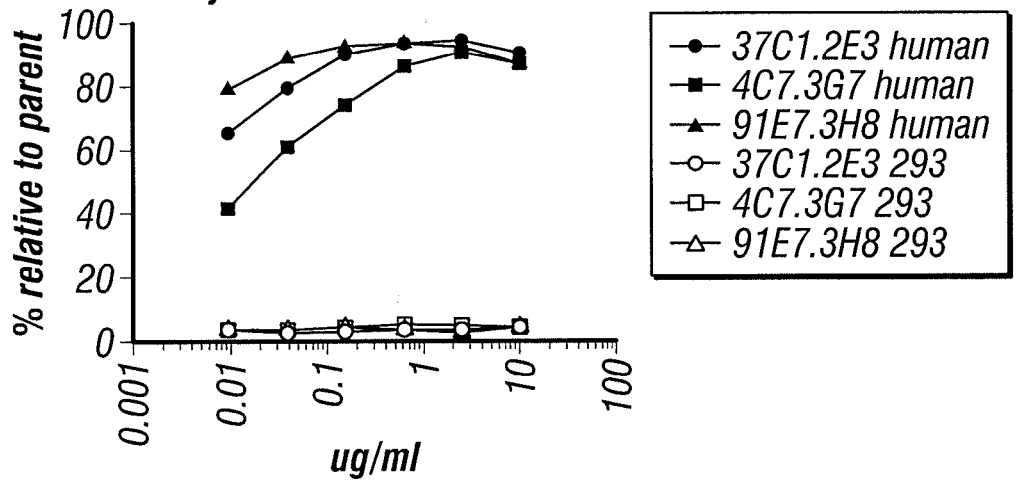
Figure 13:
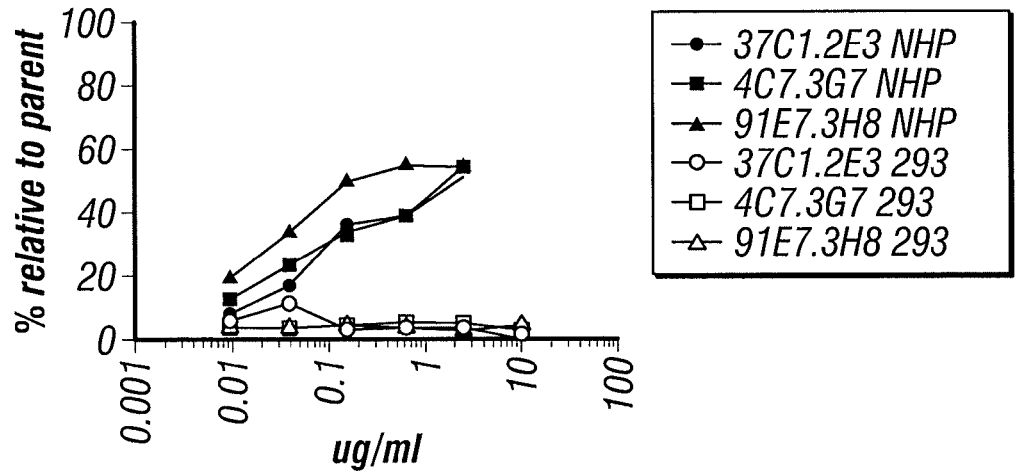

FIG. 13—FACS analysis on Langerin clones: 293F cells were transiently transfected with vectors directing the expression of full-length (cell surface) langerin from human, Rhesus macaque, and mouse. Cells were stained with a dilution series of the pure monoclonal antibodies, washed, then counter-stained with an anti-mouse IgG-PE conjugate, then washed again. Cells were analyzed by flow cytometry. The data are expressed as % cells giving a positive cell surface staining signal relative to the control untransfected cells.

Figure 14:
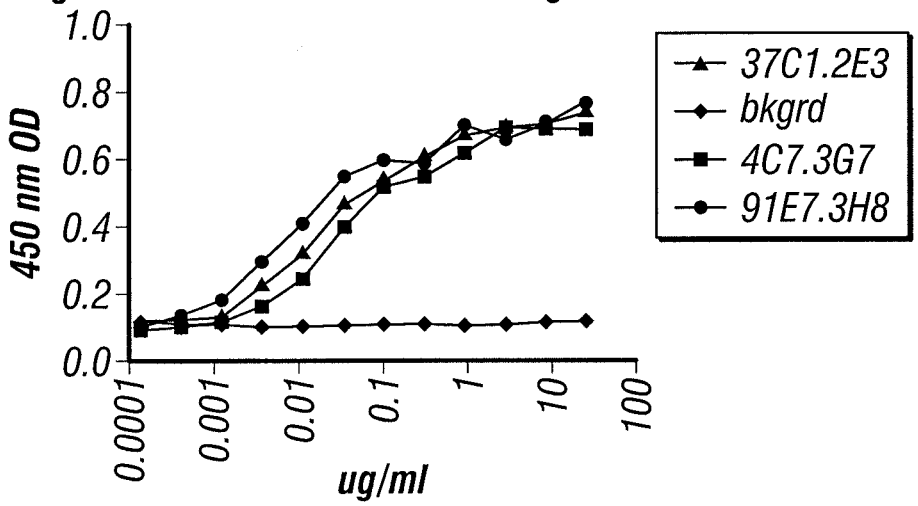
FIG. 14 show the results of ELISA binding analysis in two formats—direct (antigen bound to plate directly and bound antibody detected with an anti-mouse IgG-HRP conjugate) and capture (antibody bound to plate.
Figure 14:
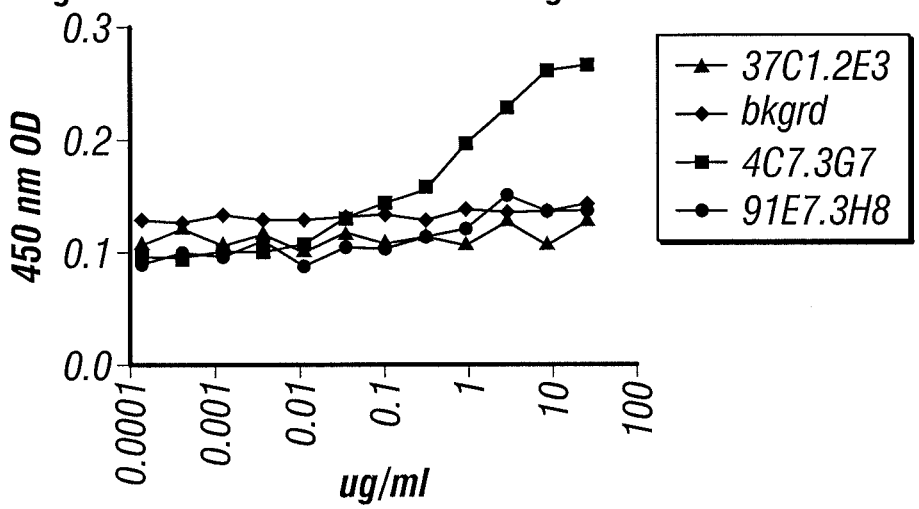
Figure 14:
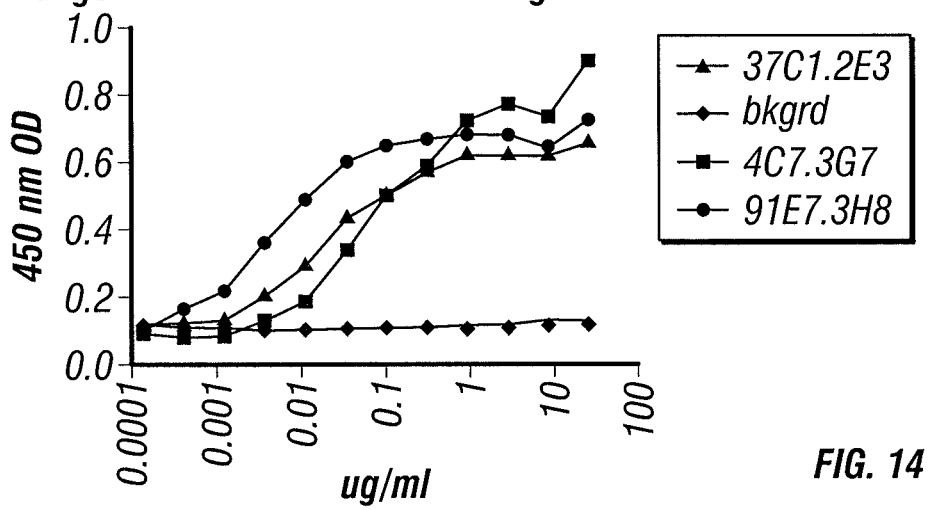
Figure 14:
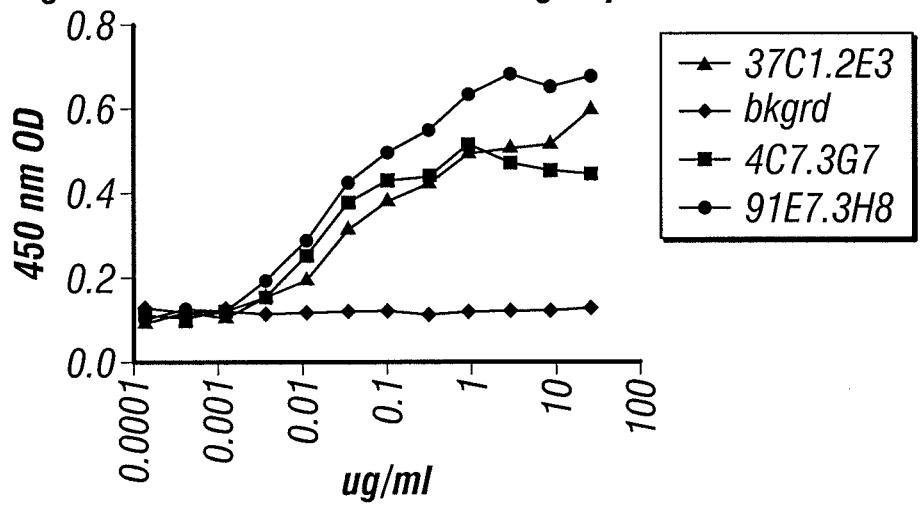
Figure 14:
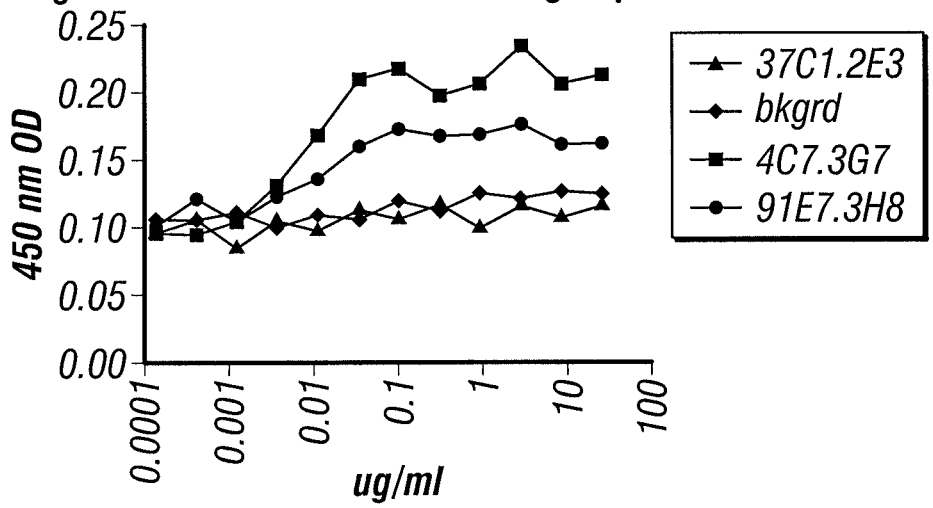
Figure 14:
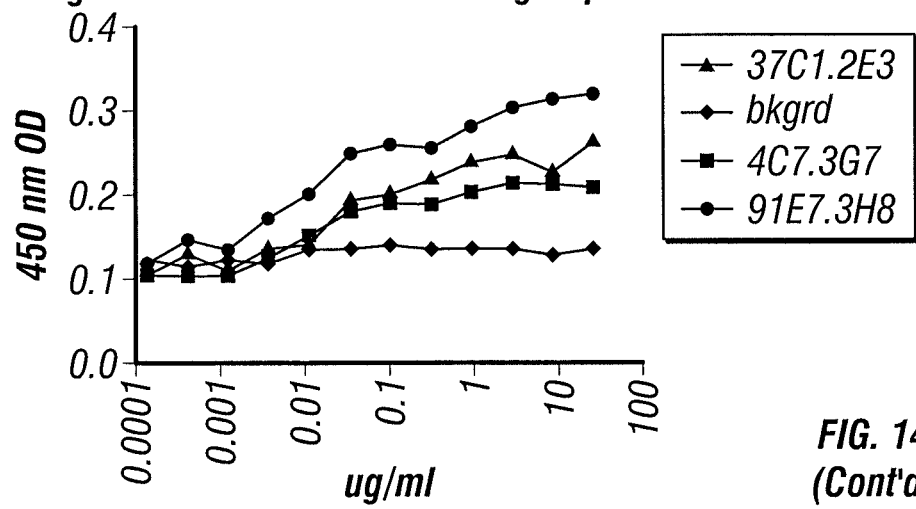

FIG. 14—ELISA analysis in two formats—direct (antigen bound to plate directly and bound antibody detected with an anti-mouse IgG-HRP conjugate) and capture (antibody bound to plate, capturing a fixed concentration of biotinylated Langerin ectodomain protein, detected with a neutravidin-HRP reagent). ELISA data for human, Rhesus macaque, and mouse Langerin ectodomain proteins are shown.

TABLE 1

Immunogenicity in cynomolgus macaques of anti-Langerin-Gag and anti-DCIR-Gag fusion protein, for FIG. 12.
Group 1 (n = 6) 0.25 mg anti-Langerin-Gag
Group 2 (n = 6) 0.25 mg anti-Langerin-Gag + 0.25 mg PolyIC
Group 3 (n = 6) 0.25 mg anti-DCIR-Gag
Group 4 (n = 6) 0.25 mg anti-DCIR-Gag + 0.25 mg PolyIC
Group 5 (n = 3) 0.25 mg IgG4-Gag
Group 6 (n = 3) 0.25 mg IgG4-Gag + 0.25 mg PolyIC
Group 7 (n = 3) 0.0635 mg Gag
Group 8 (n = 3) 0.0635 mg Gag + 0.25 mg PolyIC

| | Timepoints (weeks) post priming | Blood PBMC | Blood Micorarray | Plasma | Rectal Wash |
|---|---|---|---|---|---|
| | −3 | X | X | X | |
| | −2 | X | | X | X |
| | −1 | X | | X | |
| Vaccination | 0 | | | X | X |
| | 2 | X | | X | X |
| Vaccination | 6 | X | | X | X |
| | 8 | X | X | X | X |
| | 10 | | | X | X |
| Vaccination | 12 | | | X | X |
| | 13 | | X | X | x |
| | 14 | | X | X | X |
| | 15 | X | | X | X |
| | 16 | | X | X | X |
| | 18 | X | | X | X |
| | 22 | X | X | X | X | mAnti-Langerin 91E7K Light Chain Sequence (SEQ ID NO.: 51)
ATGGATTTTCAGATGCAGATTATCAGCTTGCTGCTAATCAGTGTCACAGT

CATAGTGTCTAATGGAGAAATTGTGCTCACCCAGTCTCCAACCACCATGG

CTGCATCTCCCGGGGAGAAGATCACTATCACCTGCAGTGCCAGCTCAAGT

ATAAGTTCCCATTACTTACATTGGTATCAGCAGAAGCCAGGATTCTCCCC

TAAACTCTTGATTTATAGGACATCCAATCTGGCTTCTGGAGTCCCAGCTC

GCTTCAGTGGCAGTGGGTCTGGGACCTCTTACTCTCTCACAATTGACACC

ATGGAGGCTGAAGATGTTGCCACTTACTACTGCCAGCAGGGTAGTAGTAT

ACCATTCACGTTCGGCTCGGGGACAAAGTTGGAAATAAAACGGGCTGATG

CTGCACCAACTGTATCCATCTTCCCACCATCCAGTGAGCAGTTAACATCT

GGAGGTGCCTCAGTCGTGTGCTTCTTGAACAACTTCTACCCCAAAGACAT

CAATGTCAAGTGGAAGATTGATGGCAGTGAACGACAAAATGGCGTCCTGA

ACAGTTGGACTGATCAGGACAGCAAAGACAGCACCTACAGCATGAGCAGC

ACCCTCACGTTGACCAAGGACGAGTATGAACGACATAACAGCTATACCTG

TGAGGCCACTCACAAGACATCAACTTCACCCATCGTCAAGAGCTTCAACA

GGAATGAGTGTTAG mAnti-Langerin 91E7K Light Chain Sequence (SEQ ID NO.: 52)
EIVLTQSPTTMAASPGEKITITCSASSSISSHYLHWYQQKPGFSPKLLIYRTSNLAS

GVPARFSGSGSGTSYSLTIDTMEAEDVATYYCQQGSSIPFTFGSGTKLEIKRADAAPTVSI

FPPSSEQLTSGGASVVCFLNNFYPKDINVKWKIDGSERQNGVLNSWTDQDSKDSTYSM

SSTLTLTKDEYERHNSYTCEATHKTSTSPIVKSFNRNEC mAnti-Langerin 91E7H [Mouse IgG2a] Heavy Chain
ATGAGATCACTGTTCTCTTTACAGTTACTGAGCACACAGGACCTCGCCATGGGATGGAGCTGTATCATCCTCTTCTTGGTAGCAACAGCTACAGGTGTCCACTCTCAGGTCCAACTGCAGCAGCCTGGGGCTGAACTTGTGAAGCCTGGGGCTTCAGTGAAGCTGTCCTGCAAGGCTTCTGGCTACACCTTCACCAGTTACTGGATGCAGTGGGTAAAGCAGAGGCCTGGACAGGGCCTTGAGTGGATCGGAGAGATTGATCCTTCTGATAGCTATACTAACTACAATCAAAGGTTCAAGGGCAAGGCCACATTGACTGTGGACACATCCTCCAGCACAGCCTACATACAGCTCAGCAGCCTGACGTCTGAGGACTCTGCGGTCTGTTTCTGTGCAAGACGCTACTATGGTAACTACGATGGGTTTGCTTACTGGGGCCAAGGGACTCTGGTCACTGTCTCTGCAGCCAAAACAACAGCCCCATCGGTCTATCCACTGGCCCCTGTGTGTGGAGGTACAACTGGCTCCTCGGTGACTCTAGGATGCCTGGTCAAGGGTTATTTCCCTGAGCCAGTGACCTTGACCTGGAACTCTGGATCCCTGTCCAGTGGTGTGCACACCTTCCCAGCTCTCCTGCAGTCTGGCCTCTACACCCTCAGCAGCTCAGTGACTGTAACCTCGAACACCTGGCCCAGCCAGACCATCACCTGCAATGTGGCCCACCCGGCAAGCAGCACCAAAGTGGACAAGAAAATTGAGCCCAGAGTGCCCATAACACAGAACCCCTGTCCTCCACTCAAAGAGTGTCCCCCATGCGCAGCTCCAGACCTCTTGGGTGGACCATCCGTCTTCATCTTCCCTCCAAAGATCAAGGATGTACTCATGATCTCCCCGAGCCCCATGGTCACATGTGTGGTGGTGGATGTGAGCGAGGATGACCCAGACGTCCAGATCAGCTGGTTTGTGAACAACGTGGAAGTACACACAGCTCAGACACAAACCCATAGAGGAGGATTACAACAGTACTCTCCGGGTGGTCAGTGCCCTCCCCATCCAGCACCAGGACTGGATGAGTGGCAAGGAGTTCAAATG-CAAGGTCAACAACAGAGCCCTCCCATCCCCCATCGAGAAAACCATCTCAAAACCCAGAGGGCCAGTAAGAGCTCCACAGGTATATGTCTTGCCTCCACCAGCAGAAGAGATGACTAAGAAAGAGTTCAGTCTGACCTGCATGATCACAGGCTTCTTACCTGCCGAAATTGCTGTGGACTGGACCAGCAATGGGCGTACAGAGCAAAACTACAAGAACACCGCAACAGTCCTGGACTCTGATGGTTCTTACTTCATGTACAGCAAGCTCAGAGTACAAAAGAGCACTTGGGAAAGAGGAAGTCTTTTCGCCTGCTCAGTGGTCCACGAGGGTCTGCACAATCACCTTACGACTAAGACCATCTCCCGGTCTCTGGGTAAAGCTAGCTGA [GCTAGC in bold is for the in-frame fusion of antigens at the H-chain C-terminus] (SEQ ID NO.: 53)

mAnti-Langerin 91E7H [Mouse IgG2a] Mature H Heavy Chain Sequence (SEQ ID NO.: 54)
QVQLQQPGAELVKPGASVKLSCKASGYTFTSYWMQWVKQRPGQGLEWIGEID

PSDSYTNYNQRFKGKATLTVDTSSSTAYIQLSSLTSEDSAVCFCARRYYGNYDGFAYW

GQGTLVTVSAAKTTAPSVYPLAPVCGGTTGSSVTLGCLVKGYFPEPVTLTWNSGSLSSG

VHTFPALLQSGLYTLSSSVTVTSNTWPSQTITCNVAHPASSTKVDKKIEPRVPITQNPCPP

LKECPPCAAPDLLGGPSVFIFPPKIKDVLMISPSPMVTCVVVDVSEDDPDVQISWFVNNV

EVHTAQTQTHREDYNSTLRVVSALPIQHQDWMSGKEFKCKVNNRALPSPIEKTISKPRG

PVRAPQVYVLPPPAEEMTKKEFSLTCMITGFLPAEIAVDWTSNGRTEQNYKNTATVLDS

DGSYFMYSKLRVQKSTWERGSLFACSVVHEGLHNHLTTKTISRSLGKAS mAnti-Langerin 37C1K Light Chain (SEQ ID NO.: 55)
ATGAGGGCCCCTGCTCAGTTTTTTGGGATCTTGTTGCTCTGGTTTCCAGG

TATCAGATGTGACATCAAGATGACCCAGTCTCCATCCTCCATGTATGCAT

CGCTGGGAGAGAGTCACTATTACTTGCAAGGCGAGTCAGGACATTAAA

AGCTATTTAACTTGGTACCAGCAGAAACCATGGAAATCTCCTAAGACCCT

GATCAATTATGCAACAAGCTTGGCAGATGGGGTCCCATCAAGATTCAGTG

GCAGTGGATCTGGACAAGATTATTCTCTAACCATCAGCAGCCTGGAGTCT

GACGATACAGCAACTTATTACTGTCTACAGCATGGTCAGAGTCCGTTCAC

GTTCGGAGGGGGGACCAGGCTGGAGATAAAACGGGCTGATGCTGCACCAA

CTGTATCCATCTTCCCACCATCCAGTGAGCAGTTAACATCTGGAGGTGCC

TCGGTCGTGTGCTTCTTGAACAACTTCTACCCCAAAGACATCAATGTCAA

GTGGAAGATTGATGGCAGTGAACGACAAAATGGCGTCCTGAACAGTTGGA

CTGATCAGGACAGCAAAGACAGCACCTACAGCATGAGCAGCACCCTCACG

TTGACCAAGGACGAGTATGAACGACATAACAGCTATACCTGTGAGGCCAC

TCACAAGACATCAACTTCACCCATCGTCAAGAGCTTCAACAGGAATGAGT

GTTAG mAnti-Langerin 37C1K Light Chain (SEQ ID NO.: 56)

DIKMTQSPSSMYASLGERVTITCKASQDIKSYLTWYQQKPWKSPKTLINYATSL

ADGVPSRFSGSGSGQDYSLTISSLESDDTATYYCLQHGQSPFTFGGGTRLEIKRADAAPT

VSIFPPSSEQLTSGGASVVCFLNNFYPKDINVKWKIDGSERQNGVLNSWTDQDSKDSTY

SMSSTLTLTKDEYERHNSYTCEATHKTSTSPIVKSFNRNEC mAnti-Langerin 37C1H [Mouse IgG2a] Heavy Chain (SEQ ID NO.: 57)

ATGAGATCACTGTTCTCTTTACAGTTACTGAGCACACAGGACCTCGCCAT

GGGATGGAGCTGTATCATCCTCTTCTTGGTAGCAACAGCTACAGGTGTCC

ACTCTCAGGTCCAACTGCAGCAGCCTGGGGCTGAGCTTGTGAAGCCTGGG

GCTTCAGTGAAGCTGTCCTGCAAGGCTTCTGGCTACACCTTCACCAGTTA

CTGGATGCAGTGGGTAAAGCAGAGGCCTGGACAGGGCCTTGAGTGGACCG

GAGAGATTGATCCTTCTGATAGCTATACTAACTACAATCAAAGGTTCAAG

GGCAAGGCCACATTGACTGTGGACACATCCTCCAGCACAGCCTACACACA

GCTCAGCAGCCTGACGTCTGAGGACTCTGCGGTCCATTTCTGTGCAAGAC

GCTACTATGGTAACTACGATGGGTTTGCTTACTGGGGCCAAGGGACTCTG

GTCACTGTCTCTGCAGCCAAAACAACAGCCCCATCGGTCTATCCACTGGC

CCCTGTGTGTGGAGGTACAACTGGCTCCTCGGTGACTCTAGGATGCCTGG

TCAAGGGTTATTTCCCTGAGCCAGTGACCTTGACCTGGAACTCTGGATCC

CTGTCCAGTGGTGTGCACACCTTCCCAGCTCTCCTGCAGTCTGGCCTCTA

CACCCTCAGCAGCTCAGTGACTGTAACCTCGAACACCTGGCCCAGCCAGA

CCATCACCTGCAATGTGGCCCACCCGGCAAGCAGCACCAAAGTGGACAAG

AAAATTGAGCCCAGAGTGCCCATAACACAGAACCCCTGTCCTCCACTCAA

AGAGTGTCCCCCATGCGCAGCTCCAGACCTCTTGGGTGGACCATCCGTCT

TCATCTTCCCTCCAAAGGTCAAGGATGTACTCATGATCTCCCTGAGCCCC

ATGGTCACATGTGTGGTGGTGGATGTGAGCGAGGATGACCCAGACGTCCA

GATCAGCTGGTTTGTGAACAACGTGGAAGTACACACAGCTCAGACACAAA

CCCATAGAGAGGATTACAACAGTACTCTCCGGGTGGTCAGTGCCCTCCCC

ATCCAGCACCAGGACTGGATGAGTGGCAAGGAGTTCAAATGCAAGGTCAA

CAACAGAGCCCTCCCATCCCCCATCGAGAAAACCATCTCAAAACCCAGAG

GGCCAGTAAGAGCTCCACAGGTATATGTCTTGCCTCCACCAGCAGAAGAG

ATGACTAAGAAAGAGTTCAGTCTGACCTGCATGATCACAGGCTTCTTACC

TGCCGAAATTGCTGTGGACTGGACCAGCAATGGGCGTACAGAGCAAAACT

ACAAGAACACCGCAACAGTCCTGGACTCTGATGGTTCTTACTTCATGTAC

AGCAAGCTCAGAGTACAAAAGAGCACTTGGGAAAGAGGAAGTCTTTTCGC

CTGCTCAGTGGTCCACGAGGGTCTGCACAATCACCTTACGACTAAGACCA

TCTCCCGGTCTCTGGGTAAAGCTAGCTGA mAnti-Langerin 37C1H [Mouse IgG2a] Heavy Chain (SEQ ID NO.: 58)

QVQLQQPGAELVKPGASVKLSCKASGYTFTSYWMQWVKQRPGQGLEWTGEID

PSDSYTNYNQRFKGKATLTVDTSSSTAYTQLSSLTSEDSAVHFCARRYYGNYDGFAYW

GQGTLVTVSAAKTTAPSVYPLAPVCGGTTGSSVTLGCLVKGYFPEPVTLTWNSGSLSSG

VHTFPALLQSGLYTLSSSVTVTSNTWPSQTITCNVAHPASSTKVDKKIEPRVPITQNPCPP

LKECPPCAAPDLLGGPSVFIFPPKVKDVLMISLSPMVTCVVVDVSEDDPDVQISWFVNN

VEVHTAQTQTHREDYNSTLRVVSALPIQHQDWMSGKEFKCKVNNRALPSPIEKTISKPR

GPVRAPQVYVLPPPAEEMTKKEFSLTCMITGFLPAEIAVDWTSNGRTEQNYKNTATVL

DSDGSYFMYSKLRVQKSTWERGSLFACSVVHEGLHNHLTTKTISRSLGKAS mAnti-Langerin 4C7K (Light Chain)

(SEQ ID NO.: 77)

ATGGATTTTCAAGTGCAGATTTTCAGCTTCCTGCTAATCAGTGCTTCAGT

CATAATGTCCAGAGGACAAATTGTTCTCTCCCAGTCTCCAGCAATCCTGT

CTGCATCTCCAGGGGAGAAGGTCACAATGACTTGCAGGGCCAGCTCAAGT

GTAAGTTACATGCACTGGTACCAGCGGAAGCCAGGATCCTCCCCCAAACC

```
CTGGATTTATGCCACATCCAACCTGGCTTCTGGAGTCCCTGCTCGCTTCA
GTGGCAGTGGGTCTGGGACCTCTTATTCTCTCACAATCAGCAGAGTGGAG
GCTGAAGATGCTGCCACTTATTACTGCCAGCAGTGGAGTAGTAACCCGCT
CACGTTCGGTGCTGGGACCAAGCTGGAGCTGAAACGGGCTGATGCTGCAC
CAACTGTATCCATCTTCCCACCATCCAGTGAGCAGTTAACATCTGGAGGT
GCCTCAGTCGTGTGCTTCTTGAACAACTTCTACCCCAAAGACATCAATGT
CAAGTGGAAGATTGATGGCAGTGAACGACAAAATGGCGTCCTGAACAGTT
GGACTGATCAGGACAGCAAAGACAGCACCTACAGCATGAGCAGCACCCTC
ACGTTGACCAAGGACGAGTATGAACGACATAACAGCTATACCTGTGAGGC
CACTCACAAGACATCAACTTCACCCATCGTCAAGAGCTTCAACAGGAATG
AGTGTTAG
```
(SEQ ID NO.: 78)
```
QIVLSQSPAILSASPGEKVTMTCRASSSVSYMHWYQRKPGSSPKPWIYAT
SNLASGVPARFSGSGSGTSYSLTISRVEAEDAATYYCQQWSSNPLTFGAG
TKLELKRADAAPTVSIFPPSSEQLTSGGASVVCFLNNFYPKDINVKWKID
GSERQNGVLNSWTDQDSKDSTYSMSSTLTLTKDEYERHNSYTCEATHKTS
TSPIVKSFNRNEC
``` mAnti-Langerin 4C7H [Mouse IgG2a] Heavy Chain (SEQ ID NO.: 79)
```
ATGGAATGGAGCTGGGTCTTTCTCTTCCTCCTGTCAGTAATTGCAGGTGT
CCAATCCCAGGTTCAGCTGCAGCAGTCTGGGGCTGAGCTGGTGAGGCCTG
GGGCTTCAGTGACGCTGTCCTGCAAGGCTTCGGGCTACACATTTATTGAC
CATGATATGCACTGGGTGCAGCAGACACCTGTGTATGGCCTGGAATGGAT
CGGAGCTATTGATCCTGAAACTGGTGATACTGGCTACAATCAGAAGTTCA
AGGGCAAGGCCATACTGACTGCAGACAAATCCTCCAGGACAGCCTACATG
GAACTCCGCAGCCTGACATCTGAGGACTCTGCCGTCTATTACTGTACAAT
CCCCTTCTACTATAGTAACTACAGCCCGTTTGCTTACTGGGGCCAAGGGG
CTCTGGTCACTGTCTCTGCAGCCAAAACAACAGCCCCATCGGTCTATCCA
CTGGCCCCTGTGTGTGGAGGTACAACTGGCTCCTCGGTGACTCTAGGATG
CCTGGTCAAGGGTTATTTCCCTGAGCCAGTGACCTTGACCTGGAACTCTG
GATCCCTGTCCAGTGGTGTGCACACCTTCCCAGCTCTCCTGCAGTCTGGC
CTCTACACCCTCAGCAGCTCAGTGACTGTAACCTCGAACACCTGGCCCAG
CCAGACCATCACCTGCAATGTGGCCCACCCGGCAAGCAGCACCAAAGTGG
ACAAGAAAATTGAGCCCAGAGTGCCCATAACACAGAACCCCTGTCCTCCA
CTCAAAGAGTGTCCCCCATGCGCAGACCTCTTGGGTGGACCATCCGTCTT
CATCTTCCCTCCAAAGATCAAGGATGTACTCATGATCTCCCTGAGCCCCA
TGGTCACATGTGTGGTGGTGGATGTGAGCGAGGATGACCCAGACGCCCAG
ATCAGCTGGTTTGTGAACAACGTGGAAGTACACACAGCTCAGACACAAAC
CCATAGAGAGGATTACAACAGTACTCTCCGGGTGGTCAGTGCCCTCCCCA
TCCAGCACCAGGACTGGATGAGTGGCAAGGAGTTCAAATGCAAGGTCAAC
AACAGAGCCCTCCCATCCCCCATCGAGAAAACCATCTCAAAACCCAGAGG
GCCAGTAAGAGCTCCACAGGTATATGTCTTGCCTCCACCAGCAGAAGAGA
TGACTAAGAAAGAGTTCAGTCTGACCTGCATGATCACAGGCTTCTTACCT
GCCGAAATTGCTGTGGACTGGACCAGCAATGGGCGTACAGAGCAAAACTA
CAAGAACACCGCAACAGTCCTGGACTCTGATGGTTCTTACTTCATGTACA
GCAAGCTCAGAGTACAAAAGAGCACTTGGGAAAGAGGAAGTCTTTTCGCC
TGCTCAGTGGTCCACGAGGGTCTGCACAATCACCTTACGACTAAGACCAT
CTCCCGGTCTCTGGGTAAAGCTAGCTGA
``` mAnti-Langerin 4C7H [Mouse IgG2a] Heavy Chain (SEQ ID NO.: 80)
```
QVQLQQSGAELVRPGASVTLSCKASGYTFIDHDMHWVQQTPVYGLEWIGAIDP
ETGDTGYNQKFKGKAILTADKSSRTAYMELRSLTSEDSAVYYCTIPFYYSNYSPFAYW
GQGALVTVSAAKTTAPSVYPLAPVCGGTTGSSVTLGCLVKGYFPEPVTLTWNSGSLSS
GVHTFPALLQSGLYTLSSSVTVTSNTWPSQTITCNVAHPASSTKVDKKIEPRVPITQNPC
PPLKECPPCADLLGGPSVFIFPPKIKDVLMISLSPMVTCVVVDVSEDDPDAQISWFVNNV
EVHTAQTQTHREDYNSTLRVVSALPIQHQDWMSGKEFKCKVNNRALPSPIEKTISKPRG
PVRAPQVYVLPPPAEEMTKKEFSLTCMITGFLPAEIAVDWTSNGRTEQNYKNTATVLDS
DGSYFMYSKLRVQKSTWERGSLFACSVVHEGLHNHLTTKTISRSLGKAS
```

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. As used herein, the phrase "consisting essentially of" limits the scope of a claim to the specified materials or steps and those that do not materially affect the basic and novel characteristic(s) of the claimed invention. As used herein, the phrase "consisting of" excludes any element, step, or ingredient not specified in the claim except for, e.g., impurities ordinarily associated with the element or limitation.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. Banchereau J, Steinman R M. Dendritic cells and the control of immunity. Nature. 1998; 392:245-252.
2. Pascual V, Banchereau J, Palucka A. The Central Role of Dendritic Cells and Interferon-alpha in SLE. Curr Opin Rheumatol. 2003; in press.
3. Palucka K, Banchereau J. Dendritic cells: a link between innate and adaptive immunity. J Clin Immunol. 1999; 19:12-25.
4. Di Pucchio T, Chatterjee B, Smed-Sorensen A, et al. Direct proteasome-independent cross-presentation of viral antigen by plasmacytoid dendritic cells on major histocompatibility complex class I. Nat Immunol. 2008; 9:551-557.
5. Kadowaki N, Antonenko S, Lau J Y, Liu Y J. Natural interferon alpha/beta-producing cells link innate and adaptive immunity. J Exp Med. 2000; 192:219-226.
6. Fonteneau J F, Gilliet M, Larsson M, et al. Activation of influenza virus-specific CD4+ and CD8+ T cells: a new role for plasmacytoid dendritic cells in adaptive immunity. Blood. 2003; 101:3520-3526.
7. Randolph G J, Beaulieu S, Lebecque S, Steinman R M, Muller W A. Differentiation of monocytes into dendritic cells in a model of transendothelial trafficking. Science. 1998; 282:480-483.
8. Chomarat P, Dantin C, Bennett L, Banchereau J, Palucka A K. TNF skews monocyte differentiation from macrophages to dendritic cells. J Immunol. 2003; 171:2262-2269.
9. Romani N, Gruner S, Brang D, et al. Proliferating dendritic cell progenitors in human blood. J Exp Med. 1994; 180: 83-93.
10. Sallusto F, Lanzavecchia A. Efficient presentation of soluble antigen by cultured human dendritic cells is maintained by granulocyte/macrophage colony-stimulating factor plus interleukin 4 and downregulated by tumor necrosis factor a. J Exp Med. 1994; 179:1109-1118.
11. Peters J H, Xu H, Ruppert J, Ostermeier D, Friedrichs D, Gieseler R K. Signals required for differentiating dendritic cells from human monocytes in vitro. Adv Exp Med Biol. 1993; 329:275-280.
12. Paquette R L, Hsu N C, Kiertscher S M, et al. Interferon-alpha and granulocyte-macrophage colony-stimulating factor differentiate peripheral blood monocytes into potent antigen-presenting cells. J Leukoc Biol. 1998; 64:358-367.
13. Luft T, Jefford M, Luetjens P, et al. Functionally distinct dendritic cell (DC) populations induced by physiologic stimuli: prostaglandin E(2) regulates the migratory capacity of specific DC subsets. Blood. 2002; 100:1362-1372.
14. He B, Xu W, Santini P A, et al. Intestinal bacteria trigger T cell-independent immunoglobulin A(2) class switching by inducing epithelial-cell secretion of the cytokine APRIL. Immunity. 2007; 26:812-826.
15. Blanco P, Palucka A K, Gill M, Pascual V, Banchereau J. Induction of dendritic cell differentiation by IFN-alpha in systemic lupus erythematosus. Science. 2001; 294:1540-1543.

16. Mohamadzadeh M, Berard F, Essert G, et al. Interleukin 15 skews monocyte differentiation into dendritic cells with features of Langerhans cells. J Exp Med. 2001; 194:1013-1020.
17. Caux C, Massacrier C, Vanbervliet B, et al. CD34+ hematopoietic progenitors from human cord blood differentiate along two independent dendritic cell pathways in response to granulocyte-macrophage colony-stimulating factor plus tumor necrosis factor alpha: II. Functional analysis. Blood. 1997; 90:1458-1470.
18. Caux C, Vanbervliet B, Massacrier C, et al. CD34+ hematopoietic progenitors from human cord blood differentiate along two independent dendritic cell pathways in response to GM-CSF+TNF alpha. J Exp Med. 1996; 184: 695-706.
19. Seifert U, Maranon C, Shmueli A, et al. An essential role for tripeptidyl peptidase in the generation of an MHC class I epitope. Nat Immunol. 2003; 4:375-379.
20. Dudziak D, Kamphorst A O, Heidkamp G F, et al. Differential antigen processing by dendritic cell subsets in vivo. Science. 2007; 315:107-111.
21. Shortman K, Liu Y J. Mouse and human dendritic cell subtypes. Nature Rev Immunol. 2002; 2:151-161.
22. Maldonado-Lopez R, De Smedt T, Michel P, et al. CD8alpha+ and CD8alpha-subclasses of dendritic cells direct the development of distinct T helper cells in vivo. J Exp Med. 1999; 189:587-592.
23. Pulendran B, Smith J L, Caspary G, et al. Distinct dendritic cell subsets differentially regulate the class of immune response in vivo. Proc Natl Acad Sci. 1999; 96:1036-1041.
24. Pulendran B, Kumar P, Cutler C W, Mohamadzadeh M, Van Dyke T, Banchereau J. Lipopolysaccharides from distinct pathogens induce different classes of immune responses in vivo. J Immunol. 2001; 167:5067-5076.
25. Rissoan M C, Soumelis V, Kadowaki N, et al. Reciprocal control of T helper cell and dendritic cell differentiation. Science. 1999; 283:1183-1186.

What is claimed is:

1. An isolated Langerin binding antibody or antigen binding fragment thereof comprising:
   i) an antibody light chain variable domain comprising light chain complementarity regions CDR1L, CDR2L and CDR3L from SEQ ID NO: 2 and an antibody heavy chain variable domain comprising heavy chain complementarity regions CDR1H, CDR2H and CDR3H from SEQ ID NO: 4 or,
   ii) an antibody light chain variable domain comprising light chain complementarity regions CDR1L, CDR2L and CDR3L from SEQ ID NO: 6 and an antibody heavy chain variable domain comprising heavy chain complementarity regions CDR1H, CDR2H and CDR3H from SEQ ID NO: 8.

2. The antibody or antigen binding fragment thereof of claim 1, wherein the antibody comprises
   the light chain variable domain sequence of SEQ ID NO: 2 and the heavy chain variable domain sequence of SEQ ID NO: 4 or,
   the light chain variable domain sequence of SEQ ID NO: 6 and the heavy chain variable domain sequence of SEQ ID NO: 8.

3. The antibody of claim 1, the antibody comprising an antibody light chain of SEQ ID NO: 2 and an antibody heavy chain of SEQ ID NO: 4 or an antibody light chain of SEQ ID NO: 6 and an antibody heavy chain of SEQ ID NO 8.

4. The antibody or antigen binding fragment thereof of claim 1, wherein the antibody or antigen binding fragment is humanized.

5. The antibody of claim 1, wherein the antibody is produced by the 15B10 hybridoma having ATCC Accession No. PTA-9852 or the 2G3 hybridoma having ATCC Accession No. PTA-9853.

6. The antigen binding fragment thereof of claim 1, wherein the antigen binding fragment is an Fv, Fab, Fab', F(ab')2 or ScFv.

7. The antibody or antigen binding fragment thereof of claim 1, wherein the antibody or antigen binding fragment is the expression product of SEQ ID NO: 1 and 3 or SEQ ID NO: 5 and 7.

* * * * *